(12) United States Patent
Shakeel et al.

(10) Patent No.: US 11,624,061 B2
(45) Date of Patent: Apr. 11, 2023

(54) COMPOSITIONS AND METHODS FOR ENZYME IMMOBILIZATION

(71) Applicant: AgroSpheres, Inc., Charlottesville, VA (US)

(72) Inventors: Ameer Hamza Shakeel, Leesburg, VA (US); Zachery George Davis, Charlottesville, VA (US); Joseph Thomas Frank, Charlottesville, VA (US); Sepehr Zomorodi, Charlottesville, VA (US); Payam Pourtaheri, Charlottesville, VA (US)

(73) Assignee: AgroSpheres, Inc., Charlottesville, VA (US)

( * ) Notice: Subject to any disclaimer, the term of this patent is extended or adjusted under 35 U.S.C. 154(b) by 90 days.

(21) Appl. No.: 16/606,595

(22) PCT Filed: Apr. 30, 2018

(86) PCT No.: PCT/US2018/030328
§ 371 (c)(1),
(2) Date: Oct. 18, 2019

(87) PCT Pub. No.: WO2018/201160
PCT Pub. Date: Nov. 1, 2018

(65) Prior Publication Data
US 2020/0123527 A1     Apr. 23, 2020

Related U.S. Application Data

(60) Provisional application No. 62/491,603, filed on Apr. 28, 2017.

(51) Int. Cl.
| | |
|---|---|
| *C12N 11/16* | (2006.01) |
| *C07K 14/005* | (2006.01) |
| *C07K 14/21* | (2006.01) |
| *C07K 14/415* | (2006.01) |
| *C12N 1/20* | (2006.01) |
| *C12N 9/20* | (2006.01) |
| *C12N 9/86* | (2006.01) |
| *C12N 15/70* | (2006.01) |
| *C12N 15/74* | (2006.01) |
| *B82Y 5/00* | (2011.01) |

(52) U.S. Cl.
CPC ............ *C12N 11/16* (2013.01); *C07K 14/005* (2013.01); *C07K 14/21* (2013.01); *C07K 14/415* (2013.01); *C12N 1/20* (2013.01); *C12N 9/20* (2013.01); *C12N 9/86* (2013.01); *C12N 15/70* (2013.01); *C12N 15/74* (2013.01); *B82Y 5/00* (2013.01); *C07K 2319/03* (2013.01); *C07K 2319/735* (2013.01); *C12Y 301/01034* (2013.01); *C12Y 301/03001* (2013.01); *C12Y 305/02006* (2013.01)

(58) Field of Classification Search
None
See application file for complete search history.

(56) References Cited

U.S. PATENT DOCUMENTS

| | | |
|---|---|---|
| 4,613,355 A | 9/1986 | Omura et al. |
| 6,071,725 A | 6/2000 | Pan et al. |
| 7,183,105 B2 | 2/2007 | Sabbadini et al. |
| 7,396,822 B2 | 7/2008 | Sabbadini et al. |
| 7,871,815 B2 | 1/2011 | Sabbadini et al. |
| 8,101,396 B2 | 1/2012 | Sabbadini et al. |
| 8,129,166 B2 | 3/2012 | Sabbadini et al. |
| 8,524,484 B2 | 9/2013 | Sabbadini et al. |
| 9,017,986 B2 | 4/2015 | Sabbadini et al. |
| 9,045,761 B2 | 6/2015 | Giacalone et al. |
| 9,267,108 B2 | 2/2016 | Giacalone |
| 9,566,321 B2 | 2/2017 | Giacalone |
| 9,670,270 B2 | 6/2017 | Sabbadini et al. |
| 10,005,820 B2 | 6/2018 | Giacalone et al. |
| 10,039,817 B2 | 8/2018 | Giacalone |
| 10,124,024 B2 | 11/2018 | Giacalone et al. |
| 10,913,940 B2 | 2/2021 | Pourtaheri et al. |
| 11,219,679 B2 | 1/2022 | Giacalone |
| 11,312,954 B2 | 4/2022 | Linke et al. |

(Continued)

FOREIGN PATENT DOCUMENTS

| | | |
|---|---|---|
| CA | 3056801 A1 | 11/2018 |
| CN | 101935669 A | 1/2011 |

(Continued)

OTHER PUBLICATIONS

Thomassin et al., "OmpT Outer Membrane Proteases of Enterohemorrhagic and Enteropathogenic *Escherichia coli* Contribute Differently to the Degradation of Human LL-37", Infection and Immunity, Feb. 2012, 80(2):483-492.*
Sauerbrei et al., "Lon Protease Removes Excess Signal Recognition Particle Protein in *Escherichia coli* ", J. Bacteriology, 2020, 202(14):e00161-20. 15 pages.*
Jeong et al., "Complete Genome Sequence of *Escherichia coli* Strain BL21", Genome Announcement, 2015, 3(2):e00134-15.*
Ha et al., "The minicell generation in *Escherichia coli* harboring minD of Lactobacillus", J. Chemical and Pharmaceutical Research, 2016, 8(7):328-331.*
Bhosale et al., "Molecular and Industrial Aspects of Glucose Isomerase," Microbiological Reviews, Jun. 1996, p. 280-300, vol. 60, No. 2.

(Continued)

*Primary Examiner* — Suzanne M Noakes
(74) *Attorney, Agent, or Firm* — Cooley LLP

(57) ABSTRACT

The present disclosure relates to compositions of immobilized enzymes on the surface of achromosomal and/or anucleate cells and uses thereof. In particular, the present disclosure provides genetically engineered minicells with enzymes self-assembled on their surface. The immobilized enzymes on the surface of achromosomal and/or anucleate minicells, has agricultural, industrial, and environmental applications due to their improved stability durability and, reusability. Also, provided are methods for producing and purifying enzyme-immobilized minicells.

36 Claims, 27 Drawing Sheets

Specification includes a Sequence Listing.

(56) References Cited

U.S. PATENT DOCUMENTS

| | | |
|---|---|---|
| 2003/0166099 A1 | 9/2003 | Sabbadini et al. |
| 2003/0166279 A1 | 9/2003 | Sabbadini et al. |
| 2003/0203481 A1 | 10/2003 | Surber et al. |
| 2004/0109853 A1 | 6/2004 | McDaniel |
| 2005/0176117 A1 | 8/2005 | Russell et al. |
| 2005/0222057 A1 | 10/2005 | Brahmbhatt et al. |
| 2006/0014291 A1 | 1/2006 | Kebeler et al. |
| 2006/0039870 A1 | 2/2006 | Turner |
| 2006/0084136 A1 | 4/2006 | Kudlicki et al. |
| 2006/0225154 A1 | 10/2006 | Kasukabe et al. |
| 2006/0270040 A1 | 11/2006 | Filutowicz et al. |
| 2007/0048852 A1 | 3/2007 | Holker et al. |
| 2011/0045975 A1 | 2/2011 | Ehr et al. |
| 2011/0104786 A1 | 5/2011 | Van Kimmenade et al. |
| 2012/0107875 A1 | 5/2012 | Liu et al. |
| 2012/0207754 A1 | 8/2012 | Giacalone et al. |
| 2013/0084559 A1 | 4/2013 | Simpson et al. |
| 2013/0316007 A1 | 11/2013 | Ma et al. |
| 2013/0337545 A1 | 12/2013 | Sabbadini et al. |
| 2014/0045692 A1 | 2/2014 | Rossines et al. |
| 2014/0051571 A1 | 2/2014 | Asolkar et al. |
| 2014/0147873 A1 | 5/2014 | Clubb et al. |
| 2015/0087029 A1 | 3/2015 | Tan et al. |
| 2015/0140037 A1 | 5/2015 | Galan et al. |
| 2015/0218254 A1 | 8/2015 | Sabbadini et al. |
| 2015/0264938 A1 | 9/2015 | Gage et al. |
| 2017/0268002 A1 | 9/2017 | Esau et al. |
| 2019/0169582 A1 | 6/2019 | Pourtaheri et al. |
| 2020/0113177 A1 | 4/2020 | Shakeel et al. |
| 2020/0267971 A1 | 8/2020 | Shakeel et al. |
| 2020/0399618 A1 | 12/2020 | Pourtaheri et al. |
| 2022/0008557 A1 | 1/2022 | Von Maltzahn et al. |
| 2022/0031862 A1 | 2/2022 | Fisher et al. |
| 2022/0042042 A1 | 2/2022 | Weinstein et al. |
| 2022/0064661 A1 | 3/2022 | Van Rooijen et al. |
| 2022/0073950 A1 | 3/2022 | Weinstein et al. |
| 2022/0105166 A1 | 4/2022 | Sharei et al. |
| 2022/0152139 A1 | 5/2022 | Van Rooijen et al. |
| 2022/0192201 A1 | 6/2022 | Van Rooijen et al. |
| 2022/0195364 A1 | 6/2022 | Sharei et al. |
| 2022/0202950 A1 | 6/2022 | Brahmbhatt et al. |

FOREIGN PATENT DOCUMENTS

| | | |
|---|---|---|
| CN | 102021185 A | 4/2011 |
| CN | 111328803 A | 6/2020 |
| DK | 2865755 T3 | 5/2017 |
| WO | WO 03/106490 A1 | 12/2003 |
| WO | WO 2016/198852 A1 | 12/2016 |
| WO | WO 2017/180650 A1 | 10/2017 |
| WO | WO 2018/201160 A1 | 11/2018 |
| WO | WO 2018/201161 A1 | 11/2018 |
| WO | WO 2019/060903 A1 | 3/2019 |
| WO | WO-2019222379 A1 | 11/2019 |
| WO | WO2021133846 A2 | 7/2021 |
| WO | WO2021236799 A2 | 11/2021 |
| WO | WO-2021257788 A1 | 12/2021 |
| WO | WO-2021257803 A1 | 12/2021 |
| WO | WO-2022010889 A1 | 1/2022 |
| WO | WO-2022076877 A1 | 4/2022 |
| WO | WO-2022108944 A1 | 5/2022 |
| WO | WO-2022125996 A1 | 6/2022 |
| WO | WO-2022140638 A1 | 6/2022 |
| WO | WO-2022140639 A1 | 6/2022 |

OTHER PUBLICATIONS

Datta et al., "Enzyme immobilization: an overview on techniques and support materials," 3 Biotech. Feb. 2013;3(1):1-9.

Giacalone et al., "Toxic protein expression in Escherichia coli using a rhamnose-based tightly regulated and tunable promoter system," Biotechniques, (2006) 40, 355-364.

Giacalone et al., "The use of bacterial minicells to transfer plasmid DNA to eukaryotic cells," Cellular Microbiology (2006), 8(10), 1624-1633.

Giacalone et al., "Immune responses elicited by bacterial minicells capable of simultaneous DNA and protein antigen delivery," Vaccine, 24 (2006), 6009-6017.

Giacalone et al., "Immunization with non-replicating E. coli minicells delivering both protein antigen and DNA protects mice from lethal challenge with lymphocytic choriomeningitis virus," Vaccine,25;12 (2007), 2279-2287.

International Search Report and Written Opinion dated Jul. 19, 2018, for International Application No. PCT/US2018/030328, 20 pages.

Jarmander et al., "A dual tag system for facilitated detection of surface expressed proteins in Escherichia coli," Microb Cell Fact. Sep. 3, 2012;11:118.

Kirk et al., "Industrial enzyme applications," Curr Opin Biotechnol. Aug. 2002;13(4):345-351.

Maurer et al., "Autodisplay: One-Component System for Efficient Surface Display and Release of Soluble Recombinant Proteins from Escherichia coli," Journal of Bacteriology, Feb. 1997, p. 794-804, vol. 179, No. 3.

Mitra et al., "Right Place, Right Time: Focalization of Membrane Proteins in Gram-Positive Bacteria," Trends in Microbiology, 2016, 24(8), 611-621.

Parker et al., "High fructose corn syrup: Production, uses and public health concerns," Biotechnology and Molecular Biology Reviews, Sep. 30, 2010 (30.092(J10), vol. 5, No. 5, pp. 71-78.

Sun et al., "BrkAutoDisplay: functional display of multiple exogenous proteins on the surface of Escherichia coli by using BrkA autotransporter," Microb Cell Fact. Sep. 4, 2015;14:129.

Tsuji et al., "An Efficient Thermoinducible Bacterial Suicide System—Elimination of Viable Parental Bacteria from Minicells," (2010) BioProcess International, vol. 8, No. 4, 28-40.

Ulmanen et al., "Transcription and Translation of Foreign Genes in Bacillus subtilis by the Aid of a Secretion Vector," Journal of Bacteriology, Apr. 30, 1985 (Apr. 30, 1985), vol. 162, No. 1, pp. 176-182.

Yamamoto et al., "Localization of the Vegetative Cell Wall Hydrolases LytC, LytE, and LytF on the Bacillus subtilis Cell Surface and Stability of These Enzymes to Cell Wall-Bound or Extracellular Proteases," Journal of Bacteriology, Nov. 30, 2003 (Nov. 30, 2003), vol. 185, No. 22, pp. 6666-6677.

Yang et al., "Comparison of Autotransporter and Ice Nucleation Protein as Carrier Proteins for Antibody Display on The Cell Surface of Escherichia coli," Progress in Biochemistry and Biophysics 40(12):1209-1219.

Zeigler D.R. "New! Protease-free Bacillus subtilis host," Bacillus Genetic Stock Center News, Jun. 30, 2016 (Jun. 30, 2016), pp. 1-3. Retrieved from the Internet:<http:/www.bgsc.org/new.php?page=2> on Jul. 4, 2018 (Jul. 4, 2018).

Zhang et al., "Surface Immobilization of Human Arginase-1 with an Engineered Ice Nucleation Protein Display System in E. coli," PLoS One. Aug. 1, 2016;11(8).

International Search Report and Written Opinion dated Mar. 16, 2022, for International Application No. PCT/US2021/065009, 13 pages.

International Search Report, dated Mar. 15, 2022, for International Application No. PCT/US2021/059571, 5 pages.

Burwood-Taylor, "Brief: AgroSpheres raises $4m Series A with Ospraie, Wilbur Ellis, for 'Minicell' pesticide tech," AgFunder Network Partners (Aug. 28, 2019) <https://agfundernews.com/agrospheres-raises-4m-series-a-with-ospraie-wilbur-ellis-forminicell-pesticide-tech>: pp. 1-2.

Islam et al., "Minicell-based fungal RNAi delivery for sustainable crop protection," Microbial Technology, vol. 14, Issue 4; (Feb. 24, 2021); pp. 1847-1856.

Islam et al., "RNAi-Based Biofungicides as a Promising Next-Generation Strategy for Controlling Devastating Gray Mold Diseases," International Journal of Molecular Sciences, vol. 21, Issue 6, (Mar. 18, 2020); pp. 1-10.

Kiernan, "Ospraie Ag Science Leads Rounds Totaling $49M for Two Separate Crop Protection Startups," Global AgInvesting (Sep. 10, 2019) <https://www.globalaginvesting.com/ospraie-ag-science-leads-rounds-totaling-49m-two-separate-crop-protection-startups/>: pp. 1-3. (A, used:2, 10,20).

(56) References Cited

OTHER PUBLICATIONS

Nguyen et al., "Nanosized Minicells Generated by Lactic Acid Bacteria for Drug Delivery", Journal of Nanomaterials, vol. 2017, Article 6847297 (Sep. 7, 2017): pp. 1-11.
Extended European Search Report for Application No. 18791868.5, dated Dec. 7, 2020, 7 pages.
Extended European Search Report dated Jun. 14, 2021, in European Application No. 18859413.9, 10 pages.
International Search Report dated Jul. 10, 2017, issued in PCT Application No. PCT/US2017/027048, 3 pages.
International Search Report and Written Opinion dated Jul. 10, 2018, for International Application No. PCT/US2018/030329, 18 pages.
International Search Report and Written Opinion dated Jan. 16, 2019, for International Application No. PCT/US2018/052690, 16 pages.
International Search Report and Written Opinion dated Feb. 18, 2022, for International Application No. PCT/US2021/054259, 24 pages.
International Search Report, dated Aug. 31, 2021, for International Application No. PCT/US2020/066706, 4 pages.
International Search Report, dated Nov. 10, 2021, for International Application No. PCT/US2021/033208, 6 pages.
Written Opinion dated Jul. 10, 2017, issued in PCT Application No. PCT/US2017/027048, 7 pages.
Written Opinion dated Aug. 31, 2021, issued in PCT Application No. PCT/US2020/066706, 8 pages.
Written Opinion dated Nov. 10, 2021, issued in PCT Application No. PCT/US2021/033208, 9 pages.
Aislabie et al., "A review of bacterial degradation of pesticides", Aust. J. Soil. Res., 1995; 33: 925-942.
Andrews et al., "Protective efficacy of recombinant Yersinia outer proteins against bubonic plague caused by encapsulated and nonencapsulated Yersinia pestis," Infection and Immunity, Mar. 1, 1999 (Mar. 1, 1999), vol. 67, pp. 1533-1537.
Beys da Silva et al., "Metarhizium anisopliae lipolytic activity plays a pivotal role in Rhipicephalus (Boophilus) microplus infection," Fungal Biology, 2010, 114(1), 10-15.
Cid et al., "Recognition of the helical structure of beta-1,4-galactan by a new family of carbohydrate-binding modules," J Biol Chem. Nov. 12, 2010;285(46):35999-36009.
Colla et al., "Biostimulant Action of Protein Hydrolysates: Unraveling Their Effects on Plant Physiology and Microbiome," Frontiers in Plant Science, Dec. 2017, vol. 8, Article 2202 pp. 1-14.
Crowet et al., "Modeling of non-covalent complexes of the cell-penetrating peptide CADY and its siRNA cargo," Biochemica et Biophysica Acta, Feb. 2013, vol. 1828, No. 2; pp. 499-509.
Farley et al., "Minicells, Back in Fashion," J Bacteriol. Mar. 31, 2016; 198(8):1186-95.
García-Sosa et al., "Peptide-Ligand Binding Modeling of siRNA with Cell-Penetrating Peptides," BioMed Research International, Jul. 24, 2014, vol. 2014, Article ID 257040 pp. 1-7.
Hallmann, et al., Bacterial endophytes in agricultural crops. Canadian Journal of 4 Microbiology. 1997, vol. 43, No. 10; pp. 895-914.
Huang et al., "A super long-acting and anti-photolysis pesticide release platform through self-assembled natural polymer-based polyelectrolyte", Reactive and Functional Polymers, Jan. 2020, vol. 146, No. 104429, pp. 1-8.
Huang et al., "Structural Investigation of a Self-Cross-Linked Chitosan/Alginate Dialdehyde Multilayered Film within Situ QCM.D and Spectroscopic Ellipsometry", ACS Omega, 2019, vol. 4, pp. 2019-2029.
Jog et al., "Plant growth promoting potential and soil enzyme production of the most abundant Streptomyces spp. from wheat rhizosphere," Journal of Applied Microbiology, 2012, 113(5), 1154-1164.
Jose et al., "Autodisplay of enzymes—molecular basis and perspectives," J Biotechnol. Oct. 15, 2012;161(2):92-103.
Kanchiswamy et al., "Bioprospecting bacterial and fungal volatiles for sustainable agriculture," Trends in Plant Science, 2015, 20(4), 206-211.
Kourti et al., "In Search of New Methodologies for Efficient Insect Pest Control: "The RNAi Movement"", Biological Control of Pest and Vector Insects, Apr. 5, 2017, InTech, XP055810178, ISBN: 978-953-51-3036-9 pp. 71-96, DOI: 10.5772/66633.
Li et al., "Preparation of antifogging and enhanced antimicrobial biopolymer coating and its applications in lettuce preservation", LWT. Jul. 30, 2020, vol. 133, No. 109941, pp. 1-7.
Linder et al., "The roles and function of cellulose-binding domains," Journal of Biotechnology, 57(1), 15-28.
MacDiarmid et al., "Bacterially derived 400 nm particles for encapsulation and cancer cell targeting of chemotherapeutics," Cancer Cell. May 2007;11(5):431-445.
Madhavi et al., "A Scrupulous Overview on Controlled Release Fertilizers," Research Reviews: Journal of Agriculture and Alfred Sciences, Mar. 17, 2016 (Mar. 17, 2016), vol. 5, Issue. 1, pp. 1-8.
Mayne et al., "The cellular membrane as a mediator for small molecule interaction with membrane proteins," Biochimica et Biophysica Acta, May 6, 2016 (May 6, 2016), vol. 1858, pp. 2290-2304.
Nuruzzaman et al., "Nanoencapsulation, Nano-guard for Pesticides: A New Window for Safe Application," J Agric Food Chem. Feb. 24, 2016;64(7):1447-83.
Pichyangkura et al., "Biostimulant activity of chitosan in horticulture," Scientia Horticulturae, 2015, 196, 49-65.
Ryu et al., "Bacterial volatiles promote growth in Arabidopsis," Proceedings of the National Academy of Sciences, Apr. 2003, 100(8), 4927-4932.
Ryu, et al., "Bacterial Volatiles Induce Systemic Resistance in Arabidopsis," Plant Physiology, 2004, 134(3), 1017-1026.
Sathya et al., Plant growth-promoting actinobacteria: a new strategy for enhancing sustainable production and protection of grain legumes, 3 Biotech, 2017, 7(102) pp. 1-10.
Shoseyov et al., "Carbohydrate binding modules: biochemical properties and novel applications," Microbiol Mol Biol Rev. Jun. 2006; 70(2):283-295.
Singh et al., "Microbial degradation of organophosphorus compounds", FEMS Microbiol. Rev. 30, Apr. 2006, 428-471.
Souza et al., "Plant growth-promoting bacteria as inoculants in agricultural soils," Genetics and Molecular Biology, 2015, 38(4), 401-419.
St. Leger et al., "New perspectives on insect pathogens," Fungal Biology Reviews, Apr. 2011, 25(2), 84-88.
Varley et al., "The divIVB region of the Bacillus subtilis chromosome encodes homologs of Escherichia coli septum placement (minCD) and cell shape (mreBCD) determinants," Journal of Bacteriology, Nov. 1, 1992 (Nov. 1, 1992), vol. 174, pp. 6729-6742.
Witzgall et al., "Sex Pheromones and Their Impact on Pest Management," Journal of Chemical Ecology, Jan. 2010, 36(1), 80-100.
Extended European Search Report for Application No. 18791775.2, dated Apr. 28, 2021, 10 pages.
Nakatani et al., "Cell surface protein engineering for high-performance whole-cell catalysts," Front. Chem. Sci. Eng. 2017, 11(1): 46-57.
Ota et al., "Display of Clostridium cellulovorans Xylose Isomerase on the Cell Surface of Saccharomyces cerevisiae and its Direct Application to Xylose Fermentation," Biotechnology Progress, vol. 29, No. 2, Mar. 1, 2013, pp. 346-351.
Schüürmann et al., "Bacterial whole-cell biocatalysts by surface display of enzymes: toward industrial application," Appl Microbiol Biotechnol (2014) 98:8031-8046.
Supplemental European Search Report for European Application No. 18791775.2, dated Jan. 25, 2021, 15 pages.
International Preliminary Report on Patentability for Application No. PCT/US2020/066706, dated Jul. 7, 2022, 10 pages.
Lasko et al., "On-Line Monitoring of Intracellular ATP Concentration in Escherichia coli Fermentations," Biotechnology and Bioengineering, Nov. 1996, vol. 52, pp. 364-372.
Manwaring et al., "Nucleoside Triphosphate Pools in Minicells of Escherichia coli," Journal of Bacteriology, May 1977, pp. 960-962.

(56) References Cited

OTHER PUBLICATIONS

Mathis et al., "ATP concentration in *Escherichia coli* during oxygen toxicity," Biochimica et Biophysica Act, Sep. 1976, 440(3), pp. 723-732.
Mempin et al., "Release of extracellular ATP by bacteria during growth," BMC Microbiology, Dec. 2013, 13:301, 13 pages.
Mendelson et al., "Physiological Studies of Bacillus subtilis Minicells," Journal of Bacteriology, Mar. 1974, vol. 117, No. 3, pp. 1312-1319.
Rampley et al., "Development of SimCells as a novel chassis for functional biosensors," Scientific Reports, Aug. 2017, 7(1):7261, 10 pages.
Schneider et al., "Relationship between Growth Rate and ATP Concentration in *Escherichia coli*," The Journal of Biological Chemistry, Feb. 27, 2004, vol. 279, No. 9, pp. 8262-8268.
Soini et al., "Transient increase of ATP as a response to temperature up-shift in *Escherichia coli*," Microbial Cell Factories, Apr. 2005, 4:9 doi:10.1186/1475-2859-4-9, 8 pages.
Yaginuma et al., "Diversity in ATP concentrations in a single bacterial cell population revealed by quantitative single-cell imaging," Scientific Reports, Oct. 6, 2014, 4:6522, 7 pages.
Zhang et al., "*E. coli* Nissle 1917-Derived Minicells for Targeted Delivery of Chemotherapeutic Drug to Hypoxic Regions for Cancer Therapy," Theranostics, Feb. 2018, vol. 8 Issue 6, pp. 1690-1705.
International Search Report and Written Opinion, dated Apr. 15, 2022, for International Application No. PCT/US2021/062964, 16 pages.
International Search Report and Written Opinion dated Mar. 28, 2022, for International Application No. PCT/US2021/065010, 9 pages.
Elish et al., "Biochemical analysis of spontaneous fepA mutants in *Escherichia coli*," Journal of General Microbiology, May 1988, 134(5), pp. 1355-1364.

\* cited by examiner

COMPOSITIONS AND METHODS FOR ENZYME IMMOBILIZATION

CROSS-REFERENCE TO RELATED APPLICATIONS

This application is a U.S. National Phase application, filed under 35 U.S.C. § 371, of International Application No. PCT/US2018/030328, filed Apr. 30, 2018, which claims the benefit of priority to U.S. provisional application No. 62/491,603 filed on Apr. 28, 2017, which is hereby incorporated by reference in its entirety.

FIELD

The present disclosure is generally directed to compositions and methods for immobilizing enzymes on the surface of achromosomal and/or anucleate cells. The immobilized enzymes on the surface of achromosomal and/or anucleate cells, described herein provide improved stability and efficiency for agricultural, industrial, and environmental applications. Also, disclosed herein are methods for producing achromosomal and/or anucleate cells with enzymes immobilized.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AGRO_001_01WP_SeqList_ST25.txt. The text file is 104 KB, was created on Apr. 27, 2018, and is being submitted electronically via EFS-Web.

BACKGROUND

Due to the evolution of modern biotechnology, the enzyme industry has been rapidly developed over the past decades. Enzymes found in nature have been used since ancient times in the production of food products, such as cheese, sourdough, beer, wine and vinegar, and in the manufacture of commodities such as leather, indigo and linen. In these processes enzymes were not used in any pure or well-characterized form, but for example, enzymes produced by spontaneously growing microorganisms. Along with the development of fermentation processes, the production of enzymes by use of selected production strains, made it possible to manufacture enzymes as purified, well-characterized preparations even on a large scale.

Despite their excellent catalytic capabilities and properties of enzymes, enzymes prior to implementation have issues to be improved, such as stability, activity, inhibition by reaction products, selectivity towards non-natural substrates and reusability. Currently, many immobilization techniques to immobilize enzymes on a solid material, such as a porous support aim to simplify the recovery process, enhances process control, and reduces operational costs. However, these immobilization processes are associated with toxic reagents and/or chemical reactions to ensure stability of the enzymes on a solid material.

Thus, there is a great need in the art for the technical development of enzyme immobilization on enzyme-friendly supports, which make production of industrial enzymes in more environment-friendly, process-efficient, and cost-efficient manners. Also, there is a need for the production of enzyme-immobilized minicells such as described herein which are easily recoverable, recyclable, durable, and stable with extended active life cycle of enzyme to increase the usage of immobilized enzymes in industry.

SUMMARY OF THE DISCLOSURE

The present disclosure provides compositions and methods for immobilizing enzymes on the surface of achromosomal and/or anucleate cells. In particular, the present disclosure provides compositions and methods for production of minicells having immobilized enzymes on their surface and uses thereof.

The present disclosure is directed to an industrially suitable anucleated cell-based enzyme immobilization and delivery platform and a composition thereof. Also, disclosed herein a method of producing an industrially suitable anucleated cell-based enzyme immobilization and delivery platform and applications thereof.

In some embodiments, an industrially suitable anucleated cell-based enzyme immobilization and delivery platform, is provided, which comprising: a) an intact anucleated cell derived from a protease deficient parental cell, wherein said anucleated cell comprising an expressed self-assembled enzyme immobilized to the surface of said cell. In embodiments, the expressed self-assembled enzyme is heterologous to the parental cell. In embodiments, the expressed self-assembled enzyme is at least one selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase. In embodiments, the expressed self-assembled enzyme is lipase. In embodiments, glucose isomerase. In embodiments, said intact anucleated cell is derived from a prokaryotic cell. In embodiments, said intact anucleated cell is a bacterially derived minicell. In embodiments, said intact anucleated cell is produced from a gram negative bacterial genus. In embodiments, said intact anucleated cell is produced from a bacterial genus selected from the group consisting of: *Escherichia, Salmonella, Shigella, Pseudomonas*, and *Agrobacterium*. In embodiments, said intact anucleated cell is produced from a bacterial species selected from the group consisting of: *Escherichia coli, Salmonella typhimurium, Shigella flexneri*, and *Pseudomonas aeruginosa*. In embodiments, said intact anucleated cell is produced from a gram positive bacterial genus. In embodiments, said intact anucleated cell is produced from a bacterial genus selected from the group consisting of: *Bacillus, Corynebacterium*, and *Lactobacillus*. In embodiments, said intact anucleated cell is produced from a bacterial species selected from the group consisting of: *Bacillus subtilis, Corynebacterium glutamicum*, and *Lactobacillus acidophilus*. In embodiments, intact anucleated cell is a bacterially derived minicell that is produced from a parental bacterial cell deficient in WprA protease. In embodiments, said intact anucleated cell is a bacterially derived minicell that is produced from a protease deficient *B. subtilis* parental bacterial cell. In embodiments, said intact anucleated cell is a bacterially derived minicell that is produced from a protease deficient KO7 *B. subtilis* parental bacterial cell. In embodiments, said intact anucleated cell is a bacterially derived minicell that is produced from a protease deficient *B. subtilis* parental bacterial cell selected from the group consisting of: (1) CU403,DIVIVA; (2) CU403,DIVIVB,SPO-; (3) CU403,DIVIVB; and (4) CU403,DIVIVB1, wherein at least one protease encoding gene has been repressed, deleted, or silenced. In embodiments, said intact anucleated cell is a bacterially derived minicell that is produced from a parental bacterial cell deficient in Lon and OmpT proteases. In embodiments, said intact anucleated cell is a bacterially derived minicell that is produced from a protease deficient *E. coli* parental bacterial cell. In embodiments, said intact anucleated cell is a bacterially derived minicell that is produced from a protease deficient *E. coli* parental bacterial cell selected from the group consisting of: BL21, BL21(DE3), BL21-AI, LPS-modified BL21 (DE3) and B8. In embodiments, said intact anucleated cell is derived from a eukaryotic cell.

In some embodiments, an industrially suitable anucleated cell-based enzyme immobilization and delivery platform, is provided, which comprising: a) an intact anucleated cell derived from a protease deficient parental cell, wherein said anucleated cell comprising an expressed self-assembled enzyme immobilized to the surface of said cell. In embodiments, the expressed self-assembled enzyme is a fusion protein. In embodiments, the expressed self-assembled enzyme is a fusion protein, comprising at least one surface expressing moiety and at least one enzymatically active moiety. In embodiments, the expressed self-assembled enzyme is a fusion protein, comprising at least one surface expressing moiety and at least one enzymatically active moiety, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence). In embodiments, the expressed self-assembled enzyme is a fusion protein, comprising at least one surface expressing moiety and at least one enzymatically active moiety, wherein said surface expressing moiety comprises an exported bacterial protein and is selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

In some embodiments, the anucleated cell expresses a second polypeptide on its surface, in addition to the self-assembled enzyme. In embodiments, the anucleated cell expresses a heterologous polypeptide on its surface, in addition to the self-assembled enzyme. In embodiments, the anucleated cell expresses a fusion protein on its surface, in addition to the self-assembled enzyme. In embodiments, the anucleated cell expresses a fusion protein on its surface, in addition to the self-assembled enzyme, said fusion protein comprising: at least one surface expressing moiety and at least one plant cell adhesion moiety. In embodiments, the anucleated cell expresses a fusion protein on its surface, in addition to the self-assembled enzyme, said fusion protein comprising: at least one surface expressing moiety and at least one plant cell adhesion moiety, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence). In embodiments, the anucleated cell expresses a fusion protein on its surface, in addition to the self-assembled enzyme, said fusion protein comprising: at least one surface expressing moiety and at least one plant cell adhesion moiety, wherein said surface expressing moiety comprises an exported bacterial protein and is selected from the group consisting of: LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III). In embodiments, the anucleated cell expresses a fusion protein on its surface, in addition to the self-assembled enzyme, said fusion protein comprising: at least one surface expressing moiety and at least one plant cell adhesion moiety, wherein said plant cell adhesion moiety comprises a carbohydrate binding module. In embodiments, the anucleated cell expresses a fusion protein on its surface, in addition to the self-assembled enzyme, said fusion protein comprising: at least one surface expressing moiety and at least one plant cell adhesion moiety, wherein said plant cell adhesion moiety comprises a carbohydrate binding module selected from the group consisting of: a cellulose binding domain, a xylan binding domain, a chitin binding domain, and a lignin binding domain. In embodiments, the anucleated cell expresses a polypeptide on its surface that increases adhesion to a plant surface, in addition to the self-assembled enzyme. In embodiments, the anucleated cell expresses a plant adhesion polypeptide on its surface, in addition to the self-assembled enzyme. In embodiments, the anucleated cell expresses a carbohydrate binding module that is displayed on its surface, in addition to the self-assembled enzyme. In embodiments, the anucleated cell expresses a heterologous carbohydrate binding module that is displayed on its surface, in addition to the self-assembled enzyme. In embodiments, the anucleated cell expresses a cellulose binding domain that is displayed on its surface, in addition to the self-assembled enzyme In embodiments, the anucleated cell expresses a heterologous cellulose binding domain that is displayed on its surface, in addition to the self-assembled enzyme.

In some embodiments, the anucleated cell is used as a resin for immobilizing a polypeptide, wherein the anucleated cell expresses endogenous surface expressing moiety that have a binding domain, and wherein the binding domain is capable of binding to the polypeptide that has a binding site. the anucleated cell is used for purifying a polypeptide, wherein the polypeptide is immobilized to the anucleated cell by incubation.

In some embodiments, a method of improving activity and stability of an anucleated cell-based enzyme, is provided, which comprises: applying the anucleated cell-based enzyme immobilization and delivery platform to a substrate, wherein the anucleated cell is derived from a protease deficient parental cell, and wherein the anucleated cell comprises an expressed self-assembled enzyme immobilized to the surface of said cell. In embodiments, the expressed self-assembled enzyme is heterologous to the parental cell. In embodiments, the expressed self-assembled enzyme is at least one selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase. In embodiments, the expressed self-assembled enzyme is lipase. In embodiments, the expressed self-assembled enzyme is lipase, wherein the substrate is reacted with the lipase for enzymatic activity. In embodiments, the expressed self-assembled enzyme is lipase, wherein the substrate is reacted with the lipase for enzymatic activity, and wherein said enzymatic activity is associated with fatty acid and oily stain removal, biodiesel production via transesterification, dough stability and conditioning in baking, pitch control and contaminant control for production of pulp and paper, and resolution of chiral alcohols and amines. In embodiments, the expressed self-assembled enzyme is glucose isomerase. In embodiments, the expressed self-assembled enzyme is glucose isomerase, wherein the substrate is reacted with the glucose isomerase for enzymatic activity. In embodiments, the expressed self-assembled enzyme is glucose isomerase, wherein the substrate is reacted with the glucose isomerase for enzymatic activity, and wherein said enzymatic activity is associated with glucose to fructose conversion for production of high-fructose corn syrup.

In some embodiments, the anucleated cell comprises at least two expressed self-assembled enzymes immobilized to the surface of said cell. In embodiments, each of the expressed self-assembled enzymes is a fusion protein, comprising at least one surface expressing moiety and at least one enzymatically active moiety. In embodiments, each of the expressed self-assembled enzymes is heterologous to the parental cell. In embodiments, each of the expressed self-assembled enzymes is a fusion protein, comprising at least one surface expressing moiety and at least one enzymatically active moiety, wherein said enzymatically active moiety is selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase. In embodiments, one of the expressed self-assembled enzymes is lipase. In embodiments, one of the expressed self-assembled enzymes is glucose isomerase. In embodiments, one of the expressed self-assembled enzymes is protease. In embodiments, each of the expressed self-assembled enzymes is a fusion protein, comprising at least one surface expressing moiety and at least one enzymatically active moiety, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence). In embodiments, each of the expressed self-assembled enzymes is a fusion protein, comprising at least one surface expressing moiety and at least one enzymatically active moiety, wherein said surface expressing moiety comprises an exported bacterial protein and is selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III). In embodiments, the at least two expressed self-assembled enzymes are co-localized to a desired locus, wherein each of the expressed self-assembled enzymes have its enzymatic activity at the desired locus. In embodiments, the expressed self-assembled enzymes are lipase and protease. In embodiments, the expressed self-assembled enzymes are glucose isomerase and protease. In embodiments, the at least two expressed self-assembled enzymes have a complimentary function. In embodiments, the at least two expressed self-assembled enzymes act synergistically. In embodiments, the at least two expressed self-assembled enzymes each work to carry out a portion of an overall enzymatic reaction.

BRIEF DESCRIPTION OF THE FIGURES

FIG. 10A shows His-Tag staining of lipases expressed from non-permeabilized protease-deficient minicells. FIG. 10B shows His-Tag staining of lipases expressed from permeabilized protease-deficient minicells. FIG. 10C shows no or little lipase expression from non-permeabilized control minicells. FIG. 10D also shows no or little lipase expression from permeabilized control minicells. Arrow points out the expressed lipases.

FIG. 11A shows activity of lipase purified from protease-deficient minicells expressing the recombinant AIDA-1 lipase fusion expression vector. FIG. 11B shows activity of lipase purified from protease-deficient minicells expressing the recombinant Brk-lipase fusion expression vector. FIG. 11C shows that activity of lipase purified from protease-deficient minicells expressing the recombinant InaK-lipase fusion expression vector. (Protease Deficient control: protease-deficient B8 strain without fusion lipase, Wild Strain Control: wild type p678-54 strain without fusion lipase, Fusion Protein Control: his-tag purified CBM protein without lipase activity)

FIG. 12A shows activity of surface-expressed lipase that is fused to AIDA-1. FIG. 12B shows activity of surface-expressed lipase that is fused to BRK. FIG. 12C shows activity of surface-expressed lipase that is fused to InaK.

DETAILED DESCRIPTION

Figure 1:
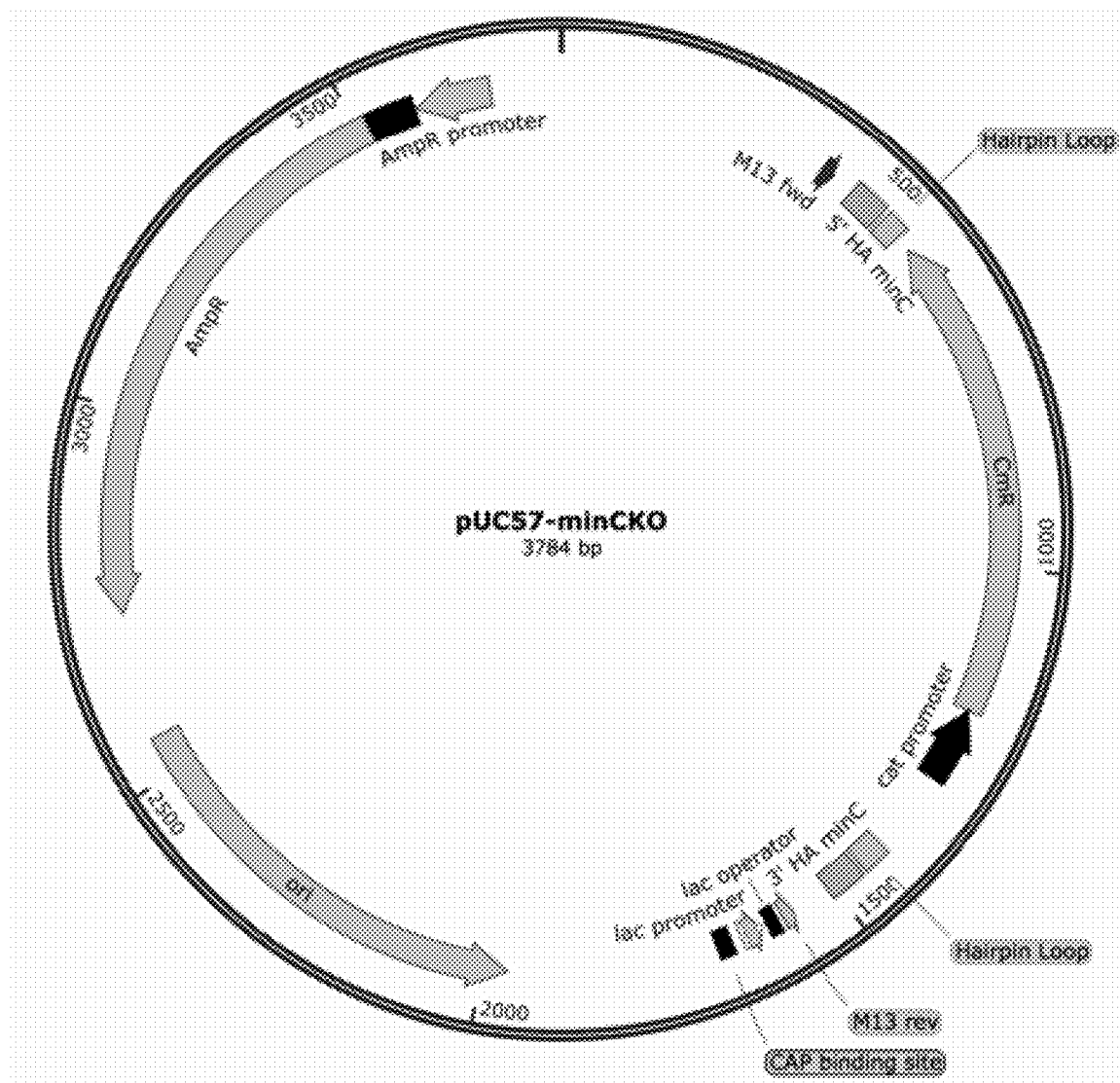
FIG. 1 illustrates an exemplary bacterial minicell-inducing vector for a minC knockout to produce protease-deficient minicells. The pUC57 vector was inserted with a recombinant DNA insert comprising 5' end nucleotide sequence of minC gene, a chloramphenicol resistant gene (CmR) with cat promoter, and 3' end nucleotide sequence of minC gene. The hairpin loops flanked by 5' and 3' ends of minC gene are inserted into the insert to stop transcriptional regulation of other neighboring genes in the genome where the insert is integrated.

The present disclosure relates generally to compositions and methods for immobilizing enzymes of interest on the surface of achromosomal and/or anucleate cells. In particular, the present disclosure provides compositions and methods for production of minicells having immobilized enzymatically active polypeptides on their surface and uses thereof.

In some embodiments, the present disclosure provides compositions and methods for immobilizing enzymatically active polypeptides including, but are not limited to, lipases, phospholipases, transacylases, transaminases, pectinase, proteases, amylases, cellulases, cutinases, esterases, acylases, invertases, isomerases, lyases, glucosidases, oxidoreductases, transferases, ligases, and amidases, displayed on the surface of achromosomal and/or anucleate cells. In other embodiments, enzymatically active polypeptides comprise lipase, glucose isomerase, alpha amylase, cellulase (endoglucanases, exoglucanases, beta-glucosidases), beta amylase, pectin lyase, isomerase, protease, transglutaminase, desaturase, peroxidase, lipoxygenase, catalase, alkaline phosphatase, tyrosinase, urease, dehydrogenases (e.g.

alcohol dehydrogenases, lactate dehydrogenases, acetaldehyde dehydrogenases, aldehyde dehydrogenases, pyruvate dehydrogenases, and succinate dehydrogenases), xylanase, phytase, mannanase, and laccase. Also, enzymatically active polypeptides further comprise amyloglucosidase, pullulanase, cyclodextrin-glycosyltransferase, pectin methyl esterase, glucose oxidase, lactase, beta-glucanase, acetolactate decarboxylase, pectate lyase, nitrilase, and amyloglucosidase. In some embodiments, the enzymatically active polypeptide is lipase. In some embodiments, the enzymatically active polypeptide is glucose isomerase.

In some embodiments, the achromosomal and/or anucleate cells are derived from eubacterial, archaebacterial, and/or eukaryotic cell. In other embodiments, minicells having immobilized enzymes on their surface can have applications for agriculture, animal feed, food, beverages, industrial enzymes, textiles, pulp and paper, biofuels, fermentation, bioremediation, bioenergy, electronics, defense, bioenergy, household care, pharmaceuticals, and others uses.

Definitions

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified. In the disclosure, "wild type strain" or "wild strain" or "wild type cell line" refers to a cell strain/line that can produce minicells. In some embodiments, wild type bacterial strains and/or cell lines such as *E. coli* strain p678-54 and *B. subtilis* strain CU403 can make miniature cells deficient in DNA. Methods for producing such minicells are known in the art. See, for example, Adler et al., 1967, *Proc. Natl. Acad. Sci. USA* 57:321-326; Inselburg J, 1970 *J. Bacteriol.* 102(3):642-647; Frazer 1975, *Curr. Topics Microbiol. Immunol.* 69:1-84, Reeve et al 1973, *J. Bacteriol.* 114(2):860-873; and Mendelson et al 1974 *J. Bacteriol.* 117(3): 1312-1319.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that rearranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, a "synthetic amino acid sequence" or "synthetic peptide" or "synthetic protein" is an amino acid sequence that is not known to occur in nature or that is not naturally occurring. Generally, such a synthetic protein sequence will comprise at least one amino acid difference when compared to any other naturally occurring protein sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode an enzymatically active portion of a genetic regulatory element. An enzymatically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3$^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. Also, "construct", "vector", and "plasmid" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218: 78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

As used herein, the term "display" refers to the exposure of the polypeptide of interest on the outer surface of the minicell. By way of non-limiting example, the displayed polypeptide may be a protein or a protein domain which is either expressed on the minicell membrane or is associated with the minicell membrane such that the extracellular domain or domain of interest is exposed on the outer surface of the minicell (expressed and displayed on the surface of the minicell or expressed in the parental cell to be displayed on the surface of the segregated/budded minicell). In all instances, the "displayed" protein or protein domain is available for interaction with extracellular components. A membrane-associated protein may have more than one extracellular domain, and a minicell of the disclosure may display more than one membrane-associated protein.

As used herein, the terms "polypeptide", "protein" and "protein domain" refer to a macromolecule made up of a single chain of amino acids joined by peptide bonds. Polypeptides of the invention may comprise naturally occurring amino acids, synthetic amino acids, genetically encoded amino acids, non-genetically encoded amino acids, and combinations thereof. Polypeptides may include both L-form and D-form amino acids.

As used herein, the term "enzymatically active polypeptide" refers to a polypeptide which encodes an enzymatically functional protein. The term "enzymatically active polypeptide" includes but not limited to fusion proteins which perform a biological function. Exemplary enzymatically active polypeptides, include but not limited to enzymes/enzyme moiety (e.g. wild type, variants, or engineered variants) that specifically bind to certain receptors or biological/chemical substrates to effect a biological function such as biological signal transduction or chemical inactivation.

As used herein, "industrially suitable" refers to utilization, and applications, of the anucleated cell-based enzyme immobilization and delivery platform, in contexts outside of internally administered animal host applications, e.g. outside of administered human therapeutics.

As used herein, the term "protease-deficient strain" refers to a strain that is deficient in one or more endogenous proteases. For example, protease deficiency can be created by deleting, removing, knock-out, silencing, suppressing, or otherwise downregulating at lease on endogenous protease. Said proteases can include catastrophic proteases. For example, BL21 (DE3) E. coli strain is deficient in proteases Lon and OmpT. E. coli strain has cytoplasmic proteases and membrane proteases that can significantly decrease protein production and localization to the membrane. In some embodiments, a protease-deficient strain can maximize production and localization of a protein of interest to the membrane of the cell.

As used herein, the term "anucleated cell" refers to a cell that lacks a nucleus and also chromosomal DNA and which can also be termed as an "anucleate cell". Because eubacterial and archaebacterial cells, unlike eukaryotic cells, naturally do not have a nucleus (a distinct organelle that contains chromosomes), these non-eukaryotic cells are of course more accurately described as being "without chromosomes" or "achromosomal." Nonetheless, those skilled in the art often use the term "anucleated" when referring to bacterial minicells in addition to other eukaryotic minicells. Accordingly, in the present disclosure, the term "minicells" encompasses derivatives of eubacterial cells that lack a chromosome; derivatives of archaebacterial cells that lack their chromosome(s), and anucleate derivatives of eukaryotic cells that lack a nucleus and consequently a chromosome. Thus, in the present disclosure, "anucleated cell" or "anucleate cell" can be interchangeably used with the term "achromosomal cell."

As used herein, the term "binding site," means a molecular structure or compound, such as a protein, a polypeptide, a polysaccharide, a glycoprotein, a lipoprotein, a fatty acid, a lipid or a nucleic acid or a particular region in such molecular structure or compound or a particular conformation of such molecular structure or compound, or a combination or complex of such molecular structures or compounds. In certain embodiments, at least one binding site is on an intact living plant. An "intact living plant," as used herein, means a plant as it grows, whether it grows in soil, in water or in artificial substrate, and whether it grows in the field, in a greenhouse, in a yard, in a garden, in a pot or in hydroponic culture systems. An intact living plant preferably comprises all plant parts (roots, stem, branches, leaves, needles, thorns, flowers, seeds etc.) that are normally present on such plant in nature, although some plant parts, such as, e.g., flowers, may be absent during certain periods in the plant's life cycle.

A "binding domain," as used herein, means the whole or part of a proteinaceous (protein, protein-like or protein containing) molecule that is capable of binding using specific intermolecular interactions to a target molecule. A binding domain can be a naturally occurring molecule, it can be derived from a naturally occurring molecule, or it can be entirely artificially designed. A binding domain can be based on domains present in proteins, including but not limited to microbial proteins, protease inhibitors, toxins, fibronectin, lipocalins, single-chain antiparallel coiled coil proteins or repeat motif proteins. Non-limiting examples of such binding domains are carbohydrate binding modules (CBM) such as cellulose binding domain to be targeted to plants. In some embodiments, a cell adhesion moiety comprises a binding domain.

Minicells

Minicells are the result of aberrant, asymmetric cell division, and contain membranes, peptidoglycan, ribosomes, RNA, protein, and often plasmids but no chromosome. (Frazer A C and Curtiss III, Production, Properties and Utility of Bacterial Minicells, *Curr. Top. Microbial. Immunol.* 69:1-84 (1975)). Because minicells lack chromosomal DNA, minicells cannot divide or grow, but they can continue other cellular processes, such as ATP synthesis, replication and transcription of plasmid DNA, and translation of mRNA. Although chromosomes do not segregate into minicells, extrachromosomal and/or episomal genetic expression elements may segregate, or may be introduced into minicells after segregation from parent cells.

In embodiments, the minicells described herein are non-naturally occurring.

In some embodiments, the disclosure provides a composition comprising a plurality of minicells, wherein each minicell of said plurality comprises an enzymatically active polypeptide displayed on the surface of the minicell, wherein said enzymatically active polypeptide has enzymatic activity. The enzymatic activity is derived from enzymatically active polypeptides disclosed in the present disclosure. In some embodiments, the invention provides a composition comprising a plurality of intact, bacterially-derived minicells, wherein each minicell of said plurality comprises an enzymatically active polypeptide displayed on the surface of the bacterial minicell, wherein said enzymatically active polypeptide has enzymatic activity. In some embodiments, the composition comprises minicells which further comprise a second polypeptide displayed on the surface of the bacterial minicell, to increase adhesion to a subject and/or subjects including, but are not limited to substrates of enzymes, receptors, metal, plastic, soil, bacteria, fungi, pathogens, germs, plants, animals, human, and the like. In some embodiments, the composition comprises a mixture of minicells, wherein certain minicells within the mixed minicell population display the enzymatically active polypeptide or display the second polypeptide including subject adhesion increasing polypeptide or display both.

Eubacterial Minicells

One type of minicell is a eubacterial minicell. For reviews of eubacterial cell cycle and division processes, see Rothfield et al., *Annu. Rev. Genet.*, 33:423-48, 1999; Jacobs et al., *Proc. Natl. Acad. Sci. USA*, 96:5891-5893, May, 1999; Koch, *Appl. and Envir. Microb.*, Vol. 66, No. 9, pp. 3657-3663; Bouche and Pichoff, *Mol Microbiol*, 1998. 29: 19-26; Khachatourians et al., *J Bacteriol*, 1973. 116: 226-229; Cooper, *Res Microbiol*, 1990. 141: 17-29; and Danachie and Robinson, "Cell Division: Parameter Values and the Process," in: *Escherichia Coli and Salmonella Typhimurium: Cellular and Molecular Biology*, Neidhardt, Frederick C., Editor in Chief, American Society for Microbiology, Washington, D.C., 1987, Volume 2, pages 1578-1592, and references cited therein; and Lutkenhaus et al., "Cell Division," Chapter 101 in: *Escherichia coli and Salmonella typhimurium: Cellular and Molecular Biology*, $2^{nd}$ Ed., Neidhardt, Frederick C., Editor in Chief, American Society for Microbiology, Washington, D.C., 1996, Volume 2, pages 1615-1626, and references cited therein. When DNA replication and/or chromosomal partitioning is altered, membrane-bounded vesicles "pinch off" from parent cells before transfer of chromosomal DNA is completed. As a result of this type of dysfunctional division, minicells are produced which contain an intact outer membrane, inner membrane, cell wall, and all of the cytoplasm components but do not contain chromosomal DNA.

In some embodiments, the bacterially-derived minicells are produced from a strain, including, but are not limited to a strain of *Escherichia coli*, *Bacillus* spp., *Salmonella* spp., *Listeria* spp., *Mycobacterium* spp., *Shigella* spp., or *Yersinia* spp. In some embodiments, the bacterially-derived minicells are produced from a strain that naturally produces minicells. Such natural minicell producing strains produce minicells, for example, at a 2:1 ratio (2 bacterial cells for every one minicell). In certain embodiments, exemplary bacterial strains that naturally produce minicells include, but are not limited to *E. coli* strain number P678-54, *Coli* Genetic Stock Center (CGSC) number: 4928 and *B. subtilis* strain CU403.

As one example, mutations in *B. subtilis* smc genes result in the production of minicells (Britton et al., 1998, *Genes and Dev.* 12:1254-1259; Moriya et al., 1998, *Mol Microbiol* 29:179-87). Disruption of smc genes in various cells is predicted to result in minicell production therefrom.

As another example, mutations in the divIVA gene of *Bacillus subtilis* results in minicell production. When expressed in *E. coli*, *B. subtilis* or yeast *Schizosaccharomyces pombe*, a DivIVA-GFP protein is targeted to cell division sites therein, even though clear homologs of DivIVA do not seem to exist in *E. coli*, *B. subtilis* or *S. pombe* (David et al., 2000, EMBO J. 19:2719-2727. Over- or under-expression of *B. subtilis* DivIVA or a homolog thereof may be used to reduce minicell production in a variety of cells.

In some embodiments, the minicell-producing bacteria is a Gram-negative bacteria. The Gram-negative bacteria includes, but is not limited to, *Escherichia coli*, *Salmonella* spp. including *Salmonella typhimurium*, *Shigella* spp. including *Shigella flexneri*, *Pseudomonas aeruginosa*, *Agrobacterium*, *Campylobacter jejuni*, *Lactobacillus* spp., *Neisseria gonorrhoeae*, and *Legionella pneumophila*. In some embodiments, the minicell-producing gram-negative bacteria can produce minicells naturally caused by endogenous or exogenous mutation(s) associated with cell division and/or chromosomal partitioning. In some embodiments, the minicell-producing bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing gram-negative bacteria is deficient in protease and/or its activity naturally and/or by genetic engineering techniques disclosed herein. In some embodiments, the protease-deficient minicell-producing gram-negative bacteria comprises a recombinant expression vector comprising a gene or genes that is involved in a protein of interest disclosed in the present disclosure.

In some embodiments, the minicell-producing bacteria can be a Gram-positive bacteria. The Gram-positive bacteria includes, but is not limited to, *Bacillus subtilis*, *Bacillus cereus*, *Corynebacterium Glutamicum*, *Lactobacillus acidophilus*, *Staphylococcus* spp., or *Streptococcus* spp. In some embodiments, the minicell-producing gram-positive bacteria can produce minicells naturally caused by endogenous or exogenous mutation(s) associated with cell division and/or chromosomal partitioning. In some embodiments, the minicell-producing gram-positive bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing gram-positive bacteria is deficient in protease and/or its activity naturally and/or by genetic engineering techniques disclosed herein. In some embodiments, the protease-deficient minicell-producing gram-positive bacteria comprises a recombinant expression vector comprising a gene or genes that is involved in a protein of interest disclosed in the present disclosure.

The minicell-producing bacteria can be a Extremophilic bacteria. The Extremophilic bacteria includes, but is not limited to, Thermophiles including *Thermus aquaticus*, Psychrophiles, Piezophiles, Halophilic bacteria, Acidophile, Alkaliphile, Anaerobe, Lithoautotroph, Oligotroph, Metallotolerant, Oligotroph, Xerophil or Polyextremophile. In some embodiments, the minicell-producing Extremophilic bacteria can produce minicells naturally caused by endogenous or exogenous mutation(s) associated with cell division and/or chromosomal partitioning. In some embodiments, the minicell-producing Extremophilic bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing Extremophilic bacteria is deficient in protease and/or its activity naturally and/or by genetic engineering techniques disclosed herein. In some embodiments, the protease-deficient minicell-producing Extremophilic bacteria comprises a recombinant expression vector comprising a gene or genes that is involved in a protein of interest disclosed in the present disclosure.

Eukaryotic Minicells

Achromosomal eukaryotic minicells (i.e., anucleate cells) are within the scope of the disclosure. Yeast cells are used to generate fungal minicells. See, e.g., Lee et al., Ibd1p, a possible spindle pole body associated protein, regulates nuclear division and bud separation in *Saccharomyces cerevisiae*, Biochim Biophys Acta 3:239-253, 1999; Kopecka et al., A method of isolating anucleate yeast protoplasts unable to synthesize the glucan fibrillar component of the wall J Gen Microbiol 81:111-120, 1974; and Yoo et al., Fission yeast Hrp1, a chromodomain ATPase, is required for proper chromosome segregation and its overexpression interferes with chromatin condensation, Nucl Acids Res 28:2004-2011, 2000. Cell division in yeast is reviewed by Gould and Simanis, The control of septum formation in fission yeast, Genes & Dev 11:2939-51, 1997).

In some embodiments, the eukaryotic minicells can be produced from yeast cells, such as *Saccharomyces cerevisiae, Pichia pastoris* and/or *Schizosaccharomyces pombe.*

As one example, mutations in the yeast genes encoding TRF topoisomerases result in the production of minicells, and a human homolog of yeast TRF genes has been stated to exist (Castano et al., 1996, *Nucleic Acids Res* 24:2404-10). Mutations in a yeast chromodomain ATPase, Hrp1, result in abnormal chromosomal segregation; (Yoo et al., 2000 *Nuc. Acids Res.* 28:2004-2011). Disruption of TRF and/or Hrp1 function is predicted to cause minicell production in various cells. Genes involved in septum formation in fission yeast (see, e.g., Gould et al., 1997 *Genes and Dev.* 11:2939-2951) can be used in like fashion.

Platelets are a non-limiting example of eukaryotic minicells. Platelets are anucleate cells with little or no capacity for de novo protein synthesis. The tight regulation of protein synthesis in platelets (Smith et al., 1999, Vasc Med 4:165-72) may allow for the over-production of exogenous proteins and, at the same time, under-production of endogenous proteins. Thrombin-activated expression elements such as those that are associated with Bcl-3 (Weyrich et al., Signal-dependent translation of a regulatory protein, Bcl-3, in activated human platelets, Cell Biology 95:5556-5561, 1998) may be used to modulate the expression of exogenous genes in platelets.

As another non-limiting example, eukaryotic minicells are generated from tumor cell lines (Gyongyossy-Issa and Khachatourians, Tumour minicells: single, large vesicles released from cultured mastocytoma cells (1985) Tissue Cell 17:801-809; Melton, Cell fusion-induced mouse neuroblastomas HPRT revertants with variant enzyme and elevated HPRT protein levels (1981) *Somatic Cell Genet.* 7: 331-344).

Yeast cells are used to generate fungal minicells. See, e.g., Lee et al., Ibd1p, a possible spindle pole body associated protein, regulates nuclear division and bud separation in *Saccharomyces cerevisiae*, Biochim Biophys Acta 3:239-253, 1999; Kopecka et al., A method of isolating anucleate yeast protoplasts unable to synthesize the glucan fibrillar component of the wall J Gen Microbiol 81:111-120, 1974; and Yoo et al., Fission yeast Hrp1, a chromodomain ATPase, is required for proper chromosome segregation and its overexpression interferes with chromatin condensation, Nucl Acids Res 28:2004-2011, 2000. Cell division in yeast is reviewed by Gould and Simanis, The control of septum formation in fission yeast, Genes & Dev 11:2939-51, 1997). In some embodiments, the present disclosure teaches production of yeast minicells.

Archaebacterial Minicells

The term "archaebacterium" is defined as is used in the art and includes extreme thermophiles and other Archaea (Woese, C. R., L. Magrum. G. Fox. 1978. Archaebacteria. *Journal of Molecular Evolution.* 11:245-252). Three types of Archaebacteria are halophiles, thermophiles and methanogens. By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage. Non-limiting examples of halophiles include *Halobacterium cutirubrum* and *Halogerax mediterranei*. Non-limiting examples of methanogens include *Methanococcus voltae; Methanococcus vanniela; Methanobacterium thermoautotrophicum; Methanococcus voltae; Methanothermus fervidus*; and *Methanosarcina barkeri*. Non-limiting examples of thermophiles include *Azotobacter vinelandii; Thermoplasma acidophilum; Pyrococcus horikoshii; Pyrococcus furiosus*; and *Crenarchaeota* (extremely thermophilic archaebacteria) species such as *Sulfolobus solfataricus* and *Sulfolobus acidocaldarius*.

Archaebacterial minicells are within the scope of the invention. Archaebacteria have homologs of eubacterial minicell genes and proteins, such as the MinD polypeptide from *Pyrococcus furiosus* (Hayashi et al., *EMBO J.* 20:1819-28, 2001). It is thus possible to create Archaebacterial minicells by methods such as, by way of non-limiting example, overexpressing the product of a min gene isolated from a prokaryote or an archaebacterium; or by disrupting expression of a min gene in an archaebacterium of interest by, e.g., the introduction of mutations thereof or antisense molecules thereto. See, e.g., Laurence et al., *Genetics* 152: 1315-1323, 1999.

By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage. In some embodiments, the present disclosure teaches production of archaeal minicells.

Bacterial Minicell Production

Minicells are produced by parent cells having a mutation in, and/or overexpressing, or under expressing a gene involved in cell division and/or chromosomal partitioning, or from parent cells that have been exposed to certain conditions, that result in aberrant fission of bacterial cells and/or partitioning in abnormal chromosomal segregation during cellular fission (division). The term "parent cells" or "parental cells" refers to the cells from which minicells are produced. Minicells, most of which lack chromosomal DNA (Mulder et al., *Mol Gen Genet*, 221: 87-93, 1990), are generally, but need not be, smaller than their parent cells. Typically, minicells produced from *E. coli* cells are generally spherical in shape and are about 0.1 to about 0.3 um in diameter, whereas whole *E. coli* cells are about from about 1 to about 3 um in diameter and from about 2 to about 10 um in length. Micrographs of *E. coli* cells and minicells that have been stained with DAPI (4:6-diamidino-z-phenylindole), a compound that binds to DNA, show that the minicells do not stain while the parent *E. coli* are brightly stained. Such micrographs demonstrate the lack of chromosomal DNA in minicells. (Mulder et al., *Mol. Gen. Genet.* 221:87-93, 1990).

Minicells are achromosomal, membrane-encapsulated biological nanoparticles (≤400 nm) that are formed by bacteria following a disruption in the normal division apparatus of bacterial cells. Minicells can also be 400 nm to 650 nm in size. In essence, minicells are small, metabolically active replicas of normal bacterial cells with the exception that they contain no chromosomal DNA and as such, are non-dividing and non-viable. Although minicells do not contain chromosomal DNA, the ability of plasmids, RNA, native and/or recombinantly expressed proteins, and other metabolites have all been shown to segregate into minicells. Some methods of construction of minicell-producing bacterial strains are discussed in detail in U.S. patent application Ser. No. 10/154,951 (US Publication No. US/2003/0194798 A1), which is hereby incorporated by reference in its entirety.

Disruptions in the coordination between chromosome replication and cell division lead to minicell formation from the polar region of most rod-shaped prokaryotes. Disruption of the coordination between chromosome replication and cell division can be facilitated through the overexpression of some of the genes involved in septum formation and binary fission. Alternatively, minicells can be produced in strains that harbor mutations in genes that modulate septum formation and binary fission. Impaired chromosome segregation mechanisms can also lead to minicell formation as has been shown in many different prokaryotes.

Plasmid Based Methods of Minicell Production

In some embodiments, minicell production can be achieved by the overexpression or mutation of genes involved in the segregation of nascent chromosomes into daughter cells. For example, mutations in the parC or mukB loci of *E. coli* have been demonstrated to produce minicells. Both affect separate requisite steps in the chromosome segregation process in bacteria. Manipulation of wild type levels of any given gene involved in the chromosome segregation process that result in minicell production will have similar effects in other family members.

Because the cell division and chromosome replication processes are so critical to survival, there exists a high level of genetic and functional conservancy amongst prokaryotic family members with respect to genes responsible for these processes. The overexpression or mutation of a cell division gene capable of driving minicell production in one family member, can be used to produce minicells in another. For example, it has been shown that the overexpression *E. coli* ftsZ gene in other Enterobacteriacea family members such as *Salmonella* spp. and *Shigella* spp as well as other class members such as *Pseudomonas* spp. will result in similar levels of minicell production.

In some embodiments, minicells can be produced in *E. coli* by the overproduction of the protein FtsZ which is an essential component of the Min division system by which *E. coli* operates. This protein polymerizes during cell division to form a ring-like structure at the potential site of division. This ring recruits other proteins which complete the division. Overproduction of this protein in *E. coli* results in the inability for this ring to be spatially restricted to the mid-section of the cell, thus resulting in production of minicells upon cell division. Because the overproduction of FtsZ can create minicells, it can be overexpressed using a plasmid based system.

The same can be demonstrated in the mutation-based minicell producing bacterial strains. For example, deletion of the Min locus in any of bacterial strains results in minicell production. Cell division genes in which mutation can lead to minicell formation include but are not limited to the min genes (such as minC, minD, and minE).

In some embodiments, *E. coli* rely on the min system in order to ensure proper replication of parent cells into daughter cells. This min system (known as the minB operon) consists of 3 parts, minD, minC, and minE. These genes work together in order to control the placement of the Z-ring which is comprised of polymerized FtsZ protein. MinC consists of two distinct domains, both of which interact directly with the FtsZ protein in order to inhibit polymerization (Z-ring formation). MinD is a protein that is associated with the membrane that forms at one of the cell's poles and polymerizes toward the cell's mid-point. It binds MinC which is distributed throughout the cytoplasm. MinE is a protein that binds to MinD as well and releases MinC. It polymerizes into a ring like shape and oscillates from pole to pole in the cell.

This system results in the sequestering of MinC bound to FtsZ (inactivating it) to the polar ends of the cell. By doing this, and due to the oscillating effect of MinE, the system creates a high chance that FtsZ polymerizes in the middle of cell and forms a Z-ring. This sets the division septum of the cell at the midpoint in the cell, which results in two cells with equal genetic information upon completion of division.

In some embodiments, this system can be manipulated in order to shift the Z-ring to a polar end of the cell which excludes the nucleoid DNA upon completion of replication. The Z-ring can be shifted by not allowing the cell to sequester MinC to the polar ends of the cell. In the absence of MinC or MinD, or overexpression of MinE, *E. coli* cells will form achromosomal and/or anucleate cells. The FtsZ and the Min systems for causing asymmetrical cell division are exemplified by Piet et al, 1990, *Proc. Natl. Acad. Sci. USA* 87:1129-1133 and Xuan-Chuan et al, 2000, *J. Bacteriol.* 182(21):6203-62138, each of which is incorporated herein by reference.

In some embodiments, the present disclosure is compatible with all genetic design and cloning methods. That is, in some embodiments, the present disclosure teaches the use of traditional cloning techniques such as polymerase chain reaction, restriction enzyme digestions, ligation, homologous recombination, RT PCR, and others generally known in the art and are disclosed in for example: Sambrook et al. (2001) Molecular Cloning: A Laboratory Manual ($3^{rd}$ ed., Cold Spring Harbor Laboratory Press, Plainview, N.Y.), incorporated herein by reference.

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

In some embodiments, minicells are produced by deleting, mutating, knocking out, or disrupting minC, minD, and/or minC and minD gene(s) in bacteria by traditional gene engineering techniques including homologous recombination. In other embodiments, minicells are produced by overexpressing certain genes such as ftsZ and/or minE in bacteria.

Controlled Production of Minicells

In some embodiments, the present disclosure teaches mutating cell populations by introducing, deleting, or replacing selected portions of genomic DNA. Thus, in some embodiments, the present disclosure teaches methods for targeting mutations to a specific locus such as ftsZ, minC, minD, minC/D, and minE. In other embodiments, the present disclosure teaches the use of gene editing technologies such as ZFNs, TALENS, CRISPR or homing endonucleases, to selectively edit target DNA regions. In aspects, the targeted DNA regions is ftsZ, minC, minD, minC/D, and minE.

Engineered nucleases such as zinc finger nucleases (ZFNs), Transcription Activator Like Effector Nucleases (TALENs), engineered homing endonucleases, and RNA or DNA guided endonucleases, such as CRISPR/Cas such as Cas9 or CPF1, are particularly appropriate to carry out some of the methods of the present disclosure. Additionally or alternatively, RNA targeting systems can use used, such as CRISPR/Cas systems have RNA targeting nucleases.

In some embodiments, the present disclosure teaches uses of gene editing using a Type II CRISPR system such as Cas9 Type II CRISPR systems, or "Cas9-like" systems. Type II systems rely on a i) single endonuclease protein, ii) a transactivating crRNA (tracrRNA), and iii) a crRNA where a ~20-nucleotide (nt) portion of the 5' end of crRNA (i.e. "guide sequence" or "spacer") is complementary to a target nucleic acid.

In some embodiments, the tracrRNA and crRNA components of a Type II system can be replaced by a single-guide RNA (sgRNA). The sgRNA can include, for example, a nucleotide sequence that comprises an at least 12-20 nucleotide sequence complementary to the target DNA sequence (guide sequence) and can include a common scaffold RNA sequence at its 3' end. As used herein, "a common scaffold RNA" refers to any RNA sequence that mimics the tracrRNA sequence or any RNA sequences that function as a tracrRNA.

Cas9 endonucleases produce blunt end DNA breaks, and are recruited to target DNA by a combination of a crRNA and a tracrRNA oligos, which tether the endonuclease via complementary hybridization of the RNA CRISPR complex. DNA recognition by the crRNA/endonuclease complex requires additional complementary base-pairing with a protospacer adjacent motif (PAM) (e.g., 5'-NGG-3') located in a 3' portion of the target DNA, downstream from the target protospacer. (Jinek, M., et. al., Science. 2012:337; 816-821). In some embodiments, the PAM motif recognized by a Cas9 varies for different Cas9 proteins.

In some embodiments, one skilled in the art can appreciate that the Cas9 disclosed herein can be any variant described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M. et al. Science. 2012 337:816-21; and Jinek M. et al. Science. 2014 Mar. 14; 343(6176); see also U.S. patent application Ser. No. 13/842,859 filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild type Cas9 protein having double-stranded nuclease activity, Cas9 mutants that act as single stranded nickases, deactivated Cas9 (dCas9) that has no nuclease activity, or other mutants with modified nuclease activity.

In some examples, a Type II nuclease may be catalytically dead (e.g. dCas9, "dead Cas9," "deactivated Cas9") such that it binds to a target sequence, but does not cleave.

In some embodiments, minicell production results from the disruption of the Min division system. This can be done with overexpression of FtsZ in a plasmid based system like described above, or by stopping expression of a gene within the Min system. Stopping expression of gene can be done by removing the gene (non-inducible minicell formation) or it can be done by knocking down the gene. Knocking down the gene allows for controllable repression or expression of the gene of interest. In some embodiments, the present disclosure teaches to integrate a dCAS9 gene within a non-essential operon within the E. coli genome. dCAS9 is a variant of the CAS9 protein (CRISPR) that has had its active site altered to no longer be able to edit genomes, but can still bind to highly specific segments of the genome using a guide RNA. This protein can stop transcription of the gene if bound.

In some embodiments, the dCAS9 gene can be placed under inducible control so that its expression would be controlled. The guide RNA corresponding to the knockout within the Min system could be included on a plasmid or cut into the genome and placed under inducible control. Upon induction with this system, the guide RNA would direct the dCAS9 protein to the gene within the Min system in order to stop its expression. The stopping of expression of this gene such as minC, minD, and minC/D would result in the formation of minicells.

Antibiotic Resistance Knock in-Knock Out

In some embodiments, the present disclosure teaches uses of the genetic manipulation technique using Lambda-Red recombination system in order to edit genome integrated with exogenous expression cassette such as an selectable marker such as antibiotic resistant gene. In some embodiments, an selectable marker such as antibiotic resistant gene is integrated into the host genome (e.g. bacteria) in order to knockout minC/D/CD gene for inducing minicell production. If the marker with antibiotic resistance is no longer desired after successfully selecting the minicells in which the target gene (such as minC/D/CD) is knocked out, the flippase can be used to remove the integrated antibiotic resistant gene cassette from the host genome. A fragment of linear DNA is inserted into the genome directed by that fragment homology to the genome. This can be used to knock in genes of interest or to knockout genes of interest by replacing them with an antibiotic resistance cassette such as Chloramphenicol-resistant gene, kanamycin-resistant gene, spectinomycin-resistant gene, streptomycin-resistant gene, ampicillin-resistant gene, tetracycline-resistant gene, erythromycin-resistant gene, bleomycin-resistant gene, and bleomycin-resistant gene. A successful genetic manipulation is then selected for using this antibiotic resistance cassette. If a flippase recombination target (FRT) site is included within the resistance cassette for further genetic manipulations, it can be used for removing the antibiotic resistant gene integrated into the genome in vivo after selection of target minicells. The enzyme used for this is recombinase flippase and is often expressed from a plasmid that can be removed from the cell line using a temperature sensitive origin of replication. Recombinase flippase recognizes two identical FRT sites on both the 5' and 3' ends of the antibiotic resistance cassette and removes the DNA between the two sites. In some embodiments, the FRT site can be included within an antibiotic resistance cassette to remove the antibiotic resistance cassette after its use.

Strains for Minicell Production

A E. coli P678-54 strain is obtained from Coli Genetic Stock Center (CGSC), and is used to produce minicells (Adler et al., 1967, Proc. Natl. Acad. Sci. USA 57:321-326; Inselburg J, 1970 J. Bacteriol. 102(3):642-647; Frazer 1975, Curr. Topics Microbiol. Immunol. 69:1-84).

Protease-Deficient Bacterial Strains

The present disclosure provides the production of minicells from B strains using genetically-engineering techniques including B strains including BL21, BL21 (DE3), and BL21-AI are deficient in Lon protease (cytoplasm) and OmpT protease (outer membrane). Accordingly, B strains as protease-deficient strains can be utilized to create protease-deficient and/or protease-deficient minicells. The DE3 designation means that respective strains contain the λDE3 lysogen that carries the gene for T7 RNA polymerase under control of the lacUV5 promoter. IPTG is required to maximally induce expression of the T7 RNA polymerase in order to express recombinant genes cloned downstream of a T7 promoter. BL21(DE3) is suitable for expression from a T7 or T7-lac promoter or promoters recognized by the E. coli RNA polymerase: e.g. lac, tac, trc, ParaBAD, PrhaBAD and also the T5 promoter. The genotype of BL21 (DE3) is: fhuA2 [lon] ompT gal (λ DE3) [dcm] ΔhsdS λ DE3=λ sBamHIo ΔEcoRI-B int::(lacI::PlacUV5::T7 gene1) i21 Δnin5.

BL21-AI E. coli contains a chromosomal insertion of the gene encoding T7 RNA polymerase (RNAP) into the araB locus of the araBAD operon, placing regulation of T7 RNAP under the control of the arabinose-inducible araBAD promoter. Therefore, this strain is especially useful for the expression of genes that may be toxic to other BL21 strains where basal expression of T7 RNAP is leaky. The BL21-AI strain does not contain the lon protease and is deficient in the outer membrane protease, OmpT. The genotype of BL21-AI is F$^-$ompT hsdS$_B$ (r$_B^-$ m$_B^-$) gal dcm araB::T7RNAP-tetA. The BL21-AI has an arabinose promoter that controls the production T7 RNA Polymerase, while the BL21 (DE3) has a lac promoter that controls the production of the T7 RNA Polymerase. This is significant because the lac promotion system is leaky. Therefore, the BL21-AI protein production is more tightly regulated due to the arabinose promotion system.

The present disclosure teaches that LPS (Lipopolysaccharide) modified BL21 (DE3) cells can be used. The LPS of the E. Coli is modified to be significantly less toxic. This LPS modified BL21 (DE3) cells if necessary. This could also be branched out to other gram-negative bacterial cells. Safe usage of gram-negative cells can be beneficial for anucleated cell-based platform.

ClearColi® BL21(DE3) cells are the commercially available competent cells with a modified LPS (Lipid IVA) that does not trigger the endotoxic response in diverse cells. For example, ClearColi cells lack outer membrane agonists for hTLR4/MD-2 activation; therefore, activation of hTLR4/MD-2 signaling by ClearColi® is several orders of magnitude lower as compared with E. coli wild-type cells. Heterologous proteins prepared from ClearColi® are virtually free of endotoxic activity. After minimal purification from ClearColi cells, proteins or plasmids (which may contain Lipid IVA) can be used in most applications without eliciting an endotoxic response in human cells. In ClearColi cells, two of the secondary acyl chains of the normally hexaacylated LPS have been deleted, eliminating a key determinant of endotoxicity in eukaryotic cells. The six acyl chains of the LPS are the trigger which is recognized by the Toll-like receptor 4 (TLR4) in complex with myeloid differentiation factor 2 (MD-2), causing activation of NF-κB and production of proinflammatory cytokines. The deletion of the two secondary acyl chains results in lipid IVA, which does not induce the formation of the activated heterotetrameric TLR4/MD-2 complex and thus does not trigger the endotoxic response. In ClearColi® BL21(DE3) Electrocompetent Cells 4 MA145 Rev. 31 Oct. 2016 addition, the oligosaccharide chain is deleted, making it easier to remove the resulting lipid IVA from any downstream product.

In some embodiments, protease-deficient minicells disclosed herein are produced from protease-deficient parental strains including, but are not limited to, BL21 (DE3), BL21-AI and LPS-modified BL21 (DE3). In other embodiments, BL21 (DE3), BL21-AI and LPS-modified BL21 (DE3) strains are genetically engineered by deleting, mutating, knocking out, or disrupting minC, minD, and/or minC and minD gene(s) to induce minicell production. In other embodiments, BL21 (DE3), BL21-AI and LPS-modified BL21 (DE3) strains are genetically engineered by overexpressing ftsZ and/or minE genes to induce minicell production.

In further embodiments, the present disclosure provides a new minicell-producing strain named as B8. This strain is the protease-deficient minicell-producing strain without the T7 RNA Polymerase. This minicell strain is produced from the BL21 (DE3) strain. While knocking out minC/D/CD, the T7 RNA Polymerase was silenced due to the homology of the introduced knockout via Lambda Red Transformation. This strain can be used for a need of a protease-deficient minicell, but not having the T7 RNA Polymerase. In some embodiments, minicells displayed an enzymatically active polypeptide such as complicated or toxic proteins on their surface, need to be more controlled and slower expression of the desired but complicated or toxic proteins.

The present disclosure teaches genotypes of newly-generated protease-deficient minicell strains comprising i) minC-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC, ii) minD-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminD, iii) minC/D-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC ΔminD; iv) minC-deleted BL21-AI; F$^-$ompT hsdS$_B$ (r$_B^-$ m$_B^-$) gal dcm araB::T7RNAP-tetA ΔminC, v) minD-deleted BL21-AI; F$^-$ompT hsdS$_B$ (r$_B^-$ m$_B^-$) gal dcm araB::T7RNAP-tetA ΔminD, vi) minC/D-deleted BL21-AI; F$^-$ompT hsdS$_B$ (r$_B^-$ m$_B^-$) gal dcm araB::T7RNAP-tetA ΔminC ΔminD; vii) minC-deleted LPS-modified BL21 (DE3); msbA148 ΔgutQ ΔkdsD ΔlpxL ΔlpxM ΔpagP ΔlpxP ΔeptA ΔminC, viii) minD-deleted LPS-modified BL21 (DE3); msbA148 ΔgutQ ΔkdsD ΔlpxL ΔlpxM ΔpagP ΔlpxP ΔeptA ΔminD, ix) minC/D-deleted LPS-modified BL21 (DE3); msbA148 ΔgutQ ΔkdsD ΔlpxL ΔlpxM ΔpagP ΔlpxP ΔeptA ΔminC, ΔminD, x) minC-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC; xi) minD-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminD; and xii) minC/D-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC ΔminD.

Minicells that have segregated from parent cells lack chromosomal and/or nuclear components, but retain the cytoplasm and its contents, including the cellular machinery required for protein expression. In some embodiments, minicells are protease-deficient because the parent cells are protease-deficient strains. Although chromosomes do not segregate into minicells, extrachromosomal and/or episomal genetic expression elements may segregate, or may be introduced into minicells after segregation from parent cells. In some embodiments, the disclosure is drawn to protease-deficient minicells comprising an expression element, which may be an inducible expression element. The inducible expression element such as an inducible promoter can be introduced to a recombinant plasmid used for homologous recombination to knock out and/or delete gene(s) involved to cell division and/or chromosomal partitioning such as minC, minD, and minC/D, a recombinant expression vector to overexpress gene(s) involved to cell division and/or chromosomal partitioning such as ftsZ and minE, and a recombinant expression vector for expressing an enzymatically active polypeptide including a protein of interest disclosed herein. In further embodiments, the inducible expression element comprises expression sequences operably linked to an open reading frame (ORF) that encodes proteins of interest disclosed herein. Optionally, at any point in the method, an inducing agent is provided in order to induce expression of an ORF that encodes proteins of interest disclosed herein.

In some embodiments, the disclosure teaches methods of making a protease-deficient bacterial minicell comprising a recombinant fusion protein that is not naturally found in parental cells. In some embodiment, the disclosure teaches method of preparing protease-deficient minicells from the host cells.

Figure 18:
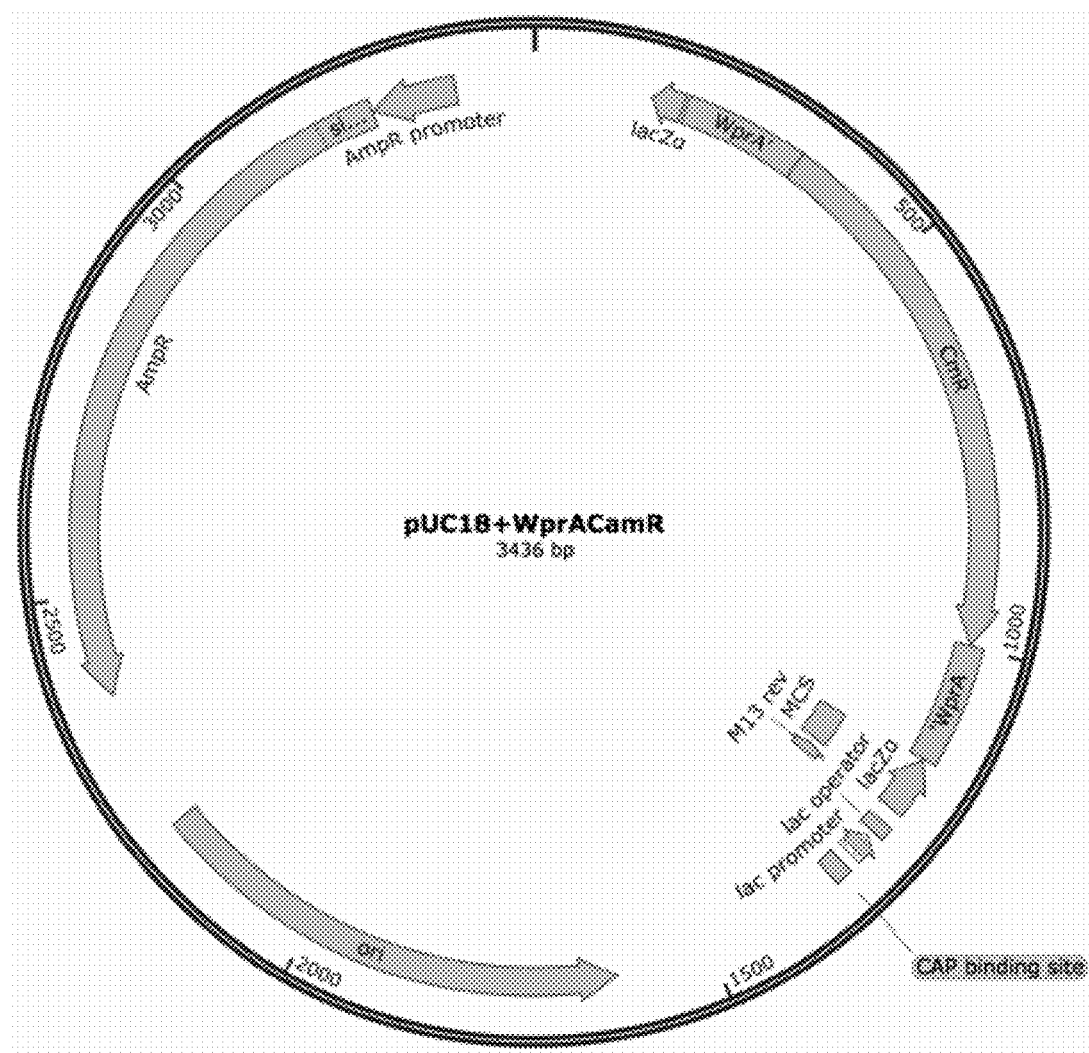
FIG. 18 illustrates an exemplary pUC18 vector for a protease WprA knockout to produce protease-deficient minicells from bacterial strains with WprA protease. The pUC18 vector was inserted with a recombinant DNA insert comprising 5' end nucleotide sequence of WprA gene, a chloramphenicol resistant gene (CmR) with cat promoter, and 3' end nucleotide sequence of WprA gene. The hairpin loops flanked by 5' and 3' ends of wprA gene are inserted into the insert to stop transcriptional regulation of other neighboring genes in the genome where the insert is integrated.

In other embodiments, the present disclosure teaches production of protease-deficient minicells from $B.$ $subtilis$ strains such as CU403 DIVIVA, CU403,DIVIVB,SPO-, CU403,DIVIVB and CU403,DIVIVB1 using by deleting, mutating, knocking out, or disrupting gene encoding WprA protease. FIG. 18 illustrate an exemplary recombinant vector for this purpose of suppressing and/or removing WprA protease activity to make protease-deficient condition in $B.$ $subtilis$.

$B.$ $subtilis$ genetic manipulations work slightly differently than genetic manipulations in $E.$ $coli$. $B.$ $subtilis$ is known to readily undergo homologous recombination if DNA containing homology to the existing genome is inserted. This is unlike $E.$ $coli$; $E.$ $coli$ has mechanisms in place to degrade any non-natural linear DNA present. This difference can be utilized in order to knockout genes by designing an antibiotic resistance cassette flanked by homologous arms which correspond to the start and end of the gene that is desired to be knockout out.

The present disclosure provides the production of minicells from $B.$ $subtilis$ using genetically-engineering techniques. In some embodiments, $B.$ $subtilis$ strains including, but are not limited to CU403 DIVIVA (BGSC No. 1A196), CU403,DIVIVB,SPO- (BGSC No. 1A197), CU403,DI-VIVB (BGSC No. 1A292), CU403,DIVIVB1 (BGSC No. 1A513), KO7 can be used as parental bacterial cells to produce minicells. $B.$ $subtilis$ strains are the commercially available and can be obtained from $Bacillus$ Genetic Stock Center (BGSC). The catalog of strains is available on the document provided by publicly accessible BGSC webpage (www.bgsc.org/_catalogs/Catpart1.pdf).

In some embodiments, $Bacillus$ $Subtilis$ stains including, but are not limited to CU403 DIVIVA, CU403,DIVIVB, SPO-, CU403,DIVIVB and CU403,DIVIVB1 can be genetically modified by knocking out gene encoding WprA Protease in these strains. WprA protease is known as one of the harshest proteases.

In order to knock out, delete, and or remove WprA-encoding gene from $B.$ $subtilis$ strains, the pUC18 WprA-CamR vector is used as illustrated in FIG. 18. This vector has the homologous arms corresponding to the gene coding for WprA cell wall protease that naturally occurs in $B.$ $subtilis$ which is undesirable for protein surface expression. These homologous arms flank a chloramphenicol resistance cassette in order to allow for selection. After the homologous recombination via the homologous arms within the host cells, the WprA-encoding nucleotide except the homologous arm is replaced with the chloramphenicol selection marker gene. This plasmid can replicate within $E.$ $coli$ due to its origin of replication, thus when transformed into $B.$ $subtilis$ it cannot replicate. After transformation, colonies are selected for using chloramphenicol in order to isolate the colonies in which the knockout of WprA successfully occurs. Because the plasmid cannot replicate in $B.$ $subtilis$, only the cells can survive against the presence of chloramphenicol if the recombinant cassette having the chloramphenicol resistant marker gene is integrated to the genome of the $B.$ $subtilis$ cell by homologous recombination.

$B.$ $subtilis$ secretes no fewer than seven proteases during vegetative growth and stationary phase. Strains in which multiple protease genes have been inactivated have proved to be superior to wild type strains in production of foreign proteins. The KO7 is prototrophic, free of secreted proteases, and have marker-free deletions in PY79 genetic background. This KO7 is available from the BGSC as accession number 1A1133. KO7 Genotype: ΔnprE ΔaprE Δepr Δmpr ΔnprB Δvpr Δbpr In some embodiments, a seven-protease deletion strain, $B.$ $subtilis$ KO7, can be used for $B.$ $subtilis$ minicell production by knocking out DIV-IVA and DIV-IVB using genetic engineering techniques described in the present disclosure.

Minicell Separation and Purification

A variety of methods are used to separate minicells from parent cells (i.e., the cells from which the minicells are produced) in a mixture of parent cells and minicells. In general, such methods are physical, biochemical and genetic, and can be used in combination.

Physical Separation of Minicells from Parent Cells

By way of non-limiting example, minicells are separated from parent cells glass-fiber filtration (Christen et al., Gene 23:195-198, 1983), and differential and zonal centrifugation (Barker et al., J. Gen. Microbiol. 111:387-396, 1979), size-exclusion chromatography, e.g. gel-filtration, differential sonication (Reeve, J. N., and N. H. Mendelson. 1973. Biochem. Biophys. Res. Commun. 53:1325-1330), and UV-irradiation (Tankersley, W. G., and J. M. Woodward. 1973. Proc Soc Exp Biol Med. 1974 March; 145(3):802-805).

Some techniques involve different centrifugation techniques, e.g., differential and zonal centrifugation. By way of non-limiting example, minicells may be purified by the double sucrose gradient purification technique described by Frazer and Curtiss, Curr. Topics Microbiol. Immunol. 69:1-84, 1975. The first centrifugation involves differential centrifugation, which separates parent cells from minicells based on differences in size and/or density. The percent of sucrose in the gradient (graduated from about 5 to about 20%), Ficol or glycerol is designed to allow only parent cells to pass through the gradient.

The supernatant, which is enriched for minicells, is then separated from the pellet and is spun at a much higher rate (e.g., ≥11,000 g). This pellets the minicells and any parent cells that did not pellet out in the first spin. The pellet is then resuspended and layered on a sucrose gradient.

The band containing minicells is collected, pelleted by centrifugation, and loaded on another gradient. This procedure is repeated until the minicell preparation is essentially depleted of parent cells, or has a concentration of parent cells that is low enough so as to not interfere with a chosen minicell application or activity. By way of non-limiting example, buffers and media used in these gradient and resuspension steps may be LB, defined minimal media, e.g. M63 salts with defined carbon, nitrogen, phosphate, magnesium, and sulfate levels, complex minimal media, e.g.

defined minimal media with casamino acid supplement, and/or other buffer or media that serves as an osmo-protectant, stabilizing agent, and/or energy source, or may contain agents that limit the growth of contaminating parental cells, e.g azide, antibiotic, or lack an auxotrophic supplemental requirement, e.g. thiamine.

Other physical methods may also be used to remove parent cells from minicell preparations. By way of non-limiting example, mixtures of parent cells and minicells are frozen to −20° C. and then thawed slowly (Frazer and Curtiss, Curr. Topics Microbiol. Immunol. 69:1-84, 1975).

Biochemical Separation of Minicells from Parent Cells

Contaminating parental cells may be eliminated from minicell preparations by incubation in the presence of an agent, or under a set of conditions, that selectively kills dividing cells. Because minicells can neither grow nor divide, they are resistant to such treatments.

Examples of biochemical conditions that prevent or kill dividing parental cells is treatment with an antibacterial agent, such as penicillin or derivatives of penicillin. Penicillin has two potential affects. First, penicillin prevent cell wall formation and leads to lysis of dividing cells. Second, prior to lysis dividing cells form filaments that may assist in the physical separation steps described above. In addition to penicillin and its derivatives, other agents may be used to prevent division of parent cells. Such agents may include azide. Azide is a reversible inhibitor of electron transport, and thus prevents cell division. As another example, D-cycloserine or phage MS2 lysis protein may also serve as a biochemical approach to eliminate or inhibit dividing parental cells. (Markiewicz et al., FEMS Microbiol. Lett. 70:119-123, 1992). Khachatourians (U.S. Pat. No. 4,311,797) states that it may be desirable to incubate minicell/parent cell mixtures in brain heart infusion broth at 36° C. to 38° C. prior to the addition of penicillin G and further incubations.

Genetic Separation of Minicells from Parent Cells

Alternatively or additionally, various techniques may be used to selectively kill, preferably lyse, parent cells. For example, although minicells can internally retain M13 phage in the plasmid stage of the M13 life cycle, they are refractory to infection and lysis by M13 phage (Staudenbauer et al., Mol. Gen. Genet. 138:203-212, 1975). In contrast, parent cells are infected and lysed by M13 and are thus selectively removed from a mixture comprising parent cells and minicells. A mixture comprising parent cells and minicells is treated with M13 phage at an M.O.I.=5 (phage cells). The infection is allowed to continue to a point where ≥50% of the parent cells are lysed, preferably ≥75%, more preferably ≥95% most preferably ≥99%; and ≤25% of the minicells are lysed or killed, preferably ≤15%, most preferably ≤1%.

As another non-limiting example of a method by which parent cells can be selectively killed, and preferably lysed, a chromosome of a parent cell may include a conditionally lethal gene. The induction of the chromosomal lethal gene will result in the destruction of parent cells, but will not affect minicells as they lack the chromosome harboring the conditionally lethal gene. As one example, a parent cell may contain a chromosomal integrated bacteriophage comprising a conditionally lethal gene. One example of such a bacteriophage is an integrated lambda phage that has a temperature sensitive repressor gene (e.g., lambda cI857). Induction of this phage, which results in the destruction of the parent cells but not of the achromosomal minicells, is achieved by simply raising the temperature of the growth media. A preferred bacteriophage to be used in this method is one that kills and/or lyses the parent cells but does not produce infective particles. One non-limiting example of this type of phage is one that lyses a cell but which has been engineered to as to not produce capsid proteins that are surround and protect phage DNA in infective particles. That is, capsid proteins are required for the production of infective particles.

As another non-limiting example of a method by which parent cells can be selectively killed or lysed, toxic proteins may be expressed that lead to parental cell lysis. By way of non-limiting example, these inducible constructs may employ a system to control the expression of a phage holing gene. Holin genes fall with in at least 35 different families with no detectable orthologous relationships (Grundling, A., et al. 2001. Proc. Natl. Acad. Sci. 98:9348-9352) of which each and any may be used to lyse parental cells to improve the purity of minicell preparations.

In some embodiments, minicells are substantially separated from the minicell-producing parent cells in a composition comprising minicells. After separation, the compositions comprising the minicells is at least about 99.9%, about 99.8%, about 99.7%, about 99.6%, about 99.5%, about 99.4%, about 99.3%, about 99.2%, about 99.1%, about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 65%, about 60%, about 55%, about 50%, about 45%, about 40%, about 35%, about 30%, about 25% or about 20% free of minicell-producing parent cells. Thus, the compositions of the disclosure can comprise minicells that are substantially free of the parental cell.

In some aspects, the present invention provides a method for making minicells, the method comprising (a) culturing a minicell-producing parent cell, wherein the parent cell comprises an recombinant construct, wherein the recombinant construct comprises a nucleotide sequence homologous to a target gene associated with regulating cell division, and (b) separating the minicells from the parent cell, thereby generating a composition comprising minicells. In some embodiments, the method further comprises (c) purifying the minicells from the composition by centrifugation and/or filtration. In some embodiments, one or more additional expression constructs can be introduced into the minicell-producing parent cell which comprise genes associated with cell division. In such instances, the expression constructs may be simultaneously or sequentially introduced into the parent cell prior to induction for minicell formation, and can comprise one or more selection markers (e.g., antibiotic resistance genes) and/or reporter genes to allow for selection and/or visualization of minicells expressing the protein(s) of interest. In other embodiments, the expression construct can express one or more additional proteins, which are driven by the same or different promoters, including inducible promoters. In further embodiments, genes associated with cell division are minC, minD, and/or both minC and minD.

Eubacterial cells and minicells are bounded by an inner membrane, which is surrounded by a cell wall, wherein the cell wall is itself enclosed within an outer membrane. That is, proceeding from the external environment to the cytoplasm of a minicell, a molecule first encounters the outer membrane (OM), then the cell wall and finally, the inner membrane (IM).

In some embodiments, the present disclosure teaches disruption or degradation of the OM, cell wall or IM of a eubacterial minicell. Such treatments are used, by way of non-limiting example, in order to increase or decrease the immunogenicity, and/or to alter the permeability characteristics, of a minicell.

In some embodiments, minicells are (i) fully intact, (ii) protoplasts (outer membrane and cell wall removed) or, (iii) poroplasts (outer membrane removed or permeabilized) in which surface-expressing moieties such as membrane-associated protein, transmembrane protein/domain, and linker protein/domain are found. In some embodiments, the surface-expressing moieties can be fused to enzymatically active polypeptides including, but are not limited to lipases, phospholipases, transacylases, transaminases, pectinase, proteases, amylases, cellulases, cutinases, esterases, acylases, invertases, isomerases, lyases, glucosidases, oxidoreductases, transferases, ligases, and amidases, displayed on the surface of achromosomal and/or anucleate cells. In other embodiments, enzymatically active polypeptides comprise lipase, glucose isomerase, alpha amylase, cellulase (endoglucanases, exoglucanases, beta-glucosidases), beta amylase, pectin lyase, isomerase, protease, transglutaminase, desaturase, peroxidase, lipoxygenase, catalase, alkaline phosphatase, tyrosinase, urease, dehydrogenases (e.g. alcohol dehydrogenases, lactate dehydrogenases, acetaldehyde dehydrogenases, aldehyde dehydrogenases, pyruvate dehydrogenases, and succinate dehydrogenases), xylanase, phytase, mannanase, and laccase. Also, enzymatically active polypeptides further comprise amyloglucosidase, pullulanase, cyclodextrin-glycosyltransferase, pectin methyl esterase, glucose oxidase, lactase, beta-glucanase, acetolactate decarboxylase, pectate lyase, nitrilase, and amyloglucosidase. In some embodiments, the enzymatically active polypeptide is lipase. In some embodiments, the enzymatically active polypeptide is glucose isomerase.

Eubacterial cells and minicells with altered membranes and/or cell walls are called "poroplasts" "spheroplasts," and "protoplasts." Herein, the terms "spheroplast" and "protoplast" refer to spheroplasts and protoplasts prepared from minicells. In contrast, "cellular spheroplasts" and "cellular protoplasts" refer to spheroplasts and protoplasts prepared from cells. Also, as used herein, the term "minicell" encompasses not only minicells per se but also encompasses poroplast, spheroplasts and protoplasts.

In a poroplast, the eubacterial outer membrane (OM) and LPS have been removed. In a spheroplast, portions of a disrupted eubacterial OM and/or disrupted cell wall either may remain associated with the inner membrane of the minicell, but the membrane and cell wall is nonetheless porous because the permeability of the disrupted OM and cell wall has been increased. A membrane is said to be "disrupted" when the membrane's structure has been treated with an agent, or incubated under conditions, that leads to the partial degradation of the membrane, thereby increasing the permeability thereof. In contrast, a membrane that has been "degraded" is essentially, for the applicable intents and purposes, removed. In preferred embodiments, irrespective of the condition of the OM and cell wall, the eubacterial inner membrane is not disrupted, and membrane proteins displayed on the inner membrane are accessible to compounds that are brought into contact with the minicell, poroplast, spheroplast, protoplast or cellular poroplast, as the case may be.

Enzyme Immobilization

A variety of enzyme immobilization techniques have been developed to improve the efficiency of enzymes. The process of immobilizing enzymes began in 1916 with the invertase being immobilized on aluminum hydroxide (Fersht A. Structure and mechanism in protein science: a guide to enzyme catalysis and protein folding. New York: W. H. Freeman & Company; 1998. p. 615; Powers R. *Struct Funct Bioinf.* 2006; 65:124-35.) Since then, enzyme immobilization techniques have been advanced in many ways. Enzyme immobilization adds various valuable properties to enzymes. It improves the stability, reusability, storage time, recovery, and range of activities in the presence of various physical and chemical factors.

In the early phase of enzyme immobilization, invertases was reversibly immobilized on aluminum hydroxide through a physical adsorption method. This laid the groundwork for enzyme immobilization (Nelson J M et al., Hitchcock D I. 1921, *J Am Chem Soc.* 43:1956-61). From 1940 to 1965, the physical adsorption method was transitioned to adsorption based on ionic adsorption to various organic, synthetic, and inorganic materials. There were also many unsuccessful attempts at immobilizing enzymes through covalent methods at this time (Mclaren A D. 1957, *Science.* 125:697. By 1970, the covalent method of immobilizing enzymes had been successfully completed with various chemical cross-linkers and acrylamide polymers (Mosbach K et al. 1966, *Acta Chem Scand.* 20:2807-10) By 1980, the basis for enzyme immobilization methods in covalent bonding, adsorption, entrapment, and encapsulation had been developed. Affinity binding and coordination binding on novel matrices arose in this decade. This was also the decade where a multi-enzyme system was immobilized rather than a single enzyme (Chen L F et al. 1974 *Pharmacol Res Commun.* 6:273-80; Kennedy J F et al. 1975, *Carbohydr Res.* 41:227-33; Cordonnier M et al. 1975, *FEBS Lett.* 59:263-7; Sin M L et al. 2014 *Expert Rev Mol Diagn.* 14:225-44; Horton H R et al. 1976, *Methods Enzymol.* 44:516-26). During this time, designing immobilized enzymes with very high selectivity and specificity were tried to replace most chemical-based processes. Discoveries in the structure and specificity of immobilized enzymes led to breakthroughs in various industries including pharmaceuticals, agriculture, and industry.

From the 1990s to present day, research has been heavily focused on developing advanced immobilization techniques. The goal has been to create immobilized enzymes that have similar catalytic ability to that of soluble enzymes but with higher operational stability. Cross-linked enzyme crystals and cross-linked enzyme aggregates have showed that enzyme immobilization is possible in the absence of a carrier. The development of nano-structured materials and the use of computer modeling have significantly improved the processes involved with enzyme immobilization. Currently, there are two overarching methods involved in immobilizing enzymes: physical methods and chemical methods. Physical methods include: entrapment, adsorption, and microencapsulation. Chemical methods include covalent attachment, cross-linking, ionic binding, and conjugation by affinity ligands.

Entrapment involves the cross linking of enzymes to a polymer, allowing the permeation of substrates and release of product molecules (Das N et al. *Biotechnol Appl Biochem.* 1998; 27:25-9; Nakarani M et al. *Orient Pharm Exp Med.* 2007; 7:79-84.) Adsorption involves attaching enzymes to support materials through ionic or hydrophobic interactions, hydrogen bonding, and van der Waals forces (Alloue W A et al. 2008 *Appl Biochem Biotechnol.* 150:51-63. Hage D S et al. 1986 *Anal Chem.* 58:274-9; Marquez L D S et al. 2008 *J Mol Catal B: Enzym.* 51:86-92). Microencapsulation involves enclosing enzymes within spherical, semi-permeable polymer membranes with controlled porosity (Iso M et al. 1989, *J Microencapsul.* 6:165-76; Iso M et al. 1985, *J Microencapsul.* 2:275-87; Mauguet M C et al. 2002, *J Microencapsul.* 19:377-384).

Covalent attachment involves attaching enzymes by means of covalent bonds, including diazotization, amino bond, Schiff's base formation, amidation reactions, thiol-disulfide, peptide bond and alkylation reactions (Kayastha A M et al. 2003, J Bioact Compat Polym. 18; 113-124) Cross-linking involves covalently bonding multiple enzymes together to then bond to a matrix (Dwevedi A et al. 2009, *Bioresour Technol.* 100:2667-75). Ionic binding involves immobilizing enzymes to a charged matrix through a method similar to physical adsorption (Kayastha A M et al. 2001, 96:41-53). Conjugation by affinity ligands involves attaching an enzyme to a matrix using specific ligands, such as artificially adding a histidine tag or utilizing the existing ligands on the unmodified enzyme (DeLouise L A. et al. 2005 *Anal Chem.* 77:1950-1956; Reddy K R C et al. 2005, *Anal Chem.* 77:5063-7).

The present disclosure teaches enzyme immobilization by covalent attachment via self assembly, rather than synthetic force. Self-assembly is the process by which an organized structure spontaneously forms from individual components, as a result of specific, local interactions among the components. When the constitutive components are molecules, the process is termed molecular self-assembly as described in the following webpage (www.nature.com/subjects/self-assembly). In some embodiments, a self assembling enzyme immobilization process where the enzyme is secreted and attached to the outer membrane of the minicell in one step has been developed for standardized enzyme purification and efficacious enzyme delivery. Self-assembly is achieved through the means of targeted linker proteins and signaling sequences. These linker proteins and signaling sequences guide the expressed protein of interest to bind to the surface of the cell, exposing the expressed protein of interest to the exterior of the cell membrane.

Enzyme

In some embodiments, the enzymatically active polypeptide comprises a fusion protein. In some embodiments, the fusion protein comprises at least one surface-expressing moiety, and at least one enzyme moiety.

Enzymatically active polypeptides that are within the scope of the present disclosure include, but are not limited to, enzymes/enzyme moieties such as lipases, phospholipases, transacylases, transaminases, pectinase, proteases, amylases, cellulases, cutinases, esterases, acylases, invertases, isomerases, lyases, glucosidases, oxidoreductases, transferases, ligases, and amidases. In some embodiments, the enzymes/enzyme moieties comprise lipase, glucose isomerase, alpha amylase, cellulase (endoglucanases, exoglucanases, beta-glucosidases), beta amylase, pectin lyase, isomerase, protease, transglutaminase, desaturase, peroxidase, lipoxygenase, catalase, alkaline phosphatase, tyrosinase, urease, dehydrogenases (e.g. alcohol dehydrogenases, lactate dehydrogenases, acetaldehyde dehydrogenases, aldehyde dehydrogenases, pyruvate dehydrogenases, and succinate dehydrogenases), xylanase, phytase, mannanase, and laccase. Also, in other embodiments, enzymes/enzyme moieties further comprise amyloglucosidase, pullulanase, cyclodextrin-glycosyltransferase, pectin methyl esterase, glucose oxidase, lactase, beta-glucanase, acetolactate decarboxylase, pectate lyase, nitrilase, and amyloglucosidase. In some embodiments, the enzymes/enzyme moieties is lipase. In some embodiments, the enzymes/enzyme moieties is glucose isomerase.

In some embodiments, the enzymatically active polypeptide displayed by the minicells of the invention comprises a lipase. Exemplary lipase that is within the scope of the disclosure include, but are not limited to sequences corresponding to Genbank Accession No. AY787835.2. In some embodiments, the enzyme/enzyme moieties described above is fused to surface-expressing moiety. In other embodiments, the lipase is fused to surface-expressing moiety.

In some embodiments, the enzymatically active polypeptide displayed by the minicells of the invention comprises a glucose isomerase. Molecular and industrial aspects of glucose isomerase is reported by Bhosale S H et al 1996, Microbiological reviews, p 280-300, which is herein incorporated by reference in its entirety. In some embodiments, the enzyme/enzyme moieties described above is fused to surface-expressing moiety. In other embodiments, the glucose isomerase is fused to surface-expressing moiety and is displayed on the surface of the minicells.

Binding Domain for Cell Adhesion

In some embodiments, the anucleated cell-based platform described herewith express binding domains. These domains allow for better retention of the minicells on plant surfaces, which prevents runoff or drift of agrochemicals encapsulated within the minicells. They can also improve adhesion to the targeted pests to ensure the administration of an effective dose of the agrochemicals. Once the minicells are on the plant, the chemical will slowly release into the environment.

In some embodiments, the anucleated cell described herewith expresses a fusion protein, which comprises at least one surface expressing moiety and at least one plant cell adhesion moiety. The plant cell adhesion moiety comprises a carbohydrate binding module comprising a carbohydrate binding module selected from the group consisting of: a cellulose binding domain, a xylan binding domain, a chitin binding domain, and a lignin binding domain.

In some embodiments, the anucleated cell expresses a polypeptide on its surface that increases adhesion to a plant surface. The polypeptide is a plant adhesion polypeptide on its surface. In some embodiments, the polypeptide is a carbohydrate binding module that is displayed on its surface. In other embodiments, the polypeptide is a carbohydrate binding module that is displayed on its surface.

A carbohydrate-binding module (CBM) is a protein domain found in carbohydrate-active enzymes (for example glycoside hydrolases). The majority of these domains have carbohydrate-binding activity. Some of these domains are found on cellulosomal scaffoldin proteins. CBMs are also known as cellulose-binding domains. CBMs are classified into numerous families, based on amino acid sequence similarity. CBMs of microbial glycoside hydrolases play a central role in the recycling of photosynthetically fixed carbon through their binding to specific plant structural polysaccharides. CBMs can recognize both crystalline and amorphous cellulose forms. CBMs are the most common non-catalytic modules associated with enzymes active in plant cell-wall hydrolysis. Many putative CBMs have been identified by amino acid sequence alignments but only a few representatives have been shown experimentally to have a carbohydrate-binding function. By binding to polysaccharides, CBMs bring appended catalytic domains into intimate contact with target substrates and thus potentiate catalysis. CBMs with the capacity to bind cellulose are associated with enzymes that hydrolyze both cellulose and other cell wall polymers such as xylan, mannan, pectin, and noncellulosic β-glucans.

Cellulose binding domains (CBDs) have been described as useful agents for attachment of molecular species to cellulose (U.S. Pat. Nos. 5,738,984 and 6,124,117). Indeed, as cotton is made up of 90% cellulose, CBDs have proved useful for delivery of so called "benefit agents" onto cotton fabrics, as is disclosed in WO9800500 where direct fusions between a CBD and an enzyme were used utilizing the affinity of the CBD to bind to cotton fabric. The use of similar multifunctional fusion proteins for delivery of encapsulated benefit agents was claimed in WO03031477, wherein the multifunctional fusion proteins consist of a first binding domain which is a cellulose binding domain and a second binding domain, wherein either the first binding domain or the second binding domain can bind to a microparticle. WO03031477 is exemplified using a bifunctional fusion protein consisting of a CBD and an anti-RR6 antibody fragment binding to a microparticle, which complex is deposited onto cotton treads or cut grass.

In some embodiments, the enzymatically active polypeptide displayed by the minicells of the invention comprises a CBM. Exemplary CBM from *Cellulomonas fimi* that is within the scope of the disclosure is used. In some embodiments, the cell adhesion moiety is fused to surface-expressing moiety. In other embodiments, the CBM is fused to surface-expressing moiety and is displayed on the surface of the minicells.

In some embodiments, the present disclosure provides the genetic engineering techniques to make minicell-based platform with binding domains/motifs that functionalize the surface of the minicell. Proteins including specific binding domains and/or motifs are expressed on the surface of the minicells and specifically target binding sites that are present on the surface of plants or pests.

In some embodiments, minicell-based platform can be functionalized by proteins with carbohydrate binding modules (CBMs) that can target and bind to carbohydrates such as cellulose, xylan, chitin, and lignin, which are important and ubiquitous structural components of plant cell walls. Because CBMs can recognize their binding site present on a subject such as a plant or a pest, the minicell-based platform comprising the functionalized binding domain allows for targeting with high specificity.

Surface Expression System

In some embodiments, the present disclosure teaches surface-expressing moiety that is fused to enzyme moiety. The surface-expressing moiety can be transmembrane protein and/or transmembrane domains that function as a linker protein to display the enzymatically active polypeptides having enzyme moiety on the surface of cells.

In some embodiments, surface-expressing moiety can be membrane-associated proteins including, but not limited to, transmembrane protein, membrane-anchoring protein, linker protein and/or domain thereof.

In some embodiments, the invention is drawn to display produced membrane-associated protein(s) fused to proteins of interest disclosed herein on the surface of the minicell. By way of non-limiting example, this structure may be an internally expressed membrane protein or chimeric construct to be inserted in or associated with the minicell membrane such that the extracellular domain or domain of interest is exposed on the outer surface of the minicell (expressed and displayed on the surface of the minicell or expressed in the parental cell to be displayed on the surface of the segregated minicell).

The displayed domain fused to a membrane-associated linker protein may be an enzymatic domain such as having lipases, phospholipases, transacylases, transaminases, pectinase, proteases, amylases, cellulases, cutinases, esterases, acylases, invertases, isomerases, lyases, glucosidases, oxidoreductases, transferases, ligases, and amidases activity. In other embodiments, the displayed domain fused to a membrane-associated linker protein may be an enzymatic domain such as having lipase, glucose isomerase, alpha amylase, cellulase (endoglucanases, exoglucanases, beta-glucosidases), beta amylase, pectin lyase, isomerase, protease, transglutaminase, desaturase, peroxidase, lipoxygenase, catalase, alkaline phosphatase, tyrosinase, urease, dehydrogenases (e.g. alcohol dehydrogenases, lactate dehydrogenases, acetaldehyde dehydrogenases, aldehyde dehydrogenases, pyruvate dehydrogenases, and succinate dehydrogenases), xylanase, phytase, mannanase, and laccase activity. In other embodiments, the displayed domain fused to a membrane-associated linker protein may be an enzymatic domain such as having amyloglucosidase, pullulanase, cyclodextrin-glycosyltransferase, pectin methyl esterase, glucose oxidase, lactase, beta-glucanase, acetolactate decarboxylase, pectate lyase, nitrilase, and amyloglucosidase activity. In some embodiments, the displayed domain fused to a membrane-associated linker protein may be an enzymatic domain such as having lipase activity. In some embodiments, the displayed domain fused to a membrane-associated linker protein may be an enzymatic domain such as having glucose isomerase activity.

Contacting such minicells with the appropriate substrate of the enzyme allows the substrate to be converted to reactant. When either the substrate or reactant is detectable, the reaction catalyzed by the membrane-bound enzyme may be quantified. In the latter instance, the minicells may be used to identify and isolate, from a pool of compounds, one or more compounds that inhibit or stimulate the activity of the enzyme represented by the displayed enzymatic moiety.

In some embodiments, the membrane-associated protein can be a fusion protein, i.e., a protein that comprises a first polypeptide having a first amino acid sequence and a second polypeptide having a second amino acid sequence, wherein the first and second amino acid sequences are not naturally present in the same polypeptide. At least one polypeptide in a membrane fusion protein is a "transmembrane protein/domain" "membrane-anchoring protein/domain" or "linker protein/domain". The transmembrane and membrane-anchoring domains of a fusion protein may be selected from membrane proteins that naturally occur in a prokaryote such as bacteria, a eukaryote, such as a fungus, a unicellular eukaryote, a plant and an animal, such as a mammal including a human. Such domains may be from a viral membrane protein naturally found in a virus such as a bacteriophage or a eukaryotic virus, e.g., an adenovirus or a retrovirus. Such domains may be from a membrane protein naturally found in an archaebacterium such as a thermophile.

Exemplary surface-expressing moieties include but are not limited to ice nucleation protein (INP) *Bordetella* serum-resistance killing protein (BRK), Adhesin Involved in Diffuse Adherence protein (AIDA) and/or an exported bacterial protein. "Exported bacterial proteins," generally refers to bacterial proteins that are transported across the plasma membrane and function as an anchor for membrane proteins. Exemplary exported bacterial proteins encompassed by the present invention, include, but are not limited to LamB (GenBank Accession No. AMC96895), OprF (GenBank Accession No. NP_792118), OmpA (GenBank Accession No. AIZ93785), Lpp (GenBank Accession No. P69776), MalE (GenBank Accession No. P0AEX9), PhoA (GenBank Accession No. AIZ92470.1), Bla (GenBank Accession No. P62593), F1 or M13 major coat (J7I0P6—Uniprot No.), and F1 or M13 minor coat (P69168—Uniprot No.).

In some embodiments, for gram negative bacterial expression systems, enzymes of interest disclosed herein are immobilized to the surface of the minicells via wild type or mutant versions of the exported bacterial proteins such as LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), F1 or M13 minor coat (Gene III).

In other embodiments, a wild type and/or truncated version of the Ice Nucleation Protein (INP) can be used to immobilize enzymes on the surface of bacteria.

Surface Display System

Bacterial surface display technique enables the exogenous proteins or polypeptides displayed on the bacterial surface, while maintaining their relatively independent spatial structures and biological activities. The technique makes recombinant bacteria possess the expectant functions, subsequently, directly used for many applications. Many proteins could be used to achieve bacterial surface display, among them, autotransporter, a member of the type V secretion system of gram-negative bacteria, has been extensively studied because of its modular structure and apparent simplicity. However, autotransporter has not been widely used at present due to lack of a convenient genetic vector system.

The present disclosure teaches that autodisplay of an protein/polypeptide of interest requires an autotransporter protein in order to surface display a protein or peptide in a gram negative bacteria. The autotransporter proteins are broken down into 3 different subgroups, classical autotransporters (type Va), trimeric autotransporters adhesins (type Vb), and two partner secretion systems (type Vc).

Classic autotransporters (type Va) are thought to all share a common general structure which consists of a N-terminus signal peptide fused to the passenger protein that takes place of autotransport precursor protein, which provides transport across the cytoplasmic membrane. The N-terminus signal peptide normally utilizes the Secretion machinery in order to provide transport. This signal peptide is cleaved once the protein crosses the inner membrane. Outer membrane translocation is facilitated by the C-terminal domain of the autotransporter. This domain, known as the translocator domain, forms a β-barrel within the outer membrane. This autotransporter requires an additional linker domain due to the β-strand that closes barrel is directed towards the periplasm. Over 30 different proteins have been expressed as the passenger protein using this mechanism.

The trimeric autotransporters (type Vb) are similar to the classical autotransporters except that they cannot transport just one protein to the surface, they transport 3 (trimeric) proteins to the surface.

Type Vc autotransporters consist of a passenger and translocation domain, however both domains are expressed in separate genes. Both domains are transported across the inner membrane by the Secretion machinery, but interact with the periplasm via the polypeptide transport associated domain (POTRA). Due to the similarities between this mechanism of transport and the systems of transport that exist in chloroplasts and mitochondria, this system is expected to be able to transport extremely complex protein structures, but Vb or Vc systems of autotransport have been rarely used.

Enzymes are immobilized to the surface of the minicell by means of protein mediated membrane localization mechanisms including, but are not limited to the following linking proteins and mechanisms. In some embodiments, these systems include the BrkA protein, and AIDA-1 protein. The comparison of autotransporter and Ice Nucleation Protein as carrier proteins for protein display on the cell surface of *E. coli* is reported by Yang et al. 2013, Progress in Biochemistry and Biophysics 40(12):1209-1219, which is herein incorporated by reference in its entirety.

AIDA-I Autotransporter System

One of the most widely studied autotransporter is AIDA-1 which naturally occurs in *E. coli*. It was originally discovered in a pathogenic strain of *E. coli* but was subsequently transferred to laboratory *E. coli* strains using both the pAIDA-1 plasmid and the pDT1 plasmids.

Figure 4A:
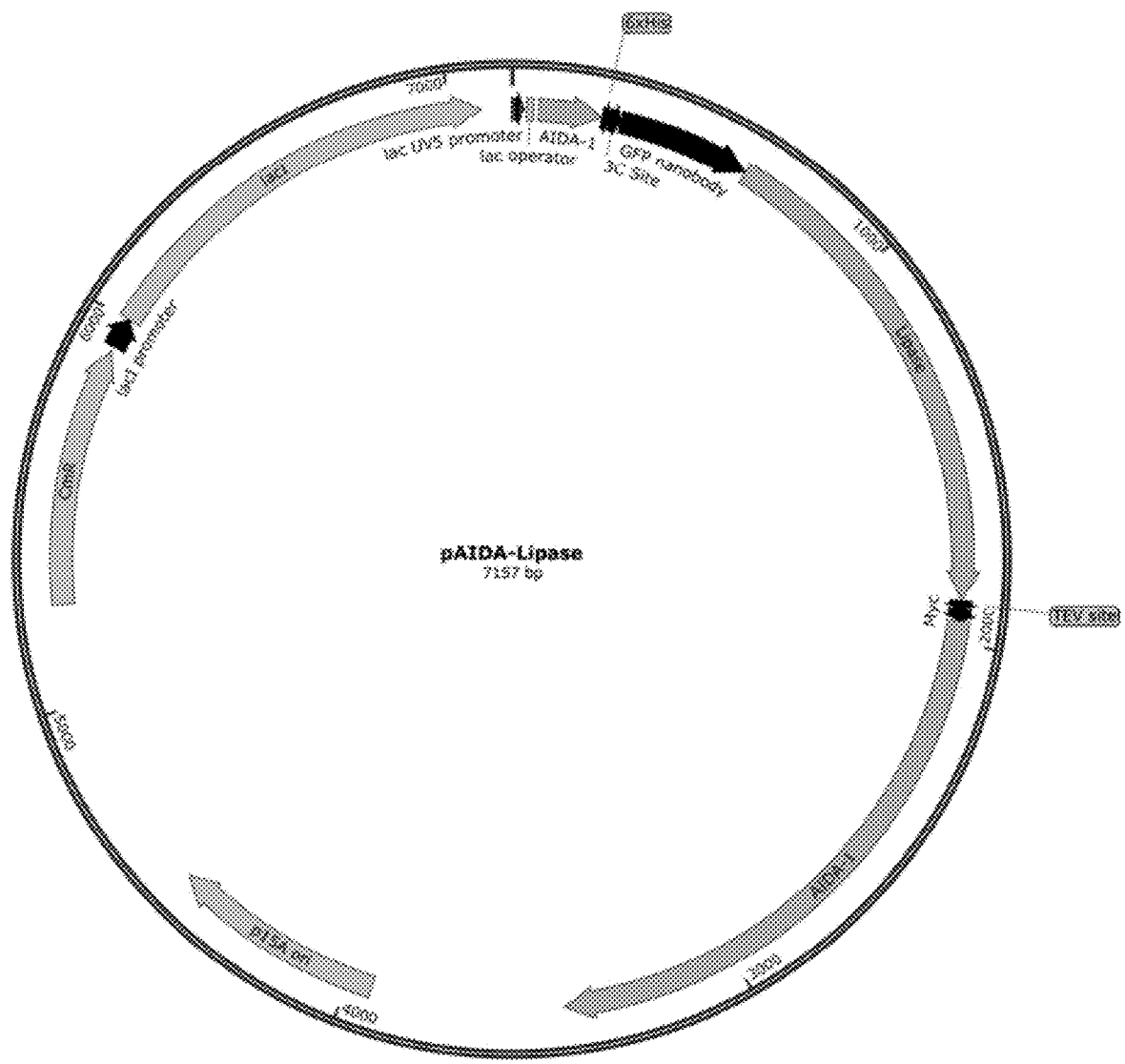
FIG. 4A illustrates an exemplary pAIDA-1-Lipase vector with an AIDA-1 surface expression system for display of a lipase protein flanked by 6×His, GFP nanobody and Myc tags on the surface of minicells.
Figure 4B:
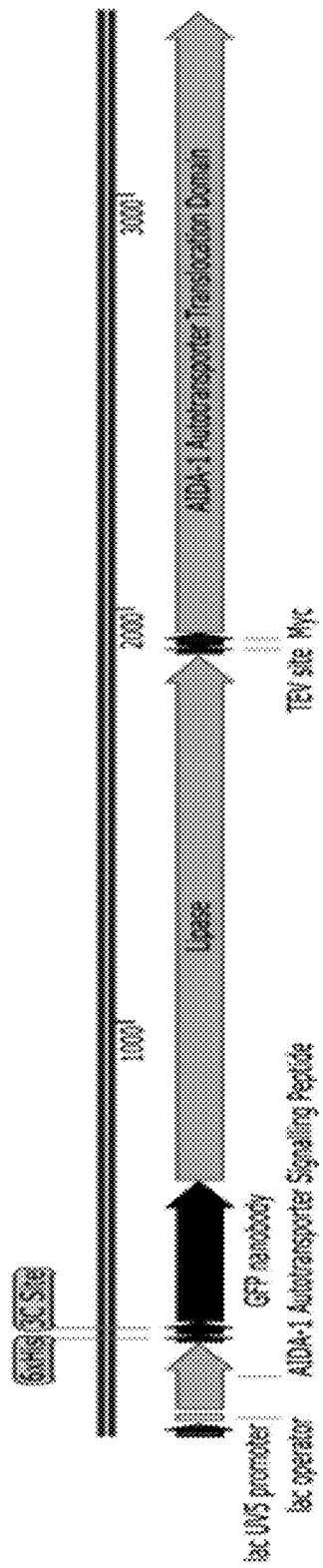
FIG. 4B illustrates an exemplary pAIDA-1 lipase surface expression cassette, comprising nucleotide sequences encoding AIDA-1 Autotransporter signal peptide, GFP nanobody, lipase, and AIDA-1 autotransporter translocation domain with tags including 6×His Tag and Myc Tag as well as two protease cleavage sites including HRV3C and TEV.

In some embodiments, the present disclosure provides the pAIDA-1 expression vector in which a polynucleotide sequence encoding a protein of interest including lipase. For example, the recombinant pAIDA-1 expression vector with lipase-encoding gene is illustrated in FIGS. 4A and 4B. The AIDA-I autotransport system consists of an N-terminus 5 kDa signaling peptide, a 5 kDa linker region, and a 47 kDA C-terminus translocation unit. The passenger domain is located between the signaling peptide and the linker domain. This autotransporter with no protein in its passenger domain is a total of 63 kDa. The protein of interest is inserted into the passenger domain in order to enable surface expression. This corresponds genetically to the signaling peptide region of the protein being located between the NdeI and SalI, the passenger domain between KpnI and SacI, the linker region of the peptide between the XbaI and NotI restriction sites, and the rest of the protein corresponding to the C-terminus translocation unit.

The pAIDA-1-lipase expression vector contains the AIDA-I gene under inducible control with a lacUV5 promoter and includes 2 protein tags (6×His Tag and Myc Tag) and 2 protease cleavage sites (HRV3C and TEV) in order to enable surface expression analysis. FIGS. 4A and 4B illustrates the pAIDA-1 lipase expression vector. The TEV site is an amino acid sequence recognized by the tobacco etch virus. It is a well-known, highly specific protease. The HRV3C site is another highly specific protease cleavage site located C-terminus to the 6× His tag. Both of these protease cleavage sites are used for protein tag removal for analytical purposes if desired. The 6× His tag is located between the SalI and the KpnI site. This 6× his tag was used for immunofluorescent staining with THE™ His Tag antibody [FITC] from Genscript® as well as used for Cobalt Immobilized Metal Affinity Chromatography for purification of the protein for assay confirmation of presence. The TEV site is N-terminus of the Myc tag and located between SacI and XbaI restriction site within the AIDA-I gene located in the pAIDA-I plasmid. The Myc tag present on the plasmid can be used for immunofluorescent staining, however this capability was not utilized.

Further components of the plasmid include a lac operator and a lad repressor gene placed under control of the lad promoter. These three components work in conjunction with the lacUV promoter in order to regulate expression of the AIDA-I gene. The pAIDA-1 plasmid maintained in vivo by the p15a origin of replication which is a medium copy origin of replication. This differs from a low copy or high copy origin of replication simply by the relative number of copies of the plasmid maintained within the cell. The antibiotic resistance gene for this plasmid is chloramphenicol (CmR) under control of its own promoter.

Brk Auto Display

The Brk has been recently discovered as autotransporter (autodisplay) protein. An autotransporter domain is a structural domain found in some bacterial outer membrane proteins. The domain is located at the C-terminal end of the protein and forms a beta-barrel structure. The barrel is oriented in the membrane such that the N-terminal portion of the protein, termed the passenger domain, is presented on the cell surface. With recently characterized autotransporter BrkA (*Bordetella* serum-resistance killing protein A) from *Bordetella pertussis*, BrkAutoDisplay system works better for surface display compared to other systems such as using the Ice Nucleation Protein (INP). The BrkAutoDisplay system for functional display of multiple exogenous proteins on the *E. coli* surface using BrkA autotransporter is exemplified by Sun et al. 2015, Microb. Cell Fact. 14:129, which is herein incorporated by reference in its entirety.

The BrkA protein (GenBank WP_010931506.1) is found as a 1010 amino acid chain length protein in its native form. The first 59 amino acids represent the signal peptide and the Beta barrel is formed between amino acids 693-1010. The Translocation domain corresponds to amino acids 545-1010. The passenger domain corresponds to amino acids 60-544, which is replaced with the proteins of interest such as lipase and/or glucose isomerase. The first 59 amino acids and the Beta barrel region, 693-1010, represent the minimal translocation domain.

Figure 6A:
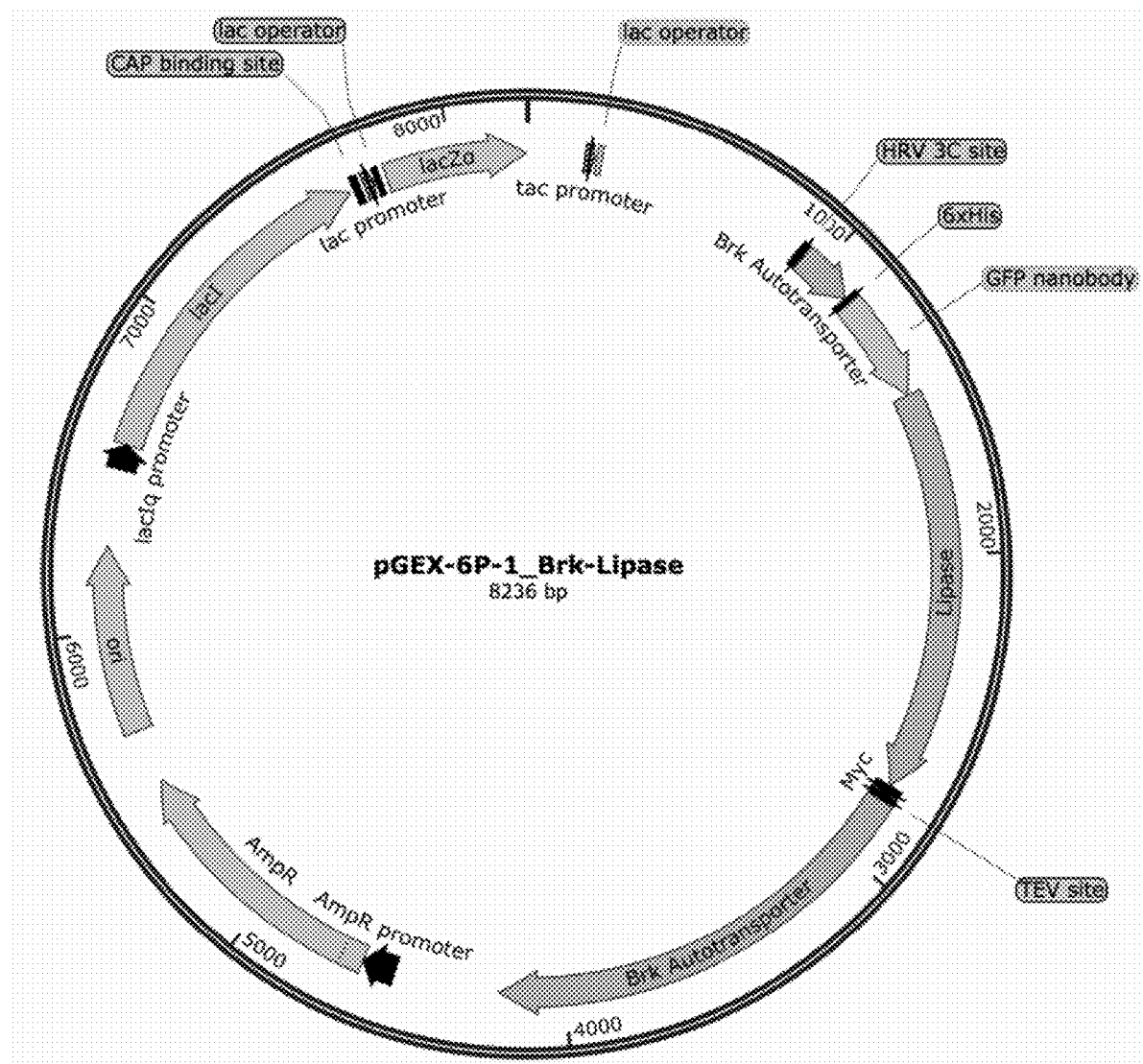
FIG. 6A illustrates an exemplary pGEX-6P-1 Brk-Lipase vector with a serum resistance autotransporter Brk surface expression system for display of a lipase protein flanked by 6×His, GFP nanobody and Myc tags on the surface of minicells.
Figure 6B:
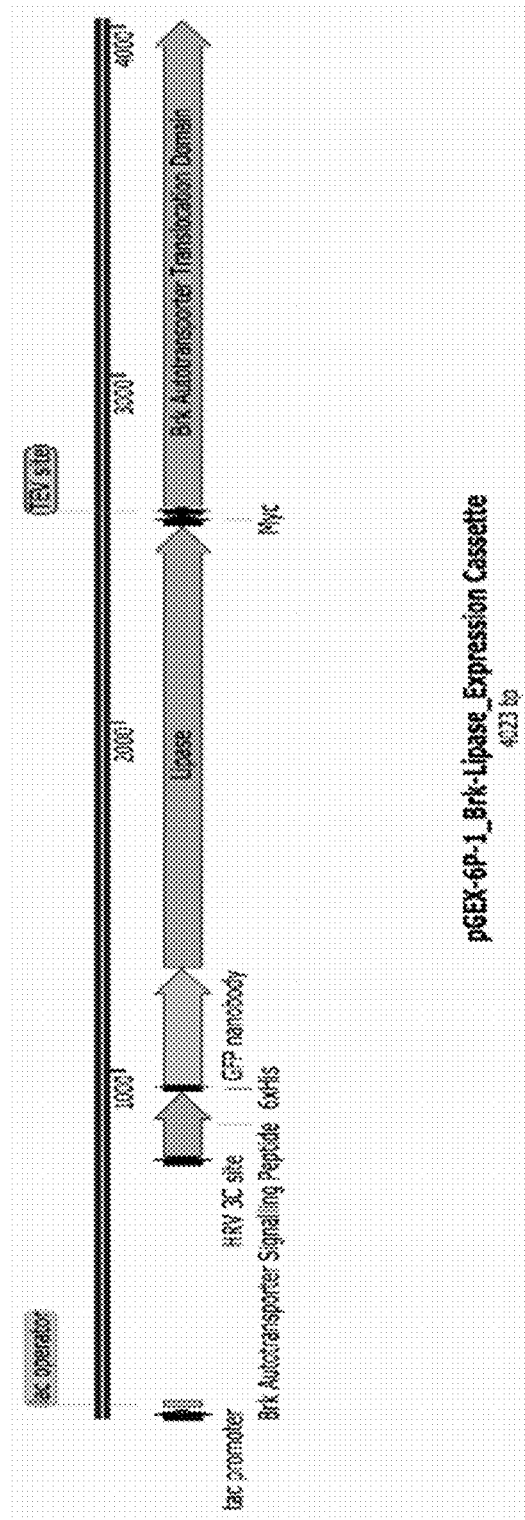
FIG. 6B illustrates an exemplary Brk-lipase surface expression cassette, comprising nucleotide sequences encoding Brk Autotransporter signal peptide, GFP nanobody, lipase, and Brk autotransporter translocation domain with tags including 6×His Tag and Myc Tag as well as two protease cleavage sites including HRV3C and TEV.

The present disclosure teaches that a recombinant expression vector/construct for expression a fusion protein possesses two polynucleotide sequences encoding i) the first 228 amino acids (signal peptide and 5' partial passenger domain) and ii) the 694-1010 amino acid (Beta barrel domain) sequence of the BrkA protein. In this recombinant expression vector, polynucleotide sequences encoding protein of interest such as lipase are inserted between these two segments (i) one for the signal peptide and 5' partial passenger domain, and ii) the other for the Beta barrel domain) of the BrkA protein. Once the fusion protein is trafficked to the membrane, it is cleaved between the Asn731 and Ala732 residues corresponding to location of the wild-type BrkA protein, upon which the protein of interest including lipase located between the signal peptide and the B-barrel translocation domain, adopts its mature conformation and is displayed externally on the surface of the cells. The recombinant expression vector used herein is illustrated in FIGS. 6A and 6B. The pGEX-6P-1 Brk-lipase expression vector contains the AIDA-I gene under control with a tac promoter and includes protein tags (6×His Tag and Myc Tag) and two protease cleavage sites (HRV3C and TEV) in order to enable surface expression analysis. The uses of 6×His tag and Myc tag are well described above.

In further embodiments, the BrkAutodisplay system in the *E coli* B strains including, but are not limited to BL21, BL21(DE3), LPS-modified BL21(DE3), B8 and BL21-AI shows a greater aggregation towards the polar ends of the cell membrane, resulting in a greater retention in the minicells because minicells bud off the polar ends from the parent cells. However, this phenomenon is not observed in the other minicell-producing cell lines such as the wild type P678-54 strain. The present disclosure teaches that the application of this autotransporter with *E coli* B strain derivatives provides an advantage of greater retention of the surface displayed protein/enzyme of interest in the final minicell product.

Vectors

In some embodiments, pUC-57 vector is used for knocking out a gene of target including minC, minD, and minC/D for including the production of minicells from the protease-deficient strain. From the 5' and 3' ends of the gene of target, about 50 base pairs of nucleotide sequence (homologous arms) corresponding to the gene of target within the genome are used for homologous recombination to knock out the gene of target. This directs the gene of interest to the place in the genome to replace the gene of target that are aimed to be knocked out. Just inside of the homologous arms, hairpin loops were inserted. These hairpin loops, when transcribed to mRNA, do not allow for any translation of what is contained between the loops in which the translation starts outside of the hairpin loops. These hairpin loops are formed upon translation of DNA to RNA and are also known as stem loops. This allows for the insert to not interfere with the native promotion of the other genes in the min system. Due to the hairpin loops, the chloramphenicol cassette (CmR) that was contained within the insert was placed under control of its own promoter, the cat promoter. By including the hairpin loops, this promoter would also not affect the regulation of any genes.

Figure 8A:
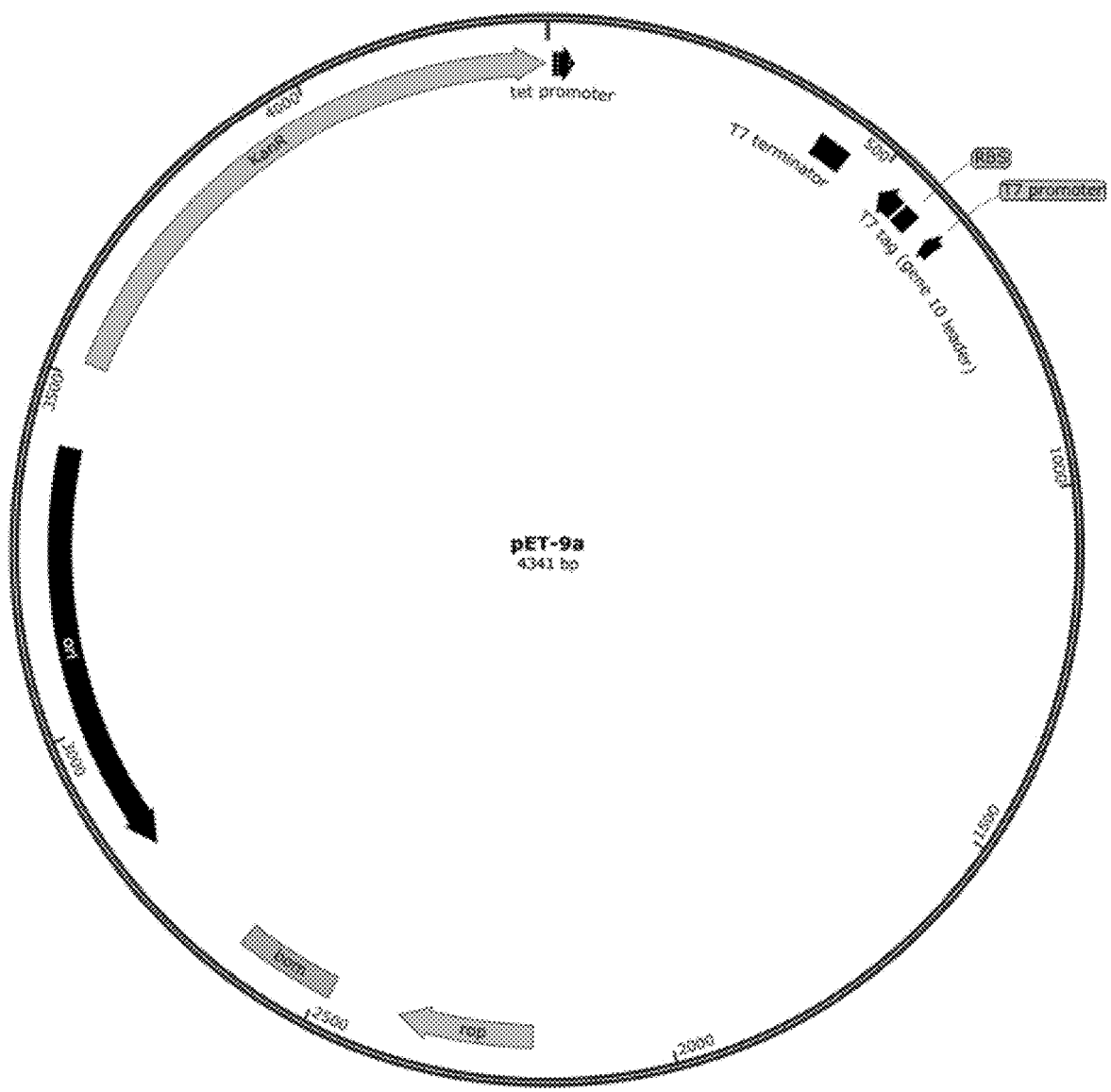
FIG. 8A illustrates an exemplary pET-9a vector for expression of a protein of interest in the protease-deficient strain with T7 RNA polymerase.

In some embodiments, the pET-9a plasmid can be used for expressing a protein of interest when the protease-deficient strain in which the protein of interest can be expressed has its own T7 RNA polymerase activity. The pEF-9a expression vector is illustrated in FIG. 8A. This plasmid is operated under the T7 promotion system which includes a promoter region upstream of the gene of interest. This promoter sequence is essentially a recognition site of the T7 RNA polymerase located under inducible control within the genome of the cell line in which the vector is transformed. Thus, production of the protein of interest is controlled by the promoter that controls the T7 rather than a promoter present on the plasmid. Because the plasmid is under control of the T7 promoter, directly after the gene is a T7 terminator region. This is to ensure that only the gene of interest is overexpressed. C-terminus to the protein of interest is the T7 epitope tag which can be used for immunofluorescent staining purposes. This plasmid is maintained in vivo by the pBR322 origin of replication which is normally a high copy origin of replication. However, T7 promotion with a high copy origin of replication is undesirable (toxic levels of protein) so the rop gene was also included in order to keep the copy number low. This plasmid contains a kanamycin resistance cassette (KanR) under control of its own promoter and thus is selected for with kanamycin.

Figure 8B:
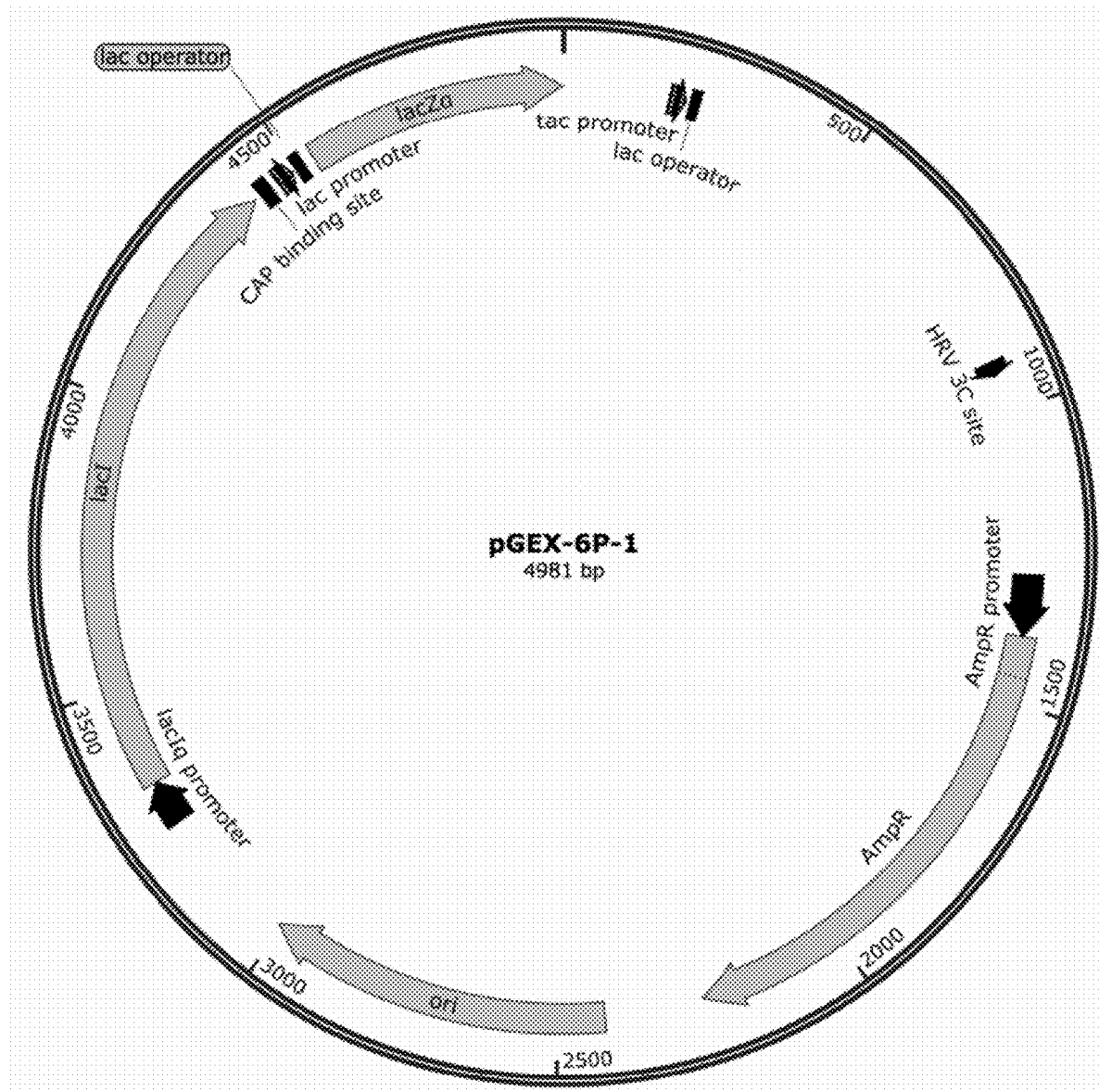
FIG. 8B illustrates an exemplary pGEX-6P-1 vector for expression of a protein of interest in the protease-deficient strain without T7 RNA polymerase.

In some embodiments, the pGEX-6P-1 plasmid can be used for expressing a protein of interest when the protease-deficient strain in which the protein of interest can be expressed does not have a T7 RNA polymerase activity. The pGEX-6P-1 expression vector is illustrated in FIG. 8B. The pGEX-6P-1 is operated under the tac promotion system. The tac promotion system is a hybrid promotion system between the trp promoter and the lac promoter. By hybridizing the promotion system, the binding/release lad protein (inhibitor) is the mechanism of modulation of the promotion system, but it allows for tunable expression levels by varying the concentration of the induction agent (normally IPTG). This lad gene and its promoter are included on the plasmid in order to mitigate any basal level of gene expression thus enhancing the degree of expression control resulting from the tac promoter.

This pGEX plasmid normally contains a glutathione S-transferase tag (GST) which enables for protein purification or immunochemical applications. However, given the purpose of the present disclosure, the start codon (ATG) for the GST tag was removed from the pGEX-6P-1 plasmid in order to decrease the size of the overall protein of interest to ensure adequate overexpression. This plasmid also contains an HRV3C cleavage site for removal of the tag post purification.

This plasmid is maintained in vivo by the pBR322 origin of replication which is a high copy origin of replication. Unlike the T7 promotion system, the level of protein accumulated using the tac promotion system with a high copy plasmid is not toxic due to the use of the native RNA polymerase for mRNA production. This pGEX plasmid contains an ampicillin resistance cassette (AmpR) under the control of its own promoter.

Enzyme Immobilization on surface of Gram Positive Bacterial Derivatives

Enzymes are immobilized to the surface of the minicell by means of protein mediated membrane localization mechanisms including but not limited to the following linking proteins and mechanisms: Sortase linking mechanism. Sortase is one of autotransporters for enzyme immobilization that specifically works in gram positive bacteria cells like *Bacillus Subtilis*. This sortase is induced with D (+) xylose. Sortase is a transpeptidase that attaches surface proteins to the cell wall; it cleaves between the Gly and Thr of the LPXTG motif and catalyzes the formation of an amide bond between the carboxyl-group of threonine and the amino-group of the cell-wall peptidoglycan. In some embodiments, the LPXTG motif can be inserted into the end of the C-terminus of the enzymatically active polypeptide of interest to express on the surface of gram positive bacterial cell. The Sortase can recognize this motif and covalently bind the enzymatically active polypeptide to the surface of the gram positive bacterial cell.

Likewise, minicells can be engineered from Extremophiles such that they retain the resilient physical and chemical properties of the parent species. For instance minicells from thermophiles would retain the resistance to high temperatures. Fluorescent protein fusions, ATP synthase mediated protein localization, Succinate dehydrogenase mediated protein localization. The focalization of membrane proteins and linking mechanisms in Gram-Positive Bacteria is reported by Mitra S D et al 2016, Trends in Microbiology, 24 (8):611-621, which is herein incorporated by reference in its entirety.

Enzyme Immobilization on the Surface of Yeast Derivatives

Enzymes can be immobilized to the surface of the yeast minicell via surface display proteins. Minicells can be produced from yeast strains, including but not limited to *Saccharomyes cervisiae, Pichia pastoris* and *Schizosaccharomyces pombe*.

The crystal structures of mammalian membrane proteins derived from recombinant sources were solved from protein expressed in yeast cells: the $Ca^{2+}$-ATPase (SERCA1a) from rabbit. This protein was overexpressed in *Saccharomyces cerevisiae*. Also, the rat voltage-dependent potassium ion channel, Kv1.2 was produced in *Pichia pastoris* to understand its structure. Since then, several other host cells have been used for eukaryotic membrane protein production including *Escherichia coli*, baculovirus-infected insect cells and mammalian cell-lines. Whilst all host systems have advantages and disadvantages, yeasts have remained a consistently-popular choice in the eukaryotic membrane protein field. As microbes, they are quick, easy and cheap to culture; as eukaryotes they are able to post-translationally process eukaryotic membrane proteins. Very recent crystal structures of recombinant transmembrane proteins produced in yeast include those of human aquaporin 2, chicken bestrophin-1, the human TRAAK channel, human leukotriene $C_4$ synthase, an algal P-glycoprotein homologue and mouse P-glycoprotein using *P. pastoris*-derived samples; the structures of the *Arabidopsis thaliana* NRT1.1 nitrate transporter, a fungal plant pathogen TMEM16 lipid scramblase and the yeast mitochondrial ADP/ATP carrier were solved using recombinant protein produced in *S. cerevisiae*. Due to its features as an eukaryotic cells, yeast cells can be used for the purpose of enzyme-immobilized minicell production.

The yeast membrane differs in composition from that of mammalian membranes. This is relevant to subsequent structural and functional studies of recombinant membrane proteins produced in yeast because lipids have a particularly important role in the normal function of membrane proteins by contributing to membrane fluidity and may directly interact with membrane proteins.

In an attempt to "humanize" the yeast membrane, yeast strains have been developed that synthesize cholesterol rather than the native yeast sterol, ergosterol. This was achieved by replacing the ERGS and ERG6 genes of the ergosterol biosynthetic pathway with the mammalian genes DHRC24 and DHRC7 and, respectively. The gene products of DHRC7 and DHRC24 were identified as key enzymes that saturate sterol intermediates at positions C7 and C24 in cholesterol (but not ergosterol) synthesis. Erg5p introduces a double bond at position C22 and Erg6p adds a methyl group at position C24 in the ergosterol biosynthetic pathway and therefore competes with the gene product of DHRC24 for its substrate.

In addition to the open reading frame (ORF) of the gene of interest, a typical expression plasmid usually incorporate a number of other sequences in its expression cassette. The *S. cerevisiae* α-mating factor signal sequence is a common addition to commercial expression plasmids because it is believed to correctly-target recombinant membrane proteins to the yeast membrane. For example, its presence had a positive impact on the yield of the mouse $5$-$HT_{5A}$ serotonin receptor but dramatically reduced expression of the histamine Hi receptor. Alternative signal sequences have been used (albeit much less frequently) such as the STE2 leader sequence of the fungal GPCR, Ste2p. The known signal sequences in yeast can be another advantage for trafficking a protein of interest fused to membrane-associated protein/domain and immobilizing the protein of interest on the surface of yeast cell.

Uses of Enzyme Immobilization Platform

When using enzyme-immobilized minicells can be used as a platform for improving enzyme activity and stability, when harsh conditions are required for desired enzymatic reactions than normal conditions, and/or when high cycles with prolonged reaction time are required from the enzyme.

In some embodiments, the minicell-based enzyme immobilization platform is used to purify enzymes that are not easily purified. For example, if an enzyme of interest is difficult to be extracted and purified from the lysed cells, the enzyme can be immobilized to the minicell and the minicell can be purified, instead of the enzyme.

In other embodiments, the minicell-based enzyme immobilization platform can be used as an immobilization chassis. Minicells purified from the parental cells can be used for post fermentation incubation with any enzyme of choice. For the post fermentation incubation, two independent fermentations are required; i) the minicell fermentation and 2) the enzyme fermentation. After the minicell and the enzyme are isolated, respectively, the minicells can be incubated with the enzyme that is either purified or non-purified so that the enzyme may bind to the surface of the minicell. In one process, the minicells is fermented to have surface-expressing moiety X. In the other process, the enzyme is fermented to have a binding moiety complementary to moiety X. After separating minicells that express moiety X on the surface, they can be incubated with an enzyme solution, where the enzyme has a complementary moiety that recognizes and binds to moiety X. From this post fermentation incubation, the enzyme of choice can be captured by the minicells and surface displayed.

In other embodiments, the present disclosure teaches co-localization of surface immobilized enzymes that described herein. More than one enzyme are expressed on the anucleated cell, and work symbiotically for an intended outcome. One enzyme can bind to a substrate for its own enzymatic activity while another enzyme function with another substrate for its own enzymatic activity. This can be exemplified by how a cellulosome would work, when three cellulases work together synergistically to break down cellulose. For example, lipase can be used in conjunction with protease in biological detergents in order to break down and digest the substances in stains into smaller and more water soluble substances when both lipase and protease are surface-expressed and immobilized to minicells.

In some embodiments, the anucleated cell comprises at least two expressed self-assembled enzymes immobilized to the surface of said cell. In other embodiments, the at least two expressed self-assembled enzymes are co-localized to a desired locus, wherein each of the expressed self-assembled enzymes have its enzymatic activity at the desired locus. In some embodiments, the expressed self-assembled enzymes are lipase and protease. In other embodiments, the expressed self-assembled enzymes are glucose isomerase and protease. In further embodiments, the at least two expressed self-assembled enzymes have a complimentary function. In some embodiments, the at least two expressed self-assembled enzymes act synergistically. In some embodiments, at least two expressed self-assembled enzymes each work to carry out a portion of an overall enzymatic reaction.

Enzyme-Immobilized Minicell Applications

The present disclosure is directed to uses and/or application of enzyme-immobilized minicells disclosed herein. There are various potential commercial applications for immobilized enzymes. The unique features of enzymes immobilized on minicells can make the production of industrial enzymes cheaper and more efficient, while making the enzymes more efficacious, easier to recycle, and increasing their active life cycles. Immobilizing enzymes can also open doors to various markets outside the enzyme industry. These applications can include preventing frost on crops and infrastructure (roads, airplanes, etc.), heavy metal and antibiotic remediation in bodies of water, the removal and degradation of chemical agents, nitrogen fixation, and antimicrobial medicines.

The present disclosure teaches compositions and methods for the immobilization of enzymes on the surface of achromosomal and/or anucleate cells, including but are not limited to anucleate cells derived from eubacteria, archaebacteria, and yeast, in applications such as agriculture, animal feed, food, beverages, industrial enzymes, textiles, pulp and paper, biofuels, fermentation, bioremediation, bioenergy, electronics, defense, bioenergy, household care, pharmaceuticals, and others uses.

In some embodiments, the development of enzyme-immobilized minicells allowed the introduction of enzymes into true industrial products and processes, for example, within the detergent (including laundry and dish wash) industries, starch and fuel industries, food including dairy industries, baking industries, animal feed industries, beverage industries, textile industries, pulp and paper industries, fats and oils industries, organic synthesis industries, leather industries, and/or personal care industries. In some embodiments, enzymes expressed on the surface of minicells disclosed herein can have applications in various industrial segments as illustrated in Table 1. In some embodiments, the present disclosure teaches production, uses, and/or application of lipase-immobilized minicells. In some embodiments, the present disclosure teaches production, uses, and/or application of glucose isomerase-immobilized minicells.

TABLE 1

Applications of exemplary enzymes in various industrial segments

| Industry | Enzyme class | Application |
| --- | --- | --- |
| Detergent (laundry and dish wash) | Protease | Protein stain removal |
| | Amylase | Starch stain removal |
| | Lipase | Lipid stain removal |
| | Cellulase | Cleaning, color clarification, anti-redeposition (cotton) |
| | Mannanase | Mannanan stain removal (reappearing stains) |
| Starch and fuel | Amylase | Starch liquefaction and saccharification |
| | Amyloglucosidase | Saccharification |
| | Pullulanase | Saccharification |
| | Glucose isomerase | Glucose to fructose conversion |
| | Cyclodextrin-glycosyltransferase | Cyclodextrin production |
| | Xylanase | Viscosity reduction (fuel and starch) |
| | Protease | Protease (yeast nutrition-fuel) |
| Food (including dairy) | Protease | Milk clotting, infant formulas (low allergenic), flavor |
| | Lipase | Cheese flavor |
| | Lactase | Lactose removal (milk) |
| | Pectin methyl esterase | Firming fruit-based products |
| | Pectinase | Fruit-based products |
| | Transglutaminase | Modify visco-elastic properties |
| Baking | Amylase | Bread softness and volume, flour adjustment |
| | Xylanase | Dough conditioning |
| | Lipase | Dough stability and conditioning (in situ emulsifier) |
| | Phospholipase | Dough stability and conditioning (in situ emulsifier) |

TABLE 1-continued

Applications of exemplary enzymes in various industrial segments

| Industry | Enzyme class | Application |
|---|---|---|
| | Glucose oxidase | Dough strengthening |
| | Lipoxygenase | Dough strengthening, bread whitening |
| | Protease | Biscuits, cookies |
| | Transglutaminase | Laminated dough strengths |
| Animal feed | Phytase | Phytate digestibility-phosphorus release |
| | Xylanase | Digestibility |
| | beta-Glucanase | Digestibility |
| Beverage | Pectinase | De-pectinization, mashing |
| | Amylase | Juice treatment, low calorie beer |
| | Beta-Glucanase | Mashing |
| | Acetolactate decarboxylase | Maturation (beer) |
| | Laccase | Clarification (juice), flavor (beer), cork stopper treatment |
| Textile | Cellulase | Denim finishing, cotton softening |
| | Amylase | De-sizing |
| | Pectate lyase | Scouring |
| | Catalase | Bleach termination |
| | Laccase | Bleaching |
| | Peroxidase | Excess dye removal |
| Pulp and paper | Lipase | Pitch control, contaminant control |
| | Protease | Biofilm removal |
| | Amylase | Starch-coating, de-inking, drainage improvement |
| | Xylanase | Bleach boosting |
| | Cellulase | De-inking, drainage improvement, fiber modification |
| Fats and oils | Lipase | Transesterification |
| | Phospholipase | De-gumming, lyso-lecithin production |
| Organic synthesis | Lipase | Resolution of chiral alcohols and amides |
| | Acylase | Synthesis of semisynthetic penicillin |
| | Nitrilase | Synthesis of enantiopure carboxylic acids |
| Leather | Protease | Unhearing, bating |
| | Lipase | De-pickling |
| Personal care | Amyloglucosidase | Antimicrobial (combined with glucose oxidase) |
| | Glucose oxidase | Bleaching, antimicrobial |
| | Peroxidase | Antimicrobial |

In some embodiments, the present disclosure teaches use of immobilized lipase. Lipases are one of the most commonly used classes of enzymes in biocatalysis. Lipases catalyze the hydrolysis of triacylglycerols to diacylglycerol, monoacylglycerol, glycerol and free fatty acids. The reaction reverses under anhydrous conditions and the enzyme is able to synthesize new molecules by esterification, alcoholysis and transesterification. All reactions can be performed with high regio- and enantioselectivity under mild reaction conditions. Lipases have been used on a variety of substrates and show very broad substrate specificity due to the ubiquity in nature and the heterogeneity of lipases from different sources. For example, Candida antarctica can be a source of industrially important lipases. Immobilized Candida antarctica lipase can be used to catalyze the regioselective acylation of flavonoids or the direct acetylation with phenolic acids. Lipase can from Candida antarctica (Lipase B). In the detergent industry, immobilized lipases are used for fatty acid and oily stain removal, In the fuel industry, immobilized lipases are used for biodiesel production. Biodiesel is a fatty acid alkyl ester that can be derived from any vegetable oil or animal fat via the process of transesterification that can be catalyzed by lipase. In the food industry, immobilized lipases are used in dairy and baking. In the chemical industry, immobilized lipases are used for resolution of chiral alcohols and amines.

Production of high-fructose corn syrup (HFCS) is the biggest industrial use of immobilized enzymes. The enzyme glucose isomerase is immobilized, and this enzyme converts the glucose in the corn syrup to fructose, which makes it sweeter. HFCS is used as a sweetener in place of sucrose, especially in the USA where sugar prices are high. It is not widely used in Europe, because sucrose is cheaper there and there are concerns about the health risks of HFCS.

Immobilized lactase can be used to produce lactose-free milk: normal milk is poured down a column containing the immobilized lactase enzymes, which break down the lactose. After the milk has passed through this platform, it will only contain the products of the reaction (glucose and galactose), so lactose-intolerant people (and cats) can drink it.

Immobilized pectinase can be used to break down these pectins, loosening the connections between cells. This increases the amount of juice obtained from the fruit, makes the juice runnier and gets rid of the cloudiness that pectins can cause.

Immobilized Protease (also known as a proteolytic enzyme, peptidase or proteinase) can function mainly to help us digest different kinds of proteins. Protease breaks down the bonds by a process known as hydrolysis and convert proteins into smaller chains called peptides or even smaller units called amino acids.

Commercial Applications of Enzymes

Enzymes now have a large number of commercial applications. They carry many advantages, with one important one being that enzymes are specific to only one catalytic reaction and so they therefore do not produce a range of unwanted by-products.

Enzymes are widely used in the textile industry. They are used for improving production methods and for fabric finishing. In this industry, a very common application is the use of the enzyme amylase in order to remove starch size. The threads (the longitudinal threads) of the fabrics are often coated in starch. This prevents them from breaker when weaving takes place. In the textile industry, a process called scouring is used (the cleaning of fabrics by removing any impurities such as waxes, pectins and any mineral salts from cellulose fibers). Pectin can act as a glue between the core of the fibers and the waxes, but this can be destroyed by an alkaline called pectinase. Cellulases have quite recently become the tool for fabric finishing. This began in denim finishing where it was discovered that cellulases could achieve the fashionable stonewashed look traditionally achieved through the abrasive action of pumice stones. Cellulases are also quite often used in order to prevent pilling and improve the smoothness and color brightness of cotton fabrics. In addition, a softer handle is obtained. Catalases can also be used for degrading residual hydrogen peroxide after the bleaching of cotton. Hydrogen peroxide has to be removed before dyeing. Protease enzymes are used for wool treatment and the degumming of raw silk. Examples of enzymes that may be used in the textile industry: Cellulase—for stonewashing denim, polishing of cotton; Catalase—removing hydrogen peroxide; Pectinase—for bioscouring (a way to scour fabrics); Alpha amylase—for desizing at low temperatures.

The food and drink industry has to be one of the largest markets for enzymes. In the baking industry, enzymes are added to the dough when baking bread to ensure that the bread is high in quality and has a better volume (that there is more of it). Enzymes also have the ability to preserve bread; keeping it fresh for a longer period of time and therefore increasing its shelf life. In the dairy industry, enzymes are used in cheese making to help bring about the coagulation of milk. In these applications, enzymes from microbial and animal sources are used. Industrial enzymes are added to control the brewing process in alcohol making and the brewing industry. This also helps to produce consistent and high quality beer. When making wines and juices, enzymes are used to break down cell walls of plants when extracting plant material. This use of enzymes would give higher juice yields and also improves the color and smell of the extracted substances. Examples of enzymes that may be used in the baking industry: Fungal alpha amylase—for dough improvement in the bread making industry; Glucoamylase—used in fermentation; Papain enzymes—for fermentation in the brewing industry; Beta glucanse—for filtration; Protease—used in biscuit production.

Enzymes are also used in the pulp and paper industry. Amylase is used for modification of starch coating and xylanases to reduce the consumption of bleach chemicals are known applications, but nowadays lipases for is used for pitch control, esterases is used for stickies removal and amylases and cellulases are used for improved deinking and cellulases for fiber modification have become an integral part of the chemical solutions used in the pulp and paper mills.' In the manufacturing of coated papers, a starch-based coating formulation is used in order to coat the surface of the paper. Compared with the uncoated paper, the coating provides a number of benefits, including; improved gloss, a smoother texture, and printing properties. Examples of enzymes that may be used in the pulp and paper industry: Cellulase—can be used for pulp deinking and pulp refining; Xylanase—for pulp bleaching; Alpha amylase—starch modification.

Enzymes are used in detergents and in personal care and hygiene. They are used in many household and industrial detergents. This industry, in addition to the food processing industry is currently one of the largest application areas for enzymes. This is because the enzymes are very effective at relatively low temperatures and pH values. They contribute to a: better overall cleaning performance; they are biodegradable so they do not really effect the environment that much; they reduce water consumption through more effective release of soil.

Bioethanol is a type of biofuel. It may be used when adding fuel to a vehicle. This biofuel is able to be produced from starchy plant materials with the use of enzymes that are capable of efficiently making this conversion. At the moment, corn is widely used as a source of starch, however increasing interest in bioethanol is raising concerns as corn prices rise and corn as a food supply is being threatened. Other plants including wheat, bamboo, or other grasses are possible candidate sources of starch for bioethanol production. Bioethanol production (the growing of crops, shipping and manufacturing) still requires a large input of non-renewable resources. Technological research and manipulation of enzymes to make the process more efficient, thus requiring less plant material or consuming less fossil fuels, are in the works, to improve on this area of biotechnology.

Protease enzyme is used in the manufacturing of baby foods to predigest proteins.

Lipase can be used in conjunction with protease in biological detergents in order to break down and digest the substances in stains into smaller and more water soluble substances.

Carbohydrase can be used to convert starch syrup into sugar syrup. This is done during the manufacturing of sports drinks; sugar syrup is much more valuable than starch syrup, which is relatively cheap. Isomerase can be used in slimming foods/weight loss products. It converts the glucose syrup into fructose syrup (fructose is much sweeter than glucose so it can be used in much smaller amounts, thus saving money during the production processes).

Zymase can be used in alcohol manufacturing. Fermentation is another method used for manufacturing alcohol. During the fermentation process, carbohydrates are converted into ethanol (with carbon dioxide as a byproduct). The carbohydrate is usually a sugar or a starch. The ethanol that is produced during the fermentation process may have an alcohol concentration of up to 14%. The fermentation process is carried out at quite low temperatures using used. It is the zymase enzymes that are present in the yeast that actually catalyse the fermentation reactions. The reaction takes places at temperatures between 25° C. and 37° C. This is because zymase would begin to denature at temperatures above 37° C. and it would therefore begin to lose its function and efficiency, whereas at temperature bellow 25° C. the reaction would be too slow. Zymase also stops functioning at an alcohol concentration of above 14%.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will occur to those skilled in the art.

Example 1. Production of Protease-Deficient Minicells

In order to create protease-deficient minicells, the genes (minC and minD) that guide replication in a protease-deficient BL21 (DE3) *E. coli* strain were knocked out. Also, BL21-AI strain was used for producing protease-deficient minicells. BL21-AI strain is the same as the BL21 (DE3) strain, except for one major difference. While BL21-AI uses an arabinose promoter that controls the production of T7 RNA polymerase, a lac promoter controls the production of T7 RNA polymerase in the BL21(DE3) strain. When comparing to the wild type minicell-producing p678-54 strain, BL21 and BL21-AI are deficient in ion and ompT proteases, which make them protease-deficient bacterial strains.

Figure 17A:
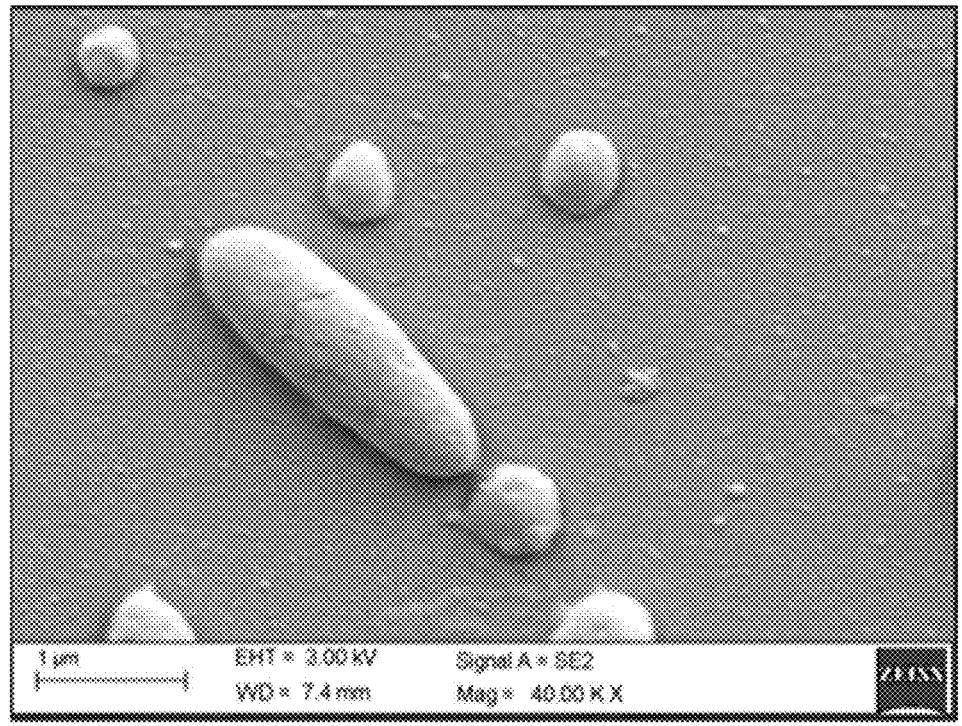
FIG. 17A-B shows scanning electron micrograph images of minicell formation in *E. coli* (FIG. 17A) and of protease-deficient minicells in which minC gene is knocked out and/or removed (FIG. 17B). The size of exemplary minicells is less than one micrometer as shown in FIG. 17B.
Figure 17B:
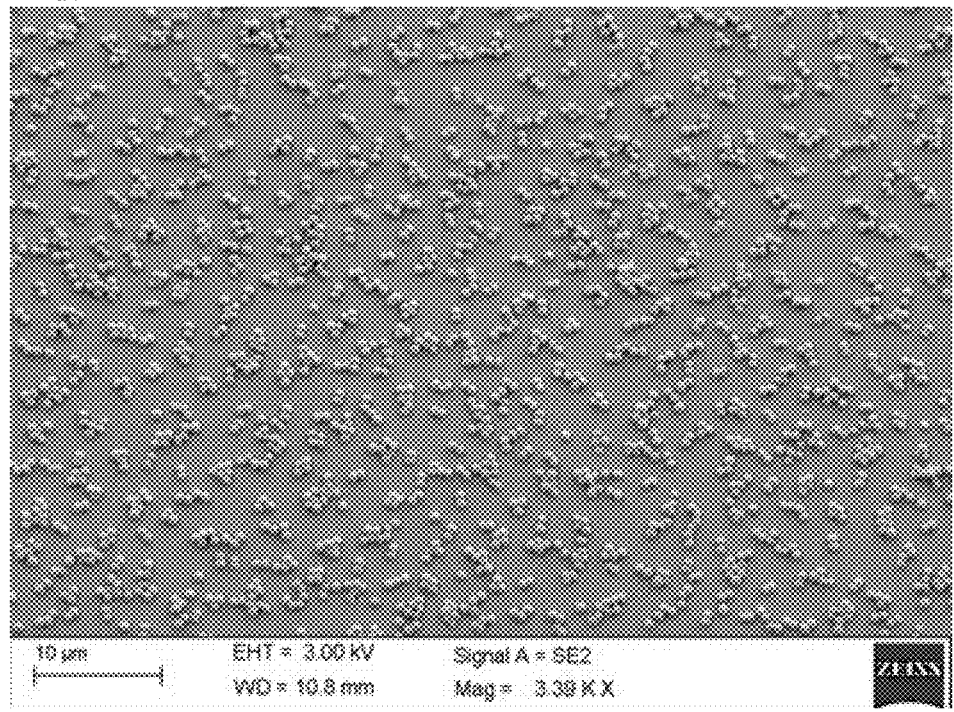

The success of these knockouts was determined by PCR amplification (Eppendorf Mastercycler 5333) and morphological characterization using the Laxco LMC4000 microscope (40× Objective, brightfield and fluorescent LED light sources) in conjunction with the Zeiss Sigma VP HD field SEM (UVA Advanced Microscopy Core). Based on the results shown in FIGS. 17A and 17B, it was determined that the minC, minD, and/or minC/D knockouts produced the minicells closest in morphological characteristics to the original wild type P678-54 strain producing minicells (Adler et al., 1967, *Proc. Natl. Acad. Sci. USA* 57:321-326; Inselburg J, 1970 *J. Bacteriol.* 102(3):642-647; Frazer 1975, *Curr. Topics Microbiol. Immunol.* 69:1-10). As an example, FIG. 17B shows the minicells in which minC gene is deleted.

To further investigate which gene knockout was responsible for producing minicells closest to the minicell-producing wild type p678-54 strains, the Lambda Red homologous recombination system was used. This lambda red recombinant-engineering system relies on three different proteins (Beta, Gam, and Exo) required for facilitating insertion of double stranded linear DNA into the genome guided by homology to the already existing genome, as exemplified by Murphy K C, 2011 Methods Mol. Biol. 765:27-42. All of these proteins are expressed via a plasmid with the pSC101 origin of replication containing the RepA protein which only allows for plasmid replication at 30° C. Thus, once the genetic manipulation is complete, the plasmid is removed from the cell line by growth at 37° C.

The genes that were inserted into the genome were designed to have 50 base pairs of homology to both the 5' and 3' ends of a targeted gene to be knocked out. The homology corresponded to 50 base pairs at the 5' (SEQ ID NO:1) and 3' end (SEQ ID NO:2) of minC in order to knockout minC, at the 5' (SEQ ID NO:3) and 3' end (SEQ ID NO:4) of minD in order to knockout minD, or 5' end (SEQ ID NO:3) of minD and 3' end (SEQ ID NO:2) of minC in order to knockout minCD, respectively. A chloramphenicol cassette with its promoter flanked by two hairpin loops was inserted in place of either minC, minD, or minC/D. The hairpin loops were included in the insert in order to not interfere with the regulation of other genes in the same area of the genome, due to their ability to stop transcription.

Figure 2:
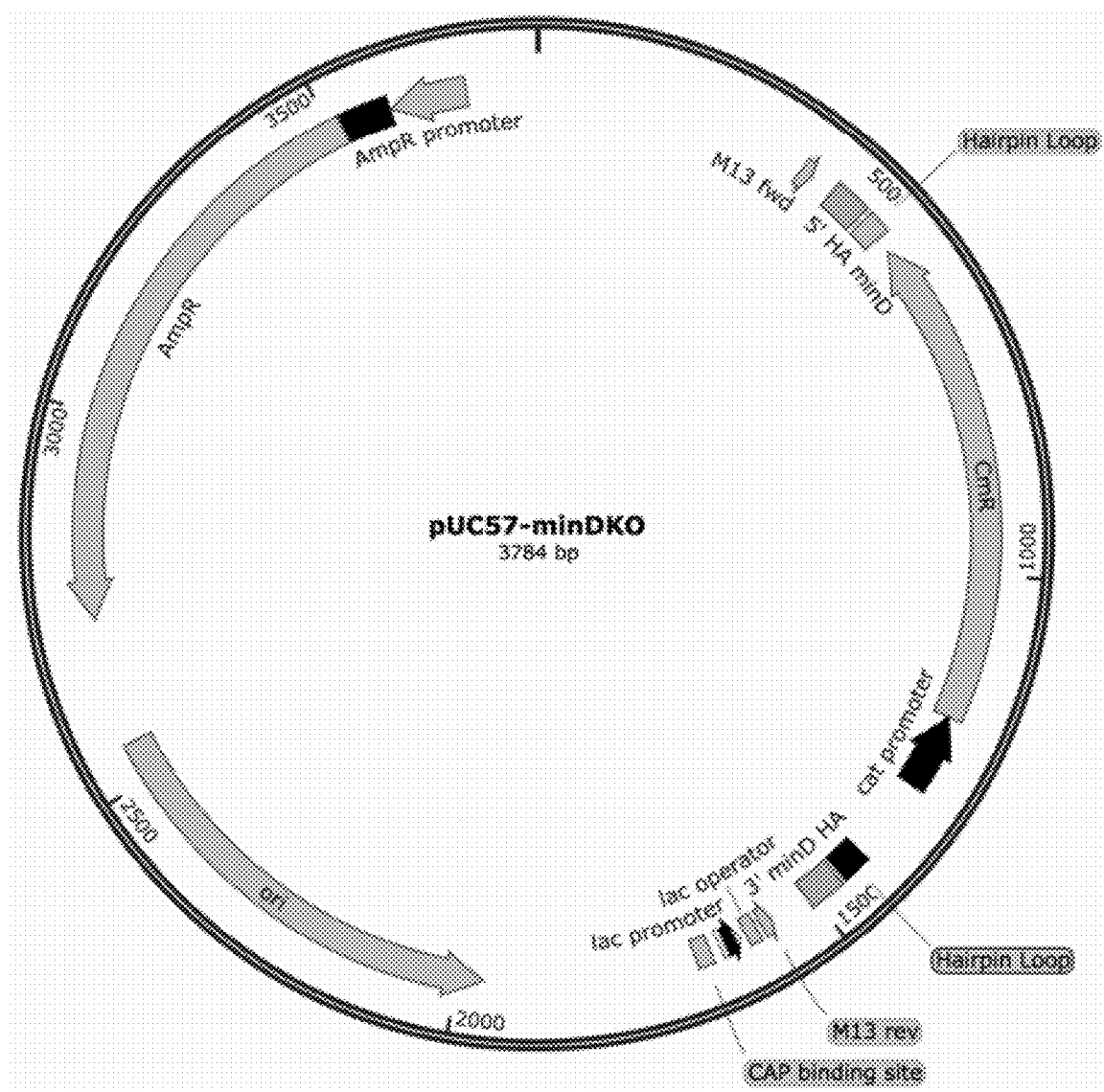
FIG. 2 illustrates an exemplary bacterial minicell-inducing vector for a minD knockout to produce protease-deficient minicells. The pUC57 vector was inserted with a recombinant DNA insert comprising 5' end nucleotide sequence of minD gene, a chloramphenicol resistant gene (CmR) with cat promoter, and 3' end nucleotide sequence of minD gene. The hairpin loops flanked by 5' and 3' ends of minD gene are inserted into the insert to stop transcriptional regulation of other neighboring genes in the genome where the insert is integrated.
Figure 3:
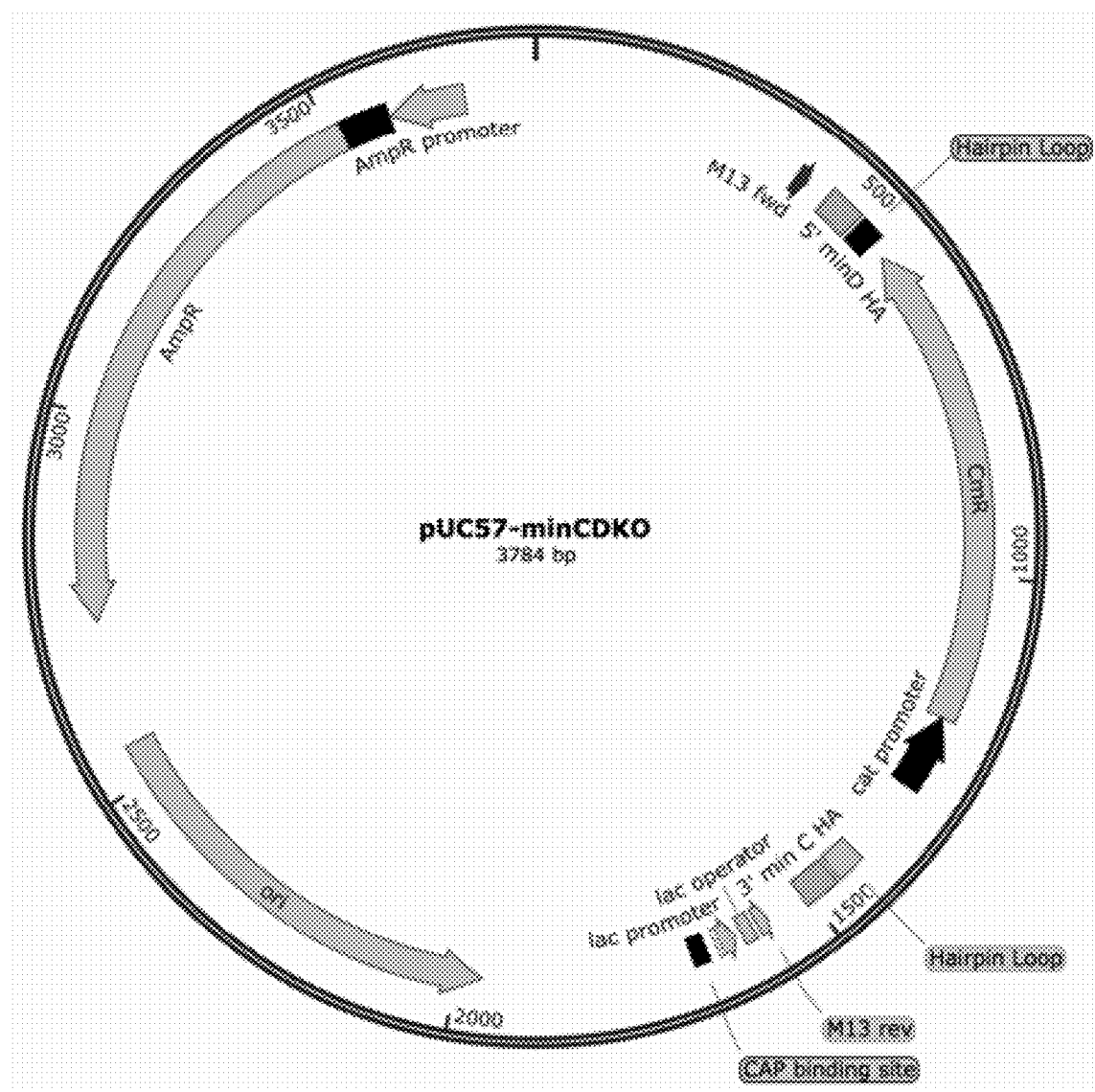
FIG. 3 illustrates an exemplary bacterial minicell-inducing vector for a minC/minD knockout to produce protease-deficient minicells. The pUC57 vector was inserted with a recombinant DNA insert comprising 5' end nucleotide sequence of minD gene, a chloramphenicol resistant gene (CmR) with cat promoter, and 3' end nucleotide sequence of minC gene. The hairpin loops, flanked by 5' end of minD gene and 3' ends of minC gene, are inserted into the insert to stop transcriptional regulation of other neighboring genes in the genome where the insert is integrated.

These genes were inserted into a pUC57 backbone as shown in FIGS. 1-3. This plasmid was used as a template to then amplify out the gene of interest to verify that the sequence information is accurate before integrate them into the host genome. All amplifications were run across 6 different annealing temperatures with the following components and conditions as shown in Tables 3 and 4. Table 2 displays that two different sets of primers were designed per each gene knockout amplification. All primers were synthesized by the service provider, Integrated DNA Technologies (IDT).

TABLE 2

Information on primer sets for testing min gene knockout; SEQ ID Nos: 25-36, in order of appearance.

| Name | Sequence | Amplification Designation |
|---|---|---|
| F2 minCKO | AACAACAATAATGCGTGCCAT | A |
| R2 minCKO | GCGCTGGCGATGATTAATAG | A |
| F9 minCKO | AGTAACAACAATAATGCGTGCC | B |
| R9 minCKO | CGCGCTGGCGATGATT | B |
| F7 minDKO | TTCCGCGAGAGAAAGAAATCG | C |
| R7 minDKO | GACCGTTCAACCGTTAAATTGAT | C |
| F10 minDKO | CTGTGTTTTCTTCCGCGAG | D |
| R10 minDKO | TCAACCGTTAAATTGATCCCTTTTT | D |
| F6 minCDKO | TCCGCGAGAGAAAGAAATCG | E |
| R6 minCDKO | CGCGCTGGCGATGATTA | E |
| F9 minCDKO | CTGTGTTTTCTTCCGCGAG | F |
| R9 minCDKO | CGCGCTGGCGATGATT | F |

TABLE 3

Components for PCR reaction

| Contents Component | Volume (uL) | Final Concentration |
|---|---|---|
| Nuclease Free Water | 17.5 | N/A |
| Template DNA (5 ng/uL) | 1 | 5 ng |
| 10 uM Forward Primer | 2.5 | 500 nM |
| 10 uM Reverse Primer | 2.5 | 500 nM |
| DMSO | 1.5 | 3% |
| Phusion HF Master Mix | 25 | 1X |

TABLE 4

Conditions for PCR reaction

| Conditions Steps | 55 Cycles Temperature (° C.) | Time (seconds) |
|---|---|---|
| Initial Denaturation | 98 | 30 |
| Cycle Denaturation | 98 | 10 |
| Cycle Annealing | 64, 4° Gradient | 30 |
| Cycle Extension | 72 | 30 |
| Final Extension | 72 | 600 |
| Hold | 4 | N/A |

Six series amplifications from A to F (Table 2) were run with each of the following annealing temperatures shown in Table 5. The number following the letter correspond to the position on the PCR plate with a gap between each well because of the slight increase in temperature from well to well. (example: well number A2 was the A series amplification run with Tm 1; A4—A series amplification run with Tm 2; A6—A series amplification run with Tm 3; A8—A series amplification run with Tm 4; A10—A series amplification run with Tm 5; A12—A series amplification run with Tm 6; and A1, A3, A5, A7, A9, and A11 are empty wells)

TABLE 5

Information on annealing temperatures for PCR reaction

| Annealing Temperatures Tm Number | Tm ° C. |
|---|---|
| 1 | 59.8 |
| 2 | 60.8 |
| 3 | 62.8 |
| 4 | 65.1 |
| 5 | 66.9 |
| 6 | 67.6 |

All amplifications were cleaned up using the Monarch® PCR and DNA Cleanup kit according to their standard protocol. All DNA was eluted with enough elution buffer in order to provide for adequate DNA quantification and quality determination. After cleanup, all amplifications were run on a gel against the 1 kB plus ladder from Invitrogen® to determine success of the PCR reaction. All amplifications run at all annealing temperatures were successful by visualization of a single band at about 1080 base pairs. All DNA visualization was accomplished using a 1% Agarose (w/v) gel prepared with 1×TAE and SYBR safe stain in conjunction with the Invitrogen Safe Imager 2.0.

These bands were extracted from the gel using the disposable scalpels and the Monarch® DNA gel extraction kit according to their standard protocol. After extraction the DNA was quantified, its quality was determined before sending off for sequencing from Eton Biosciences. Primers used for amplification (Table 2) were used for sequencing determination. All sequences came back with ~99% identity, thus they were deemed suitable for insertion into the genome.

The lambda red plasmid was transformed into a chemically competent protease-deficient E. coli strain via the heat shock method (see examples; Rahimzadeh et al. 2016, Mol. Boil. Res. Commun. 5(4):257-261). It was plated on a selective LB Agar plate, and re-streaked the following day in order to be sure that a single colony was isolated for lambda red recombination.

In order to introduce the PCR generated DNA into the genome, the TransformAid Bacterial Transformation Kit from Thermon Scientific™ was used with a modified protocol.

A single colony was grown in C-medium at 30° C. overnight. Next day, a 1:100 dilution of the cultured cells were inoculated into fresh C-medium. This was grown at 30° C. until it reached an optical density of about 0.2 (measured at 600 nm). This culture was induced with 1 mM IPTG for 20 minutes to allow for sufficient production and accumulation of the three proteins vital for this procedure (Beta, Gam, and Exo). After induction for every 1.5 mL of inoculated culture volume, the cells were pelleted for 1 minute at 10,000 rcf and resuspended in 300 uL of cold T-solution and incubated for 5 minutes. The cells were then pelleted again and resuspended in 120 uL of cold T-solution for 5 minutes. After the final incubation step, 50 uL of cells and 50 ng of PCR amplification were combined for each transformation and incubated on ice for 5 minutes. From here, 250 uL of SOC medium was added to each transformation and let grow for 90 minutes at 37° C. After the 90 minute outgrowth, all 300 uL of transformation was plated on Chloramphenicol LB Agar plates (10 ug/mL) and let the transformed cells grow overnight.

This protocol resulted in the successful transformation of almost all of the genes attempted (3 from each series). The morphology of the transformed cells was examined from each successful transformant on the Laxco LMC4000 (40× objective, brightfield) and it was determined that the minC knockouts (A and B) produced the most morphologically similar minicells to the control p678-54 strain from which minicells were discovered. These BL21 and BL21-AI strains were two strains that were used for protease-deficient minicells and analyzed genetically.

In order to confirm presence of the knockouts in the genome, primers were designed to amplify out specific parts of the knockouts of minC and/or minD. The 5' and 3' end of the insert was confirmed by having the primers span regions both inside and outside of the insert. The primers in Table 6 were used according to the following conditions in Tables 7-9.

TABLE 6

Information on primer sets for testing min gene knockout; SEQ ID Nos: 37-44, in order of appearance.

| Name | Annealing Sequence | Designation |
|---|---|---|
| 3'minCKO_1 | GGCCGGATAAAACTTGTGCT | 1 |
| 3'minCKO_2 | AGTCTTCGGAACATCATCGC | 2 |
| 5'minCKO_1 | CCCTTTGCCCGAAGTAACAA | 3 |
| 5'minCKO_2 | ACGGTGAAAACCTGGCCTAT | 4 |
| minC_check_4_1 | TCAATTTAACGGTTGAACGGTCA | 5 |
| minC_check_4_2 | ATGTCAAACACGCCAATCGA | 6 |
| minD_check_2_1 | TTATCCTCCGAACAAGCGTTTGA | 7 |
| minD_check_2_2 | ATGGCACGCATTATTGTTGTTAC | 8 |

TABLE 7

Components for PCR reaction

| Component | 50 uL Reaction | Final Concentration |
|---|---|---|
| 10 uM Forward Primer | 2.5 uL | 0.5 uM |
| 10 uM Reverse Primer | 2.5 uL | 0.5 uM |
| DMSO | 1.5 uL | 3% |
| 2X Phusion Master Mix | 25 uL | 1x |
| Genomic DNA | 1 uL | 2 ng/uL |
| Nuclease Free Water | 17.5 uL | N/A |

TABLE 8

Conditions for PCR reaction

| Conditions Steps | 55 Cycles Temperature (° C.) | Time (seconds) |
|---|---|---|
| Initial Denaturation | 98 | 30 |
| Cycle Denaturation | 98 | 10 |
| Cycle Annealing | 65, 5° Gradient | 30 |
| Cycle Extension | 72 | 30 |

TABLE 8-continued

Conditions for PCR reaction

| Conditions Steps | 55 Cycles Temperature (° C.) | Time (seconds) |
|---|---|---|
| Final Extension | 72 | 600 |
| Hold | 4 | N/A |

TABLE 9

Information on annealing temperatures for PCR reaction

| Annealing Temperatures Tm Number | Tm ° C. |
|---|---|
| 1 | 59.9 |
| 2 | 61.3 |
| 3 | 63.8 |
| 4 | 66.6 |
| 5 | 69.7 |
| 6 | 67.6 |

After PCR amplification, all products were cleaned up using either the Monarch® PCR and DNA Clean up Kit or the DNA Clean & Concentrator Kit™-5 with Zymo-Spin IC Columns. The purified PCR amplicants were then run in a DNA Agarose gel with the above conditions and visualized the same way. For both the A and B series, reactions using a pair of primers 1-2 and another pair of primers 3-4 produced primarily a single band at the appropriate size, respectively. Reaction with a set of primers 7-8 produced only a single band corresponding to the minD gene. Reaction using a set of primers 5-6 was run to check for presence of minC, and this reaction produced a stratification of bands indicating a nonspecific PCR product which is to be expected after knocking out minC. All of these reactions were also run on the wild type genome for comparison. Reactions using sets of primers 1-2 and 3-4 produced a stratification of bands which is to be expected from BL21 and/or BL21-AI strains with the insert of min C and/or D knock-out system, but not in the wild type because the recombinant insert was not present in the wild type genome. Reactions using sets of primers 5-6 and 7-8 produced a single band indicating a specific PCR product, respectively.

All bands indicating a specific PCR product were extracted from the gel using the Monarch® gel extraction kit and the DNA sequences were analyzed by Eton Biosciences. All DNA sequencing results showed almost identical (99%) sequence homology to the expected sequence with min C and/or D knocked out.

To isolation minicells from parental cells, the entire culture including parent cells and minicells is spun down at 2,000 rcf for 10 minutes to pellet the parental cells. The supernatant is then collected and spun down again at 10,000 rcf for 10 minutes to pellet the minicells. The supernatant is discarded and the pelleted minicells are resuspended in PBS or any other buffer based on their intended use.

TABLE 10

Listing of Sequences in Sequence File

| SEQ ID NO | Type | Description |
|---|---|---|
| 1 | DNA | minC 5' recombination site (5' Homologous Arm of minC) |
| 2 | DNA | minC 3' recombination site (3' Homologous Arm of minC) |
| 3 | DNA | minD 5' recombination site (5' Homologous Arm of minD) |
| 4 | DNA | minD 5' recombination site (3' Homologous Arm of minD) |
| 5 | DNA | AIDA-1 surface expression cassette |
| 6 | DNA | BrkAutoTransporter surface expression cassette |
| 7 | DNA | BrkAutoTransporter surface expression cassette fused with CBM-encoding nucleic acid |
| 8 | DNA | BrkAutoTransporter surface expression cassette fused with lipase-encoding nucleic acid |
| 9 | DNA | CBM (Carbohydrate Binding Module)-encoding nucleic acid |
| 10 | DNA | GFP-Nanobody sequence with CBM-encoding nucleic acid |
| 11 | DNA | GFP-Nanobody sequence with lipase-encoding nucleic acid |
| 12 | DNA | InaK surface expression cassette |
| 13 | DNA | InaK surface expression cassette with CBM-encoding nucleic acid |
| 14 | DNA | InaK surface expression cassette with lipase-encoding nucleic acid |
| 15 | DNA | The optimized Lipase-encoding nucleic acid (*Bacillus* sp. 42 thermostable organic solvent tolerant lipase gene) |
| 16 | DNA | pAIDA-1 vector |
| 17 | DNA | pAIDA-1 vector with CBM-encoding nucleic acid |
| 18 | DNA | pAIDA-1 vector with lipase-encodig nucleic acid |
| 19 | DNA | pET-9a vector |
| 20 | DNA | pGEX-6P-1 vector without ATG for GST tag |
| 21 | DNA | pGEX-6P-1 vector without ATG for GST tag, containing BrkAutoTransporter surface expression cassette fused with CBM-encoding nucleic acid |
| 22 | DNA | pGEX-6P-1 vector without ATG for GST tag, containing BrkAutoTransporter surface expression cassette fused with lipase-encoding nucleic acid |
| 23 | DNA | pGEX-6P-1 vector without ATG for GST tag, containing InaK surface expression cassette fused with CBM-encoding nucleic acid |
| 24 | DNA | pGEX-6P-1 vector without ATG for GST tag, containing InaK surface expression cassette fused with lipase-encoding nucleic acid |

TABLE 10-continued

Listing of Sequences in Sequence File

| SEQ ID NO | Type | Description |
|---|---|---|
| 25 | DNA | F2 minCKO primer |
| 26 | DNA | R2 minCKO primer |
| 27 | DNA | F9 minCKO primer |
| 28 | DNA | R9 minCKO primer |
| 29 | DNA | F7 minDKO primer |
| 30 | DNA | R7 minDKO primer |
| 31 | DNA | F10 minDKO primer |
| 32 | DNA | R10 minDKO primer |
| 33 | DNA | F6 minCDKO primer |
| 34 | DNA | R6 minCDKO primer |
| 35 | DNA | F9 minCDKO primer |
| 36 | DNA | R9 minCDKO primer |
| 37 | DNA | 3'minCKO_1 primer |
| 38 | DNA | 3'minCKO_2 primer |
| 38 | DNA | 5'minCKO_1 primer |
| 40 | DNA | 5'minCKO_2 primer |
| 41 | DNA | minC_check_4_1 primer |
| 42 | DNA | minC_check_4_2 primer |
| 43 | DNA | minD_check_2_1 primer |
| 44 | DNA | 3'minCKO_1 primer |

Example 2. Transformation of Lipase Expression Cassette into Minicells

The genetically modified minicell-producing bacterial strain was transformed with a linker protein fused lipase expression plasmid.

The lipase-encoding gene was inserted into the AIDA-1 surface expression cassette of the pAIDA-1 vector using KpnI and SacI restriction sites, which allows the lipase protein to be expressed and displayed by the fusion with the transmembrane autotransporter protein AIDA-1 (Adhesin Involved in Diffuse Adherence) as shown in FIG. 4B. This construction was conducted with primarily designed pAIDA-1 plasmid (from Addgene, Cambirdge, Mass.) in which the lipase-encoding gene was ligated into the passenger domain within the AIDA-I autotransporter using KpnI and SacI sites as illustrated in FIG. 4A. The tags existed on the pAIDA-1 plasmid prior were used for further analysis on lipase expression. After the ligation is completed, the 6× His tag and HRV3C site are located at N-terminus of the lipase-encoding gene and the Myc tag and TEV site are placed at C-terminus of the lipase-encoding gene. The 6× His tag, which is the 5' end of the surface-expressed fusion lipase protein was used for Cobalt immobilized metal affinity chromatography (IMAC) and for immunofluorescent staining with THE His Tag antibody [FITC] from Genscript. The pAIDA-1 vector has a chloramphenicol resistant gene so that the recombinant pAIDA-lipase expression vector can be transformed into p567-48 wild type strain, BL21 (DE3) strain, and BL21-AI strain. In order to induce minicell production from BL21 (DE3) strain and BL21-AI strain, the present disclosure uses a minC, minD, and/or minC/D knockout system by replacing the min locus with a chloramphenicol resistant gene. In this case, the new protease-deficient minicell-producing strains (e.g. minC, D, or C/D-depleted BL21 (DE3) strain and/or minC, D, or C/D-depleted BL21-AI strain) cannot be transformed with the recombinant pAIDA-1 lipase expression vector due to the presence of the same chloramphenicol resistant gene in both vector and the minicell-producing strains.

Figure 5A:
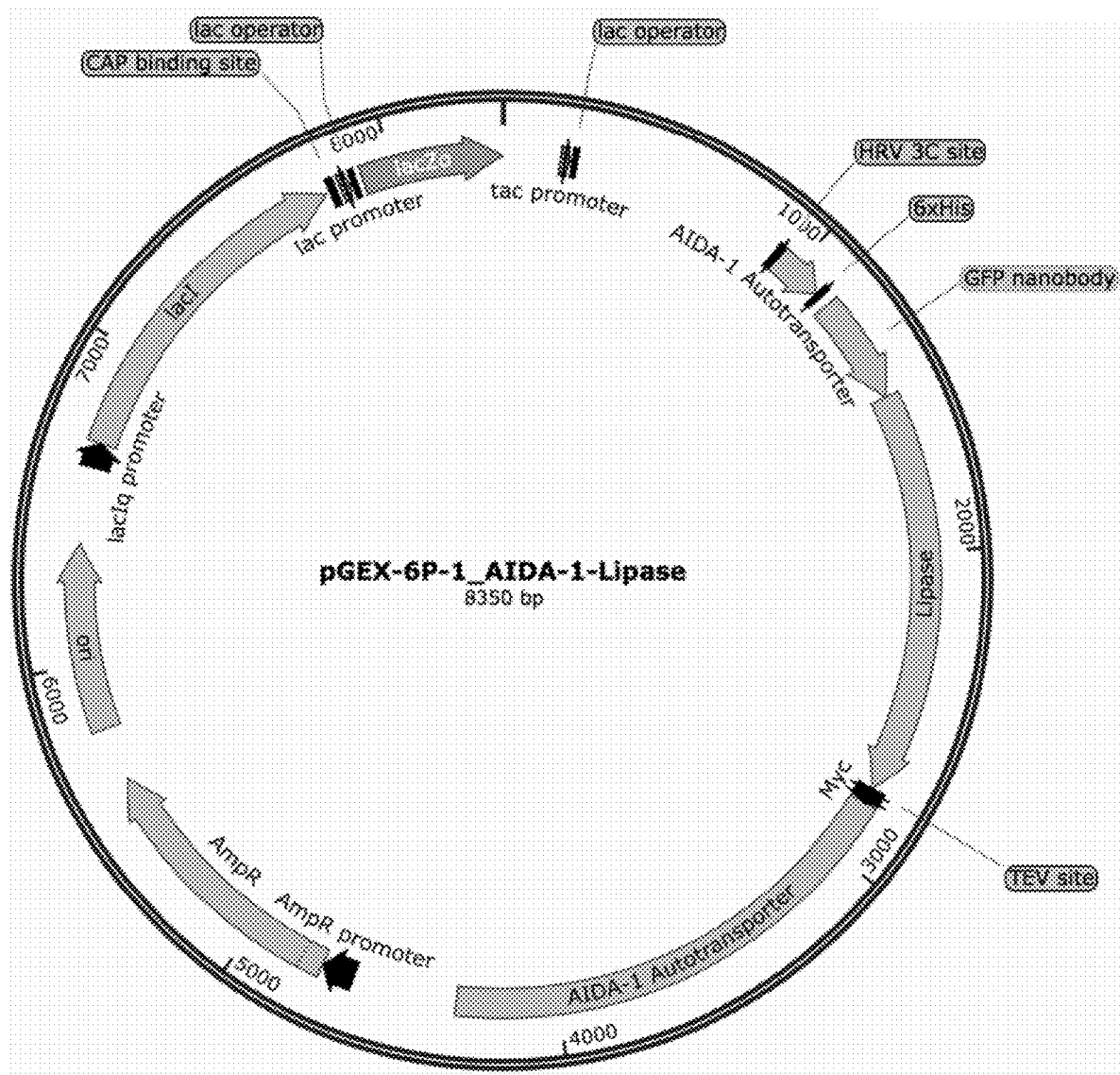
FIG. 5A illustrates an exemplary pGEX-6P-1 AIDA-1-Lipase vector with AIDA-1 surface expression system for display of a lipase protein flanked by 6×His, GFP nanobody and Myc tags on the surface of minicells.
Figure 5B:
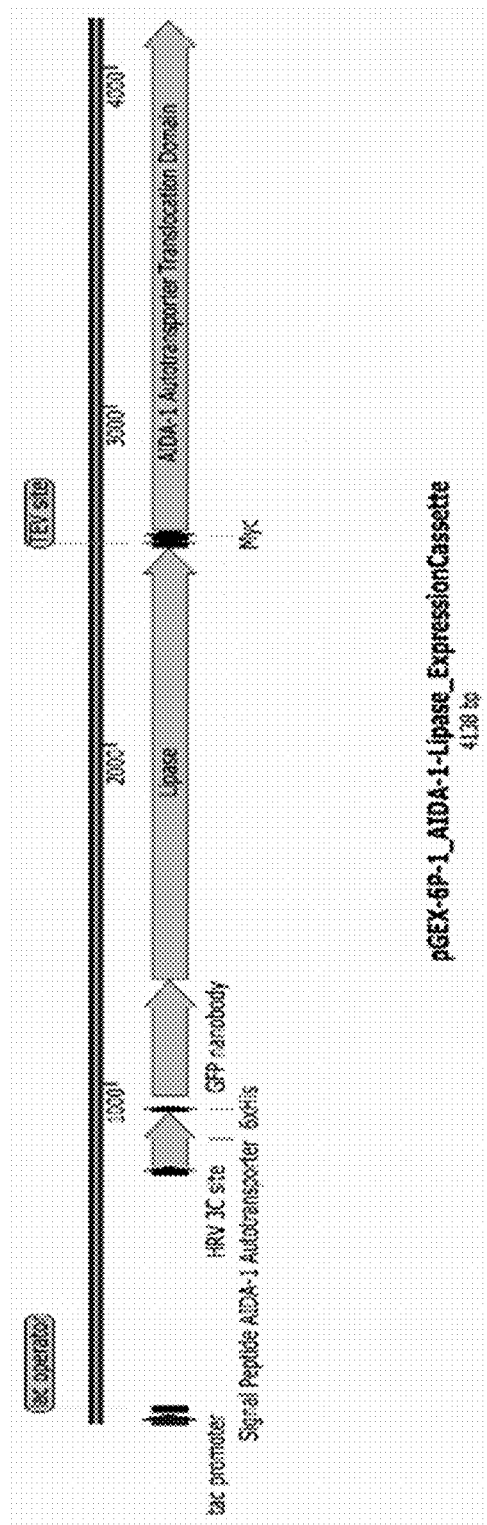
FIG. 5B illustrates an exemplary AIDA-1 lipase surface expression cassette, comprising nucleotide sequences encoding AIDA-1 Autotransporter signal peptide, GFP nanobody, lipase, and AIDA-1 autotransporter translocation domain with tags including 6×His Tag and Myc Tag as well as two protease cleavage sites including HRV3C and TEV.

In order to express the AIDA-1 lipase fusion protein, another recombinant AIDA-Lipase expression plasmid was constructed in the backbone of pGEX-6P-1 vector. The AIDA-1 lipase surface expression cassette was cut from the pAIDA-1 lipase expression vector and cloned into the pGEX-6P-1 vector as illustrated in FIG. 5A. In this way, the new protease-deficient minicells, which has chloramphenicol resistant gene, can be selected with chloramphenicol because the pGEX-6P-1 AIDA-1-lipase vector possess Amphicilin-resistant gene.

For a bacterial surface display system named as BrkAutoDisplay based on the structure of autotransporter BrkA (Bordetella serum-resistance killing protein A) was used to host an exogenous gene encoding lipase. To construct a recombinant Brk-lipase expression vector, Brk autotransporter gene was first cloned into the pGEX-6P-1 plasmid. Using BamHI and EcoRI restriction sites, the lipase-encoding gene was ligated with the Brk autotransporter gene, as illustrated in FIG. 6A. As illustrated in FIG. 6B, the lipase-encoding gene was inserted into the passenger domain of BrkA autotransporter gene. The first 177 nucleotides of the expression cassette correspond to the signaling peptide portion of the Brk autotransporter. This is the most N-terminus region of the fusion protein. This portion is cleaved during the translocation process. Immediately at the end of C-terminus of the signaling peptide is located the 6× His tag used for purification and staining. This 6× His tag is the surface expressed N-terminus end of the fusion protein after the signal peptide is cut off. C-terminus to the His tag is fused to the lipase-encoding gene, which is followed by the Myc tag and the TEV site sequentially. Then, the translocation domain of the BrkA autotransporter is located right after the TEV site. This translocation domain of the fusion protein is the most C-terminus region of the protein that is embedded in the membrane.

Figure 7A:
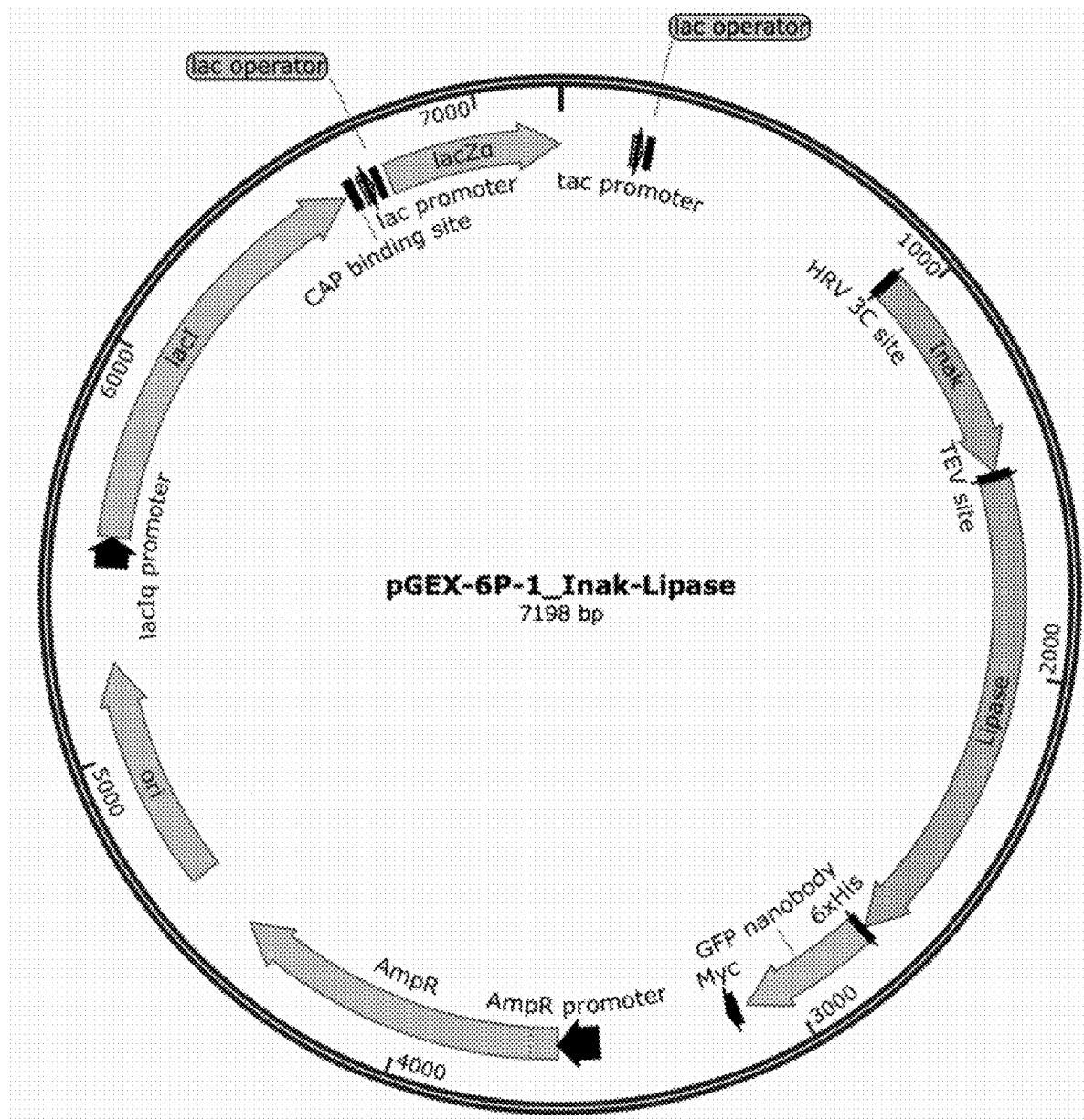
FIG. 7A illustrates an exemplary pGEX-6P-1 Inak-Lipase vector with an Ice Nucleation Protein InaK surface expression system for display of a lipase protein on the surface of minicells. The lipase-encoding nucleotide sequence is ligated at its 5' end to Inak and at its 3' end to 6×His, GFP nanobody and Myc tags.
Figure 7B:
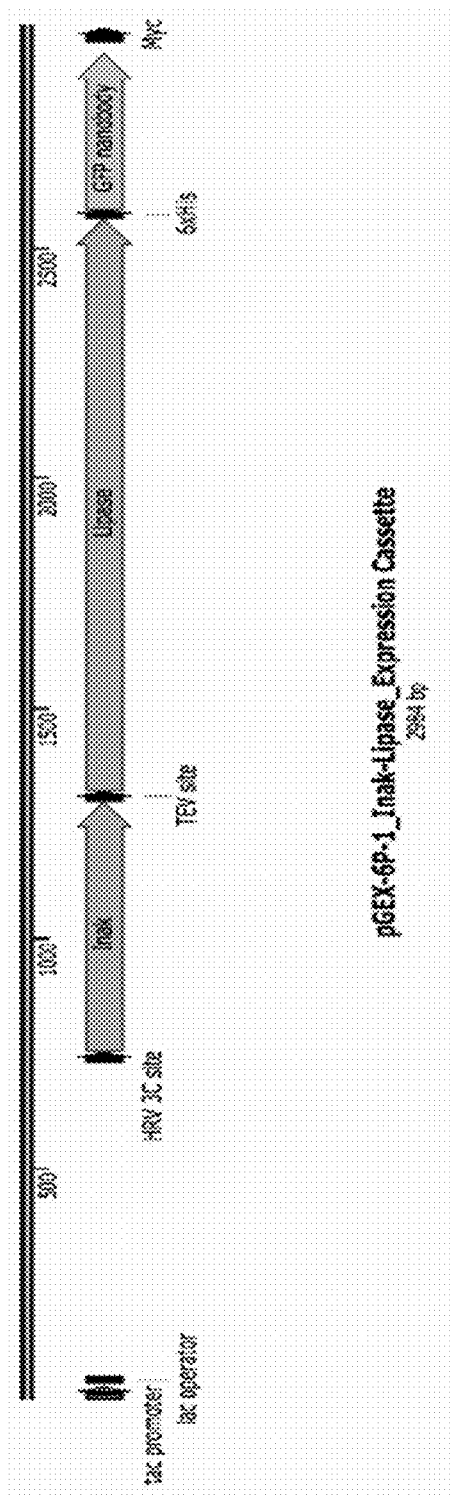
FIG. 7B illustrates an exemplary Inak-lipase surface expression cassette, comprising nucleotide sequences encoding Inak translocation domain, lipase, and GFP nanobody, with tags including 6×His Tag and Myc Tag as well as two protease cleavage sites including HRV3C and TEV.

Another bacterial surface display protein, Ice Nucleation Protein K (InaK) was used for expressing recombinant lipase proteins fused to anchoring linker protein (motif) that direct the incorporated fusion protein on the surface of minicells. Like BrkAutoDisplay, polynucleotide encoding InaK transmembrane protein and the lipase-encoding gene were inserted into the pGEX-6P-1 vector for producing the bacterial surface display lipase protein as illustrated in FIG. 7A. For all InaK-lipase fusions, the lipase-encoding gene has a 6× His tag and an Myc tag at the C-terminus, while the TEV site is fused to N-terminus of the lipase-encoding gene.

In this construct, the polynucleotide sequence encoding InaK is located before N-terminus of the TEV site. Since C-terminus of InaK protein is surface expressed and the N-terminus end becomes embedded in the membrane, the lipase-encoding gene is inserted after InaK-encoding polynucleotide sequence, which allows the lipase to be displayed on the surface while the InaK can function as a membrane anchor. The 6× His tag was used for the Cobalt immobilized metal affinity chromatography (IMAC) and for immunofluorescent staining with THE His Tag antibody [FITC] from Genscript®. The Myc tag can be used for immunofluorescent staining. The TEV site can be used for digesting off the protein of interest such as lipase for surface expression confirmation.

After construction of bacterial expression vectors for bacterial surface display fusion proteins using AIDA-1, BrkA, and InaK system was completed, transformation of each expression vector was conducted using the TransformAid Bacterial Transformation Kit (Thermo Scientific™) according to their standard protocol into the protease-deficient cell lines, BL21 and/or BL21-AI strains. The lipase was fused to each linker protein of AIDA-1, BrkA, and InaK to ensure surface-expression of the lipase. These expression plasmid can be transformed into the wild-type p678-54 strain and protease-deficient minicell-producing bacterial strains generated by the method taught in the present disclosure (e.g. minC, D, or C/D-depleted BL21 (DE3) strain and/or minC, D, or C/D-depleted BL21-AI strain).

In order to confirm presence of plasmid in the transformed bacterial strains, a miniprep was done on a culture from the strains using GeneJet Plasmid MiniPrep Kit, and the purified plasmid was submitted for DNA sequencing analysis. All sequencing confirmed the presence of the surface expression lipase plasmids in the transformed bacterial strains.

Example 3. Protein Production

The transformed strain was grown overnight in a 5 mL culture with the appropriate antibiotic. The next day, 1:100 inoculation of the cultured strain (2.5 mL of overnight culture in 250 mL of 2×YT media) was performed in 2×YT media plus appropriate antibiotic. The 2×YT media provided the surplus of nutrients necessary for efficient protein production. Once the culture reached the exponential growth stage (OD about 0.4), it was induced with 1 mM IPTG and is incubated at 30° C. overnight. The culture then was analyzed the next day for lipase production.

Example 4. Protein Imaging/Staining

The cultured cells are subjected to staining in order to determine the presence surface-expressed lipase. Slides were developed for both the Lipase-expressing minicell-producing bacterial BL21 and/or BL21-AI strain and the minicell-producing bacterial p678-54 strain that has not been transformed with the recombinant linker protein-fused lipase expression plasmid. 250 uL of poly-L-lysine was pipetted on slides for 15 minutes. After washing three times with 500 uL PBS, 500 uL of the correct cell type was pipetted on slides for 15 minutes. After washing three times with 500 uL PBS, 750 uL of 4% paraformaldehyde was pipetted on slides for 15 minutes in order to fix the cell samples to the slides. After washing three times with PBS, 500 uL of 0.1% triton x-100 PBS was added to slides allocated as permeabilized samples for 10 minutes. For non-permeabilized samples, 500 uL of PBS was added to slides during this step. After washing three times with PBS, 100 uL of 2% bovine serum albumin was pipetted on all slides as a blocking agent. After washing three times with PBS, on the slides it was pipetted 100 uL of 1 mg/mL GenScript® THE™ His Tag Antibody [FITC], mAb, Mouse antibody, which binds to the 6×-HIS tag component of the Lipase fusion protein. Then, the slides were incubated with the antibody at room temperature for 1 hour while protected from light. After washing 5-10 times with PBS, 3-4 drops of Fluoroshield Mounting Medium with DAPI were added before mounting coverslips to the slides. Fluorescent microscopy can then be implemented to analyze localization between brightfield cells and fluorescent probes that are indicative of cell presence and surface-expressed protein presence.

Figure 9A:
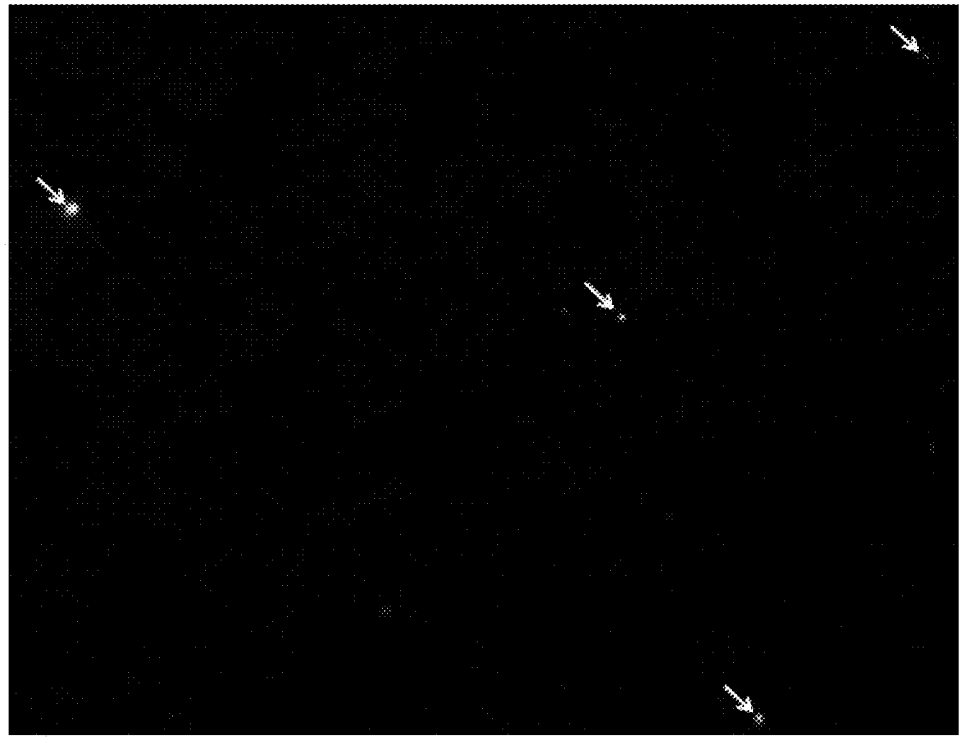
FIG. 9A shows His-Tag staining of the expressed lipase protein fused with Adhesin Involved in Diffuse Adherence 1 protein (AIDA-1) on the surface of non-permeabilized minicells. The fusion AIDA-1 lipases were expressed on the surface of the transformed minicells (FIG. 9A), compared to control minicells that did not have the recombinant fusion lipase expression vector (FIG. 9C).
Figure 9B:
FIG. 9B also shows His-Tag staining of the expressed lipase protein fused with *Bordetella* serum-resistance killing protein (BRK) on the surface of non-permeabilized protease-deficient minicells. The fusion Brk-lipases were expressed on the surface of the transformed minicells (FIG. 9B), compared to control minicells that did not have the recombinant fusion lipase expression vector (FIG. 9D).
Figure 9C:
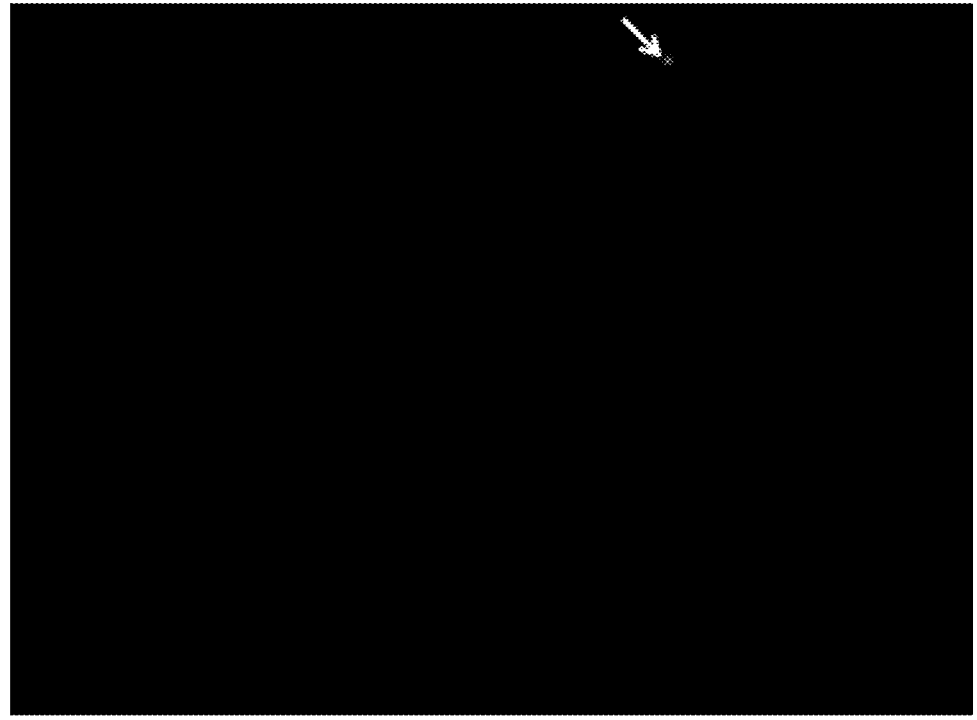
FIGS. 9C and 9D show no or little lipase expression from non-permeabilized control minicells. Arrow points out the expressed lipases.
Figure 9D:
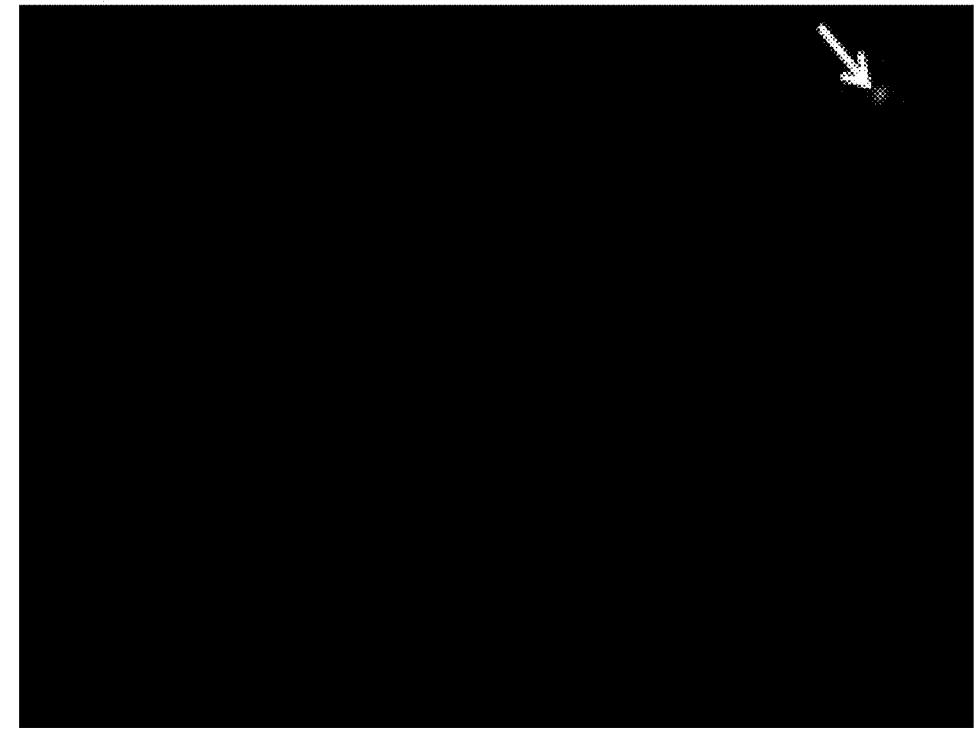

For identifying surface expression, cells were not permeabilized so that the stain cannot enter the cells and stain for internally expressed lipases. Thus, the non-permiabilized minicell stained with His-tag antibody presents the fusion lipase expression on the minicell surface. At first, FIG. 9A shows the expression of AIDA-1 lipase fusion protein on the surface of non-permeabilized minicells, when compared to control minicells that did not have the recombinant fusion lipase expression vector (FIG. 9C). This surface expressed lipase proteins indicates that lipase is immobilized on the surface of the minicells via the membraned-associated autotransporter AIDA-1 protein. Also, the detection of Brk-lipase fusion protein as shown in FIG. 9B demonstrates that lipase is stabilized on the surface of the minicells through the another autotransporter Brk protein, when compared to control minicells that did not have the recombinant fusion lipase expression vector (FIG. 9D). FIGS. 9C and 9D show no or little lipase expression from non-permeabilized control minicells.

Figure 10A:
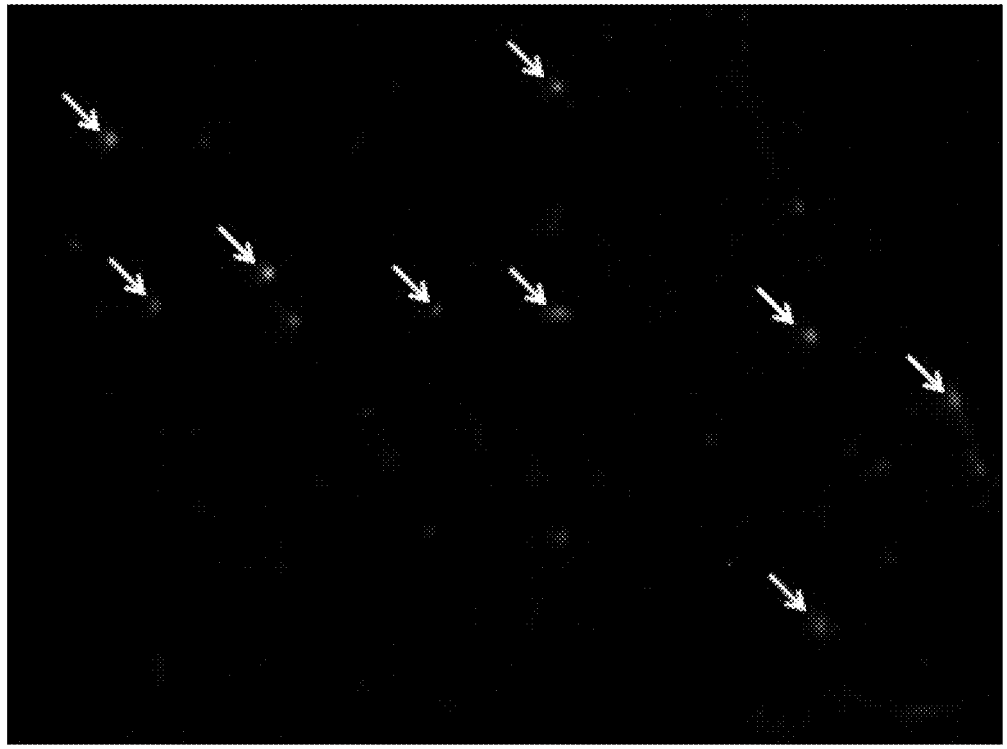
FIG. 10A-D shows His-Tag staining results of lipase protein fused with Ice Nucleation Activation K (InaK) linker protein on the surface of minicells. The minicells were either non-permeabilized (FIGS. 10A and 10C) or permeabilized (FIGS. 10B and 10D). The fusion lipases were expressed on the surface of the transformed minicells (FIGS. 10A and 10B), compared to control minicells that did not have the recombinant AIDA-1 lipase expression vector (FIGS. 10C and 10D).
Figure 10B:
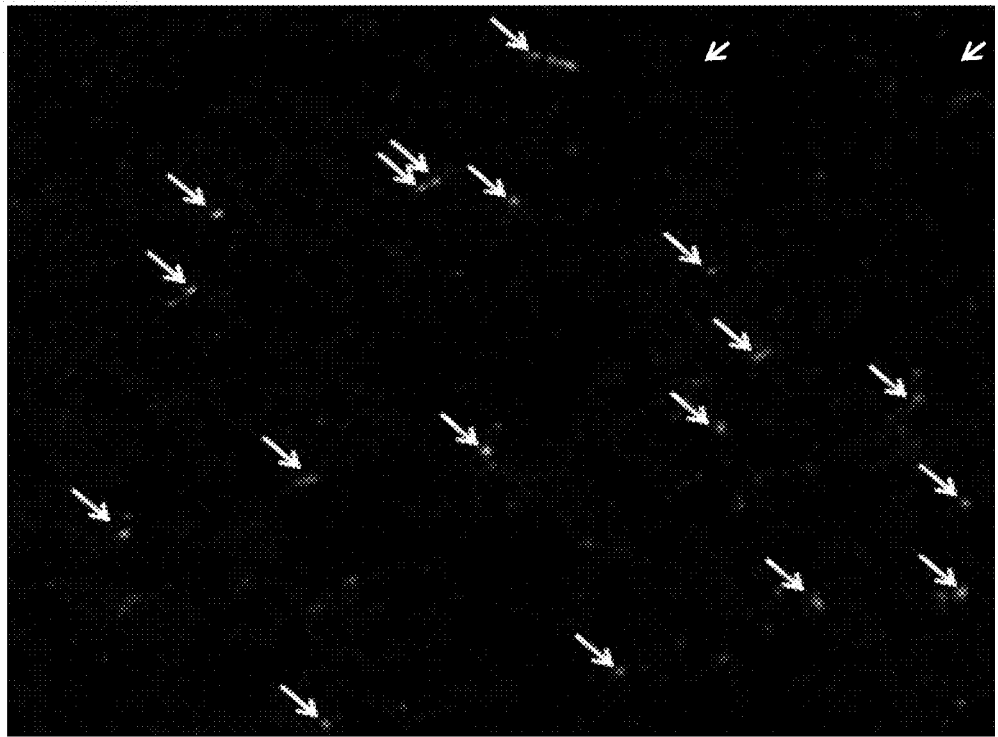
Figure 10C:
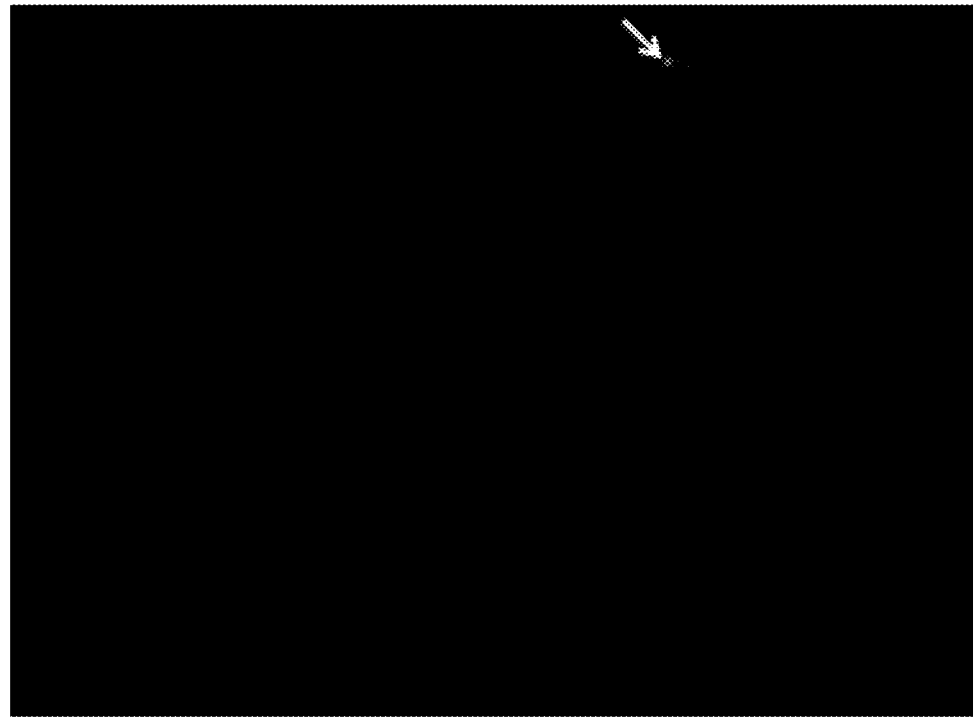
Figure 10D:
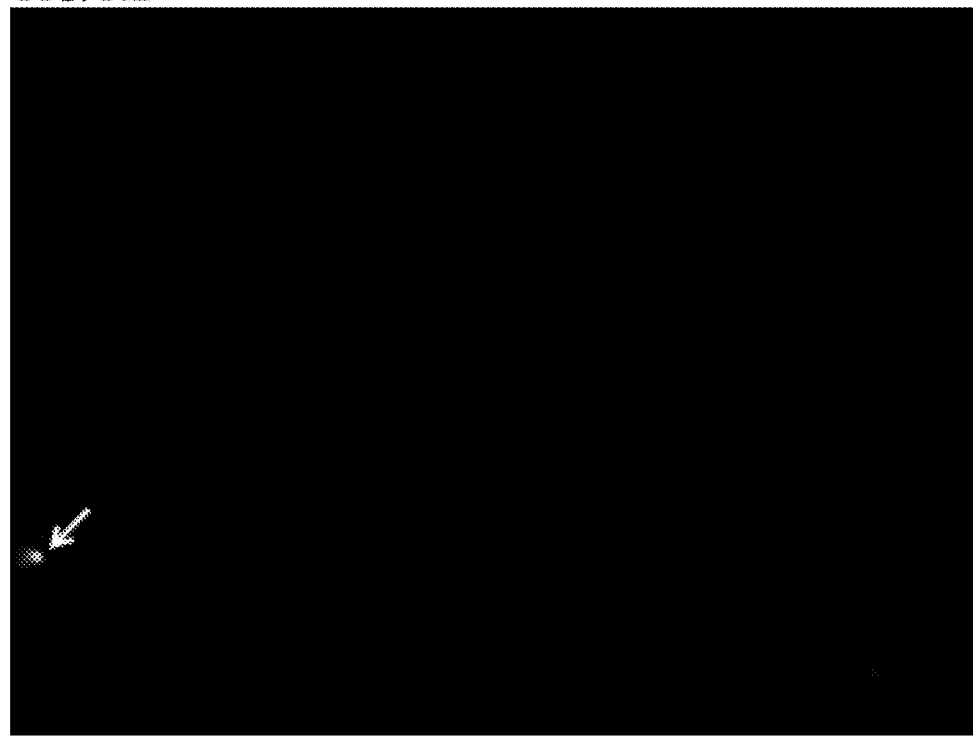

In both permeabilized and nonpermeabilized minicells, the staining with His-tag antibody showed a strong signal in a majority of the population of the cells that expressing InaK-lipase fusion proteins (FIGS. 10A and 10B). However, the His-tag antibody detected little to no signal in the control samples (FIGS. 10C and 10D). The control samples are wild type p678-54 minicells that do not contain the recombinant lipase expressing plasmid so that the fusion protein cannot be detectable. Therefore, the His tag staining results indicate the expression of the fusion lipase from the minicells transformed with the recombinant lipase expression plasmid, but not the control cells. Non-permeabilized minicells (FIG. 10A) show the surface expressed lipase proteins, indicating that lipase is immobilized via the InaK linker protein on the surface of the minicells. However, the recombinant lipase is not all surface expressed from the comparison of non-permeabilized cells with permeabilized cells (FIG. 10B), indicating that endogenous lipases and/or recombinant fusion lipase minicells can be also expressed within the minicells. On the other hand, a false positive by staining any endogenously produced lipases within the transformed minicells can be detected as illustrated in the control minicells (FIGS. 10C and 10D).

Example 5. Protein Purification

Once the protein production was confirmed, the cells are ready to undergo protein purification for functional studies. The cells were incubated with Lysis Buffer for at least six hours at 37° C. They were then frozen at −20° C. They underwent at least one more freeze-thaw cycle prior to purification. Once the lysis process was complete, the cell samples are centrifuged at 10,000 rcf for 10 minutes to pellet the cell debris. The supernatant was then filtered through a Puradisc 25 mm, sterile Whatman 0.45 uM filter prior to the protein purification process.

Figure 11A:
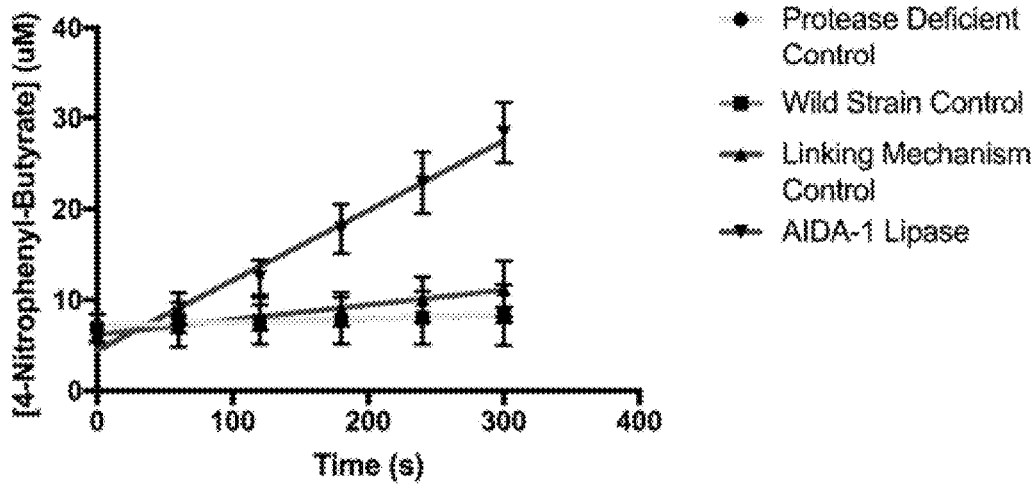
FIG. 11A-C shows lipase activity results of the purified lipase protein fused with three surface expression mechanisms, including AIDA-1, BRK, and InaK, respectively. The lipase was purified from the minicells and tested for its activity using lipase probe 4-nitrophenyl-butyrate.
Figure 11B:
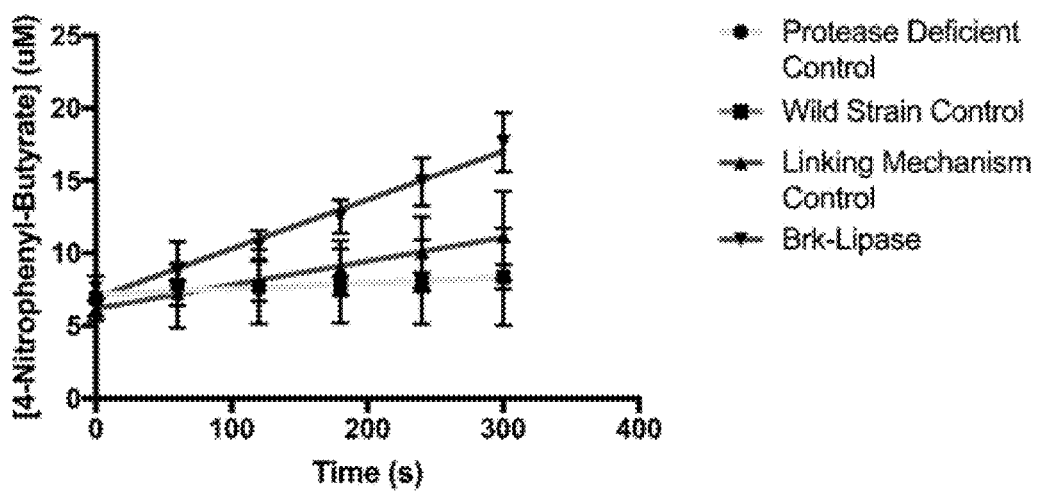
Figure 11C:
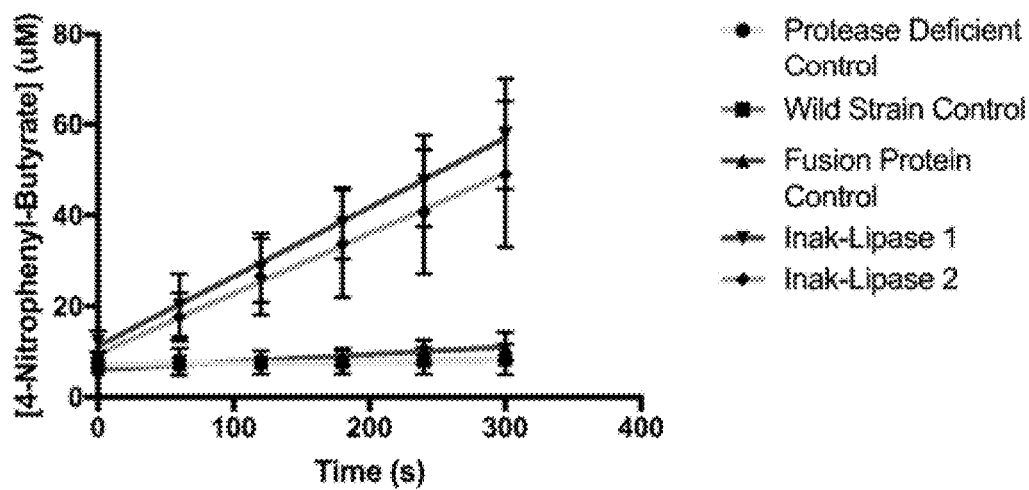

The supernatant was incubated in a 20 mL Econopac Gravity Flow column with about 2 mL of HisPur™ Cobalt Superflow Agarose that had been equilibrated with 4 mL of Equilibration Buffer for 30 minutes in an end over end rotary mixer. The supernatant was flowed through the column. Then, the resin was washed three times with 4 mL of wash buffer before elution with 4 fractions of 2 mL each of elution buffer. Equal volumes of glycerol was added to elution fractions 1 and 2 and were dialyzed overnight in 50% glycerol (v/v) and 50 mM Sodium Phosphate buffer solution pH 7.2. After dialysis, the elution fractions were checked for presence of the fusion protein using the lipase assay. Presence of the lipase in each elution fraction was elucidated from the lipase assay described below using 50 mM 4-nitrophenyl-butyrate against a variety of control purifications. At first, the protease-deficient B8 and P678-54 cell lines were used for control, as they contained no recombinant lipase expression plasmids. Thus they do not have recombinant proteins, resulting in no lipase activity in the lipase assay. While P678-54 strain is the wild type minicell-producing strain that is commercially available, the B8 minicell strain was produced from the BL21 (DE3) strain, but the T7 RNA Polymerase activity was additionally silenced along with minC/minD/minCD knock-out effect. This B8 strain is the protease-deficient producing minicell strain without the T7 RNA Polymerase, which make it suitable for lipase assay as a negative control. The protease-deficient B8 strain without fusion lipase is used as Protease Deficient Control. Furthermore, the Brk-CBM and Inak-CBM (CBM: cellulose-binding domain) fusion protein was also used as another Linking Mechanism Control displaying the purified active CBM fusion enzyme that cannot act on the substrate given for the lipase assay. As shown in FIGS. 11A and 11B, both Brk-lipase and the Inak-lipase produced measurable lipase activity compared to protease-deficient control, wild strain control and linking mechanism control, respectively, thus demonstrating production of recombinant lipases in the BL21(DE3)-derived minicells.

Example 6. Functional Lipase Activity Analysis

In order to further confirm presence of the functional lipase-fusion protein in both the elution fraction from the protein purification and the surface of the cell, a lipase activity assay was designed using the lipase substrate, 4-nitrophenyl-butyrate. This assay was designed using the Sigma-Aldrich quality control assay for lipoprotein lipases (EC 3.1.1.34), which can also serve as a substrate for the same type of lipase fused to the surface expression carrier proteins, a triacylglycerol lipase, (EC 3.1.1.3) using Type II Lipase from Porcine Pancreas as well described in Enzymatic Assay of Lipoprotein Lipase protocol found in sigma aldrich online webpage. Kinetic analysis of the enzymatic reaction of lipase was conducted using a method of continuous spectrophotometric rate determination at 400 nm using Beer's law ($A=\varepsilon l C$) and the extinction coefficient 0.0148 ($uM^{-1}*cm^{-1}$). The pathlength, 0.625 cm, was calculated from the known volume of the well (200 uL) and the well's surface area (0.32 $cm^2$).

Figure 12A:
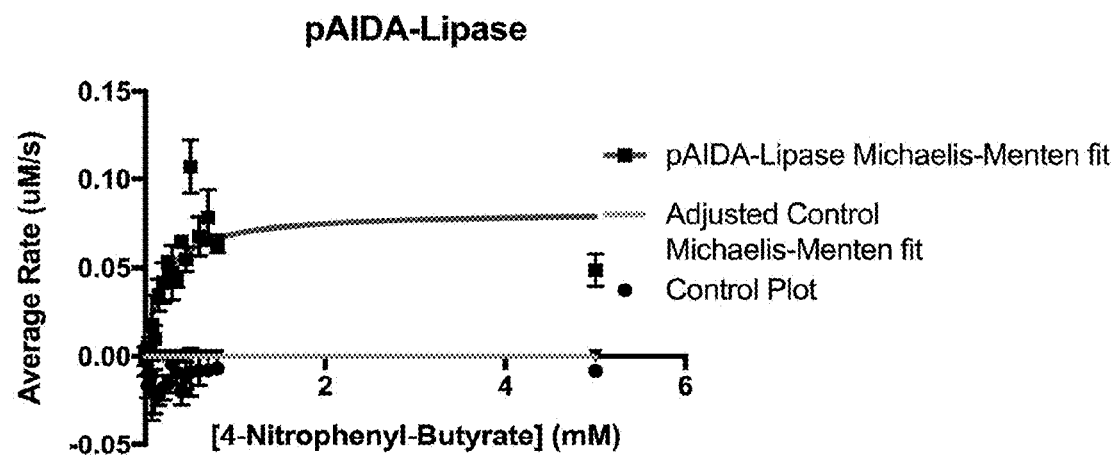
FIG. 12A-C shows lipase activity results of the fusion lipase proteins on the surface of minicells. Kinetic analysis of the reaction was analyzed by continuous spectrophotometric rate determination at 400 nm.
Figure 12B:
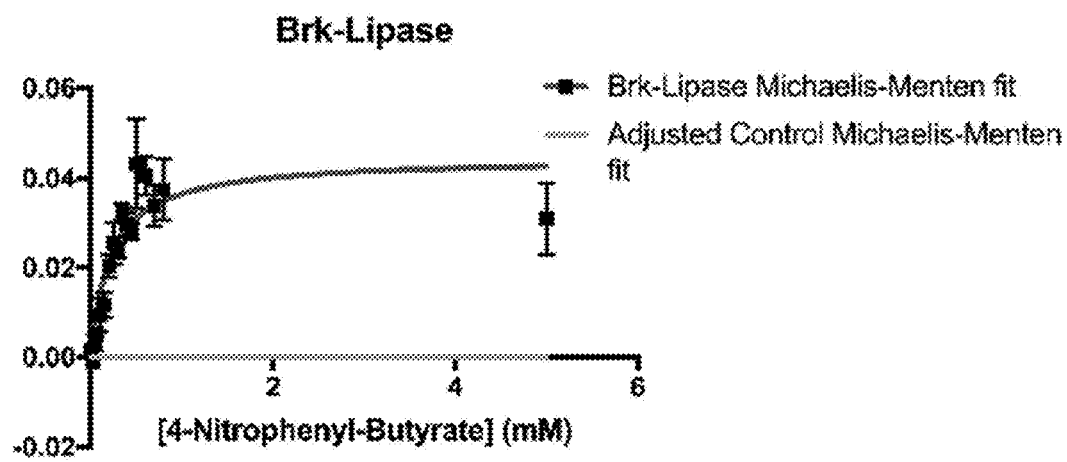
Figure 12C:
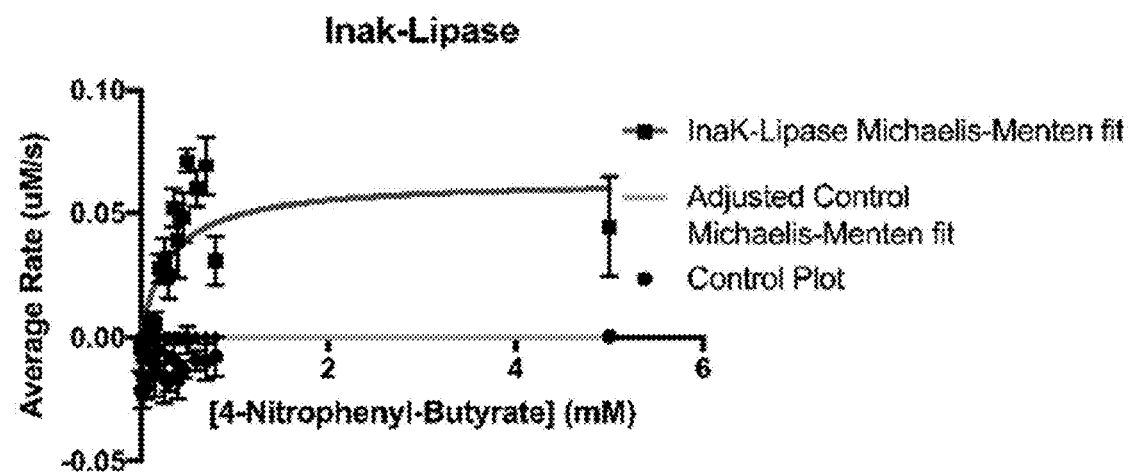
Figure 13:
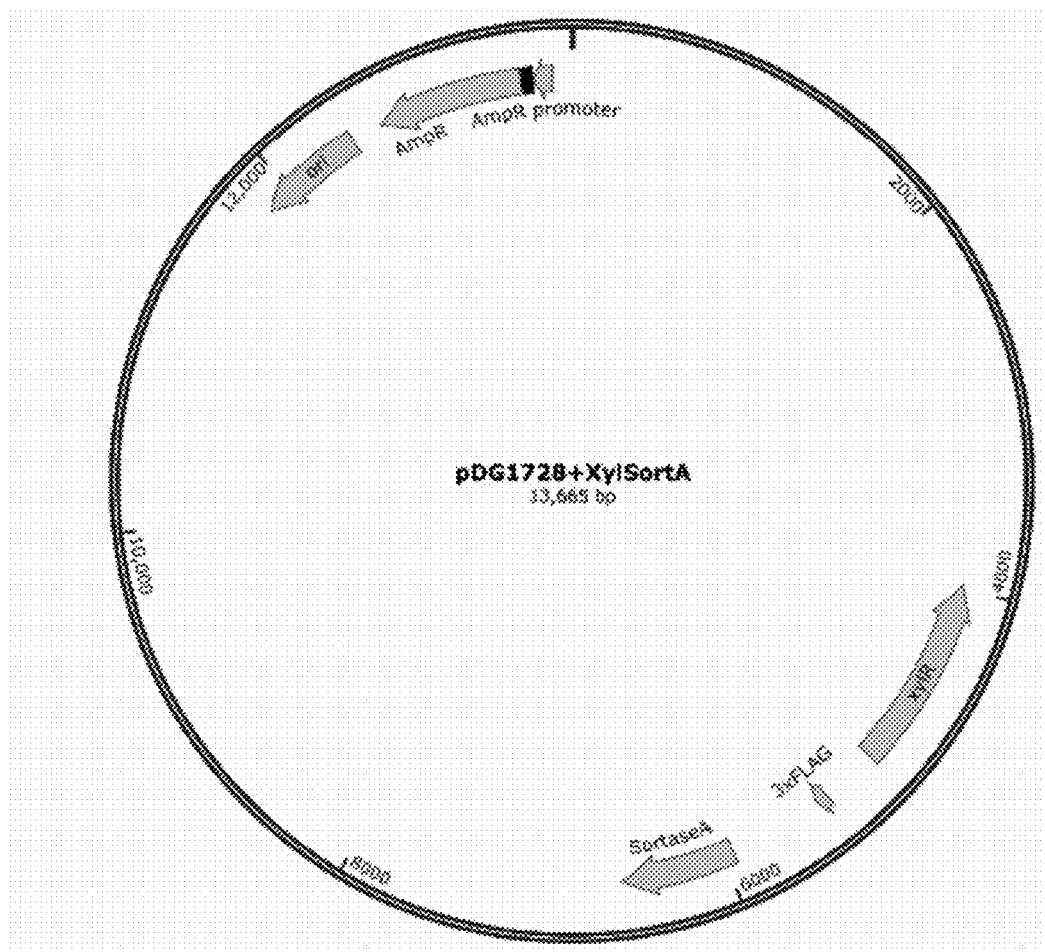
FIG. 13 illustrates an exemplary pDG1728 vector with a Sortase autotransporter for enzyme immobilization in gram positive bacteria cells. Sortase expression is induced with D(+) xylose.
Figure 14:
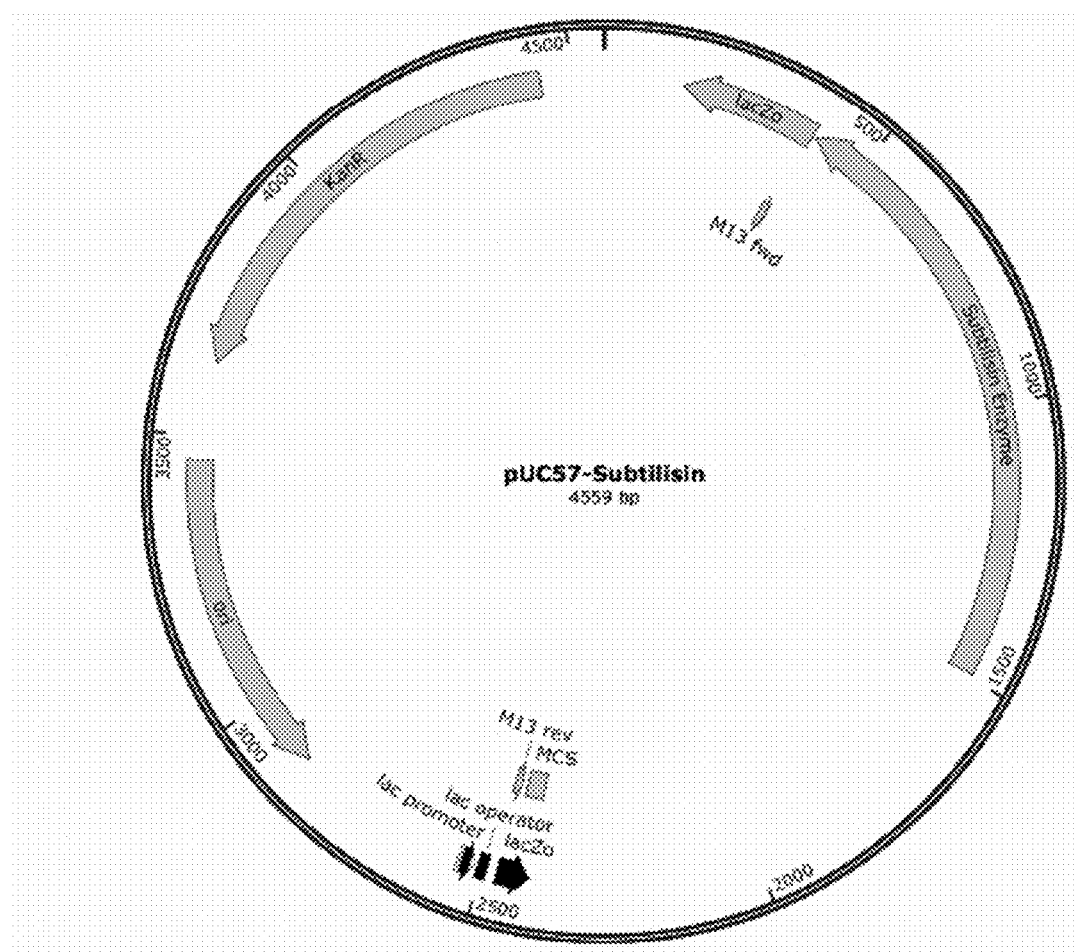
FIG. 14 illustrates an exemplary pUC57 vector for expressing a protein of interest including proteases such as a protease subtilisin on the surface of minicells by inserting surface expression mechanisms including but not limited to AIDA-1, BRK, and InaK into this vector.
Figure 15:
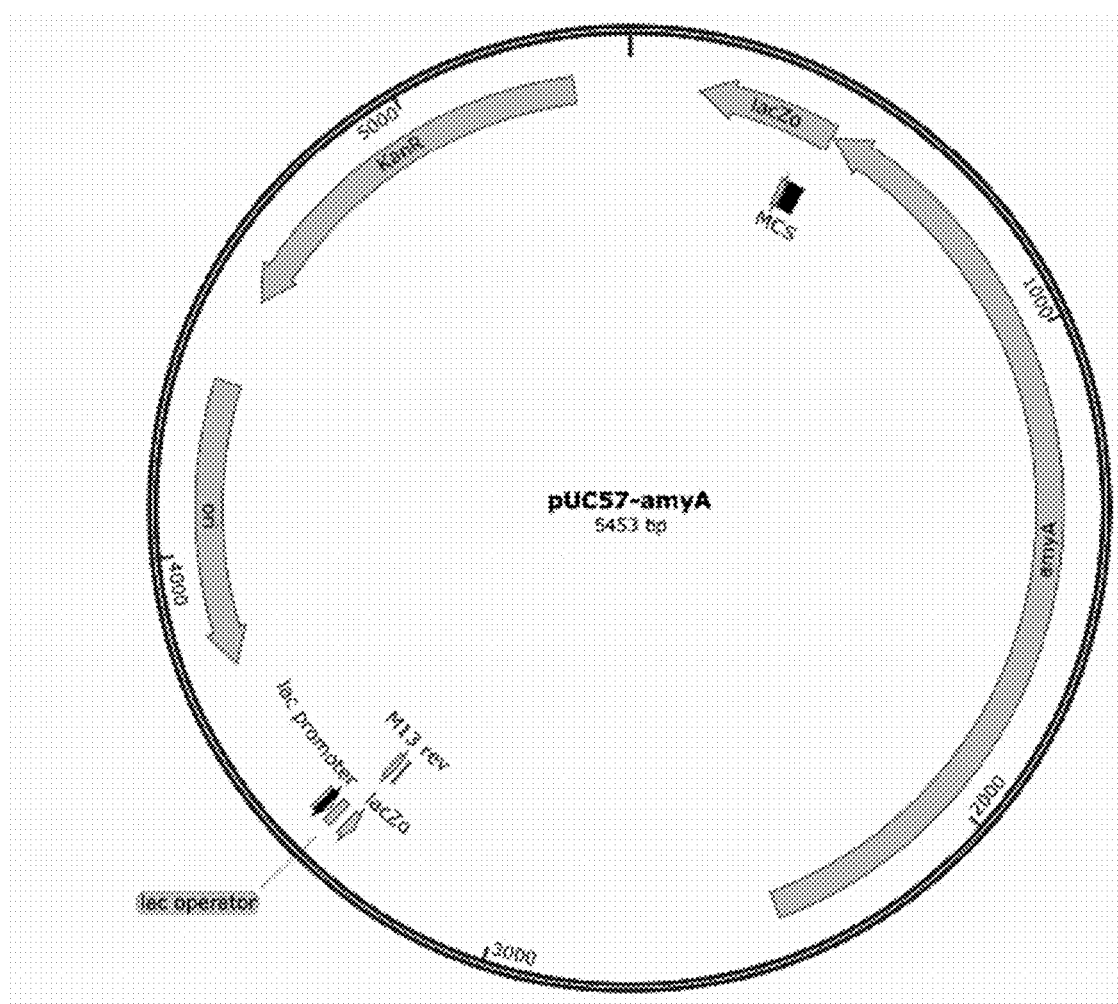
FIG. 15 illustrates an exemplary pUC57 vector for expressing an amylase A on the surface of minicells by inserting surface expression mechanisms including but not limited to AIDA-1, BRK, and InaK into this vector.
Figure 16:
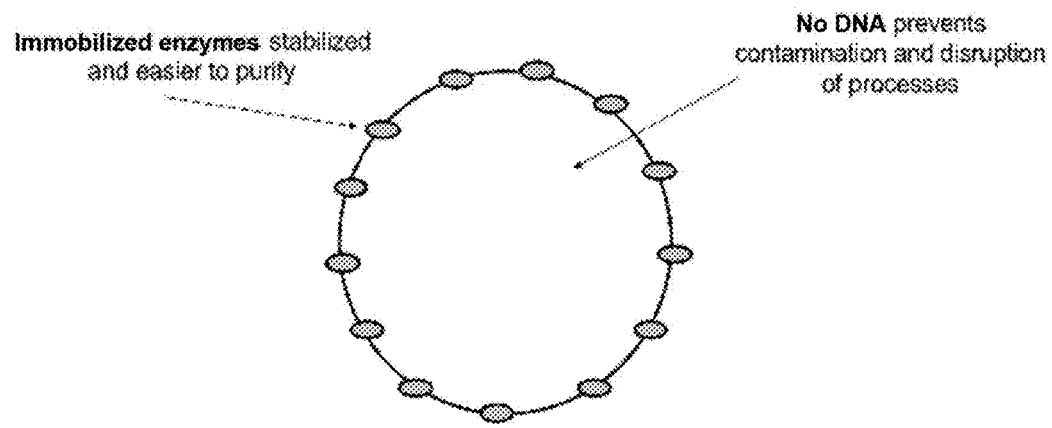
FIG. 16 illustrates delivery of self-immobilized enzymes on a minicell that can be simply purified. The enzyme-immobilized minicell is an achromosomal and/or anucleate cell that is not contaminated and/or disrupted by DNA.

For the enzymatic assay, required are the reaction buffer (100 mM Sodium Phosphate Buffer solution pH 7.2, 0.5% (v/v) Triton-X 100, 150 mM Sodium Chloride), the enzyme/cell solution in 1×PBS, and the substrate solution which is varying concentrations of 4-nitrophenyl-butyrate in acetonitrile. 148 uL of the reaction buffer, 50 uL of the enzyme/cell solution, and 2 uL of the substrate solution were loaded into each well immediate prior to the start of the continuous spectrophotometric rate determination at 37° C. for 5 minutes. Then, rates were calculated by calculating the slope of the line of the concentration increase (Beer's law) versus the time the reaction proceeded in seconds. Activity was determined from a Michaelis-Menten fit of the calculated rates resulting from varying the substrate concentration according to the Table 10. Vmax and Km were calculated using GraphPad Prism Michaelis-Menten fitting parameters. FIG. 12 shows that the enzymatic reaction of AIDA-lipase (FIG. 12A and Table 11), Brk-lipase (FIG. 12B and Table 12), and InaK-lipase (FIG. 12C and Table 13) to 4-nitrophenyl-butyrate substrate, respectively.

TABLE 10

Substrate Concentrations for calculating enzymatic reaction rate

| Stock Concentrations (mM) | Concentrations in Well (mM) |
|---|---|
| 0 | 0 |
| 2.5 | 0.025 |
| 5 | 0.05 |
| 7.5 | 0.075 |
| 10 | 0.1 |
| 15 | 0.15 |
| 20 | 0.2 |
| 25 | 0.25 |
| 30 | 0.3 |
| 35 | 0.35 |
| 40 | 0.4 |
| 45 | 0.45 |
| 50 | 0.5 |
| 60 | 0.6 |
| 70 | 0.7 |
| 80 | 0.8 |
| 500 | 5 |

TABLE 11

Enzymatic reaction rate of pAIDA-lipase

| pAIDA-Lipase | Experimental Average Rate (uM/s) |
|---|---|
| Michaelis-Menten Best-fit values | Cells/Well: 99,946,667 |
| | |
| Vmax | 0.08174 |
| Km | 0.1803 |
| Std. Error | |
| | |
| Vmax | 0.008508 |
| Km | 0.05912 |
| 95% CI (profile likelihood) | |
| | |
| Vmax | 0.06857 to 0.09734 |
| Km | 0.104 to 0.2922 |
| Goodness of Fit | |
| | |
| Degrees of Freedom | 49 |
| R square | 0.6414 |
| Absolute Sum of Squares | 0.01626 |
| Sy.x | 0.01822 |
| Constraints | |
| | |
| Km | Km > 0 |

TABLE 12

Enzymatic reaction rate of Brk-lipase

| Brk-Lipase | Brk-Lipase Average Rate (uM/s) |
|---|---|
| Michaelis-Menten Best-fit values | Cells/Well: 17,706,667 |
| Vmax | 0.04453 |
| Km | 0.2207 |
| Std. Error | |
| Vmax | 0.003487 |
| Km | 0.05025 |
| 95% CI (profile likelihood) | |
| Vmax | 0.03894 to 0.05088 |
| Km | 0.1503 to 0.3134 |
| Goodness of Fit | |
| Degrees of Freedom | 49 |
| R square | 0.7838 |
| Absolute Sum of Squares | 0.002289 |
| Sy.x | 0.006834 |
| Constraints | |
| Km | Km > 0 |

TABLE 13

Enzymatic reaction rate of Inak-lipase

| Inak-Lipase | Experimental Average Rate (uM/s) |
|---|---|
| Michaelis-Menten Best-fit values | Cells/Well: 107,840,000 |
| Vmax | 0.06354 |
| Km | 0.3015 |
| Std. Error | |
| Vmax | 0.009548 |
| Km | 0.1109 |
| 95% CI (profile likelihood) | |
| Vmax | 0.04894 to 0.08074 |
| Km | 0.1649 to 0.5114 |
| Goodness of Fit | |
| Degrees of Freedom | 49 |
| R square | 0.6375 |
| Absolute Sum of Squares | 0.009709 |
| Sy.x | 0.01539 |
| Constraints | |
| Km | Km > 0 |

Example 7. Lipase Surface Expression Via Minicell Self Assembly Technology

As described above, lipase from *Bacillus* sp. was surface expressed with three different linker proteins (Ice nucleation activation protein K (InaK), BrK AutoDisplay, and pAIDA-1). The lipase immobilized on the surface of minicells via the transmembrane linker proteins was analyzed using the His-tag staining and functional enzyme activity assay as described in Examples 4-6. General lipase expression was identified by staining permeabilized cells. Then, to identify surface expression, cells were not permeabilized, which prevents staining for internally expressed lipases within the cells. The positive staining of non-permeabilized cells indicate the exogenous expression of immobilized enzyme on the surface of the cells excluding the possibility of endogenous protein expression as false positive. As shown in Examples above, the His-tag antibody detected a strong signal in a majority of the population of the cells in both the permeabilized and non-permeabilized minicells, indicating that lipase is immobilized and stabilized by the linker protein on the surface of minicells. On the other hand, the His-tag antibody detected little to no signal in the control p678-54 strains without exogenous fusion lipase expression.

Example 8. Production of Non-Inducible Protease-Deficient Minicell and/or Inducible Protease-Deficient Minicell As described in example 1, a protease-deficient minicell producing strain is generated. The strain that spontaneously produce minicells once the knockout has been performed at all stages of cell growth. The process for producing minicell producing strain. The process for that is as follows:

A protease deficient cell line, which is the BL21 and its derivatives is used. When a strain that is not protease-deficient is used, a protease knockout vector such as the WprA-CamR vector shown in FIG. 18 can also be used to knock out protease and/or suppress protease activity in host cells via genetic engineering techniques. Interchangeably to the process described in Example 1, the following process for generating non-inducible minicell producing strain can be also used as follows:

Step 1: Transform cell-line with lambda red recombination plasmid (this plasmid codes for the Beta, Gam and Exo proteins that are involved in catalyzing homology driven recombination)

Step 2: The min knock-out construct is then used as a PCR template to amplify out the sequence of DNA that has homologous 5' and 3' ends to the intended knockout site for the min C, minD or minCD.

Step 3: The PCR amplified product is purified and transformed into the cell line from step 1. PCR product is the DNA that has homologous ends with an antibiotic marker between the ends to allow for selection of successful knockouts.

Step 4: The cell line from step 3 is then induced for protein production from the lambda red recombination plasmid. The encoded proteins catalyze the knockout.

Step 5: The cells are then selected for by using the appropriate antibiotics.

This cell line is then used for transformation and expression of the recombinant fusion constructs described in this disclosure, from which the minicells that express the fusion constructs on their surface can be produced.

Also, a strain that can be induced to initiate minicell production using inducible system at the specific stage of cell growth and/or at the desired timing can be generated. The inducible minicell production can be developed using inducible expression system for protein of interest. This inducible minicell production can be performed in protease-deficient minicell producing strains either using FtsZ and/or MinE overproduction via a recombinant expression cassette for overexpression FtsZ or negative regulation of the Min locus to allow for inducible repression of the MinC/MinD/MinCD proteins. Upon the treatment of induction at a desired timing, either the overexpression effect on FtsZ and/or MinE or the knockout effect on MinC/MinD/MinCD can allow for production of protease-deficient minicells.

NUMBERED EMBODIMENTS OF THE DISCLOSURE

Notwithstanding the appended claims, the disclosure sets forth the following numbered embodiments:

Platform
1. An industrially suitable anucleated cell-based enzyme immobilization and delivery platform, comprising:
   a. an intact anucleated cell derived from a protease deficient parental cell, said anucleated cell comprising an expressed self-assembled enzyme immobilized to the surface of said cell.
2. The anucleated cell-based enzyme immobilization and delivery platform as in any one of the preceding clauses, wherein the expressed self-assembled enzyme is heterologous to the parental cell.
3. The anucleated cell-based enzyme immobilization and delivery platform as in any one of the preceding clauses, wherein the expressed self-assembled enzyme is at least one selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase.
4. The anucleated cell-based enzyme immobilization and delivery platform as in any one of the preceding clauses, wherein the expressed self-assembled enzyme is lipase.
5. The anucleated cell-based enzyme immobilization and delivery platform as in any one of the preceding clauses, wherein the expressed self-assembled enzyme is glucose isomerase.
6. The anucleated cell-based enzyme immobilization and delivery platform as in any one of the preceding clauses, wherein said intact anucleated cell is derived from a prokaryotic cell.
7. The anucleated cell-based enzyme immobilization and delivery platform as in any one of the preceding clauses, wherein said intact anucleated cell is a bacterially derived minicell.
8. The anucleated cell-based enzyme immobilization and delivery platform as in any one of the preceding clauses, wherein said intact anucleated cell is produced from a gram negative bacterial genus.
9. The anucleated cell-based enzyme immobilization and delivery platform as in any one of the preceding clauses, wherein said intact anucleated cell is produced from a bacterial genus selected from the group consisting of: *Escherichia, Salmonella, Shigella, Pseudomonas*, and *Agrobacterium*.
10. The anucleated cell-based enzyme immobilization and delivery platform as in any one of the preceding clauses, wherein said intact anucleated cell is produced from a bacterial species selected from the group consisting of: *Escherichia coli, Salmonella typhimurium, Shigella flexneri*, and *Pseudomonas aeruginosa*.
11. The anucleated cell-based enzyme immobilization and delivery platform as in any one of the preceding clauses, wherein said intact anucleated cell is produced from a gram positive bacterial genus.
12. The anucleated cell-based enzyme immobilization and delivery platform as in any one of the preceding clauses, wherein said intact anucleated cell is produced from a bacterial genus selected from the group consisting of: *Bacillus, Corynebacterium*, and *Lactobacillus*.
13. The anucleated cell-based enzyme immobilization and delivery platform as in any one of the preceding clauses, wherein said intact anucleated cell is produced from a bacterial species selected from the group consisting of: *Bacillus subtilis, Corynebacterium glutamicum*, and *Lactobacillus acidophilus*.
14. The anucleated cell-based enzyme immobilization and delivery platform as in any one of the preceding clauses, wherein said intact anucleated cell is a bacterially derived minicell that is produced from a parental bacterial cell deficient in WprA protease.
15. The anucleated cell-based enzyme immobilization and delivery platform as in any one of the preceding clauses, wherein said intact anucleated cell is a bacterially derived minicell that is produced from a protease deficient *B. subtilis* parental bacterial cell.
16. The anucleated cell-based enzyme immobilization and delivery platform as in any one of the preceding clauses, wherein said intact anucleated cell is a bacterially derived minicell that is produced from a protease deficient KO7 *B. subtilis* parental bacterial cell.
17. The anucleated cell-based enzyme immobilization and delivery platform as in any one of the preceding clauses, wherein said intact anucleated cell is a bacterially derived minicell that is produced from a protease deficient *B. subtilis* parental bacterial cell selected from the group consisting of: (1) CU403,DIVIVA; (2) CU403,DIVIVB,SPO-; (3) CU403,DIVIVB; and (4) CU403,DIVIVB1, wherein at least one protease encoding gene has been repressed, deleted, or silenced.
18. The anucleated cell-based enzyme immobilization and delivery platform as in any one of the preceding clauses, wherein said intact anucleated cell is a bacterially derived minicell that is produced from a parental bacterial cell deficient in Lon and OmpT proteases.
19. The anucleated cell-based enzyme immobilization and delivery platform as in any one of the preceding clauses, wherein said intact anucleated cell is a bacterially derived minicell that is produced from a protease deficient *E. coli* parental bacterial cell.
20. The anucleated cell-based enzyme immobilization and delivery platform as in any one of the preceding clauses, wherein said intact anucleated cell is a bacterially derived minicell that is produced from a protease deficient *E. coli* parental bacterial cell selected from the group consisting of: BL21, BL21(DE3), BL21-AI, LPS-modified BL21 (DE3) and B8.
21. The anucleated cell-based enzyme immobilization and delivery platform as in any one of the preceding clauses, wherein said intact anucleated cell is derived from a eukaryotic cell.
22. The anucleated cell-based enzyme immobilization and delivery platform as in any one of the preceding clauses, wherein the expressed self-assembled enzyme is a fusion protein.
23. The anucleated cell-based enzyme immobilization and delivery platform as in any one of the preceding clauses, wherein the expressed self-assembled enzyme is a fusion protein, comprising at least one surface expressing moiety and at least one enzymatically active moiety.
24. The anucleated cell-based enzyme immobilization and delivery platform as in any one of the preceding clauses, wherein the expressed self-assembled enzyme is a fusion protein, comprising at least one surface expressing moiety and at least one enzymatically active moiety, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

25. The anucleated cell-based enzyme immobilization and delivery platform as in any one of the preceding clauses, wherein the expressed self-assembled enzyme is a fusion protein, comprising at least one surface expressing moiety and at least one enzymatically active moiety,
wherein said surface expressing moiety comprises an exported bacterial protein and is selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

26. The anucleated cell-based enzyme immobilization and delivery platform as in any one of the preceding clauses, wherein the anucleated cell expresses a second polypeptide on its surface, in addition to the self-assembled enzyme.

27. The anucleated cell-based enzyme immobilization and delivery platform as in any one of the preceding clauses, wherein the anucleated cell expresses a heterologous polypeptide on its surface, in addition to the self-assembled enzyme.

28. The anucleated cell-based enzyme immobilization and delivery platform as in any one of the preceding clauses, wherein the anucleated cell expresses a fusion protein on its surface, in addition to the self-assembled enzyme.

29. The anucleated cell-based enzyme immobilization and delivery platform as in any one of the preceding clauses, wherein the anucleated cell expresses a fusion protein on its surface, in addition to the self-assembled enzyme, said fusion protein comprising: at least one surface expressing moiety and at least one plant cell adhesion moiety.

30. The anucleated cell-based enzyme immobilization and delivery platform as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

31. The anucleated cell-based enzyme immobilization and delivery platform as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
wherein said surface expressing moiety comprises an exported bacterial protein and is selected from the group consisting of: LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

32. The anucleated cell-based enzyme immobilization and delivery platform as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
wherein said plant cell adhesion moiety comprises a carbohydrate binding module.

33. The anucleated cell-based enzyme immobilization and delivery platform as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
wherein said plant cell adhesion moiety comprises a carbohydrate binding module selected from the group consisting of: a cellulose binding domain, a xylan binding domain, a chitin binding domain, and a lignin binding domain.

34. The anucleated cell-based enzyme immobilization and delivery platform as in any one of the preceding clauses, wherein the anucleated cell expresses a polypeptide on its surface that increases adhesion to a plant surface, in addition to the self-assembled enzyme.

35. The anucleated cell-based enzyme immobilization and delivery platform as in any one of the preceding clauses, wherein the anucleated cell expresses a plant adhesion polypeptide on its surface, in addition to the self-assembled enzyme.

36. The anucleated cell-based enzyme immobilization and delivery platform as in any one of the preceding clauses, wherein the anucleated cell expresses a carbohydrate binding module that is displayed on its surface, in addition to the self-assembled enzyme.

37. The anucleated cell-based enzyme immobilization and delivery platform as in any one of the preceding clauses, wherein the anucleated cell expresses a heterologous carbohydrate binding module that is displayed on its surface, in addition to the self-assembled enzyme.

38. The anucleated cell-based enzyme immobilization and delivery platform as in any one of the preceding clauses, wherein the anucleated cell expresses a cellulose binding domain that is displayed on its surface, in addition to the self-assembled enzyme.

39. The anucleated cell-based enzyme immobilization and delivery platform as in any one of the preceding clauses, wherein the anucleated cell expresses a heterologous cellulose binding domain that is displayed on its surface, in addition to the self-assembled enzyme.

40. The anucleated cell-based enzyme immobilization and delivery platform as in any one of the preceding clauses, wherein the anucleated cell is used as a resin for immobilizing a polypeptide, wherein the anucleated cell expresses endogenous surface expressing moiety that have a binding domain, and wherein the binding domain is capable of binding to the polypeptide that has a binding site.

41. The anucleated cell-based enzyme immobilization and delivery platform as in any one of the preceding clauses, wherein the anucleated cell is used for purifying a polypeptide, wherein the polypeptide is immobilized to the anucleated cell by incubation.

42. A method of improving activity and stability of an anucleated cell-based enzyme, comprising: applying the anucleated cell-based enzyme immobilization and delivery platform as in any one of the preceding clauses to a substrate,
   wherein the anucleated cell is derived from a protease deficient parental cell, and wherein the anucleated cell comprises an expressed self-assembled enzyme immobilized to the surface of said cell.

43. The method as in any one of the preceding clauses, wherein the expressed self-assembled enzyme is heterologous to the parental cell.

44. The method as in any one of the preceding clauses, wherein the expressed self-assembled enzyme is at least one selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase.

45. The method as in any one of the preceding clauses, wherein the expressed self-assembled enzyme is lipase.

46. The method as in any one of the preceding clauses, wherein the expressed self-assembled enzyme is lipase, wherein the substrate is reacted with the lipase for enzymatic activity.

47. The method as in any one of the preceding clauses, wherein the expressed self-assembled enzyme is lipase, wherein the substrate is reacted with the lipase for enzymatic activity, and wherein said enzymatic activity is associated with fatty acid and oily stain removal, biodiesel production via transesterification, dough stability and conditioning in baking, pitch control and contaminant control for production of pulp and paper, and resolution of chiral alcohols and amines.

48. The method as in any one of the preceding clauses, wherein the expressed self-assembled enzyme is glucose isomerase.

49. The method as in any one of the preceding clauses, wherein the expressed self-assembled enzyme is glucose isomerase, wherein the substrate is reacted with the glucose isomerase for enzymatic activity.

50. The method as in any one of the preceding clauses, wherein the expressed self-assembled enzyme is glucose isomerase, wherein the substrate is reacted with the glucose isomerase for enzymatic activity, and wherein said enzymatic activity is associated with glucose to fructose conversion for production of high-fructose corn syrup.

51. The anucleated cell-based enzyme immobilization and delivery platform as in any one of the preceding clauses, wherein the anucleated cell comprises at least two expressed self-assembled enzymes immobilized to the surface of said cell.

52. The anucleated cell-based enzyme immobilization and delivery platform as in any one of the preceding clauses, wherein each of the expressed self-assembled enzymes is a fusion protein, comprising at least one surface expressing moiety and at least one enzymatically active moiety.

53. The anucleated cell-based enzyme immobilization and delivery platform as in any one of the preceding clauses, wherein each of the expressed self-assembled enzymes is heterologous to the parental cell.

54. The anucleated cell-based enzyme immobilization and delivery platform as in any one of the preceding clauses, wherein each of the expressed self-assembled enzymes is a fusion protein, comprising at least one surface expressing moiety and at least one enzymatically active moiety,
   wherein said enzymatically active moiety is selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase.

55. The anucleated cell-based enzyme immobilization and delivery platform as in any one of the preceding clauses, wherein one of the expressed self-assembled enzymes is lipase.

56. The anucleated cell-based enzyme immobilization and delivery platform as in any one of the preceding clauses, wherein one of the expressed self-assembled enzymes is glucose isomerase.

57. The anucleated cell-based enzyme immobilization and delivery platform as in any one of the preceding clauses, wherein one of the expressed self-assembled enzymes is protease.

58. The anucleated cell-based enzyme immobilization and delivery platform as in any one of the preceding clauses, wherein each of the expressed self-assembled enzymes is a fusion protein, comprising at least one surface expressing moiety and at least one enzymatically active moiety,
   wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

59. The anucleated cell-based enzyme immobilization and delivery platform as in any one of the preceding clauses, wherein each of the expressed self-assembled enzymes is a fusion protein, comprising at least one surface expressing moiety and at least one enzymatically active moiety,
   wherein said surface expressing moiety comprises an exported bacterial protein and is selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

60. The anucleated cell-based enzyme immobilization and delivery platform as in any one of the preceding clauses, wherein the at least two expressed self-assembled enzymes are co-localized to a desired locus, wherein each of the expressed self-assembled enzymes have its enzymatic activity at the desired locus.

61. The anucleated cell-based enzyme immobilization and delivery platform as in any one of the preceding clauses, wherein the expressed self-assembled enzymes are lipase and protease.
62. The anucleated cell-based enzyme immobilization and delivery platform as in any one of the preceding clauses, wherein the expressed self-assembled enzymes are glucose isomerase and protease.
63. The anucleated cell-based enzyme immobilization and delivery platform as in any one of the preceding clauses, wherein the at least two expressed self-assembled enzymes have a complimentary function.
64. The anucleated cell-based enzyme immobilization and delivery platform as in any one of the preceding clauses, wherein the at least two expressed self-assembled enzymes act synergistically.
65. The anucleated cell-based enzyme immobilization and delivery platform as in any one of the preceding clauses, wherein the at least two expressed self-assembled enzymes each work to carry out a portion of an overall enzymatic reaction.

Compositions

1. A composition for enzyme immobilization and delivery platform, comprising:
   a. an intact anucleated cell derived from a protease deficient parental cell, said anucleated cell comprising an expressed self-assembled enzyme immobilized to the surface of said cell.
2. The composition as in any one of the preceding clauses, wherein the expressed self-assembled enzyme is heterologous to the parental cell.
3. The composition as in any one of the preceding clauses, wherein the expressed self-assembled enzyme is at least one selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase.
4. The composition as in any one of the preceding clauses, wherein the expressed self-assembled enzyme is lipase.
5. The composition as in any one of the preceding clauses, wherein the expressed self-assembled enzyme is glucose isomerase.
6. The composition as in any one of the preceding clauses, wherein said intact anucleated cell is derived from a prokaryotic cell.
7. The composition as in any one of the preceding clauses, wherein said intact anucleated cell is a bacterially derived minicell.
8. The composition as in any one of the preceding clauses, wherein said intact anucleated cell is produced from a gram negative bacterial genus.
9. The composition as in any one of the preceding clauses, wherein said intact anucleated cell is produced from a bacterial genus selected from the group consisting of: *Escherichia, Salmonella, Shigella, Pseudomonas,* and *Agrobacterium.*
10. The composition as in any one of the preceding clauses, wherein said intact anucleated cell is produced from a bacterial species selected from the group consisting of: *Escherichia coli, Salmonella typhimurium, Shigella flexneri,* and *Pseudomonas aeruginosa.*
11. The composition as in any one of the preceding clauses, wherein said intact anucleated cell is produced from a gram positive bacterial genus.
12. The composition as in any one of the preceding clauses, wherein said intact anucleated cell is produced from a bacterial genus selected from the group consisting of: *Bacillus, Corynebacterium,* and *Lactobacillus.*
13. The composition as in any one of the preceding clauses, wherein said intact anucleated cell is produced from a bacterial species selected from the group consisting of: *Bacillus subtilis, Corynebacterium glutamicum,* and *Lactobacillus acidophilus.*
14. The composition as in any one of the preceding clauses, wherein said intact anucleated cell is a bacterially derived minicell that is produced from a parental bacterial cell deficient in WprA protease.
15. The composition as in any one of the preceding clauses, wherein said intact anucleated cell is a bacterially derived minicell that is produced from a protease deficient *B. subtilis* parental bacterial cell.
16. The composition as in any one of the preceding clauses, wherein said intact anucleated cell is a bacterially derived minicell that is produced from a protease deficient KO7 *B. subtilis* parental bacterial cell.
17. The composition as in any one of the preceding clauses, wherein said intact anucleated cell is a bacterially derived minicell that is produced from a protease deficient *B. subtilis* parental bacterial cell selected from the group consisting of: (1) CU403,DIVIVA; (2) CU403,DIVIVB,SPO-; (3) CU403,DIVIVB; and (4) CU403,DIVIVB1, wherein at least one protease encoding gene has been repressed, deleted, or silenced.
18. The composition as in any one of the preceding clauses, wherein said intact anucleated cell is a bacterially derived minicell that is produced from a parental bacterial cell deficient in Lon and OmpT proteases.
19. The composition as in any one of the preceding clauses, wherein said intact anucleated cell is a bacterially derived minicell that is produced from a protease deficient *E. coli* parental bacterial cell.
20. The composition as in any one of the preceding clauses, wherein said intact anucleated cell is a bacterially derived minicell that is produced from a protease deficient *E. coli* parental bacterial cell selected from the group consisting of: BL21, BL21(DE3), BL21-AI, LPS-modified BL21 (DE3) and B8.
21. The composition as in any one of the preceding clauses, wherein said intact anucleated cell is derived from a eukaryotic cell.
22. The composition as in any one of the preceding clauses, wherein the expressed self-assembled enzyme is a fusion protein.
23. The composition as in any one of the preceding clauses, wherein the expressed self-assembled enzyme is a fusion protein, comprising at least one surface expressing moiety and at least one enzymatically active moiety.
24. The composition as in any one of the preceding clauses, wherein the expressed self-assembled enzyme is a fusion protein, comprising at least one surface expressing moiety and at least one enzymatically active moiety,
   wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

25. The composition as in any one of the preceding clauses, wherein the expressed self-assembled enzyme is a fusion protein, comprising at least one surface expressing moiety and at least one enzymatically active moiety,
    wherein said surface expressing moiety comprises an exported bacterial protein and is selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

26. The composition as in any one of the preceding clauses, wherein the anucleated cell expresses a second polypeptide on its surface, in addition to the self-assembled enzyme.

27. The composition as in any one of the preceding clauses, wherein the anucleated cell expresses a heterologous polypeptide on its surface, in addition to the self-assembled enzyme.

28. The composition as in any one of the preceding clauses, wherein the anucleated cell expresses a fusion protein on its surface, in addition to the self-assembled enzyme.

29. The composition as in any one of the preceding clauses, wherein the anucleated cell expresses a fusion protein on its surface, in addition to the self-assembled enzyme, said fusion protein comprising: at least one surface expressing moiety and at least one plant cell adhesion moiety.

30. The composition as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
    wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

31. The composition as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
    wherein said surface expressing moiety comprises an exported bacterial protein and is selected from the group consisting of: LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

32. The composition as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
    wherein said plant cell adhesion moiety comprises a carbohydrate binding module.

33. The composition as in any one of the preceding clauses, wherein the anucleated cell expresses a fusion protein on its surface, in addition to the self-assembled enzyme, said fusion protein comprising: at least one surface expressing moiety and at least one plant cell adhesion moiety,
    wherein said plant cell adhesion moiety comprises a carbohydrate binding module selected from the group consisting of: a cellulose binding domain, a xylan binding domain, a chitin binding domain, and a lignin binding domain.

34. The composition as in any one of the preceding clauses, wherein the anucleated cell expresses a polypeptide on its surface that increases adhesion to a plant surface, in addition to the self-assembled enzyme.

35. The composition as in any one of the preceding clauses, wherein the anucleated cell expresses a plant adhesion polypeptide on its surface, in addition to the self-assembled enzyme.

36. The composition as in any one of the preceding clauses, wherein the anucleated cell expresses a carbohydrate binding module that is displayed on its surface, in addition to the self-assembled enzyme.

37. The composition as in any one of the preceding clauses, wherein the anucleated cell expresses a heterologous carbohydrate binding module that is displayed on its surface, in addition to the self-assembled enzyme.

38. The composition as in any one of the preceding clauses, wherein the anucleated cell expresses a cellulose binding domain that is displayed on its surface, in addition to the self-assembled enzyme.

39. The composition as in any one of the preceding clauses, wherein the anucleated cell expresses a heterologous cellulose binding domain that is displayed on its surface, in addition to the self-assembled enzyme.

40. The composition as in any one of the preceding clauses, wherein the anucleated cell is used as a resin for immobilizing a polypeptide, wherein the anucleated cell expresses endogenous surface expressing moiety that have a binding domain, and wherein the binding domain is capable of binding to the polypeptide that has a binding site.

41. The composition as in any one of the preceding clauses, wherein the anucleated cell is used for purifying a polypeptide, wherein the polypeptide is immobilized to the anucleated cell by incubation.

42. A method of improving activity and stability of an anucleated cell-based enzyme, comprising: applying the anucleated cell-based enzyme immobilization and delivery platform as in any one of the preceding clauses to a substrate,
    wherein the anucleated cell is derived from a protease deficient parental cell, and wherein the anucleated cell comprises an expressed self-assembled enzyme immobilized to the surface of said cell.

43. The method as in any one of the preceding clauses, wherein the expressed self-assembled enzyme is heterologous to the parental cell.

44. The method as in any one of the preceding clauses, wherein the expressed self-assembled enzyme is at least one selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase.

45. The method as in any one of the preceding clauses, wherein the expressed self-assembled enzyme is lipase.
46. The method as in any one of the preceding clauses, wherein the expressed self-assembled enzyme is lipase, wherein the substrate is reacted with the lipase for enzymatic activity.
47. The method as in any one of the preceding clauses, wherein the expressed self-assembled enzyme is lipase, wherein the substrate is reacted with the lipase for enzymatic activity, and wherein said enzymatic activity is associated with fatty acid and oily stain removal, biodiesel production via transesterification, dough stability and conditioning in baking, pitch control and contaminant control for production of pulp and paper, and resolution of chiral alcohols and amines.
48. The method as in any one of the preceding clauses, wherein the expressed self-assembled enzyme is glucose isomerase.
49. The method as in any one of the preceding clauses, wherein the expressed self-assembled enzyme is glucose isomerase, wherein the substrate is reacted with the glucose isomerase for enzymatic activity.
50. The method as in any one of the preceding clauses, wherein the expressed self-assembled enzyme is glucose isomerase, wherein the substrate is reacted with the glucose isomerase for enzymatic activity, and wherein said enzymatic activity is associated with glucose to fructose conversion for production of high-fructose corn syrup.
51. The composition as in any one of the preceding clauses, wherein the anucleated cell comprises at least two expressed self-assembled enzymes immobilized to the surface of said cell.
52. The composition as in any one of the preceding clauses, wherein each of the expressed self-assembled enzymes is a fusion protein, comprising at least one surface expressing moiety and at least one enzymatically active moiety.
53. The composition as in any one of the preceding clauses, wherein each of the expressed self-assembled enzymes is heterologous to the parental cell.
54. The composition as in any one of the preceding clauses, wherein each of the expressed self-assembled enzymes is a fusion protein, comprising at least one surface expressing moiety and at least one enzymatically active moiety,
    wherein said enzymatically active moiety is selected from the group consisting of: esterase, lipase, isomerase, glucose isomerase, amylase, alpha amylase, beta amylase, cellulase, endoglucanases, exoglucanases, beta-glucosidases, lyase, pectin lyase, protease, transglutaminase, desaturase, peroxidase, lipoxygenase, catalase, phosphatase, alkaline phosphatase, tyrosinase, urease, dehydrogenase, alcohol dehydrogenase, lactate dehydrogenase, acetaldehyde dehydrogenase, aldehyde dehydrogenase, pyruvate dehydrogenase, succinate dehydrogenase, xylanase, phytase, mannanase, and laccase.
55. The composition as in any one of the preceding clauses, wherein one of the expressed self-assembled enzymes is lipase.
56. The composition as in any one of the preceding clauses, wherein one of the expressed self-assembled enzymes is glucose isomerase.
57. The composition as in any one of the preceding clauses, wherein one of the expressed self-assembled enzymes is protease.
58. The composition as in any one of the preceding clauses, wherein each of the expressed self-assembled enzymes is a fusion protein, comprising at least one surface expressing moiety and at least one enzymatically active moiety,
    wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).
59. The composition as in any one of the preceding clauses, wherein each of the expressed self-assembled enzymes is a fusion protein, comprising at least one surface expressing moiety and at least one enzymatically active moiety,
    wherein said surface expressing moiety comprises an exported bacterial protein and is selected from the group consisting of LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).
60. The composition as in any one of the preceding clauses, wherein the at least two expressed self-assembled enzymes are co-localized to a desired locus, wherein each of the expressed self-assembled enzymes have its enzymatic activity at the desired locus.
61. The composition as in any one of the preceding clauses, wherein the expressed self-assembled enzymes are lipase and protease.
62. The composition as in any one of the preceding clauses, wherein the expressed self-assembled enzymes are glucose isomerase and protease.
63. The composition as in any one of the preceding clauses, wherein the at least two expressed self-assembled enzymes have a complimentary function.
64. The composition as in any one of the preceding clauses, wherein the at least two expressed self-assembled enzymes act synergistically.
65. The composition as in any one of the preceding clauses, wherein the at least two expressed self-assembled enzymes each work to carry out a portion of an overall enzymatic reaction.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

REFERENCES

POURTAHERI P., ZOMORODI S., DAVIS Z. G., SHAKEEL A. M., Frank J., MOSHASHA S. R., KHOKHLACHEV A., Kester M., Compositions and methods for pesticide degradation, WO2017/180650 A1

Sabbadini R., Berkley N., Surber M., Klepper R., Minicell based delivery of biologically active compounds U.S. Pat. No. 9,017,986 B2

Giacalone M. J., Maloy S., Tsuji S., Regulated genetic suicide mechanism compositions and methods, U.S. Pat. No. 9,045,761 B2

Giacalone M. J, Newman M. J., Therapeutic compositions and methods for antibody and fc-containing targeting molecule-based targeted delivery of bioactive molecules by bacterial minicells, US2/012/0207754 A1

*Enzyme Immobilization—Advances in Industry, Agriculture, |Alka Dwevedi|Springer.* (n.d.). Retrieved from http://www.springer.com/us/book/9783319414164

Gai, S. A., & Wittrup, K. D. (2007). Yeast surface display for protein engineering and characterization. *Current Opinion in Structural Biology,* 17(4), 467-473. https://doi.org/10.1016/j.sbi.2007.08.012

Karlsson, S., Holmbom, B., Spetz, P., Mustranta, A., & Buchert, J. (2001). Reactivity of Trametes laccases with fatty and resin acids. *Applied Microbiology and Biotechnology,* 55(3), 317-320.

Mitra, S. D., Afonina, I., & Kline, K. A. (2016). Right Place, Right Time: Focalization of Membrane Proteins in Gram-Positive Bacteria. *Trends in Microbiology,* 24(8), 611-621.

Lee, S. H., Lee, S. Y., & Park, B. C. (2005). Cell Surface Display of Lipase in *Pseudomonas putida* KT2442 Using OprF as an Anchoring Motif and Its Biocatalytic Applications. *Applied and Environmental Microbiology,* 71(12), 8581-8586.

Routledge, S. J., Mikaliunaite, L., Patel, A., Clare, M., Cartwright, S. P., Bawa, Z., . . . Bill, R. M. (2016). The synthesis of recombinant membrane proteins in yeast for structural studies. *Methods,* 95, 26-37.

Vinh, D. Khue, N. Study on Minicell Generation of *Lactobacillus acidophilus* VTCC-B-871 for Drug Delivery. Journal of Applied Pharmaceutical Science. Vol. 3 (05), 33-36.

Wieczorek, A. S., Biot-Pelletier, D., & Martin, V. J. J. (2013). Recombinant Cellulase and Cellulosome Systems.

Patent US20130337545 Minicell Based Delivery of Biologically Active Compounds

Fersht A. Structure and mechanism in protein science: a guide to enzyme catalysis and protein folding. New York: W. H. Freeman & Company; 1998. p. 615.

Powers R. Comparison of protein active site structures for functional annotation of Proteins and drug design. Proteins Struct Funct Bioinf. 2006; 65:124-35.

Nelson J M, Hitchcock D I. The activity of adsorbed invertase. J Am Chem Soc. 1921; 43:1956-61.

Mclaren A D. Concerning the pH dependence of enzyme reactions on cells, particulates and in solution. Science. 1957; 125:697.

Mosbach K, Mosbach R. Entrapment of enzymes and microorganisms in synthetic cross-linked polymers and their application in column techniques. Acta Chem Scand. 1966; 20:2807-10.

Chen L F, Richardson R. Enzyme derivatives containing reactive groups. Immobilization of alpha-amylase on human erythrocytes. Pharmacol Res Commun. 1974; 6:273-80.

Kennedy J F, Zamir A. The use of cellulose xanthate for the immobilisation of biological molecules. Carbohydr Res. 1975; 41:227-33.

Cordonnier M, Lawny F, Chapot D, Thomas D. Magnetic enzyme membranes as active elements of electrochemical sensors. Lactose, saccharose, maltose bienzyme electrodes.
FEBS Lett. 1975; 59:263-7.

Sin M L, Mach K E, Wong P K, Liao J C. Advances and challenges in biosensor-based diagnosis of infectious diseases. Expert Rev Mol Diagn. 2014; 14:225-44.

Horton H R, Swaisgood H E. Immobilization as a means of investigating the acquisition of
tertiary structure in chymotrypsinogen. Methods Enzymol. 1976; 44:516-26.

Das N, Kayastha A M, Malhotra O P. Immobilization of urease from pigeonpea (*Cajanus cajan* L.) on polyacrylamide gels and calcium alginate beads. Biotechnol Appl Biochem. 1998; 27:25-9.

Nakarani M, Kayastha A M. Kinetics and diffusion studies in urease-alginate biocatalyst beads. Orient Pharm Exp Med. 2007; 7:79-84.

Alloue W A, Destain J, El Medjoub T, Ghalfi H, Kabran P, Thonart P. Comparison of *Yarrowia lipolytica* lipase immobilization yield of entrapment, adsorption, and covalent bond techniques. Appl Biochem Biotechnol. 2008; 150:51-63.

Hage D S, Walters R R, Hethcote H W. Split-peak affinity chromatographic studies of the
immobilization-dependent adsorption kinetics of protein A. Anal Chem. 1986; 58:274-9.

Marquez L D S, Cabral B V, Freitas F F, Cardoso V L, Ribeiro E J. Optimization of invertase
immobilization by adsorption in ionic exchange resin for sucrose hydrolysis. J Mol Catal
B: Enzym. 2008; 51:86-92.

Das N, Prabhakar P, Kayastha A M, Srivastava R C. Enzyme entrapped inside the reverse
micelle in the fabrication of a new urea sensor. Biotechnol Bioeng. 1997; 54:329-32.

Iso M, Shirahase T, Hanamura S, Urushiyama S, Omi S. Immobilization of enzyme by microencapsulation and application of the encapsulated enzyme in the catalysis. J Microencapsul. 1989; 6:165-76.

Iso M, Kando T, Omi S. A fundamental study of the microencapsulation procedure utilizing coacervation in a polystyrene-cyclohexane solution. J Microencapsul. 1985; 2:275-87.

Mauguet M C, Legrand J, Brujes L, Carnelle G, Larre C, Popineau Y. Gliadin matrices for microencapsulation processes by simple coacervation method. J Microencapsul. 2002; 19:377-84.

Kayastha A M, Srivastava P K, Miksa B, Slomkowski S. Unique activity of ureases immobilized on poly (styrene-co-acrolein) microspheres. J Bioact Compat Polym. 2003; 18:113-24.

Reddy K R C, Kayastha A M. Improved stability of urease upon coupling to alkylamine and
arylamine glass and its analytical use. J Mol Catal B: Enzym. 2006; 38:104-12.

Trevan M D. Enzyme immobilization by covalent bonding. Methods Mol Biol. 1988; 3:495-510.

Williams R A, Blanch H W. Covalent immobilization of protein monolayers for biosensor applications. Biosens Bioelectron. 1994; 9:159-67.

Pierre S J, Thies J C, Dureault A, Cameron N R, van Hest J C M, Carette N, Michon T, Weberskirch R. Covalent enzyme immobilization onto photopolymerized highly porous monoliths. Adv Mater. 2006; 18:1822-6.

Dwevedi A, Kayastha A M. Optimal immobilization of beta-galactosidase from Pea (PsBGAL) onto Sephadex and chitosan beads using response surface methodology and its applications. Bioresour Technol. 2009; 100:2667-75.

Dwevedi A, Kayastha A M. Stabilization of beta-galactosidase (from peas) by immobilization onto amberlite MB-150 beads and its application in lactose hydrolysis. J Agric Food Chem. 2009; 57:682-8.

Mulagalapalli S, Kumar S, Kalathur R C, Kayastha A M. Immobilization of urease from pigeonpea (*Cajanus cajan*) on agar tablets and its application in urea assay. Appl Biochem Biotechnol. 2007; 142:291-7.

Das N, Kayastha A M, Malhotra O P. Immobilization of urease from pigeonpea (*Cajanus cajan* L.) in polyacrylamide gels and calcium alginate beads. Biotechnol Appl Biochem. 1998; 27:25-9.

Das N, Kayastha A M. Immobilization of urease from pigeonpea (*Cajanus cajan* L.) on flannel cloth using polyethylenimine. World J Microbiol Biotechnol. 1998; 14:927-9.

Kayastha A M, Srivastava P K. Pigeonpea (*Cajanus cajan* L.) urease immobilized on glutaraldehyde activated chitosan beads and its analytical applications. Appl Biochem Biotechnol. 2001; 96:41-53.

Tripathi P, Kumari A, Rath P, Kayastha A M. Immobilization of α-amylase from mung beans (*Vigna radiata*) on Amberlite MB 150 and chitosan beads: A comparative study. J Mol Catal B: Enzym. 2007; 49:69-74.

Kumar S, Dwevedi A, Kayastha A M. Immobilization of soybean (*Glycine max*) urease on alginate and chitosan beads showing improved stability: Analytical applications. J Mol Catal B: Enzym. 2009; 58:138-45.

Neto S A, Forti J C, Zucolotto V, Ciancaglini P, De Andrade A R. The kinetic behavior of dehydrogenase enzymes in solution and immobilized onto nanostructured carbon platforms. Process Biochem. 2011; 46:2347-52.

DeLouise L A, Miller B L. Enzyme Immobilization in porous silicon: Quantitative analysis of the kinetic parameters for glutathione-S-transferases. Anal Chem. 2005; 77:1950-6.

Reddy K R C, Turcu F, Schulte A, Kayastha A M, Schuhmann W. Fabrication of a potentiometric/amperometric bifunctional enzyme microbiosensor. Anal Chem. 2005; 77:5063-7.

Lin E-W, Boehnke N, Maynard H D. Protein-polymer conjugation via ligand affinity and photoactivation of glutathione S-transferase. Bioconjugate Chem. 2014; 25:1902-9.

Alconcel S N S, Baas A S, Maynard H D. FDA approved poly (ethylene glycol)-protein conjugate drugs. Polym Chem. 2011; 2:1442-8.

Canalle L A, Lowik D, van Hest J C M. Polypeptide-polymer bioconjugates. Chem Soc Rev. 2010; 39:329-53.

Self-assembly—Latest research and news Nature. (n.d.). Retrieved from http://www.nature.com/subjects/self-assembly Silhavy, T. J., Benson, S. A., & Emr, S. D. (1983). Mechanisms of protein localization. *Microbiological Reviews*, 47(3), 313-344.

Mitra, S. D., Afonina, I., & Kline, K. A. (2016). Right Place, Right Time: Focalization of Membrane Proteins in Gram-Positive Bacteria. *Trends in Microbiology*, 24(8), 611-621.

Routledge, S. J., Mikaliunaite, L., Patel, A., Clare, M., Cartwright, S. P., Bawa, Z., . . . Bill, R. M. (2016). The synthesis of recombinant membrane proteins in yeast for structural studies. *Methods*, 95, 26-37.

H. I. Adler, W. D. Fisher, A. Cohen and Alice A. Hardigree, Miniature *Escherichia coli* Cells Deficient in DNA *Proceedings of the National Academy of Sciences of the United States of America* Vol. 57, No. 2 (Feb. 15, 1967), pp. 321-326

PIET A. J. DE BOER, ROBIN E. CROSSLEY, AND LAWRENCE I. ROTHFIELD, (1990) Central role for the *Escherichia coli* minC gene product in two different cell division-inhibition systems, Proc. Natl. Acad. Sci. USA Vol. 87, pp. 1129-1133, Xuan-Chuan Yu and William Margolin Deletion of the min Operon Results in Increased Thermosensitivity of an ftsZ84 Mutant and Abnormal FtsZ Ring Assembly, Placement, and Disassembly, J Bacteriol. 2000 November; 182(21): 6203-6213.

Murphy K C. Targeted chromosomal gene knockout using PCR fragments. Methods Mol Biol. 2011; 765:27-42.

Maral Rahimzadeh, Majid Sadeghizadeh, Farhood Najafi, Seyed Arab, and Hamid Mobasheri Impact of heat shock step on bacterial transformation efficiency, Mol Biol Res Commun. 2016 December; 5(4): 257-261.

https://www.sigmaaldrich.com/content/dam/sigma-aldrich/docs/Sigma/General_Information/lipoprotein_lipase. pdf Mitra, S. D., Afonina, I. and Kline, K. A. (2016) Right Place, Right Time: Focalization of Membrane Proteins in Gram-Positive Bacteria. Trends in Microbiology 24(8): 611-621.

Inselburg J, Segregation into and Replication of Plasmid Deoxyribonucleic Acid in Chromosomeless Segregants of *Escherichia coli* 1970 *J. Bacteriol.* 102(3):642-647

Frazer A C, Curtiss R 3$^{rd}$, Production, properties and utility of bacterial minicells 1975, *Curr. Topics Microbiol. Immunol.* 69:1-84

Reeve, J. N., and N. H. Mendelson. 1973. Pronase digestion of amino acid binding components on the surface of *Bacillus subtilis* cells and minicells. Biochem. Biophys. Res. Commun. 53:1325-1330

Tankersley W G, Woodward J M, Brown A. Induction and isolation of a minicell-producing strain of *Salmonella typhimurium*. Proc Soc Exp Biol Med. 1974 March; 145(3):802-805

Reeve J N, Mendelson N H, Coyne S I, Hallock L L, Cole R M, Minicells of *Bacillus subtilis*, 1973, *J. Bacteriol.* 114(2):860-873

Mendelson N H, Reeve J N, Cole R M, Physiological Studies of *Bacillus subtilis* Minicells 1974 *J. Bacteriol.* 117(3): 1312-1319.

Yang X, Sun S, Wang H F, Hang H Y 2013, Comparison of Autotransporter and Ice Nucleation Protein as Carrier Proteins for Antibody Display on The Cell Surface of *Escherichia coli* Progress in Biochemistry and Biophysics 40(12):1209-1219

Bhosale S H, Rao M B, and Deshpande V V et al 1996, Molecular and Industrial Aspects of Glucose Isomerase, Microbiological reviews, p 280-300

Raza, S; Fransson, L; Hult, K (2001). "Enantioselectivity in *Candida antarctica* lipase B: A molecular dynamics study". Protein Science. 10 (2): 329-338.

What is claimed is:

1. An industrially suitable anucleated cell-based enzyme immobilization and delivery platform, comprising: an intact anucleated cell derived from a protease deficient parental cell, wherein said anucleated cell comprises
   (i) at least one expressed self-assembled enzyme immobilized to the surface of said cell and
   (ii) at least one fusion protein comprising at least one surface expressing moiety and at least one cell adhesion moiety.

2. The anucleated cell-based enzyme immobilization and delivery platform according to claim 1,
   wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

3. The anucleated cell-based enzyme immobilization and delivery platform according to claim 1,
   wherein said surface expressing moiety comprises an exported bacterial protein and is selected from the group consisting of: LamB (lambda receptor), OprF (*Pseudomonas aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

4. The anucleated cell-based enzyme immobilization and delivery platform according to claim 1,
   wherein said cell adhesion moiety comprises a carbohydrate binding module.

5. The anucleated cell-based enzyme immobilization and delivery platform according to claim 4,
   wherein said carbohydrate binding module is selected from the group consisting of: a cellulose binding domain, a xylan binding domain, a chitin binding domain, and a lignin binding domain.

6. The anucleated cell-based enzyme immobilization and delivery platform according to claim 1, wherein said fusion protein increases adhesion of said anucleated cell to a surface of a target.

7. The anucleated cell-based enzyme immobilization and delivery platform according to claim 1, wherein said cell adhesion moiety is a plant adhesion polypeptide that adheres to a plant surface.

8. The anucleated cell-based enzyme immobilization and delivery platform according to claim 1, wherein said fusion protein is present on a surface of the anucleated cell.

9. The anucleated cell-based enzyme immobilization and delivery platform according to claim 4, wherein said carbohydrate binding module is a heterologous carbohydrate binding module that is displayed on a surface of the anucleated cell.

10. The anucleated cell-based enzyme immobilization and delivery platform according to claim 9, wherein said heterologous carbohydrate binding module is a heterologous cellulose binding domain that is displayed on a surface of the anucleated cell.

11. An industrially suitable anucleated cell-based enzyme immobilization and delivery platform, comprising: an intact anucleated cell derived from a protease deficient parental cell, wherein the anucleated cell comprises at least two different expressed self-assembled enzymes immobilized to a surface of said cell, wherein each of the expressed self-assembled enzymes is a fusion protein comprising at least one surface expressing moiety and at least one enzymatically active moiety, and wherein said enzymatically active moiety of a first expressed self-assembled enzyme is lipase and said enzymatically active moiety of a second expressed self-assembled enzyme is not lipase.

12. The anucleated cell-based enzyme immobilization and delivery platform according to claim 11, wherein each of the expressed self-assembled enzymes is heterologous to the parental cell.

13. The anucleated cell-based enzyme immobilization and delivery platform according to claim 11,
    wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

14. The anucleated cell-based enzyme immobilization and delivery platform according to claim 11, wherein said surface expressing moiety comprises an exported bacterial protein and is selected from the group consisting of LamB (lambda receptor), OprF (*Pseudomonas aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

15. The anucleated cell-based enzyme immobilization and delivery platform according to claim 11, wherein the at least two different expressed self-assembled enzymes are co-localized to a desired locus, and wherein each of the expressed self-assembled enzymes have its own enzymatic activity at the desired locus.

16. The anucleated cell-based enzyme immobilization and delivery platform according to claim 11, wherein the expressed self-assembled enzymes are lipase and protease.

17. The anucleated cell-based enzyme immobilization and delivery platform according to 11, wherein the at least two different expressed self-assembled enzymes have a complimentary function.

18. The anucleated cell-based enzyme immobilization and delivery platform according to claim 11, wherein the at least two different expressed self-assembled enzymes act synergistically.

19. The anucleated cell-based enzyme immobilization and delivery platform according to claim 11, wherein the at least two different expressed self-assembled enzymes each work to carry out a portion of an overall enzymatic reaction.

20. An industrially suitable anucleated cell-based enzyme immobilization and delivery platform, comprising: an intact anucleated cell derived from a protease deficient parental cell, wherein the anucleated cell comprises at least two different expressed self-assembled enzymes immobilized to a surface of said cell, wherein each of the expressed self-assembled enzymes is a fusion protein comprising at least one surface expressing moiety and at least one enzymatically active moiety, and wherein said enzymatically active moiety of a first expressed self-assembled enzyme is glucose isomerase and said enzymatically active moiety of a second expressed self-assembled enzyme is not glucose isomerase.

21. The anucleated cell-based enzyme immobilization and delivery platform according to claim 20, wherein the expressed self-assembled enzymes are glucose isomerase and protease.

22. The anucleated cell-based enzyme immobilization and delivery platform according to claim 20, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

23. The anucleated cell-based enzyme immobilization and delivery platform according to claim 20, wherein said surface expressing moiety comprises an exported bacterial protein and is selected from the group consisting of LamB (lambda receptor), OprF (*Pseudomonas aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

24. The anucleated cell-based enzyme immobilization and delivery platform according to claim 20, wherein the at least two different expressed self-assembled enzymes are co-localized to a desired locus, and wherein each of the expressed self-assembled enzymes have its own enzymatic activity at the desired locus.

25. The anucleated cell-based enzyme immobilization and delivery platform according to 20, wherein the at least two different expressed self-assembled enzymes have a complimentary function.

26. The anucleated cell-based enzyme immobilization and delivery platform according to 20, wherein the at least two different expressed self-assembled enzymes act synergistically.

27. The anucleated cell-based enzyme immobilization and delivery platform according to 20, wherein the at least two different expressed self-assembled enzymes each work to carry out a portion of an overall enzymatic reaction.

28. An industrially suitable anucleated cell-based enzyme immobilization and delivery platform, comprising: an intact anucleated cell derived from a protease deficient parental cell, wherein the anucleated cell comprises at least two different expressed self-assembled enzymes immobilized to a surface of said cell, wherein each of the expressed self-assembled enzymes is a fusion protein comprising at least one surface expressing moiety and at least one enzymatically active moiety, and wherein said enzymatically active moiety of a first expressed self-assembled enzyme is protease and said enzymatically active moiety of a second expressed self-assembled enzyme is not protease.

29. The anucleated cell-based enzyme immobilization and delivery platform according to claim 28, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

30. The anucleated cell-based enzyme immobilization and delivery platform according to claim 28, wherein said surface expressing moiety comprises an exported bacterial protein and is selected from the group consisting of LamB (lambda receptor), OprF (*Pseudomonas aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

31. The anucleated cell-based enzyme immobilization and delivery platform according to claim 28, wherein the at least two different expressed self-assembled enzymes are co-localized to a desired locus, and wherein each of the expressed self-assembled enzymes have its own enzymatic activity at the desired locus.

32. The anucleated cell-based enzyme immobilization and delivery platform according to claim 28, wherein the expressed self-assembled enzymes are lipase and protease.

33. The anucleated cell-based enzyme immobilization and delivery platform according to claim 28, wherein the expressed self-assembled enzymes are glucose isomerase and protease.

34. The anucleated cell-based enzyme immobilization and delivery platform according to 28, wherein the at least two different expressed self-assembled enzymes have a complimentary function.

35. The anucleated cell-based enzyme immobilization and delivery platform according to 28, wherein the at least two different expressed self-assembled enzymes act synergistically.

36. The anucleated cell-based enzyme immobilization and delivery platform according to 28, wherein the at least two different expressed self-assembled enzymes each work to carry out a portion of an overall enzymatic reaction.

* * * * *

```
                               SEQUENCE LISTING

<160> NUMBER OF SEQ ID NOS: 44

<210> SEQ ID NO 1
<211> LENGTH: 50
<212> TYPE: DNA
<213> ORGANISM: Escherichia coli

<400> SEQUENCE: 1
cgaagtaaca acaataatgc gtgccataga aattccttgt taaaagggga                50

<210> SEQ ID NO 2
<211> LENGTH: 50
<212> TYPE: DNA
<213> ORGANISM: Escherichia coli

<400> SEQUENCE: 2
cctggcctta ctcaattagc tattaatcat cgccagcgcg cgatgatgtt                50

<210> SEQ ID NO 3
<211> LENGTH: 50
<212> TYPE: DNA
<213> ORGANISM: Escherichia coli

<400> SEQUENCE: 3
ttggctgtgt ttttcttccg cgagagaaag aaatcgagta atgccataac                50

<210> SEQ ID NO 4
<211> LENGTH: 50
<212> TYPE: DNA
<213> ORGANISM: Escherichia coli

<400> SEQUENCE: 4
agaaattcct tgttaaaaag ggatcaattt aacggttgaa cggtcaaagc                50

<210> SEQ ID NO 5
<211> LENGTH: 1773
<212> TYPE: DNA
<213> ORGANISM: Artificial Sequence
<220> FEATURE:
<223> OTHER INFORMATION: AIDA-1 annotated

<400> SEQUENCE: 5
atgaataagg cctacagtat catttggagc cactccagac aggcctggat tgtggcctca       60
gagttagcca gaggacatgg ttttgtcctt gcaaaaaata cactgctggt attggcggtt      120
gtttccacaa tcggaaatgc atttgcagtc gaccaccatc accatcacca tctggaagcg      180
ctgttccagg gtccgggtac ccagaaacag cgtaccgagc tcgaaaacct gtacttccag      240
ggtgaacaga aactgattag cgaagaagat ctgtctagat gaataacaa tggaagcatt       300 gtcattaata acagcattat aaacgggaat attacgaatg atgctgactt aagttttggt      360
acagcaaagc tgctctctgc tacagtgaat ggtagtcttg ttaataacaa aaatatcatt      420
cttaatccta caaaagaaag tgcggccgct ataggtaata ctcttaccgt gtcaaattat      480
actgggacac cggaagtgt tatttctctt ggtggtgtgc ttgaaggaga taattcactt      540
acggaccgtc tggtggtgaa aggtaatacc tctggtcaaa gtgacatcgt ttatgtcaat      600
gaagatggca gtggtggtca gacgagagat ggtattaata ttatttctgt agagggaaat      660
```

```
tctgatgcag aattctctct gaagaaccgc gtagttgccg gagcttatga ttacacactg    720
cagaaaggaa acgagagtgg gacagataat aagggatggt atttaaccag tcatcttccc    780
acatctgata cccggcaata cagaccggag aacggaagtt atgctaccaa tatggcactg    840
gctaactcac tgttcctcat ggatttgaat gagcgtaagc aattcagggc catgagtgat    900
aatacacagc ctgagtctgc atccgtgtgg atgaagatca ctggaggaat aagctctggt    960
aagctgaatg acgggcaaaa taaaacaaca accaatcagt ttatcaatca gctcggggga   1020
gatatttata aattccatgc tgaacaactg ggtgatttta ccttagggat tatgggagga   1080
tacgcgaatg caaaaggtaa aacgataaat tacacgagca acaaagctgc cagaaacaca   1140
ctggatggtt attctgtcgg ggtatacggt acgtggtatc agaatgggga aaatgcaaca   1200
gggctctttg ctgaaacttg gatgcaatat aactggttta atgcatcagt gaaaggtgac   1260
ggactggaag aagaaaaata taatctgaat ggtttaaccg cttctgcagg tgggggatat   1320
aacctgaatg tgcacacatg gacatcaccct gaaggaataa caggtgaatt ctggttacag   1380
cctcatttgc aggctgtctg gatggggtt acaccggata cacatcagga ggataacgga   1440
acggtggtgc agggagcagg gaaaaataat attcagacaa aagcaggtat tcgtgcatcc   1500
tggaaggtga aaagcaccct ggataaggat accgggcgga ggttccgtcc gtatatagag   1560
gcaaactgga tccataacac tcatgaattt ggtgttaaaa tgagtgatga cagccagttg   1620
ttgtcaggta gccgaaatca gggagagata agacaggta ttgaaggggt gattactcaa   1680
aacttgtcag tgaatggcgg agtcgcatat caggcaggag gtcacgggag caatgccatc   1740
tccggagcac tggggataaa atacagcttc tga                                1773

<210> SEQ ID NO 6
<211> LENGTH: 3033
<212> TYPE: DNA
<213> ORGANISM: Artificial Sequence
<220> FEATURE:
<223> OTHER INFORMATION: BrkAutoTransporter_Annotated

<400> SEQUENCE: 6
atgtatctgg atcgctttcg ccagtgcccg agcagcctgc agattccgcg cagcgcgtgg     60
cgcctgcatg cgctggcggc ggcgctggcg ctggcgggca tggcgcgcct ggcgccggcg    120
gcggcgcagg cgccgcagcc gccggtggcg ggcgcgccgc atgcgcagga tgcgggccag    180
gaaggcgaat tgatcatcg cgataacacc ctgattgcgg tgtttgatga tggcgtgggc     240
attaacctgg atgatgatcc ggatgaactg ggcgaaaccg cgccgccgac cctgaaagat    300
attcatatta gcgtggaaca taaaaacccg atgagcaaac cggcgattgg cgtgcgcgtg    360
agcggcgcgg gcgcgcgcct gaccctggcg gcagcaccca ttgatgcgac cgaaggcggc    420
attccggcgg tggtgcgccg cggcggcacc ctggaactgg atggcgtgac cgtggcgggc    480
ggcgaaggca tggaaccgat gaccgtgagc gatgcgggca gccgcctgag cgtgcgcggc    540
ggcgtgctgg gcgcgaagc gccgggcgtg ggcctggtgc gcgcggcgca gggcggccag    600
gcgagcatta ttgatgcgac cctgcagagc attctgggcc cggcgctgat tgcggatggc    660
ggcagcatta gcgtggcggg cggcagcatt gatatggata tgggcccggg ctttccgccg    720
ccgccgccgc cgctgccggg cgcgccgctg gcggcgcatc cgccgctgga tcgcgtggcg    780
gcggtgcatg cgggccagga tgcaaaagtg accctgcgcg aagtggccgct gcgcgcgcat    840 ggcccgcagg cgaccggcgt gtatgcgtat atgccgggca cgaaattac cctgcagggc    900 ggcaccgtga gcgtgcaggg cgatgatggc gcgggcgtgg tggcgggcgc gggcctgctg    960
```

```
gatgcgctgc cgccgggcgg caccgtgcgc ctggatggca ccaccgtgag caccgatggc    1020
gcgaacaccg atgcggtgct ggtgcgcggc gatgcgcgc gcgcggaagt ggtgaacacc    1080
gtgctgcgca ccgcgaaaag cctggcggcg ggcgtgagcg cgcagcatgg cggccgcgtg    1140
accctgcgcc agacccgcat tgaaaccgcg ggcgcgggcg cggaaggcat tagcgtgctg    1200
ggctttgaac cgcagagcgg cagcggcccg gcgagcgtgg atatgcaggg cggcagcatt    1260
accaccaccg gcaaccgcgc ggcgggcatt gcgctgaccc atggcagcgc gcgcctggaa    1320
ggcgtggcgg tgcgcgcgga aggcagcggc agcagcgcgg cgcagctggc gaacggcacc    1380
ctggtggtga gcgcgggcag cctggcgagc gcgcagagcg gcgcgattag cgtgaccgat    1440
accccgctga aactgatgcc gggcgcgctg gcgagcagca ccgtgagcgt gcgcctgacc    1500
gatgcgcgcc ccgcgcaggg cggcaacggc gtgtttctgc agcagcatag caccattccg    1560
gtggcggtgg cgctggaaag cggcgcgctg gcgcgcggcg atattgtggc ggatggcaac    1620
aaaccgctgg atgcgggcat tagcctgagc gtggcgagcg cgcggcgtg gcatggcgcg    1680 acccaggtgc tgcagagcgc gaccctgggc aaaggcggca cctgggtggt gaacgcggat    1740
agccgcgtgc aggatatgag catgcgcggc ggccgcgtgg aatttcaggc gccggcgccg    1800
gaagcgagct ataaaaccct gaccctgcag accctggatg gcaacggcgt gtttgtgctg    1860
aacaccaacg tggcggcggg ccagaacgat cagctgcgcg tgaccggccg cgcggatggc    1920
cagcatcgcg tgctggtgcg caacgcgggc ggcgaagcgg atagccgcgg cgcgcgcctg    1980
ggcctggtgc atacccaggg ccagggcaac gcgacctttc gcctggcgaa cgtgggcaaa    2040
gcggtggatc tgggcacctg cgctatagc ctggcggaag atccgaaaac ccatgtgtgg    2100
agcctgcagc gcgcgggcca ggcgctgagc ggcgcggcga acgcggcggt gaacgcggcg    2160
gatctgagca gcattgcgct ggcggaaagc aacgcgctgg ataaacgcct gggcgaactg    2220
cgcctgcgcg cggatgcggg cggcccgtgg gcgcgcacct ttagcgaacg ccagcagatt    2280
agcaaccgcc atgcgcgcgc gtatgatcag accgtgagcg gcctggaaat tggcctggat    2340
cgcggctgga gcgcgagcgg cggccgctgg tatgcgggcg gcctgctggg ctataccat    2400 gcggatcgca cctatccggg cgatggcggc ggcaaagtga aaggcctgca tgtgggcggc    2460
tatgcggcgt atgtgggcga tggcggctat tatctggata ccgtgctgcg cctgggccgc    2520
tatgatcagc agtataacat tgcgggcacc gatggcggcc gcgtgaccgc ggattatcgc    2580
accagcggcg cggcgtggag cctggaaggc ggccgccgct ttgaactgcc gaacgattgg    2640
tttgcggaac cgcaggcgga agtgatgctg tggcgcacca cgcaaacg ctatcgcgcg    2700 agcaacggcc tgcgcgtgaa agtggatgcg aacaccgcga ccctgggccg cctgggcctg    2760
cgctttggcc gccgcattgc gctggcgggc ggcaacattg tgcagccgta tgcgcgcctg    2820
ggctggaccc aggaatttaa aagcaccggc gatgtgcgca ccaacggcat tggccatgcg    2880
ggcgcgggcc gccatggccg cgtggaactg ggcgcgggcg tggatgcggc gctgggcaaa    2940
ggccataacc tgtatgcgag ctatgaatat gcggcgggcg atcgcattaa cattccgtgg    3000
agctttcatg cgggctatcg ctatagcttt tga                                3033
```

<210> SEQ ID NO 7
<211> LENGTH: 2343
<212> TYPE: DNA
<213> ORGANISM: Artificial Sequence
<220> FEATURE:
<223> OTHER INFORMATION: BrkAutoTransporter_CBM

<400> SEQUENCE: 7

```
atgtatctgg atcgctttcg ccagtgcccg agcagcctgc agattccgcg cagcgcgtgg      60
cgcctgcatg cgctggcggc ggcgctggcg ctggcgggca tggcgcgcct ggcgccggcg     120
gcggcgcagg cgccgcagcc gccggtggcg ggcgcgccgc atgcgcagga tgcgggccac     180
catcaccatc accatgttca gctggttgaa agcggtggtg cactggttca gcctggtggt     240
agcctgcgtc tgagctgtgc agcaagcggt tttccggtta atcgttatag catgcgttgg     300
tatcgtcagg caccgggtaa agaacgtgaa tgggttgcag gtatgagcag tgccggtgat     360
cgtagcagct acgaagatag cgttaaaggt cgttttacca tcagccgtga tgatgcacgt     420
aataccgttt atctgcaaat gaatagcctg aaaccggaag ataccgcagt gtattattgc     480
aacgttaacg tgggctttga atattggggt cagggcaccc aggttaccgt tagcagcaaa     540
ctcgagcggc cgcatcgtga cgcgtcgtct ggtcctgccg gctgccaagt cctttggggc     600
gtgaatcagt ggaacacagg tttcacggcg aatgttaccg tcaagaatac gtcctccgct     660
cctgttgacg gctggacctt gaccttcagt ttcccatcag acaacaagt cactcaagcc      720
tggtcatcta ccgtgaccca gagtggatct gcggtcacag tacgtaacgc tccgtggaac     780
ggttcgattc ccgcgggcgg gactgctcag ttcgggttta acggaagcca cactggcact     840
aatgctgcac caactgcctt ctcacttaac ggcacgccgt gcaccgtagg cgaacagaaa     900
ctgattagcg aagaagatct ggaaaacctg tacttccagg gtgcgggcat tagcctgagc     960
gtggcgagcg gcgcggcgtg gcatggcgcg acccaggtgc tgcagagcgc gaccctgggc    1020
aaaggcggca cctgggtggt gaacgcggat agccgcgtgc aggatatgag catgcgcggc    1080
ggccgcgtgg aatttcaggc gccggcgccg gaagcgagct ataaaaccct gaccctgcag    1140
accctggatg caacggcgt gtttgtgctg aacaccaacg tggcggcggg ccagaacgat     1200
cagctgcgcg tgaccggccg cgcggatggc cagcatcgcg tgctggtgcg caacgcgggc    1260
ggcgaagcgg atagccgcgg cgcgcgcctg ggcctggtgc ataccaggg ccagggcaac     1320
gcgacctttc gcctggcgaa cgtgggcaaa gcggtggatc tgggcacctg cgctatagc     1380
ctggcggaag atccgaaaac ccatgtgtgg agcctgcagc gcgcgggcca ggcgctgagc    1440
ggcgcggcga acgcggcggt gaacgcggcg gatctgagca gcattgcgct ggcggaaagc    1500
aacgcgctgg ataaacgcct gggcgaactg cgcctgcgcg cggatgcggg cggcccgtgg    1560
gcgcgcacct ttagcgaacg ccagcagatt agcaaccgcc atgcgcgcgc gtatgatcag    1620
accgtgagcg gcctggaaat tggcctggat cgcggctgga gcgcgagcgg cggccgctgg    1680
tatgcgggcg gcctgctggg ctataccat gcggatcgca cctatccggg cgatggcggc     1740
ggcaaagtga aaggcctgca tgtgggcggc tatgcgcgt atgtgggcga tggcggctat     1800
tatctggata ccgtgctgcg cctgggccgc tatgatcagc agtataacat tgcgggcacc    1860
gatggcggcc gcgtgaccgc ggattatcgc accagcggcg cggcgtggag cctggaaggc    1920
ggccgccgct ttgaactgcc gaacgattgg tttgcggaac cgcaggcgga agtgatgctg    1980
tggcgcacca gcggcaaacg ctatcgcgcg agcaacggcc tgcgcgtgaa agtggatgcg    2040
aacaccgcga ccctgggccg cctgggcctg cgctttggcc gccgcattgc gctggcgggc    2100
ggcaacattg tgcagccgta tgcgcgcctg ggctggaccc aggaatttaa aagcaccggc    2160
gatgtgcgca ccaacggcat tggccatgcg ggcgcgggcc gccatggccg cgtggaactg    2220
ggcgcgggcg tggatgcggc gctgggcaaa ggccataacc tgtatgcgag ctatgaatat    2280
gcggcgggcg atcgcattaa cattccgtgg agctttcatg cgggctatcg ctatagcttt    2340
```

| | |
|---|---:|
| tga | 2343 |

<210> SEQ ID NO 8
<211> LENGTH: 3258
<212> TYPE: DNA
<213> ORGANISM: Artificial Sequence
<220> FEATURE:
<223> OTHER INFORMATION: BrkAutoTransporter_Lipase

<400> SEQUENCE: 8

| | |
|---|---:|
| atgtatctgg atcgctttcg ccagtgcccg agcagcctgc agattccgcg cagcgcgtgg | 60 |
| cgcctgcatg cgctggcggc ggcgctggcg ctggcgggca tggcgcgcct ggcgccggcg | 120 |
| gcggcgcagg cgccgcagcc gccggtggcg ggcgcgccgc atgcgcagga tgcgggccac | 180 |
| catcaccatc accatgttca gctggttgaa agcggtggtg cactggttca gcctggtggt | 240 |
| agcctgcgtc tgagctgtgc agcaagcggt tttccggtta atcgttatag catgcgttgg | 300 |
| tatcgtcagg caccgggtaa agaacgtgaa tgggttgcag gtatgagcag tgccggtgat | 360 |
| cgtagcagct acgaagatag cgttaaaggt cgttttacca tcagccgtga tgatgcacgt | 420 |
| aataccgttt atctgcaaat gaatagcctg aaaccggaag ataccgcagt gtattattgc | 480 |
| aacgttaacg tgggctttga atattggggt cagggcaccc aggttaccgt tagcagcaaa | 540 |
| ctcgagcggc cgcatcgtga caagtgctgt cggattatgt tgtgttgct cggactgtgg | 600 |
| tttgtgttcg gcctatcggt cccgggaggg cggacggaag cggcatccct acgcgccaac | 660 |
| gacgcaccga ttgtgcttct ccacgggttt accggctggg acgagagga atgtttgga | 720 |
| ttcaagtatt ggggcggcgt gcgcggcgat atcgaacagt ggctgaacga caacggttat | 780 |
| cgaacgtata cgctggcggt cggaccgctc tcgagcaact gggaccgggc gtgtgaagcg | 840 |
| tacgctcagc ttgtcggcgg gacggtcgat tacggggcag cccacgcggc aaagcacggc | 900 |
| cacgcgcggt ttggccgcac ttatcccggc ctgttgccgg aattgaaaag ggtggccgc | 960 |
| atccatatca tcgcccacag ccaaggggg cagacggccc gcatgcttgt ctcgctccta | 1020 |
| gagaacggaa gccaagaaga gcgggagtac gccaagcgcg ataacgtgtc gttgtcaccg | 1080 |
| ttgtttgaag gtggacatca tttttgtgttg agtgtgacga ccatcgccac tcctcacgac | 1140 |
| gggacgacgc ttgtcaacat ggttgatttc accgatcgct tttttgactt gcaaaaagcg | 1200 |
| gtgttggaag cggcggctgt cgccagcaac gtgccgtaca cgagtcaagt atacgatttt | 1260 |
| aagctcgacc aatggggact gcgccgccag ccgggtgaat cgttcgacca ttattttgaa | 1320 |
| cggctcaagc gctcccctgt ttggacgtcc acagataccg cccgctacga tttatccgtt | 1380 |
| tccggagctg agaagctcaa tcagtgggtg caagcaagcc gaatacgta ttatttgagt | 1440 |
| ttctctacag aacggacgta tcgcggagcg ctcacaggca accattatcc cgaactcgga | 1500 |
| atgaacgcat tcagcgcggt cgtgtgcgct ccgtttctcg gttcgtaccg caatccgacg | 1560 |
| ctcggcattg acaccgttg gttggagaac gatggcattg tcaatacggt tccatgaac | 1620 |
| ggtccaaagc gtggatcaag cgatcggatc gtgccgtatg acgggacgtt gaaaaaaggg | 1680 |
| gtttggaacg atatgggaac gtacaacgtc gaccatttgg aaatcatcgg cgttgacccg | 1740 |
| aatccgtcat ttgatattcg cgccttttat ttgcggcttg ccgagcagtt ggcgagcttg | 1800 |
| cggcctgaac agaaactgat tagcgaagaa gatctggaaa acctgtactt ccagggtgcg | 1860 |
| ggcattagcc tgagcgtggc gagcggcgcg cgtggcatg cgcgacccca ggtgctgcag | 1920 |
| agcgcgaccc tgggcaaagg cggcacctgg gtggtgaacg cggatagccg cgtgcaggat | 1980 |

```
atgagcatgc gcggcggccg cgtggaattt caggcgccgg cgccggaagc gagctataaa    2040
accctgaccc tgcagaccct ggatggcaac ggcgtgtttg tgctgaacac caacgtggcg    2100
gcgggccaga cgatcagct gcgcgtgacc ggccgcgcgg atggccagca tcgcgtgctg    2160
gtgcgcaacg cggcggcga gcggatagc gcggcgcgc gcctgggcct ggtgcatacc    2220
cagggccagg gcaacgcgac ctttcgcctg gcgaacgtgg gcaaagcggt ggatctgggc    2280
acctggcgct atagcctggc ggaagatccg aaaacccatg tgtggagcct gcagcgcgcg    2340
ggccaggcgc tgagcggcgc ggcgaacgcg gcggtgaacg cggcggatct gagcagcatt    2400
gcgctggcgg aaagcaacgc gctggataaa cgcctgggcg aactgcgcct gcgcgcggat    2460
gcgggcggcc cgtgggcgcg caccttagc gaacgccagc agattagcaa ccgccatgcg    2520
cgcgcgtatg atcagaccgt gagcggcctg gaaattggcc tggatcgcgg ctggagcgcg    2580
agcggcggcc gctggtatgc gggcggcctg ctgggctata cctatgcgga tcgcacctat    2640
ccgggcgatg gcggcggcaa agtgaaaggc ctgcatgtgg gcggctatgc ggcgtatgtg    2700
ggcgatggcg gctattatct ggataccgtg ctgcgcctgg gccgctatga tcagcagtat    2760
aacattgcgg gcaccgatgg cggccgcgtg accgcggatt atcgcaccag cggcgcggcg    2820
tggagcctgg aaggcggccg ccgctttgaa ctgccgaacg attggttttgc ggaaccgcag    2880 gcggaagtga tgctgtggcg caccagcggc aaacgctatc gcgcgagcaa cggcctgcgc    2940
gtgaaagtga tgcgaacac cgcgaccctg gccgcctgg gcctgcgctt tggccgccgc    3000
attgcgctgg cgggcggcaa cattgtgcag ccgtatgcgc gcctgggctg gacccaggaa    3060
tttaaaagca ccggcgatgt gcgcaccaac ggcattggcc atgcgggcgc gggccgccat    3120
ggccgcgtgg aactgggcgc gggcgtggat gcggcgctgg gcaaaggcca taacctgtat    3180
gcgagctatg aatatgcggc gggcgatcgc attaacattc cgtggagctt tcatgcgggc    3240
tatcgctata gcttttga                                                 3258

<210> SEQ ID NO 9
<211> LENGTH: 330
<212> TYPE: DNA
<213> ORGANISM: Artificial Sequence
<220> FEATURE:
<223> OTHER INFORMATION: CBM

<400> SEQUENCE: 9
gcgtcgtctg gtcctgccgg ctgccaagtc ctttggggcg tgaatcagtg gaacacaggt    60
ttcacggcga atgttaccgt caagaatacg tcctccgctc ctgttgacgg ctggaccttg    120
accttcagtt tcccatcagg acaacaagtc actcaagcct ggtcatctac cgtgacccag    180
agtggatctg cggtcacagt acgtaacgct ccgtggaacg gttcgattcc cgcgggcggg    240
actgctcagt tcgggtttaa cggaagccac actggcacta atgctgcacc aactgccttc    300
tcacttaacg gcacgccgtg caccgtaggc                                    330

<210> SEQ ID NO 10
<211> LENGTH: 696
<212> TYPE: DNA
<213> ORGANISM: Artificial Sequence
<220> FEATURE:
<223> OTHER INFORMATION: GFP-Nanobody CBM

<400> SEQUENCE: 10
gttcagctgg ttgaaagcgg tggtgcactg gttcagcctg gtggtagcct gcgtctgagc    60
tgtgcagcaa gcggttttcc ggttaatcgt tatagcatgc gttggtatcg tcaggcaccg    120
```

```
ggtaaagaac gtgaatgggt tgcaggtatg agcagtgccg gtgatcgtag cagctacgaa        180
gatagcgtta aaggtcgttt taccatcagc cgtgatgatg cacgtaatac cgtttatctg        240
caaatgaata gcctgaaacc ggaagatacc gcagtgtatt attgcaacgt taacgtgggc        300
tttgaatatt ggggtcaggg cacccaggtt accgttagca gcaaactcga gcggccgcat        360
cgtgacgcgt cgtctggtcc tgccggctgc caagtccttt ggggcgtgaa tcagtggaac        420
acaggtttca cggcgaatgt taccgtcaag aatacgtcct ccgctcctgt tgacggctgg        480
accttgacct tcagtttccc atcaggacaa caagtcactc aagcctggtc atctaccgtg        540
acccagagtg gatctgcggt cacagtacgt aacgctccgt ggaacggttc gattcccgcg        600
ggcgggactg ctcagttcgg gtttaacgga agccacactg gcactaatgc tgcaccaact        660
gccttctcac ttaacggcac gccgtgcacc gtaggc                                  696

<210> SEQ ID NO 11
<211> LENGTH: 1611
<212> TYPE: DNA
<213> ORGANISM: Artificial Sequence
<220> FEATURE:
<223> OTHER INFORMATION: GFP-Nanobody Lipase

<400> SEQUENCE: 11
gttcagctgg ttgaaagcgg tggtgcactg gttcagcctg gtggtagcct gcgtctgagc         60
tgtgcagcaa gcggttttcc ggttaatcgt tatagcatgc gttggtatcg tcaggcaccg        120
ggtaaagaac gtgaatgggt tgcaggtatg agcagtgccg gtgatcgtag cagctacgaa        180
gatagcgtta aaggtcgttt taccatcagc cgtgatgatg cacgtaatac cgtttatctg        240
caaatgaata gcctgaaacc ggaagatacc gcagtgtatt attgcaacgt taacgtgggc        300
tttgaatatt ggggtcaggg cacccaggtt accgttagca gcaaactcga gcggccgcat        360
cgtgacaagt gctgtcggat tatgtttgtg ttgctcggac tgtggtttgt gttcggccta        420
tcggtcccgg gagggcggac ggaagcggca tccctacgcg ccaacgacgc accgattgtg        480
cttctccacg ggtttaccgg ctggggacga gaggaaatgt ttggattcaa gtattggggc        540
ggcgtgcgcg cgatatcga acagtggctg aacgacaacg ttatcgaac gtatacgctg        600 gcggtcggac cgctctcgag caactggac cgggcgtgtg aagcgtacgc tcagcttgtc        660
ggcgggacgg tcgattacgg ggcagcccac gcggcaaagc acggccacgc gcggtttggc        720
cgcacttatc ccggcctgtt gccggaattg aaaaggggtg gccgcatcca tatcatcgcc        780
cacagccaag gggggcagac ggcccgcatg cttgtctcgc tcctagagaa cggaagccaa        840
gaagagcggg agtacgccaa ggcgcataac gtgtcgttgt caccgttgtt tgaaggtgga        900
catcattttg tgttgagtgt gacgaccatc gccactcctc acgacgggac gacgcttgtc        960
aacatggttg atttcaccga tcgctttttt gacttgcaaa aagcggtgtt ggaagcggcg       1020
gctgtcgcca gcaacgtgcc gtacacgagt caagtatacg atttttaagct cgaccaatgg       1080 ggactgcgcc gccagccggg tgaatcgttc gaccattatt ttgaacggct caagcgctcc       1140
cctgtttgga cgtccacaga taccgcccgc tacgatttat ccgtttccgg agctgagaag       1200
ctcaatcagt gggtgcaagc aagcccgaat acgtattatt tgagtttctc tacagaacgg       1260
acgtatcgcg gagcgctcac aggcaaccat tatcccgaac tcggaatgaa cgcattcagc       1320
gcggtcgtgt gcgctccgtt tctcggttcg taccgcaatc cgacgctcgg cattgacgac       1380
cgttggttgg agaacgatgg cattgtcaat acggtttcca tgaacggtcc aaagcgtgga       1440
```
tcaagcgatc ggatcgtgcc gtatgacggg acgttgaaaa aagggtttg gaacgatatg    1500 ggaacgtaca acgtcgacca tttggaaatc atcggcgttg acccgaatcc gtcatttgat    1560
attcgcgcct tttatttgcg gcttgccgag cagttggcga gcttgcggcc t             1611

<210> SEQ ID NO 12
<211> LENGTH: 537
<212> TYPE: DNA
<213> ORGANISM: Artificial Sequence
<220> FEATURE:
<223> OTHER INFORMATION: InaK

<400> SEQUENCE: 12
atggtcttag acaaggcgct agttctacgt acctgcgcta ataatatggc cgatcactgc     60
ggcttgattt ggcctgcctc agggaccgtc gagtcaaggt attggcaatc tacacgtcgt    120
cacgagaacg gactggtagg tcttctttgg ggagcaggaa cttctgcttt cttgtcagtc    180
catgcagacg cccgctggat cgtgtgcgaa gtggctgttg ccgatattat ctccctagag    240
gagcccggaa tggttaaatt tcctcgggcc gaagtggtgc atgtgggcga tcgaatcagc    300
gcttctcatt ttatttcggc gcggcaggca gatcccgcga gtacgagtac ttcaacgtcg    360
acaagtactc ttactcccat gcccacggca atccccaccc ctatgccagc ggtggcgtca    420
gtgacgttac cggtggctga gcaagcgcgg catgaggtgt tgatgtagc tagtgtgagc    480 gccgcggctg ctcccgtgaa cactttacct gtcacgacac cccaaaacct ccagacg       537

<210> SEQ ID NO 13
<211> LENGTH: 1305
<212> TYPE: DNA
<213> ORGANISM: Artificial Sequence
<220> FEATURE:
<223> OTHER INFORMATION: InaK-TEV-CBM-His-Myc-GFPNB

<400> SEQUENCE: 13
atggtcttag acaaggcgct agttctacgt acctgcgcta ataatatggc cgatcactgc     60
ggcttgattt ggcctgcctc agggaccgtc gagtcaaggt attggcaatc tacacgtcgt    120
cacgagaacg gactggtagg tcttctttgg ggagcaggaa cttctgcttt cttgtcagtc    180
catgcagacg cccgctggat cgtgtgcgaa gtggctgttg ccgatattat ctccctagag    240
gagcccggaa tggttaaatt tcctcgggcc gaagtggtgc atgtgggcga tcgaatcagc    300
gcttctcatt ttatttcggc gcggcaggca gatcccgcga gtacgagtac ttcaacgtcg    360
acaagtactc ttactcccat gcccacggca atccccaccc ctatgccagc ggtggcgtca    420
gtgacgttac cggtggctga gcaagcgcgg catgaggtgt tgatgtagc tagtgtgagc    480 gccgcggctg ctcccgtgaa cactttacct gtcacgacac cccaaaacct ccagacggaa    540
aacctgtact ccagggtgc gtcgtctggt cctgccggct gccaagtcct tggggcgtg     600 aatcagtgga acacaggttt cacggcgaat gttaccgtca agaatacgtc ctccgctcct    660
gttgacggct ggaccttgac cttcagtttc ccatcaggac aacaagtcac tcaagcctgg    720
tcatctaccg tgacccagag tggatctgcg gtcacagtac gtaacgctcc gtggaacggt    780
tcgattcccg cggcgggac tgctcagttc gggtttaacg gaagccacac tggcactaat    840
gctgcaccaa ctgccttctc acttaacggc acgccgtgca ccgtaggcca ccatcaccat    900
caccatgttc agctggttga aagcggtggt gcactggttc agcctggtgg tagcctgcgt    960
ctgagctgtg cagcaagcgg ttttccggtt aatcgttata gcatgcgttg gtatcgtcag   1020
gcaccgggta agaacgtga atgggttgca ggtatgagca gtgccggtga tcgtagcagc   1080

```
tacgaagata gcgttaaagg tcgttttacc atcagccgtg atgatgcacg taataccgtt   1140
tatctgcaaa tgaatagcct gaaaccggaa gataccgcag tgtattattg caacgttaac   1200
gtgggctttg aatattgggg tcagggcacc caggttaccg ttagcagcaa actcgagcgg   1260
ccgcatcgtg acgaacagaa actgattagc gaagaagatc tgtga                   1305
```

<210> SEQ ID NO 14
<211> LENGTH: 2220
<212> TYPE: DNA
<213> ORGANISM: Artificial Sequence
<220> FEATURE:
<223> OTHER INFORMATION: InaK-TEV-Lipase-His-Myc-GFPNB

<400> SEQUENCE: 14

```
atggtcttag acaaggcgct agttctacgt acctgcgcta ataatatggc cgatcactgc    60
ggcttgattt ggcctgcctc agggaccgtc gagtcaaggt attggcaatc tacacgtcgt   120
cacgagaacg gactggtagg tcttctttgg ggagcaggaa cttctgcttt cttgtcagtc   180
catgcagacg cccgctggat cgtgtgcgaa gtggctgttg ccgatattat ctccctagag   240
gagcccggaa tggttaaatt tcctcggccc gaagtggtgc atgtgggcga tcgaatcagc   300
gcttctcatt ttatttcggc gcggcaggca gatcccgcga gtacgagtac ttcaacgtcg   360
acaagtactc ttactcccat gcccacggca atccccaccc ctatgccagc ggtggcgtca   420
gtgacgttac cggtggctga gcaagcgcgg catgaggtgt tgatgtagc tagtgtgagc   480 gccgcggctg ctcccgtgaa cactttacct gtcacgacac cccaaaacct ccagacggaa   540
aacctgtact ccagggtaa gtgctgtcgg attatgtttg tgttgctcgg actgtggttt   600
gtgttcggcc tatcggtccc gggagggcgg acggaagcgg catccctacg cgccaacgac   660
gcaccgattg tgcttctcca cgggtttacc ggctgggac gagaggaaat gtttggattc   720
aagtattggg gcggcgtgcg cggcgatatc gaacagtggc tgaacgacaa cggttatcga   780
acgtatacgc tggcggtcgg accgctctcg agcaactggg accgggcgtg tgaagcgtac   840
gctcagcttg tcggcgggac ggtcgattac ggggcagccc acgcggcaaa gcacggccac   900
gcgcggtttg gccgcactta tcccggcctg ttgccggaat gaaaagggg tggccgcatc   960 catatcatcg cccacagcca aggggggcag acggcccgca tgcttgtctc gctcctagag  1020
aacggaagcc aagaagagcg ggagtacgcc aaggcgcata acgtgtcgtt gtcaccgttg  1080
tttgaaggtg acatcatttt gtgttgagt gtgacgacca tcgccactcc tcacgacggg  1140
acgacgcttg tcaacatggt tgatttcacc gatcgctttt ttgacttgca aaaagcggtg  1200
ttggaagcgg cggctgtcgc cagcaacgtg ccgtacacga gtcaagtata cgattttaag  1260
ctcgaccaat ggggactgcg ccgccagccg ggtgaatcgt tcgaccatta ttttgaacgg  1320
ctcaagcgct cccctgtttg gacgtccaca gatacccccc gctacgattt atccgttttcc  1380 ggagctgaga agctcaatca gtgggtgcaa gcaagcccga atacgtatta tttgagtttc  1440
tctacagaac ggacgtatcg cggagcgctc acaggcaacc attatcccga actcggaatg  1500
aacgcattca gcgcggtcgt gtgcgctccg tttctcggtt cgtaccgcaa tccgacgctc  1560
ggcattgacg accgttggtt ggagaacgat ggcattgtca atacgtttc catgaacggt  1620 ccaaagcgtg gatcaagcga tcggatcgtg ccgtatgacg ggacgttgaa aaagggggtt  1680
tggaacgata tgggaacgta caacgtcgac catttggaaa tcatcggcgt tgacccgaat  1740
ccgtcatttg atattcgcgc cttttatttg cggcttgccg agcagttggc gagcttgcgg  1800
```

```
cctcaccatc accatcacca tgttcagctg gttgaaagcg gtggtgcact ggttcagcct    1860
ggtggtagcc tgcgtctgag ctgtgcagca agcggttttc cggttaatcg ttatagcatg    1920
cgttggtatc gtcaggcacc gggtaaagaa cgtgaatggg ttgcaggtat gagcagtgcc    1980
ggtgatcgta gcagctacga agatagcgtt aaaggtcgtt ttaccatcag ccgtgatgat    2040
gcacgtaata ccgtttatct gcaaatgaat agcctgaaac cggaagatac cgcagtgtat    2100
tattgcaacg ttaacgtggg ctttgaatat tggggtcagg caccccaggt taccgttagc    2160
agcaaactcg agcggccgca tcgtgacgaa cagaaactga ttagcgaaga agatctgtga    2220
```

<210> SEQ ID NO 15
<211> LENGTH: 1245
<212> TYPE: DNA
<213> ORGANISM: Artificial Sequence
<220> FEATURE:
<223> OTHER INFORMATION: Bacillus sp. 42 thermostable organic solvent
      tolerant lipase gene annotated

<400> SEQUENCE: 15

```
aagtgctgtc ggattatgtt tgtgttgctc ggactgtggt ttgtgttcgg cctatcggtc      60 ccggagggc ggacggaagc ggcatcccta cgcgccaacg acgcaccgat tgtgcttctc     120
cacgggttta ccggctgggg acgagaggaa atgtttggat tcaagtattg gggcggcgtg     180
cgcggcgata tcgaacagtg gctgaacgac aacggttatc gaacgtatac gctggcggtc     240
ggaccgctct cgagcaactg ggaccgggcg tgtgaagcgt acgctcagct tgtcggcggg     300
acggtcgatt acggggcagc ccacgcggca agcacggcc acgcgcggtt tggccgcact     360
tatcccggcc tgttgccgga attgaaaagg ggtggccgca tccatatcat cgcccacagc     420
caaggggggc agacgcccg catgcttgtc tcgctcctag agaacggaag ccaagaagag     480
cgggagtacg ccaaggcgca taacgtgtcg ttgtcaccgt tgtttgaagg tggacatcat     540
tttgtgttga gtgtgacgac catcgccact cctcacgacg gacgacgct tgtcaacatg     600 gttgatttca ccgatcgctt ttttgacttg caaaaagcgg tgttggaagc ggcggctgtc     660
gccagcaacg tgccgtacac gagtcaagta tacgatttta agctcgacca atggggactg     720
cgccgccagc cgggtgaatc gttcgaccat tattttgaac ggctcaagcg ctcccctgtt     780
tggacgtcca cagataccgc ccgctacgat ttatccgttt ccggagctga aagctcaat     840 cagtgggtgc aagcaagccc gaatacgtat tatttgagtt tctctacaga acggacgtat     900
cgcggagcgc tcacaggcaa ccattatccc gaactcggaa tgaacgcatt cagcgcggtc     960
gtgtgcgctc cgtttctcgg ttcgtaccgc aatccgacgc tcggcattga cgaccgttgg    1020
ttggagaacg atggcattgt caatacggtt tccatgaacg gtccaaagcg tggatcaagc    1080
gatcggatcg tgccgtatga cgggacgttg aaaaagggg tttggaacga tatgggaacg    1140
tacaacgtcg accatttgga aatcatcggc gttgacccga atccgtcatt tgatattcgc    1200 gcctttatt tgcggcttgc cgagcagttg gcgagcttgc ggcct                    1245
```

<210> SEQ ID NO 16
<211> LENGTH: 5561
<212> TYPE: DNA
<213> ORGANISM: Artificial Sequence
<220> FEATURE:
<223> OTHER INFORMATION: pAIDA-1

<400> SEQUENCE: 16

```
tttacacttt atgcttccgg ctcgtataat gtgtggaatt gtgagcggat aacaatttca      60
```

```
cacaggaaag cttcatatga ataaggccta cagtatcatt tggagccact ccagacaggc    120
ctggattgtg gcctcagagt tagccagagg acatggtttt gtccttgcaa aaaatacact    180
gctggtattg gcggttgttt ccacaatcgg aaatgcattt gcagtcgacc accatcacca    240
tcaccatctg gaagcgctgt tccagggtcc gggtacccag aaacagcgta ccgagctcga    300
aaacctgtac ttccagggtg aacagaaact gattagcgaa gaagatctgt ctagagtgaa    360
taacaatgga agcattgtca ttaataacag cattataaac gggaatatta cgaatgatgc    420
tgacttaagt tttggtacag caaagctgct ctctgctaca gtgaatggta gtcttgttaa    480
taacaaaaat atcattctta atcctacaaa agaaagtgcg gccgctatag gtaatactct    540
taccgtgtca aattatactg ggacaccggg aagtgttatt tctcttggtg gtgtgcttga    600
aggagataat tcacttacgg accgtctggt ggtgaaaggt aatacctctg gtcaaagtga    660
catcgtttat gtcaatgaag atggcagtgg tggtcagacg agagatggta ttaatattat    720
ttctgtagag ggaaattctg atgcagaatt ctctctgaag aaccgcgtag ttgccggagc    780
ttatgattac acactgcaga aaggaaacga gagtgggaca gataataagg gatggtattt    840
aaccagtcat cttcccacat ctgatacccg gcaatacaga ccggagaacg gaagttatgc    900
taccaatatg gcactggcta actcactgtt cctcatggat ttgaatgagc gtaagcaatt    960
cagggccatg agtgataata cacagcctga gtctgcatcc gtgtggatga agatcactgg   1020
aggaataagc tctggtaagc tgaatgacgg gcaaaataaa acaacaacca atcagtttat   1080
caatcagctc gggggggata tttataaatt ccatgctgaa caactgggtg attttacctt   1140
agggattatg gaggatacg cgaatgcaaa aggtaaaacg ataaattaca cgagcaacaa   1200
agctgccaga aacacactgg atggttattc tgtcgggta tacggtacgt ggtatcagaa   1260
tggggaaaat gcaacagggc tctttgctga aacttggatg caatataact ggtttaatgc   1320
atcagtgaaa ggtgacggac tggaagaaga aaaatataat ctgaatggtt taaccgcttc   1380
tgcaggtggg ggatataacc tgaatgtgca cacatggaca tcacctgaag gaataacagg   1440
tgaattctgg ttacagcctc atttgcaggc tgtctggatg ggggttacac cggatacaca   1500
tcaggaggat aacggaacgg tggtgcaggg agcaggaaa aataatattc agacaaaagc   1560
aggtattcgt gcatcctgga aggtgaaaag caccctggat aaggataccg ggcggaggtt   1620
ccgtccgtat atagaggcaa actggatcca taacactcat gaatttggtg ttaaaatgag   1680
tgatgacagc cagttgttgt caggtagccg aaatcaggga gagataaaga caggtattga   1740
aggggtgatt actcaaaaact tgtcagtgaa tggcggagtc gcatatcagg caggaggtca   1800
cgggagcaat gccatctccg gagcactggg gataaaatac agcttctgat aatgatcctg   1860
gcacgcggcg cgcccctggg tgcgcaaact attaactggc gaactactta ctctagcttc   1920
ccggcaacaa ttaatagact ggatggaggc ggataaagtt gcaggaccac ttctgcgctc   1980
ggcccttccg gctggctggt ttattgctga taaatctgga gccggtgagc gtgggtctcg   2040
cggtatcatt gcagcactgg ggccagatgg taagccctcc cgtatcgtag ttatctacac   2100
gacggggagt caggcaacta tggatgaacg aaatagacag atcgctgaga taggtgcctc   2160
actgattaag cattggtaac tgtcagacca agtttactca tatatacttt agattgattt   2220
aaaacttcat ttttaattta aaaggatcta ggtgaagatc cttttttgata atctcatgac   2280 caaaatccct taacgtgagt tttcgttcca ctgagcgtca gacccccttaa taagatgatc   2340 ttcttgagat cgttttggtc tgcgcgtaat ctcttgctct gaaaacgaaa aaaccgcctt   2400
gcagggcggt ttttcgaagg ttctctgagc taccaactct ttgaaccgag gtaactggct   2460
```

-continued

```
tggaggagcg cagtcaccaa aacttgtcct ttcagtttag ccttaaccgg cgcatgactt    2520
caagactaac tcctctaaat caattaccag tggctgctgc cagtggtgct tttgcatgtc    2580
tttccgggtt ggactcaaga cgatagttac cggataaggc gcagcggtcg gactgaacgg    2640
ggggttcgtg catacagtcc agcttggagc gaactgccta cccggaactg agtgtcaggc    2700
gtggaatgag acaaacgcgg ccataacagc ggaatgacac cggtaaaccg aaaggcagga    2760
acaggagagc gcacgaggga gccgccaggg ggaaacgcct ggtatcttta tagtcctgtc    2820
gggtttcgcc accactgatt tgagcgtcag atttcgtgat gcttgtcagg ggggcggagc    2880
ctatggaaaa acggctttgc cgcggccctc tcacttccct gttaagtatc ttcctggcat    2940
cttccaggaa atctccgccc cgttcgtaag ccatttccgc tcgccgcagt cgaacgaccg    3000
agcgtagcga gtcagtgagc gaggaagcgg aatatatcct gtatcacata ttctgctgac    3060
gcaccggtgc agcctttttt ctcctgccac atgaagcact tcactgacac cctcatcagt    3120
gccaacatag taagccagta tacactccgc tagcgctgag gtctgcctcg tgaagaaggt    3180
gttgctgact cataccaggc ctgaatcgcc ccatcatcca gccagaaagt gagggagcca    3240
cggttgatga gagctttgtt gtaggtggac cagttggtga ttttgaactt ttgctttgcc    3300
acggaacggt ctgcgttgtc gggaagatgc gtgatctgat ccttcaactc agcaaaagtt    3360
cgatttattc aacaaagcca cgttgtgtct caaaatctct gatgttacat tgcacaagat    3420
aaaaatatat catcatgaac aataaaactg tctgcttaca taaacagtaa tacaagggtg    3480
gttatgagcc atattcaacg ggaaacgtct tgctcgagta tccgctcatg agattatcaa    3540
aaaggatctt cacctagatc cttttgtaag aggttccaac tttcaccata tgaaataag    3600 atcactaccg ggcgtatttt ttgagttatc gagattttca ggagctaagg aagctaaaat    3660
ggagaaaaaa atcactggat ataccaccgt tgatatatcc caatggcatc gtaaagaaca    3720
ttttgaggca tttcagtcag ttgctcaatg tacctataac cagaccgttc agctggatat    3780
tacggccttt ttaaagaccg taaagaaaaa taagcacaag ttttatccgg cctttattca    3840
cattcttgcc cgcctgatga atgctcatcc ggagtttcgt atggcaatga agacggtga    3900 gctggtgata tgggatagtg ttcacccttg ttacaccgtt ttccatgagc aaactgaaac    3960
gttttcatcg ctctggagtg aataccacga cgatttccgg cagtttctac acatatattc    4020
gcaagatgtg gcgtgttacg gtgaaaacct ggcctatttc cctaaagggt ttattgagaa    4080
tatgtttttc gtctcagcca atccctgggt gagtttcacc agttttgatt taaacgtggc    4140
caatatggac aacttcttcg cccccgtttt caccatggga aaatattata cgcaaggcga    4200
caaggtgctg atgccgctgg cgattcaggt tcatcatgcc gtttgtgatg cttccatgt    4260 cggcagaatg cttaatgaat tacaacagta ctgcgatgag tggcagggcg gggcgtaatt    4320 ttttttaaggc gacaccatcg aatggcgcaa aacctttcgc ggtatggcat gatagcgccc    4380
ggaagagagt caattcaggg tggtgaatgt gaaaccagta acgttatacg atgtcgcaga    4440
gtatgccggt gtctcttatc agaccgtttc ccgcgtggtg aaccaggcca gccacgtttc    4500
tgcgaaaacg cgggaaaaag tggaagcgg gatggcggag ctgaattaca ttcccaaccg    4560
cgtggcacaa caactggcgg gcaaacagtc gttgctgatt ggcgttgcca cctccagtct    4620
ggccctgcac gcgccgtcgc aaattgtcgc ggcgattaaa tctcgcgccg atcaactggg    4680
tgccagcgtg gtggtgtcga tggtagaacg aagcggcgtc gaagcctgta aagcggcggt    4740
gcacaatctt ctcgcgcaac gcgtcagtgg gctgatcatt aactatccgc tggatgacca    4800
```

| | |
|---|---|
| ggatgccatt gctgtggaag ctgcctgcac taatgttccg gcgttatttc ttgatgtctc | 4860 |
| tgaccagaca cccatcaaca gtattatttt ctcccatgaa gacggtacgc gactgggcgt | 4920 |
| ggagcatctg gtcgcattgg gtcaccagca aatcgcgctg ttagcgggcc cattaagttc | 4980 |
| tgtctcggcg cgtctgcgtc tggctggctg gcataaatat ctcactcgca atcaaattca | 5040 |
| gccgatagcg gaacgggaag gcgactggag tgccatgtcc ggttttcaac aaaccatgca | 5100 |
| aatgctgaat gagggcatcg ttcccactgc gatgctggtt gccaacgatc agatggcgct | 5160 |
| gggcgcaatg cgcgccatta ccgagtccgg gctgcgcgtt ggtgcggata tctcggtagt | 5220 |
| gggatacgac gataccgaag acagctcatg ttatatcccg ccgttaacca ccatcaaaca | 5280 |
| ggattttcgc ctgctggggc aaaccagcgt ggaccgcttg ctgcaactct ctcagggcca | 5340 |
| ggcggtgaag ggcaatcagc tgttgcccgt ctcactggtg aaaagaaaaa ccaccctggc | 5400 |
| gcccaatacg caaaccgcct ctccccgcgc gttggccgat tcattaatgc agctggcacg | 5460 |
| acaggtttcc cgactgggaa gcgggcaagt gagtggataa ccgtattacc gcctttgagt | 5520 |
| gagctgatac cgggaattct cactcattag gcaccccagg c | 5561 |

<210> SEQ ID NO 17
<211> LENGTH: 6242
<212> TYPE: DNA
<213> ORGANISM: Artificial Sequence
<220> FEATURE:
<223> OTHER INFORMATION: pAIDA-1_CBM-Nanobody

<400> SEQUENCE: 17

| | |
|---|---|
| tttacactt atgcttccgg ctcgtataat gtgtggaatt gtgagcggat aacaatttca | 60 |
| cacaggaaag cttcatatga ataaggccta cagtatcatt tggagccact ccagacaggc | 120 |
| ctggattgtg gcctcagagt tagccagagg acatggtttt gtccttgcaa aaatacact | 180 |
| gctggtattg gcggttgttt ccacaatcgg aaatgcattt cagtcgacc accatcacca | 240 |
| tcaccatctg gaagcgctgt tccagggtcc gggtaccgtt cagctggttg aaagcggtgg | 300 |
| tgcactggtt cagcctggtg gtagcctgcg tctgagctgt gcagcaagcg gttttccggt | 360 |
| taatcgttat agcatgcgtt ggtatcgtca ggcaccgggg aaagaacgtg aatgggttgc | 420 |
| aggtatgagc agtgccggtg atcgtagcag ctacgaagat agcgttaaag gtcgttttac | 480 |
| catcagccgt gatgatgcac gtaataccgt ttatctgcaa atgaatagcc tgaaaccgga | 540 |
| agataccgca gtgtattatt gcaacgttaa cgtgggcttt gaatattggg gtcagggcac | 600 |
| ccaggttacc gttagcagca aactcgagcg gccgcatcgt gacgcgtcgt ctggtcctgc | 660 |
| cggctgccaa gtcctttggg gcgtgaatca gtggaacaca ggtttcacgg cgaatgttac | 720 |
| cgtcaagaat acgtcctccg ctcctgttga cggctggacc ttgaccttca gtttcccatc | 780 |
| aggacaacaa gtcactcaag cctggtcatc taccgtgacc cagagtggat ctgcggtcac | 840 |
| agtacgtaac gctccgtgga acggttcgat cccgcggggc gggactgctc agttcgggtt | 900 |
| taacggaagc cacactggca ctaatgctgc accaactgcc ttctcactta acggcacgcc | 960 |
| gtgcaccgta ggcgagctcg aaaacctgta cttccagggt gaacagaaac tgattagcga | 1020 |
| agaagatctg tctagagtga ataacaatgg aagcattgtc attaataaca gcattataaa | 1080 |
| cgggaatatt acgaatgatg ctgacttaag ttttggtaca gcaaagctgc tctctgctac | 1140 |
| agtgaatggt agtcttgtta ataacaaaaa tatcattctt aatcctacaa aagaaagtgc | 1200 |
| ggccgctata ggtaatactc ttaccgtgtc aaattatact gggacaccgg aagtgttat | 1260 |
| ttctcttggt ggtgtgcttg aaggagataa ttcacttacg gaccgtctgg tggtgaaagg | 1320 |

```
taatacctct ggtcaaagtg acatcgttta tgtcaatgaa gatggcagtg gtggtcagac     1380
gagagatggt attaatatta tttctgtaga gggaaattct gatgcagaat tctctctgaa     1440
gaaccgcgta gttgccggag cttatgatta cacactgcag aaaggaaacg agagtgggac     1500
agataataag ggatggtatt taaccagtca tcttcccaca tctgataccc ggcaatacag     1560
accggagaac ggaagttatg ctaccaatat ggcactggct aactcactgt tcctcatgga     1620
tttgaatgag cgtaagcaat tcagggccat gagtgataat acacagcctg agtctgcatc     1680
cgtgtggatg aagatcactg gaggaataag ctctggtaag ctgaatgacg ggcaaaataa     1740
aacaacaacc aatcagttta tcaatcagct cgggggggga atttataaat tccatgctga     1800
acaactgggt gattttacct tagggattat gggaggatac gcgaatgcaa aggtaaaac     1860 gataaattac acgagcaaca aagctgccag aaacacactg gatggttatt ctgtcgggt      1920 atacggtacg tggtatcaga atggggaaaa tgcaacaggg ctctttgctg aaacttggat     1980
gcaatataac tggtttaatg catcagtgaa aggtgacgga ctggaagaag aaaaatataa     2040
tctgaatggt ttaaccgctt ctgcaggtgg gggatataac ctgaatgtgc acacatggac     2100
atcacctgaa ggaataacag gtgaattctg gttacagcct catttgcagg ctgtctggat     2160
gggggttaca ccggatacac atcaggagga taacggaacg gtggtgcagg gagcagggaa     2220
aaataatatt cagacaaaag caggtattcg tgcatcctgg aaggtgaaaa gcaccctgga     2280
taaggatacc gggcggaggt tccgtccgta tatagaggca aactggatcc ataacactca     2340
tgaatttggt gttaaaatga gtgatgacag ccagttgttg tcaggtagcc gaaatcaggg     2400
agagataaag acaggtattg aagggggtgat tactcaaaac ttgtcagtga atggcggagt     2460
cgcatatcag gcaggaggtc acgggagcaa tgccatctcc ggagcactgg ggataaaata     2520
cagcttctga taatgatcct ggcacgcggc gcgccccttg gtgcgcaaac tattaactgg     2580
cgaactactt actctagctt cccggcaaca attaatagac tggatggagg cggataaagt     2640
tgcaggacca cttctgcgct cggcccttcc ggctggctgg tttattgctg ataaatctgg     2700
agccggtgag cgtgggtctc gcggtatcat tgcagcactg gggccagatg gtaagccctc     2760
ccgtatcgta gttatctaca cgacggggag tcaggcaact atggatgaac gaaatagaca     2820
gatcgctgag ataggtgcct cactgattaa gcattggtaa ctgtcagacc aagtttactc     2880
atatatactt tagattgatt taaaacttca tttttaattt aaaaggatct aggtgaagat     2940
cctttttgat aatctcatga ccaaaatccc ttaacgtgag ttttcgttcc actgagcgtc     3000
agacccctta ataagatgat cttcttgaga tcgttttggt ctgcgcgtaa tctcttgctc     3060
tgaaaacgaa aaaccgcct tgcagggcgg ttttcgaag gttctctgag ctaccaactc      3120
tttgaaccga ggtaactggc ttggaggagc gcagtcacca aaacttgtcc tttcagttta     3180
gccttaaccg gcgcatgact tcaagactaa ctcctctaaa tcaattacca gtggctgctg     3240
ccagtggtgc ttttgcatgt ctttccgggt tggactcaag acgatagtta ccggataagg     3300
cgcagcggtc ggactgaacg gggggttcgt gcatacagtc cagcttggag cgaactgcct     3360
acccggaact gagtgtcagg cgtggaatga gacaaacgcg gccataacag cggaatgaca     3420
ccggtaaacc gaaaggcagg aacaggagag cgcacgaggg agccgccagg ggaaacgcc      3480 tggtatcttt atagtcctgt cgggtttcgc caccactgat ttgagcgtca gatttcgtga     3540
tgcttgtcag ggggcggag cctatggaaa aacggctttg ccgcggccct ctcacttccc      3600
tgttaagtat cttcctggca tcttccagga aatctccgcc ccgttcgtaa gccatttccg     3660
```

| | |
|---|---|
| ctcgccgcag tcgaacgacc gagcgtagcg agtcagtgag cgaggaagcg gaatatatcc | 3720 |
| tgtatcacat attctgctga cgcaccggtg cagccttttt tctcctgcca catgaagcac | 3780 |
| ttcactgaca ccctcatcag tgccaacata gtaagccagt atacactccg ctagcgctga | 3840 |
| ggtctgcctc gtgaagaagg tgttgctgac tcataccagg cctgaatcgc ccatcatcc | 3900 |
| agccagaaag tgagggagcc acggttgatg agagctttgt tgtaggtgga ccagttggtg | 3960 |
| attttgaact tttgctttgc cacggaacgg tctgcgttgt cgggaagatg cgtgatctga | 4020 |
| tccttcaact cagcaaaagt tcgatttatt caacaaagcc acgttgtgtc tcaaaatctc | 4080 |
| tgatgttaca ttgcacaaga taaaaatata tcatcatgaa caataaaact gtctgcttac | 4140 |
| ataaacagta atacaagggg tgttatgagc catattcaac gggaaacgtc ttgctcgagt | 4200 |
| atccgctcat gagattatca aaaggatct tcacctagat ccttttgtaa gaggttccaa | 4260 |
| ctttcaccat aatgaaataa gatcactacc gggcgtattt tttgagttat cgagattttc | 4320 |
| aggagctaag gaagctaaaa tggagaaaaa aatcactgga tataccaccg ttgatatatc | 4380 |
| ccaatggcat cgtaaagaac attttgaggc atttcagtca gttgctcaat gtacctataa | 4440 |
| ccagaccgtt cagctggata ttacggcctt tttaaagacc gtaaagaaaa ataagcacaa | 4500 |
| gttttatccg gcctttattc acattcttgc ccgcctgatg aatgctcatc cggagtttcg | 4560 |
| tatggcaatg aaagacggtg agctggtgat atgggatagt gttcacccct tgttacaccgt | 4620 |
| tttccatgag caaactgaaa cgttttcatc gctctggagt gaataccacg acgatttccg | 4680 |
| gcagtttcta cacatatatt cgcaagatgt ggcgtgttac ggtgaaaacc tggcctattt | 4740 |
| ccctaaaggg tttattgaga atatgttttt cgtctcagcc aatccctggg tgagtttcac | 4800 |
| cagttttgat ttaaacgtgg ccaatatgga aacttcttc gccccgttt tcaccatggg | 4860 |
| caaatattat acgcaaggcg acaaggtgct gatgccgctg gcgattcagg ttcatcatgc | 4920 |
| cgtttgtgat ggcttccatg tcggcagaat gcttaatgaa ttacaacagt actgcgatga | 4980 |
| gtggcagggc ggggcgtaat ttttttaagg cgacaccatc gaatggcgca aaacctttcg | 5040 |
| cggtatggca tgatagcgcc cggaagagag tcaattcagg gtggtgaatg tgaaaccagt | 5100 |
| aacgttatac gatgtcgcag agtatgccgg tgtctcttat cagaccgttt cccgcgtggt | 5160 |
| gaaccaggcc agccacgttt ctgcgaaaac gcgggaaaaa gtggaagcgg cgatggcgga | 5220 |
| gctgaattac attcccaacc gcgtggcaca acaactggcg gcaaacagt cgttgctgat | 5280 |
| tggcgttgcc acctccagtc tggccctgca cgcgccgtcg caaattgtcg cggcgattaa | 5340 |
| atctcgcgcc gatcaactgg gtgccagcgt ggtggtgtcg atggtagaac gaagcggcgt | 5400 |
| cgaagcctgt aaagcggcgg tgcacaatct tctcgcgcaa cgcgtcagtg ggctgatcat | 5460 |
| taactatccg ctggatgacc aggatgccat tgctgtggaa gctgcctgca ctaatgttcc | 5520 |
| ggcgttattt cttgatgtct ctgaccagac acccatcaac agtattattt tctcccatga | 5580 |
| agacggtacg cgactgggcg tggagcatct ggtcgcattg ggtcaccagc aaatcgcgct | 5640 |
| gttagcgggc ccattaagtt ctgtctcggc gcgtctgcgt ctggctggct ggcataaata | 5700 |
| tctcactcgc aatcaaattc agccgatagc ggaacgggaa ggcgactgga gtgccatgtc | 5760 |
| cggttttcaa caaccatgc aaatgctgaa tgagggcatc gttcccactg cgatgctggt | 5820 |
| tgccaacgat cagatggcgc tgggcgcaat gcgcgccatt accgagtccg gctgcgcgt | 5880 |
| tggtgcggat atctcggtag tgggatacga cgataccgaa gacagctcat gttatatccc | 5940 |
| gccgttaacc accatcaaac aggattttcg cctgctgggg caaaccagcg tggaccgctt | 6000 |
| gctgcaactc tctcagggcc aggcggtgaa gggcaatcag ctgttgcccg tctcactggt | 6060 |

| | |
|---|---:|
| gaaaagaaaa accaccctgg cgcccaatac gcaaaccgcc tctccccgcg cgttggccga | 6120 |
| ttcattaatg cagctggcac gacaggtttc ccgactggaa agcgggcaag tgagtggata | 6180 |
| accgtattac cgcctttgag tgagctgata ccgggaattc tcactcatta ggcacccag | 6240 |
| gc | 6242 |

<210> SEQ ID NO 18
<211> LENGTH: 7157
<212> TYPE: DNA
<213> ORGANISM: Artificial Sequence
<220> FEATURE:
<223> OTHER INFORMATION: pAIDA-1_GFP-Nanobody_Lipase

<400> SEQUENCE: 18

| | |
|---|---:|
| tttacacttt atgcttccgg ctcgtataat gtgtggaatt gtgagcggat aacaatttca | 60 |
| cacaggaaag cttcatatga ataaggccta cagtatcatt tggagccact ccagacaggc | 120 |
| ctggattgtg gcctcagagt tagccagagg acatggtttt gtccttgcaa aaatacact | 180 |
| gctggtattg gcggttgttt ccacaatcgg aaatgcattt gcagtcgacc accatcacca | 240 |
| tcaccatctg gaagcgctgt tccagggtcc gggtaccgtt cagctggttg aaagcggtgg | 300 |
| tgcactggtt cagcctggtg gtagcctgcg tctgagctgt gcagcaagcg ttttccggt | 360 |
| taatcgttat agcatgcgtt ggtatcgtca ggcaccgggt aaagaacgtg aatgggttgc | 420 |
| aggtatgagc agtgccggtg atcgtagcag ctacgaagat agcgttaaag tcgttttac | 480 |
| catcagccgt gatgatgcac gtaataccgt ttatctgcaa atgaatagcc tgaaaccgga | 540 |
| agataccgca gtgtattatt gcaacgttaa cgtgggcttt gaatattggg gtcagggcac | 600 |
| ccaggttacc gttagcagca aactcgagcg gccgcatcgt gacaagtgct gtcggattat | 660 |
| gtttgtgttg ctcggactgt ggtttgtgtt cggcctatcg gtcccgggag ggcggacgga | 720 |
| agcggcatcc ctacgcgcca acgacgcacc gattgtgctt ctccacgggt ttaccggctg | 780 |
| gggacgagag gaaatgtttg gattcaagta ttggggcggc gtgcgcggcg atatcgaaca | 840 |
| gtggctgaac gacaacggtt atcgaacgta tacgctggcg gtcggaccgc tctcgagcaa | 900 |
| ctgggaccgg gcgtgtgaag cgtacgctca gcttgtcggc gggacggtcg attacgggc | 960 |
| agcccacgcg gcaaagcacg gccacgcgcg gtttggccgc acttatcccg gctgttgcc | 1020 |
| ggaattgaaa aggggtggcc gcatccatat catcgcccac agccaagggg ggcagacggc | 1080 |
| ccgcatgctt gtctcgctcc tagagaacgg aagccaagaa gagcgggagt acgccaaggc | 1140 |
| gcataacgtg tcgttgtcac cgttgtttga aggtggacat catttgtgt tgagtgtgac | 1200 |
| gaccatcgcc actcctcacg acgggacgac gcttgtcaac atggttgatt tcaccgatcg | 1260 |
| cttttttgac ttgcaaaaag cggtgttgga agcggcggct gtcgccagca acgtgccgta | 1320 |
| cacgagtcaa gtatacgatt ttaagctcga ccaatgggga ctgcgccgcc agccgggtga | 1380 |
| atcgttcgac cattattttg aacgctcaa gcgctcccct gtttgacgt ccacagatac | 1440 |
| cgcccgctac gatttatccg tttccggagc tgagaagctc aatcagtggg tgcaagcaag | 1500 |
| cccgaatacg tattatttga gtttctctac agaacggacg tatcgcggag cgctcacagg | 1560 |
| caaccattat cccgaactcg gaatgaacgc attcagcgcg gtcgtgtgcg ctccgtttct | 1620 |
| cggttcgtac cgcaatccga cgctcggcat tgacgaccgt tggttggaga acgatggcat | 1680 |
| tgtcaatacg gttccatga acggtccaaa gcgtggatca agcgatcgga tcgtgccgta | 1740 |
| tgacgggacg ttgaaaaaag gggtttggaa cgatatggga acgtacaacg tcgaccattt | 1800 |

```
ggaaatcatc ggcgttgacc cgaatccgtc atttgatatt cgcgcctttt atttgcggct    1860
tgccgagcag ttggcgagct tgcggcctga gctcgaaaac ctgtacttcc agggtgaaca    1920
gaaactgatt agcgaagaag atctgtctag agtgaataac aatggaagca ttgtcattaa    1980
taacagcatt ataaacggga atattacgaa tgatgctgac ttaagttttg gtacagcaaa    2040
gctgctctct gctacagtga atggtagtct tgttaataac aaaaatatca ttcttaatcc    2100
tacaaaagaa agtgcggccg ctataggtaa tactcttacc gtgtcaaatt atactgggac    2160
accgggaagt gttatttctc ttggtggtgt gcttgaagga gataattcac ttacggaccg    2220
tctggtggtg aaaggtaata cctctggtca aagtgacatc gtttatgtca atgaagatgg    2280
cagtggtggt cagacgagag atggtattaa tattatttct gtagagggaa attctgatgc    2340
agaattctct ctgaagaacc gcgtagttgc cggagcttat gattacacac tgcagaaagg    2400
aaacgagagt gggacagata taagggatg gtatttaacc agtcatcttc ccacatctga    2460
tacccggcaa tacagaccgg agaacggaag ttatgctacc aatatggcac tggctaactc    2520
actgttcctc atggatttga atgagcgtaa gcaattcagg gccatgagtg ataatacaca    2580
gcctgagtct gcatccgtgt ggatgaagat cactggagga ataagctctg gtaagctgaa    2640
tgacgggcaa aataaaacaa caaccaatca gtttatcaat cagctcgggg gggatattta    2700
taaattccat gctgaacaac tgggtgattt taccttaggg attatgggag gatacgcgaa    2760
tgcaaaaggt aaaacgataa attacacgag caacaaagct gccagaaaca cactggatgg    2820
ttattctgtc ggggtatacg gtacgtggta tcagaatggg gaaaatgcaa cagggctctt    2880
tgctgaaact tggatgcaat ataactggtt taatgcatca gtgaaaggtg acggactgga    2940
agaagaaaaa tataatctga atggtttaac cgcttctgca ggtgggggat ataacctgaa    3000
tgtgcacaca tggacatcac ctgaaggaat aacaggtgaa ttctggttac agcctcattt    3060
gcaggctgtc tggatggggg ttacaccgga tacacatcag gaggataacg gaacggtggt    3120
gcagggagca gggaaaaata atattcagac aaaagcaggt attcgtgcat cctgaaggt    3180 gaaaagcacc ctggataagg ataccgggcg gaggttccgt ccgtatatag aggcaaactg    3240
gatccataac actcatgaat ttggtgttaa aatgagtgat gacagccagt tgttgtcagg    3300
tagccgaaat cagggagaga taaagacagg tattgaaggg gtgattactc aaaacttgtc    3360
agtgaatggc ggagtcgcat atcaggcagg aggtcacggg agcaatgcca tctccggagc    3420
actggggata aaatacagct tctgataatg atcctggcac gcggcgcgcc ccttggtgcg    3480
caaactatta actggcgaac tacttactct agcttcccgg caacaattaa tagactggat    3540
ggaggcggat aaagttgcag gaccacttct gcgctcggcc cttccggctg ctggtttat    3600 tgctgataaa tctggagccg gtgagcgtgg gtctcgcggt atcattgcag cactggggcc    3660
agatggtaag ccctcccgta tcgtagttat ctacacgacg gggagtcagg caactatgga    3720
tgaacgaaat agacagatcg ctgagatagg tgcctcactg attaagcatt ggtaactgtc    3780
agaccaagtt tactcatata tactttagat tgatttaaaa cttcattttt aatttaaaag    3840
gatctaggtg aagatccttt ttgataatct catgaccaaa atcccttaac gtgagttttc    3900
gttccactga gcgtcagacc ccttaataag atgatcttct tgagatcgtt ttggtctgcg    3960
cgtaatctct tgctctgaaa acgaaaaaac cgccttgcag gcgcgttttt cgaaggttct    4020
ctgagctacc aactctttga accgaggtaa ctggcttgga ggagcgcagt caccaaaact    4080
tgtcctttca gtttagcctt aaccggcgca tgacttcaag actaactcct ctaaatcaat    4140
taccagtggc tgctgccagt ggtgcttttg catgtctttc cgggttggac tcaagacgat    4200
```

```
agttaccgga taaggcgcag cggtcggact gaacgggggg ttcgtgcata cagtccagct      4260
tggagcgaac tgcctacccg gaactgagtg tcaggcgtgg aatgagacaa acgcggccat      4320
aacagcggaa tgacaccggt aaaccgaaag gcaggaacag gagagcgcac gagggagccg      4380 ccaggggaa acgcctggta tctttatagt cctgtcgggt ttcgccacca ctgatttgag       4440
cgtcagattt cgtgatgctt gtcagggggg cggagcctat ggaaaaacgg ctttgccgcg      4500
gccctctcac ttccctgtta agtatcttcc tggcatcttc caggaaatct ccgcccgtt       4560 cgtaagccat ttccgctcgc cgcagtcgaa cgaccgagcg tagcgagtca gtgagcgagg      4620
aagcggaata tatcctgtat cacatattct gctgacgcac cggtgcagcc ttttttctcc      4680
tgccacatga agcacttcac tgacaccctc atcagtgcca acatagtaag ccagtataca      4740
ctccgctagc gctgaggtct gcctcgtgaa gaaggtgttg ctgactcata ccaggcctga      4800
atcgccccat catccagcca gaaagtgagg gagccacggt tgatgagagc tttgttgtag      4860
gtggaccagt tggtgatttt gaactttgc tttgccacgg aacggtctgc gttgtcggga       4920
agatgcgtga tctgatcctt caactcagca aaagttcgat ttattcaaca aagccacgtt      4980
gtgtctcaaa atctctgatg ttacattgca caagataaaa atatatcatc atgaacaata      5040
aaactgtctg cttacataaa cagtaataca aggggtgtta tgagccatat tcaacgggaa      5100
acgtcttgct cgagtatccg ctcatgagat tatcaaaaag gatcttcacc tagatccttt      5160
tgtaagaggt tccaactttc accataatga aataagatca ctaccgggcg tattttttga      5220
gttatcgaga ttttcaggag ctaaggaagc taaaatggag aaaaaaatca ctggatatac      5280
caccgttgat atatcccaat ggcatcgtaa agaacatttt gaggcatttc agtcagttgc      5340
tcaatgtacc tataaccaga ccgttcagct ggatattacg gcctttttaa agaccgtaaa      5400
gaaaaataag cacaagtttt atccggcctt tattcacatt cttgcccgcc tgatgaatgc      5460
tcatccggag tttcgtatgg caatgaaaga cggtgagctg gtgatatggg atagtgttca      5520
cccttgttac accgttttcc atgagcaaac tgaaacgttt tcatcgctct ggagtgaata      5580
ccacgacgat ttccggcagt ttctacacat atattcgcaa gatgtggcgt gttacggtga      5640
aaacctggcc tatttcccta aagggtttat tgagaatatg ttttcgtct cagccaatcc       5700 ctgggtgagt ttcaccagtt ttgatttaaa cgtggccaat atggacaact tcttcgcccc      5760
cgttttcacc atgggcaaat attatacgca aggcgacaag gtgctgatgc cgctggcgat      5820
tcaggttcat catgccgttt gtgatggctt ccatgtcggc agaatgctta atgaattaca      5880
acagtactgc gatgagtggc agggcggggc gtaattttt taaggcgaca ccatcgaatg       5940
gcgcaaaacc tttcgcggta tggcatgata gcgcccggaa gagagtcaat tcagggtggt      6000
gaatgtgaaa ccagtaacgt tatacgatgt cgcagagtat gccggtgtct cttatcagac      6060
cgtttcccgc gtggtgaacc aggccagcca cgtttctgcg aaaacgcggg aaaaagtgga      6120
agcggcgatg gcggagctga attacattcc caaccgcgtg gcacaacaac tggcgggcaa      6180
acagtcgttg ctgattggcg ttgccacctc cagtctggcc ctgcacgcgc cgtcgcaaat      6240
tgtcgcggcg attaaatctc gcgccgatca actgggtgcc agcgtggtgg tgtcgatggt      6300
agaacgaagc ggcgtcgaag cctgtaaagc ggcggtgcac aatcttctcg cgcaacgcgt      6360
cagtgggctg atcattaact atccgctgga tgaccaggat gccattgctg tggaagctgc      6420
ctgcactaat gttccggcgt tatttcttga tgtctctgac cagacaccca tcaacagtat      6480
tattttctcc catgaagacg gtacgcgact gggcgtggag catctggtcg cattgggtca      6540
```

| | |
|---|---|
| ccagcaaatc gcgctgttag cgggcccatt aagttctgtc tcggcgcgtc tgcgtctggc | 6600 |
| tggctggcat aaatatctca ctcgcaatca aattcagccg atagcggaac gggaaggcga | 6660 |
| ctggagtgcc atgtccggtt ttcaacaaac catgcaaatg ctgaatgagg gcatcgttcc | 6720 |
| cactgcgatg ctggttgcca acgatcagat ggcgctgggc gcaatgcgcg ccattaccga | 6780 |
| gtccgggctg cgcgttggtg cggatatctc ggtagtggga tacgacgata ccgaagacag | 6840 |
| ctcatgttat atcccgccgt taaccaccat caaacaggat tttcgcctgc tggggcaaac | 6900 |
| cagcgtggac cgcttgctgc aactctctca gggccaggcg gtgaagggca atcagctgtt | 6960 |
| gcccgtctca ctggtgaaaa gaaaaaccac cctggcgccc aatacgcaaa ccgcctctcc | 7020 |
| ccgcgcgttg gccgattcat taatgcagct ggcacgacag gtttcccgac tggaaagcgg | 7080 |
| gcaagtgagt ggataaccgt attaccgcct ttgagtgagc tgataccggg aattctcact | 7140 |
| cattaggcac cccaggc | 7157 |

<210> SEQ ID NO 19
<211> LENGTH: 4341
<212> TYPE: DNA
<213> ORGANISM: Artificial Sequence
<220> FEATURE:
<223> OTHER INFORMATION: pET-9a

<400> SEQUENCE: 19

| | |
|---|---|
| ttctcatgtt tgacagctta tcatcgataa gctttaatgc ggtagtttat cacagttaaa | 60 |
| ttgctaacgc agtcaggcac cgtgtatgaa atctaacaat gcgctcatcg tcatcctcgg | 120 |
| caccgtcacc ctggatgctg taggcatagg cttggttatg ccgtactgcc gggcctctt | 180 |
| gcgggatatc gtccattccg acagcatcgc cagtcactat ggcgtgctgc tagcgctata | 240 |
| tgcgttgatg caatttctat gcgcacccgt tctcggagca ctgtccgacc gctttggccg | 300 |
| ccgcccagtc ctgctcgctt cgctacttgg agccactatc gactacgcga tcatggcgac | 360 |
| cacacccgtc ctgtggatat ccggatatag ttcctccttt cagcaaaaaa cccctcaaga | 420 |
| cccgtttaga ggcccaagg ggttatgcta gttattgctc agcggtggca gcagccaact | 480 |
| cagcttcctt tcgggctttg ttagcagccg gatccgcgac ccatttgctg tccaccagtc | 540 |
| atgctagcca tatgtatatc tccttcttaa agttaaacaa aattatttct agagggaaac | 600 |
| cgttgtggtc tccctatagt gagtcgtatt aatttcgcgg gatcgagatc tcgatcctct | 660 |
| acgccggacg catcgtggcc ggcatcaccg gcgccacagg tgcggttgct ggcgcctata | 720 |
| tcgccgacat caccgatggg gaagatcggg ctcgccactt cgggctcatg agcgcttgtt | 780 |
| tcggcgtggg tatggtggca ggccccgtgg ccggggact gttgggcgcc atctccttgc | 840 |
| atgcaccatt ccttgcggcg gcggtgctca acggcctcaa cctactactg gctgcttcc | 900 |
| taatgcagga gtcgcataag ggagagcgtc gaccgatgcc cttgagagcc ttcaacccag | 960 |
| tcagctcctt ccgtgggcg cggggcatga ctatcgtcgc cgcacttatg actgtcttct | 1020 |
| ttatcatgca actcgtagga caggtgccgg cagcgctctg ggtcattttc ggcgaggacc | 1080 |
| gctttcgctg gagcgcgacg atgatcggcc tgtcgcttgc ggtattcgga atcttgcacg | 1140 |
| ccctcgctca agccttcgtc actggtcccg ccaccaaacg tttcggcgag aagcaggcca | 1200 |
| ttatcgccgg catggcggcc gacgcgctgg gctacgtctt gctggcgttc gcgacgcgag | 1260 |
| gctggatggc cttccccatt atgattcttc tcgcttccgg cggcatcggg atgcccgcgt | 1320 |
| tgcaggccat gctgtccagg caggtagatg acgaccatca gggacagctt caaggatcgc | 1380 |
| tcgcggctct taccagccta acttcgatca ctggaccgct gatcgtcacg gcgatttatg | 1440 |

```
ccgcctcggc gagcacatgg aacgggttgg catggattgt aggcgccgcc ctataccttg    1500
tctgcctccc cgcgttgcgt cgcggtgcat ggagccgggc cacctcgacc tgaatggaag    1560
ccggcggcac ctcgctaacg gattcaccac tccaagaatt ggagccaatc aattcttgcg    1620
gagaactgtg aatgcgcaaa ccaacccttg cagaacata tccatcgcgt ccgccatctc     1680
cagcagccgc acgcggcgca tctcgggcag cgttgggtcc tggccacggg tgcgcatgat    1740
cgtgctcctg tcgttgagga cccggctagg ctggcggggt tgccttactg gttagcagaa    1800
tgaatcaccg atacgcgagc gaacgtgaag cgactgctgc tgcaaaacgt ctgcgacctg    1860
agcaacaaca tgaatggtct tcggtttccg tgtttcgtaa agtctggaaa cgcggaagtc    1920
agcgccctgc accattatgt tccggatctg catcgcagga tgctgctggc taccctgtgg    1980
aacacctaca tctgtattaa cgaagcgctg gcattgaccc tgagtgattt ttctctggtc    2040
ccgccgcatc cataccgcca gttgtttacc ctcacaacgt tccagtaacc gggcatgttc    2100
atcatcagta acccgtatcg tgagcatcct ctctcgtttc atcggtatca ttaccccat     2160 gaacagaaat ccccttaca cggaggcatc agtgaccaaa caggaaaaaa ccgcccttaa     2220
catggcccgc tttatcagaa gccagacatt aacgcttctg gagaaactca acgagctgga    2280
cgcggatgaa caggcagaca tctgtgaatc gcttcacgac cacgctgatg agctttaccg    2340
cagctgcctc gcgcgtttcg gtgatgacgg tgaaaacctc tgacacatgc agctcccgga    2400
gacggtcaca gcttgtctgt aagcggatgc cgggagcaga caagcccgtc agggcgcgtc    2460
agcgggtgtt ggcgggtgtc ggggcgcagc catgacccag tcacgtagcg atagcggagt    2520
gtatactggc ttaactatgc ggcatcagag cagattgtac tgagagtgca ccatatatgc    2580
ggtgtgaaat accgcacaga tgcgtaagga gaaataccg catcaggcgc tcttccgctt     2640
cctcgctcac tgactcgctg cgctcggtcg ttcggctgcg gcgagcggta tcagctcact    2700
caaaggcggt aatacggtta tccacagaat caggggataa cgcaggaaag aacatgtgag    2760
caaaaggcca gcaaaaggcc aggaaccgta aaaaggccgc gttgctggcg ttttccata    2820 ggctccgccc ccctgacgag catcacaaaa atcgacgctc aagtcagagg tggcgaaacc    2880
cgacaggact ataaagatac caggcgtttc ccctggaag ctccctcgtg cgctctcctg     2940
ttccgaccct gccgcttacc ggatacctgt ccgcctttct cccttcggga agcgtggcgc    3000
tttctcatag ctcacgctgt aggtatctca gttcggtgta ggtcgttcgc tccaagctgg    3060
gctgtgtgca cgaaccccc gttcagcccg accgctgcgc cttatccggt aactatcgtc     3120
ttgagtccaa cccggtaaga cacgacttat cgccactggc agcagccact ggtaacagga    3180
ttagcagagc gaggtatgta ggcggtgcta cagagttctt gaagtggtgg cctaactacg    3240
gctacactag aaggacagta tttggtatct gcgctctgct gaagccagtt accttcggaa    3300
aaagagttgg tagctcttga tccggcaaac aaaccaccgc tggtagcggt ggtttttttg    3360
tttgcaagca gcagattacg cgcagaaaaa aaggatctca agaagatcct ttgatctttt    3420
ctacggggtc tgacgctcag tggaacgaaa actcacgtta agggattttg gtcatgaaca    3480
ataaaactgt ctgcttacat aaacagtaat acaggggtg ttatgagcca tattcaacgg    3540
gaaacgtctt gctcgaggcc gcgattaaat tccaacatgg atgctgattt atatgggtat    3600
aaatgggctc gcgataatgt cgggcaatca ggtgcgacaa tctatcgatt gtatgggaag    3660
cccgatgcgc cagagttgtt tctgaaacat ggcaaaggta cgttgccaa tgatgttaca    3720 gatgagatgg tcagactaaa ctggctgacg gaatttatgc ctcttccgac catcaagcat    3780
```

| | |
|---|---|
| tttatccgta ctcctgatga tgcatggtta ctcaccactg cgatcccgg gaaaacagca | 3840 |
| ttccaggtat tagaagaata tcctgattca ggtgaaaata ttgttgatgc gctggcagtg | 3900 |
| ttcctgcgcc ggttgcattc gattcctgtt tgtaattgtc cttttaacag cgatcgcgta | 3960 |
| tttcgtctcg ctcaggcgca atcacgaatg aataacggtt tggttgatgc gagtgatttt | 4020 |
| gatgacgagc gtaatggctg gcctgttgaa caagtctgga agaaatgca taagcttttg | 4080 |
| ccattctcac cggattcagt cgtcactcat ggtgatttct cacttgataa ccttattttt | 4140 |
| gacgagggga aattaatagg ttgtattgat gttggacgag tcggaatcgc agaccgatac | 4200 |
| caggatcttg ccatcctatg gaactgcctc ggtgagtttt ctccttcatt acagaaacgg | 4260 |
| cttttttcaaa aatatggtat tgataatcct gatatgaata aattgcagtt tcatttgatg | 4320 |
| ctcgatgagt ttttctaaga a | 4341 |

<210> SEQ ID NO 20
<211> LENGTH: 4981
<212> TYPE: DNA
<213> ORGANISM: Artificial Sequence
<220> FEATURE:
<223> OTHER INFORMATION: pGEX-6P-1_NoGST

<400> SEQUENCE: 20

| | |
|---|---|
| acgttatcga ctgcacggtg caccaatgct tctggcgtca ggcagccatc ggaagctgtg | 60 |
| gtatggctgt gcaggtcgta atcactgca taattcgtgt cgctcaaggc gcactcccgt | 120 |
| tctggataat gttttttgcg ccgacatcat aacggttctg gcaaatattc tgaaatgagc | 180 |
| tgttgacaat taatcatcgg ctcgtataat gtgtggaatt gtgagcggat aacaatttca | 240 |
| cacaggaaac agtattctcc cctatactag gttattggaa aattaagggc cttgtgcaac | 300 |
| ccactcgact tcttttggaa tatcttgaag aaaaatatga agagcatttg tatgagcgcg | 360 |
| atgaaggtga taaatggcga acaaaaagt tgaattggg tttggagttt cccaatcttc | 420 |
| cttattatat tgatggtgat gttaaattaa cacagtctat ggccatcata cgttatatag | 480 |
| ctgacaagca aacatgttg ggtggttgtc aaaagagcg tgcagagatt caatgcttg | 540 |
| aaggagcggt tttggatatt agatacggtg tttcgagaat tgcatatagt aaagactttg | 600 |
| aaactctcaa agttgatttt cttagcaagc tacctgaaat gctgaaaatg ttcgaagatc | 660 |
| gtttatgtca taaacatat ttaaatgtg atcatgtaac ccatcctgac ttcatgttgt | 720 |
| atgacgctct tgatgttgtt ttatacatgg acccaatgtg cctggatgcg ttcccaaaat | 780 |
| tagtttgttt taaaaaacgt attgaagcta tcccacaaat tgataagtac ttgaaatcca | 840 |
| gcaagtatat agcatggcct tgcagggct ggcaagccac gtttggtggt ggcgaccatc | 900 |
| ctccaaaatc ggatctggaa gttctgttcc agggggccct gggatcccg gaattcccgg | 960 |
| gtcgactcga gcggccgcat cgtgactgac tgacgatctg cctcgcgcgt ttcggtgatg | 1020 |
| acggtgaaaa cctctgacac atgcagctcc cggagacggt cacagcttgt ctgtaagcgg | 1080 |
| atgccgggag cagacaagcc cgtcagggcg cgtcagcggg tgttggcggg tgtcggggcg | 1140 |
| cagccatgac ccagtcacgt agcgatagcg gagtgtataa ttcttgaaga cgaaagggcc | 1200 |
| tcgtgatacg cctatttta taggttaatg tcatgataat aatggtttct tagacgtcag | 1260 |
| gtggcacttt tcggggaaat gtgcgcggaa cccctatttg tttattttc taaatacatt | 1320 |
| caaatatgta tccgctcatg agacaataac cctgataaat gcttcaataa tattgaaaaa | 1380 |
| ggaagagtat gagtattcaa catttccgtg tcgcccttat tccctttttt gcggcatttt | 1440 |
| gccttcctgt ttttgctcac ccagaaacgc tggtgaaagt aaaagatgct gaagatcagt | 1500 |

```
tgggtgcacg agtgggttac atcgaactgg atctcaacag cggtaagatc cttgagagtt    1560
ttcgccccga agaacgtttt ccaatgatga gcacttttaa agttctgcta tgtggcgcgg    1620
tattatcccg tgttgacgcc gggcaagagc aactcggtcg ccgcatacac tattctcaga    1680
atgacttggt tgagtactca ccagtcacag aaaagcatct tacgatggc atgacagtaa     1740
gagaattatg cagtgctgcc ataaccatga gtgataacac tgcggccaac ttacttctga    1800
caacgatcgg aggaccgaag gagctaaccg cttttttgca caacatgggg gatcatgtaa    1860
ctcgccttga tcgttgggaa ccggagctga atgaagccat accaaacgac gagcgtgaca    1920
ccacgatgcc tgcagcaatg gcaacaacgt tgcgcaaact attaactggc gaactactta    1980
ctctagcttc ccggcaacaa ttaatagact ggatggaggc ggataaagtt gcaggaccac    2040
ttctgcgctc ggcccttccg gctggctggt ttattgctga taaatctgga gccggtgagc    2100
gtgggtctcg cggtatcatt gcagcactgg ggccagatgg taagccctcc cgtatcgtag    2160
ttatctacac gacggggagt caggcaacta tggatgaacg aaatagacag atcgctgaga    2220
taggtgcctc actgattaag cattggtaac tgtcagacca agtttactca tatatacttt    2280
agattgattt aaaacttcat ttttaattta aaaggatcta ggtgaagatc ctttttgata    2340
atctcatgac caaaatccct taacgtgagt tttcgttcca ctgagcgtca gaccccgtag    2400
aaaagatcaa aggatcttct tgagatcctt ttttctgcg cgtaatctgc tgcttgcaaa     2460
caaaaaaacc accgctacca gcggtggttt gtttgccgga tcaagagcta ccaactcttt    2520
ttccgaaggt aactggcttc agcagagcgc agataccaaa tactgtcctt ctagtgtagc    2580
cgtagttagg ccaccacttc aagaactctg tagcaccgcc tacatacctc gctctgctaa    2640
tcctgttacc agtggctgct gccagtggcg ataagtcgtg tcttaccggg ttggactcaa    2700
gacgatagtt accggataag gcgcagcggt cgggctgaac ggggggttcg tgcacacagc    2760
ccagcttgga gcgaacgacc tacaccgaac tgagatacct acagcgtgag ctatgagaaa    2820
gcgccacgct tcccgaaggg agaaaggcgg acaggtatcc ggtaagcggc agggtcggaa    2880
caggagagcg cacgagggag cttccagggg gaaacgcctg gtatctttat agtcctgtcg    2940
ggtttcgcca cctctgactt gagcgtcgat ttttgtgatg ctcgtcaggg gggcggagcc    3000
tatgaaaaa cgccagcaac gcggcctttt tacggttcct ggccttttgc tggccttttg     3060
ctcacatgtt ctttcctgcg ttatcccctg attctgtgga taaccgtatt accgcctttg    3120
agtgagctga taccgctcgc cgcagccgaa cgaccgagcg cagcgagtca gtgagcgagg    3180
aagcggaaga gcgcctgatg cggtattttc tccttacgca tctgtgcggt atttcacacc    3240
gcataaattc cgacaccatc gaatggtgca aaacctttcg cggtatggca tgatagcgcc    3300
cggaagagag tcaattcagg gtggtgaatg tgaaaccagt aacgttatac gatgtcgcag    3360
agtatgccgg tgtctcttat cagaccgttt cccgcgtggt gaaccaggcc agccacgttt    3420
ctgcgaaaac gcgggaaaaa gtggaagcgg cgatggcgga gctgaattac attcccaacc    3480
gcgtggcaca acaactggcg ggcaaacagt cgttgctgat tggcgttgcc acctccagtc    3540
tggccctgca cgcgccgtcg caaattgtcg cggcgattaa atctcgcgcc gatcaactgg    3600
gtgccagcgt ggtggtgtcg atggtagaac gaagcggcgt cgaagcctgt aaagcggcgg    3660
tgcacaatct tctcgcgcaa cgcgtcagtg ggctgatcat taactatccg ctggatgacc    3720
aggatgccat tgctgtggaa gctgcctgca ctaatgttcc ggcgttattt cttgatgtct    3780
ctgaccagac acccatcaac agtattattt tctcccatga agacggtacg cgactgggcg    3840
```

| | |
|---|---|
| tggagcatct ggtcgcattg ggtcaccagc aaatcgcgct gttagcgggc ccattaagtt | 3900 |
| ctgtctcggc gcgtctgcgt ctggctggct ggcataaata tctcactcgc aatcaaattc | 3960 |
| agccgatagc ggaacgggaa ggcgactgga gtgccatgtc cggttttcaa caaaccatgc | 4020 |
| aaatgctgaa tgagggcatc gttcccactg cgatgctggt tgccaacgat cagatggcgc | 4080 |
| tgggcgcaat gcgcgccatt accgagtccg ggctgcgcgt tggtgcggat atctcggtag | 4140 |
| tgggatacga cgataccgaa gacagctcat gttatatccc gccgtcaacc accatcaaac | 4200 |
| aggattttcg cctgctgggg caaaccagcg tggaccgctt gctgcaactc tctcagggcc | 4260 |
| aggcggtgaa gggcaatcag ctgttgcccg tctcactggt gaaagaaaaa accaccctgg | 4320 |
| cgcccaatac gcaaaccgcc tctccccgcg cgttggccga ttcattaatg cagctggcac | 4380 |
| gacaggtttc ccgactggaa agcgggcagt gagcgcaacg caattaatgt gagttagctc | 4440 |
| actcattagg caccccaggc tttacacttt atgcttccgg ctcgtatgtt gtgtggaatt | 4500 |
| gtgagcggat aacaatttca cacaggaaac agctatgacc atgattacgg attcactggc | 4560 |
| cgtcgtttta caacgtcgtg actgggaaaa ccctggcgtt acccaactta atcgccttgc | 4620 |
| agcacatccc cctttcgcca gctggcgtaa tagcgaagag gcccgcaccg atcgcccttc | 4680 |
| ccaacagttg cgcagcctga atggcgaatg gcgctttgcc tggtttccgg caccagaagc | 4740 |
| ggtgccggaa agctggctgg agtgcgatct tcctgaggcc gatactgtcg tcgtccctc | 4800 |
| aaactggcag atgcacggtt acgatgcgcc catctacacc aacgtaacct atcccattac | 4860 |
| ggtcaatccg ccgtttgttc ccacggagaa tccgacgggt tgttactcgc tcacatttaa | 4920 |
| tgttgatgaa agctggctac aggaaggcca gacgcgaatt ttttgatg gcgttggaat | 4980 |
| t | 4981 |

<210> SEQ ID NO 21
<211> LENGTH: 7321
<212> TYPE: DNA
<213> ORGANISM: Artificial Sequence
<220> FEATURE:
<223> OTHER INFORMATION: pGEX-6P-1_NoGST_Brk-CBM

<400> SEQUENCE: 21

| | |
|---|---|
| acgttatcga ctgcacggtg caccaatgct tctggcgtca ggcagccatc ggaagctgtg | 60 |
| gtatggctgt gcaggtcgta aatcactgca taattcgtgt cgctcaaggc gcactcccgt | 120 |
| tctggataat gttttttgcg ccgacatcat aacggttctg gcaaatattc tgaaatgagc | 180 |
| tgttgacaat taatcatcgg ctcgtataat gtgtggaatt gtgagcggat aacaatttca | 240 |
| cacaggaaac agtattctcc cctatactag gttattggaa aattaagggc cttgtgcaac | 300 |
| ccactcgact tcttttggaa tatcttgaag aaaaatatga agagcatttg tatgagcgcg | 360 |
| atgaaggtga taaatggcga aacaaaaagt tgaattgggt tttggagttt cccaatcttc | 420 |
| cttattatat tgatggtgat gttaaattaa cacagtctat ggccatcata cgttatatag | 480 |
| ctgacaagca caacatgttg ggtggttgtc caaaagagcg tgcagagatt tcaatgcttg | 540 |
| aaggagcggt tttggatatt agatacggtg tttcgagaat tgcatatagt aaagactttg | 600 |
| aaactctcaa agttgatttt cttagcaagc tacctgaaat gctgaaaatg ttcgaagatc | 660 |
| gtttatgtca taaacatat ttaaatggtg atcatgtaac ccatcctgac ttcatgttgt | 720 |
| atgacgctct tgatgttgtt ttatacatgg acccaatgtg cctggatgcg ttcccaaaat | 780 |
| tagtttgttt taaaaaacgt attgaagcta tcccacaaat tgataagtac ttgaaatcca | 840 |
| gcaagtatat agcatggcct ttgcagggct ggcaagccac gtttggtggt ggcgaccatc | 900 |

```
ctccaaaatc ggatctggaa gttctgttcc aggggcccct gggatccatg tatctggatc      960
gctttcgcca gtgcccgagc agcctgcaga ttccgcgcag cgcgtggcgc ctgcatgcgc     1020
tggcggcggc gctggcgctg gcgggcatgg cgcgcctggc gccggcggcg gcgcaggcgc     1080
cgcagccgcc ggtggcgggc gcgccgcatg cgcaggatgc gggccaccat caccatcacc     1140
atgttcagct ggttgaaagc ggtggtgcac tggttcagcc tggtggtagc ctgcgtctga     1200
gctgtgcagc aagcggtttt ccggttaatc gttatagcat gcgttggtat cgtcaggcac     1260
cgggtaaaga acgtgaatgg gttgcaggta tgagcagtgc cggtgatcgt agcagctacg     1320
aagatagcgt taaaggtcgt tttaccatca gccgtgatga tgcacgtaat accgtttatc     1380
tgcaaatgaa tagcctgaaa ccggaagata ccgcagtgta ttattgcaac gttaacgtgg     1440
gctttgaata ttggggtcag ggcacccagg ttaccgttag cagcaaactc gagcggccgc     1500
atcgtgacgc gtcgtctggt cctgccggct gccaagtcct tgggcgtgaa tcagtggaa     1560 acacaggttt cacggcgaat gttaccgtca agaatacgtc ctccgctcct gttgacggct     1620
ggaccttgac cttcagtttc ccatcaggac aacaagtcac tcaagcctgg tcatctaccg     1680
tgacccagag tggatctgcg gtcacagtac gtaacgctcc gtggaacggt tcgattcccg     1740
cgggcgggac tgctcagttc gggtttaacg gaagccacac tggcactaat gctgcaccaa     1800
ctgccttctc acttaacggc acgccgtgca ccgtaggcga acagaaactg attagcgaag     1860
aagatctgga aaacctgtac ttccagggtg cgggcattag cctgagcgtg gcgagcggcg     1920
cggcgtggca tggcgcgacc caggtgctgc agagcgcgac cctgggcaaa ggcggcacct     1980
gggtggtgaa cgcggatagc cgcgtgcagg atatgagcat gcgcggcggc gcgtggaat     2040 ttcaggcgcc ggcgccggaa gcgagctata aaccctgac cctgcagacc ctggatggca     2100
acggcgtgtt tgtgctgaac accaacgtgg cggcgggcca gaacgatcag ctgcgcgtga     2160
ccggccgcgc ggatggccag catcgcgtgc tggtgcgcaa cgcgggcggc gaagcggata     2220
gccgcggcgc gcgcctgggc ctggtgcata cccagggcca gggcaacgcg acctttcgcc     2280
tggcgaacgt gggcaaagcg gtggatctgg cacctggcg ctatagcctg gcggaagatc     2340
cgaaaaccca tgtgtggagc ctgcagcgcg cgggccaggc gctgagcggc gcggcgaacg     2400
cggcggtgaa cgcggcggat ctgagcagca ttgcgctggc ggaaagcaac gcgctggata     2460
aacgcctggg cgaactgcgc ctgcgcgcgg atgcgggcgg cccgtgggcg cgcaccttta     2520
gcgaacgcca gcagattagc aaccgccatg cgcgcgcgta tgatcagacc gtgagcggcc     2580
tggaaattgg cctggatcgc ggctggagcg cgagcggcgg ccgctggtat gcgggcggcc     2640
tgctgggcta tacctatgcg gatcgcacct atccgggcga tggcggcggc aaagtgaaag     2700
gcctgcatgt gggcggctat gcggcgtatg tgggcgatgg cggctattat ctggataccg     2760
tgctgcgcct gggccgctat gatcagcagt ataacattgc gggcaccgat ggcggccgcg     2820
tgaccgcgga ttatcgcacc agcggcgcgg cgtggagcct ggaaggcggc cgccgctttg     2880
aactgccgaa cgattggttt gcggaaccgc aggcggaagt gatgctgtgg cgcaccagcg     2940
gcaaacgcta tcgcgcgagc aacggcctgc gcgtgaaagt ggatgcgaac accgcgaccc     3000
tgggccgcct gggcctgcgc tttggccgcc gcattgcgct ggcggcggc aacattgtgc     3060 agccgtatgc gcgcctgggc tggacccagg aatttaaaag caccggcgat gtgcgcacca     3120
acggcattgg ccatgcgggc gcgggccgcc atggccgcgt ggaactgggc gcgggcgtgg     3180
atgcggcgct gggcaaaggc cataacctgt atgcgagcta tgaatatgcg gcgggcgatc     3240
```

```
gcattaacat tccgtggagc tttcatgcgg gctatcgcta tagcttttga gaattcccgg   3300
gtcgactcga gcggccgcat cgtgactgac tgacgatctg cctcgcgcgt ttcggtgatg   3360
acggtgaaaa cctctgacac atgcagctcc cggagacggt cacagcttgt ctgtaagcgg   3420
atgccgggag cagacaagcc cgtcaggcg cgtcagcggg tgttggcggg tgtcggggcg   3480
cagccatgac ccagtcacgt agcgatagcg gagtgtataa ttcttgaaga cgaaagggcc   3540
tcgtgatacg cctattttta taggttaatg tcatgataat aatggtttct tagacgtcag   3600
gtggcacttt tcggggaaat gtgcgcggaa cccctatttg tttattttc taaatacatt    3660
caaatatgta tccgctcatg agacaataac cctgataaat gcttcaataa tattgaaaaa   3720
ggaagagtat gagtattcaa catttccgtg tcgcccttat tcccttttt gcggcatttt    3780
gccttcctgt ttttgctcac ccagaaacgc tggtgaaagt aaaagatgct gaagatcagt   3840
tgggtgcacg agtgggttac atcgaactgg atctcaacag cggtaagatc cttgagagtt   3900
ttcgccccga agaacgtttt ccaatgatga gcacttttaa agttctgcta tgtggcgcgg   3960
tattatcccg tgttgacgcc gggcaagagc aactcggtcg ccgcatacac tattctcaga   4020
atgacttggt tgagtactca ccagtcacag aaaagcatct tacggatggc atgacagtaa   4080
gagaattatg cagtgctgcc ataaccatga gtgataacac tgcggccaac ttacttctga   4140
caacgatcgg aggaccgaag gagctaaccg cttttttgca caacatgggg gatcatgtaa   4200
ctcgccttga tcgttgggaa ccggagctga atgaagccat accaaacgac gagcgtgaca   4260
ccacgatgcc tgcagcaatg gcaacaacgt tgcgcaaact attaactggc gaactactta   4320
ctctagcttc ccggcaacaa ttaatagact ggatggaggc ggataaagtt gcaggaccac   4380
ttctgcgctc ggcccttccg gctggctggt ttattgctga taaatctgga gccggtgagc   4440
gtgggtctcg cggtatcatt gcagcactgg ggccagatgg taagccctcc cgtatcgtag   4500
ttatctacac gacggggagt caggcaacta tggatgaacg aaatagacag atcgctgaga   4560
taggtgcctc actgattaag cattggtaac tgtcagacca agtttactca tatatacttt   4620
agattgattt aaaacttcat ttttaattta aaaggatcta ggtgaagatc ctttttgata   4680
atctcatgac caaaatccct taacgtgagt tttcgttcca ctgagcgtca gaccccgtag   4740
aaaagatcaa aggatcttct tgagatcctt ttttctgcg cgtaatctgc tgcttgcaaa    4800
caaaaaaacc accgctacca gcggtggttt gtttgccgga tcaagagcta ccaactcttt   4860
ttccgaaggt aactggcttc agcagagcgc agataccaaa tactgtcctt ctagtgtagc   4920
cgtagttagg ccaccacttc aagaactctg tagcaccgcc tacatacctc gctctgctaa   4980
tcctgttacc agtggctgct gccagtggcg ataagtcgtg tcttaccggg ttggactcaa   5040
gacgatagtt accggataag gcgcagcggt cgggctgaac ggggggttcg tgcacacagc   5100
ccagcttgga gcgaacgacc tacaccgaac tgagatacct acagcgtgag ctatgagaaa   5160
gcgccacgct tcccgaaggg agaaaggcgg acaggtatcc ggtaagcggc agggtcggaa   5220
caggagagcg cacgagggag cttccagggg gaaacgcctg gtatctttat agtcctgtcg   5280
ggtttcgcca cctctgactt gagcgtcgat ttttgtgatg ctcgtcaggg gggcggagcc   5340
tatgaaaaaa cgccagcaac gcggcctttt tacggttcct ggccttttgc tggccttttg   5400
ctcacatgtt ctttcctgcg ttatcccctg attctgtgga taaccgtatt accgcctttg   5460
agtgagctga taccgctcgc cgcagccgaa cgaccgagcg cagcgagtca gtgagcgagg   5520
aagcggaaga gcgcctgatg cggtattttc tccttacgca tctgtgcggt atttcacacc   5580
gcataaattc cgacaccatc gaatggtgca aaacctttcg cggtatggca tgatagcgcc   5640
```

```
cggaagagag tcaattcagg gtggtgaatg tgaaaccagt aacgttatac gatgtcgcag    5700
agtatgccgg tgtctcttat cagaccgttt cccgcgtggt gaaccaggcc agccacgttt    5760
ctgcgaaaac gcgggaaaaa gtggaagcgg cgatggcgga gctgaattac attcccaacc    5820
gcgtggcaca acaactggcg ggcaaacagt cgttgctgat tggcgttgcc acctccagtc    5880
tggccctgca cgcgccgtcg caaattgtcg cggcgattaa atctcgcgcc gatcaactgg    5940
gtgccagcgt ggtggtgtcg atggtagaac gaagcggcgt cgaagcctgt aaagcggcgg    6000
tgcacaatct tctcgcgcaa cgcgtcagtg ggctgatcat taactatccg ctggatgacc    6060
aggatgccat tgctgtggaa gctgcctgca ctaatgttcc ggcgttattt cttgatgtct    6120
ctgaccagac acccatcaac agtattattt ctcccatga agacggtacg cgactgggcg    6180
tggagcatct ggtcgcattg ggtcaccagc aaatcgcgct gttagcgggc ccattaagtt    6240
ctgtctcggc gcgtctgcgt ctggctggct ggcataaata tctcactcgc aatcaaattc    6300
agccgatagc ggaacgggaa ggcgactgga gtgccatgtc cggttttcaa caaaccatgc    6360
aaatgctgaa tgagggcatc gttcccactg cgatgctggt tgccaacgat cagatggcgc    6420
tgggcgcaat gcgcgccatt accgagtccg gctgcgcgt tggtgcggat atctcggtag    6480
tgggatacga cgataccgaa gacagctcat gttatatccc gccgtcaacc accatcaaac    6540
aggattttcg cctgctgggg caaaccagcg tggaccgctt gctgcaactc tctcagggcc    6600
aggcggtgaa gggcaatcag ctgttgcccg tctcactggt gaaagaaaaa accaccctgg    6660
cgcccaatac gcaaaccgcc tctccccgcg cgttggccga ttcattaatg cagctggcac    6720
gacaggtttc ccgactggaa agcgggcagt gagcgcaacg caattaatgt gagttagctc    6780
actcattagg cacccaggc tttacacttt atgcttccgg ctcgtatgtt gtgtggaatt    6840
gtgagcggat aacaatttca cacaggaaac agctatgacc atgattacgg attcactggc    6900
cgtcgtttta caacgtcgtg actgggaaaa ccctggcgtt acccaactta atcgccttgc    6960
agcacatccc cctttcgcca gctggcgtaa tagcgaagag gcccgcaccg atcgcccttc    7020
ccaacagttg cgcagcctga atggcgaatg gcgctttgcc tggtttccgg caccagaagc    7080
ggtgccggaa agctggctgg agtgcgatct tcctgaggcc gatactgtcg tcgtcccctc    7140
aaactggcag atgcacggtt acgatgcgcc catctacacc aacgtaacct atcccattac    7200
ggtcaatccg ccgtttgttc ccacggagaa tccgacgggt tgttactcgc tcacatttaa    7260
tgttgatgaa agctggctac aggaaggcca gacgcgaatt atttttgatg gcgttggaat    7320
t                                                                    7321
```

<210> SEQ ID NO 22
<211> LENGTH: 8236
<212> TYPE: DNA
<213> ORGANISM: Artificial Sequence
<220> FEATURE:
<223> OTHER INFORMATION: pGEX-6P-1_NoGST_Brk-Lipase

<400> SEQUENCE: 22

```
acgttatcga ctgcacggtg caccaatgct tctggcgtca ggcagccatc ggaagctgtg      60
gtatggctgt gcaggtcgta atcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattctcc cctatactag gttattggaa aattaagggc cttgtgcaac     300
```

```
ccactcgact tcttttggaa tatcttgaag aaaaatatga agagcatttg tatgagcgcg    360
atgaaggtga taaatggcga aacaaaaagt ttgaattggg tttggagttt cccaatcttc    420
cttattatat tgatggtgat gttaaattaa cacagtctat ggccatcata cgttatatag    480
ctgacaagca aacatgttg ggtggttgtc caaaagagcg tgcagagatt tcaatgcttg     540
aaggagcggt tttggatatt agatacggtg tttcgagaat tgcatatagt aaagactttg    600
aaactctcaa agttgatttt cttagcaagc tacctgaaat gctgaaaatg ttcgaagatc    660
gtttatgtca taaacatat ttaaatggtg atcatgtaac ccatcctgac ttcatgttgt     720
atgacgctct tgatgttgtt ttatacatgg acccaatgtg cctggatgcg ttcccaaaat    780
tagtttgttt taaaaaacgt attgaagcta tcccacaaat tgataagtac ttgaaatcca    840
gcaagtatat agcatggcct ttgcagggct ggcaagccac gtttggtggt ggcgaccatc    900
ctccaaaatc ggatctggaa gttctgttcc aggggcccct gggatccatg tatctggatc    960
gctttcgcca gtgcccgagc agcctgcaga ttccgcgcag cgcgtggcgc ctgcatgcgc    1020
tggcggcggc gctggcgctg gcgggcatgg cgcgcctggc gccggcggcg gcgcaggcgc    1080
cgcagccgcc ggtggcgggc gcgccgcatg cgcaggatgc gggccaccat caccatcacc    1140
atgttcagct ggttgaaagc ggtggtgcac tggttcagcc tggtgtagc ctgcgtctga     1200 gctgtgcagc aagcggtttt ccggttaatc gttatagcat gcgttggtat cgtcaggcac    1260
cgggtaaaga acgtgaatgg gttgcaggta tgagcagtgc cggtgatcgt agcagctacg    1320
aagatagcgt taaaggtcgt tttaccatca gccgtgatga tgcacgtaat accgtttatc    1380
tgcaaatgaa tagcctgaaa ccggaagata ccgcagtgta ttattgcaac gttaacgtgg    1440
gctttgaata ttggggtcag ggcacccagg ttaccgttag cagcaaactc gagcggccgc    1500
atcgtgacaa tgctgtcgg attatgtttg tgttgctcgg actgtggttt gtgttcggcc     1560
tatcggtccc gggagggcgg acggaagcgg catccctacg cgccaacgac gcaccgattg    1620
tgcttctcca cgggtttacc ggctgggac gagaggaaat gtttggattc aagtattggg     1680
gcggcgtgcg cggcgatatc gaacagtggc tgaacgacaa cggttatcga acgtatacgc    1740
tggcggtcga accgctctcg agcaactggg accgggcgtg tgaagcgtac gctcagcttg    1800
tcggcgggac ggtcgattac ggggcagccc acgcggcaaa gcacggccac gcgcggtttg    1860
gccgcactta tcccggcctg ttgccggaat gaaaagggg tggccgcatc catatcatcg      1920
cccacagcca aggggggcag acggcccgca tgcttgtctc gctcctagag aacggaagcc    1980
aagaagagcg ggagtacgcc aaggcgcata acgtgtcgtt gtcaccgttg tttgaaggtg    2040
gacatcattt tgtgttgagt gtgacgacca tcgccactcc tcacgacggg acgacgcttg    2100
tcaacatggt tgatttcacc gatcgctttt ttgacttgca aaaagcggtg ttggaagcgg    2160
cggctgtcgc cagcaacgtg ccgtacacga gtcaagtata cgattttaag ctcgaccaat    2220
ggggactgcg ccgccagccg ggtgaatcgt tcgaccatta ttttgaacgg ctcaagcgct    2280
cccctgtttg gacgtccaca gataccgccc gctacgattt atccgtttcc ggagctgaga    2340
agctcaatca gtgggtgcaa gcaagcccga atacgtatta tttgagtttc tctacagaac    2400
ggacgtatcg cggagcgctc acaggcaacc attatcccga actcggaatg aacgcattca    2460
gcgcggtcgt gtgcgctccg tttctcggtt cgtaccgcaa tccgacgctc ggcattgacg    2520
accgttggtt ggagaacgat ggcattgtca atacggtttc catgaacggt ccaaagcgtg    2580
gatcaagcga tcggatcgtg ccgtatgacg ggacgttgaa aaaagggggtt tggaacgata    2640 tgggaacgta caacgtcgac catttggaaa tcatcggcgt tgacccgaat ccgtcatttg    2700
```

```
atattcgcgc cttttatttg cggcttgccg agcagttggc gagcttgcgg cctgaacaga    2760
aactgattag cgaagaagat ctggaaaacc tgtacttcca gggtgcgggc attagcctga    2820
gcgtggcgag cggcgcggcg tggcatggcg cgacccaggt gctgcagagc gcgaccctgg    2880
gcaaaggcgg cacctgggtg gtgaacgcgg atagccgcgt gcaggatatg agcatgcgcg    2940
gcggccgcgt ggaatttcag gcgccggcgc cggaagcgag ctataaaacc ctgaccctgc    3000
agaccctgga tggcaacggc gtgtttgtgc tgaacaccaa cgtggcggcg ggccagaacg    3060
atcagctgcg cgtgaccggc cgcgcggatg ccagcatcg cgtgctggtg cgcaacgcgg     3120
gcggcgaagc ggatagccgc ggcgcgcgcc tgggcctggt gcatacccag ggccagggca    3180
acgcgacctt tcgcctggcg aacgtgggca agcggtgga tctgggcacc tggcgctata     3240
gcctggcgga agatccgaaa acccatgtgt ggagcctgca gcgcgcgggc caggcgctga    3300
gcggcgcggc gaacgcggcg gtgaacgcgg cggatctgag cagcattgcg ctggcggaaa    3360
gcaacgcgct ggataaacgc ctgggcgaac tgcgcctgcg cgcggatgcg gcggcccgt     3420
gggcgcgcac ctttagcgaa cgccagcaga ttagcaaccg ccatgcgcgc gcgtatgatc    3480
agaccgtgag cggcctggaa attggcctgg atcgcggctg gagcgcgagc ggcggccgct    3540
ggtatgcggg cggcctgctg ggctataccct atgcggatcg cacctatccg ggcgatggcg    3600
gcggcaaagt gaaaggcctg catgtgggcg gctatgcggc gtatgtgggc gatgcggct     3660
attatctgga taccgtgctg cgcctgggcc gctatgatca gcagtataac attgcgggca    3720
ccgatgcgg ccgcgtgacc gcggattatc gcaccagcgg cgcggcgtgg agcctggaag     3780
gcggccgccg ctttgaactg ccgaacgatt ggtttgcgga accgcaggcg gaagtgatgc    3840
tgtggcgcac cagcggcaaa cgctatcgcg cgagcaacgg cctgcgcgtg aaagtggatg    3900
cgaacaccgc gaccctgggc cgcctgggcc tgcgctttgg ccgccgcatt cgctggcgg     3960
gcggcaacat tgtgcagccg tatgcgcgcc tgggctggac ccaggaattt aaaagcaccg    4020
gcgatgtgcg caccaacggc attggccatg cgggcgcggg ccgccatggc cgcgtggaac    4080
tgggcgcggg cgtggatgcg cgcgctgggca aaggccataa cctgtatgcg agctatgaat    4140
atgcggcggg cgatcgcatt aacattccgt ggagcttca tgcgggctat cgctatagct    4200
tttgagaatt cccgggtcga ctcgagcggc cgcatcgtga ctgactgacg atctgcctcg    4260
cgcgtttcgg tgatgacggt gaaaacctct gacacatgca gctcccggag acggtcacag    4320
cttgtctgta agcggatgcc gggagcagac aagcccgtca gggcgcgtca gcgggtgttg    4380
gcgggtgtcg gggcgcagcc atgacccagt cacgtagcga tagcggagtg tataattctt    4440
gaagacgaaa gggcctcgtg atacgcctat ttttataggt taatgtcatg ataataatgg    4500
tttcttagac gtcaggtggc acttttcggg gaaatgtgcg cggaacccct atttgtttat    4560
ttttctaaat acattcaaat atgtatccgc tcatgagaca ataaccctga taaatgcttc    4620
aataatattg aaaaaggaag agtatgagta ttcaacattt ccgtgtcgcc cttattccct    4680
tttttgcggc attttgcctt cctgttttg ctcacccaga aacgctggtg aaagtaaaag    4740
atgctgaaga tcagttgggt gcacgagtgg gttacatcga actggatctc aacagcggta    4800
agatccttga gagttttcgc cccgaagaac gttttccaat gatgagcact tttaaagttc    4860
tgctatgtgg cgcggtatta tcccgtgttg acgccgggca agagcaactc ggtcgccgca    4920
tacactattc tcagaatgac ttggttgagt actcaccagt cacagaaaag catcttacgg    4980
atggcatgac agtaagagaa ttatgcagtg ctgccataac catgagtgat aacactgcgg    5040
```

```
ccaacttact tctgacaacg atcggaggac cgaaggagct aaccgctttt ttgcacaaca   5100
tgggggatca tgtaactcgc cttgatcgtt gggaaccgga gctgaatgaa gccataccaa   5160
acgacgagcg tgacaccacg atgcctgcag caatggcaac aacgttgcgc aaactattaa   5220
ctggcgaact acttactcta gcttcccggc aacaattaat agactggatg gaggcggata   5280
aagttgcagg accacttctg cgctcggccc ttccggctgg ctggtttatt gctgataaat   5340
ctggagccgg tgagcgtggg tctcgcggta tcattgcagc actggggcca gatggtaagc   5400
cctcccgtat cgtagttatc tacacgacgg ggagtcaggc aactatggat gaacgaaata   5460
gacagatcgc tgagataggt gcctcactga ttaagcattg gtaactgtca gaccaagttt   5520
actcatatat actttagatt gatttaaaac ttcatttttta atttaaaagg atctaggtga   5580
agatcctttt tgataatctc atgaccaaaa tcccttaacg tgagttttcg ttccactgag   5640
cgtcagaccc cgtagaaaag atcaaaggat cttcttgaga tcctttttttt ctgcgcgtaa   5700 tctgctgctt gcaaacaaaa aaaccaccgc taccagcggt ggtttgtttg ccggatcaag   5760
agctaccaac tcttttttccg aaggtaactg gcttcagcag agcgcagata ccaaatactg   5820
tccttctagt gtagccgtag ttaggccacc acttcaagaa ctctgtagca ccgcctacat   5880
acctcgctct gctaatcctg ttaccagtgg ctgctgccag tggcgataag tcgtgtctta   5940
ccgggttgga ctcaagacga tagttaccgg ataaggcgca gcggtcgggc tgaacggggg   6000
gttcgtgcac acagcccagc ttggagcgaa cgacctacac cgaactgaga tacctacagc   6060
gtgagctatg agaaagcgcc acgcttcccg aagggagaaa ggcggacagg tatccggtaa   6120
gcggcagggt cggaacagga gagcgcacga gggagcttcc agggggaaac gcctggtatc   6180
tttatagtcc tgtcgggttt cgccacctct gacttgagcg tcgatttttg tgatgctcgt   6240
caggggggcg gagcctatgg aaaaacgcca gcaacgcggc ctttttacgg ttcctggcct   6300
tttgctggcc ttttgctcac atgttctttc ctgcgttatc ccctgattct gtggataacc   6360
gtattaccgc ctttgagtga gctgataccg ctcgccgcag ccgaacgacc gagcgcagcg   6420
agtcagtgag cgaggaagcg gaagagcgcc tgatgcggta ttttctcctt acgcatctgt   6480
gcggtatttc acaccgcata aattccgaca ccatcgaatg gtgcaaaacc tttcgcggta   6540
tggcatgata gcgcccggaa gagagtcaat tcagggtggt gaatgtgaaa ccagtaacgt   6600
tatacgatgt cgcagagtat gccggtgtct cttatcagac cgtttcccgc gtggtgaacc   6660
aggccagcca cgtttctgcg aaaacgcggg aaaaagtgga agcggcgatg gcggagctga   6720
attacattcc caaccgcgtg gcacaacaac tggcgggcaa acagtcgttg ctgattggcg   6780
ttgccacctc cagtctggcc ctgcacgcgc cgtcgcaaat tgtcgcggcg attaaatctc   6840
gcgccgatca actgggtgcc agcgtggtgg tgtcgatggt agaacgaagc ggcgtcgaag   6900
cctgtaaagc ggcggtgcac aatcttctcg cgcaacgcgt cagtgggctg atcattaact   6960
atccgctgga tgaccaggat gccattgctg tggaagctgc ctgcactaat gttccggcgt   7020
tatttcttga tgtctctgac cagacaccca tcaacagtat tattttctcc catgaagacg   7080
gtacgcgact gggcgtggag catctggtcg cattgggtca ccagcaaatc gcgctgttag   7140
cgggcccatt aagttctgtc tcggcgcgtc tgcgtctggc tggctggcat aaatatctca   7200
ctcgcaatca aattcagccg atagcggaac gggaaggcga ctggagtgcc atgtccggtt   7260
ttcaacaaac catgcaaatg ctgaatgagg gcatcgttcc cactgcgatg ctggttgcca   7320
acgatcagat ggcgctgggc gcaatgcgcg ccattaccga gtccgggctg cgcgttggtg   7380
cggatatctc ggtagtggga tacgacgata ccgaagacag ctcatgttat atcccgccgt   7440
```

```
caaccaccat caaacaggat tttcgcctgc tggggcaaac cagcgtggac cgcttgctgc    7500
aactctctca gggccaggcg gtgaagggca atcagctgtt gcccgtctca ctggtgaaaa    7560
gaaaaaccac cctggcgccc aatacgcaaa ccgcctctcc ccgcgcgttg gccgattcat    7620
taatgcagct ggcacgacag gtttcccgac tggaaagcgg gcagtgagcg caacgcaatt    7680
aatgtgagtt agctcactca ttaggcaccc caggctttac actttatgct tccggctcgt    7740
atgttgtgtg gaattgtgag cggataacaa tttcacacag gaaacagcta tgaccatgat    7800
tacggattca ctggccgtcg ttttacaacg tcgtgactgg gaaaaccctg gcgttaccca    7860
acttaatcgc cttgcagcac atccccettt cgccagctgg cgtaatagcg aagaggcccg    7920
caccgatcgc ccttcccaac agttgcgcag cctgaatggc gaatggcgct ttgcctggtt    7980
tccggcacca gaagcggtgc cggaaagctg gctggagtgc gatcttcctg aggccgatac    8040
tgtcgtcgtc ccctcaaact ggcagatgca cggttacgat gcgcccatct acaccaacgt    8100
aacctatccc attacggtca atccgccgtt tgttcccacg gagaatccga cgggttgtta    8160
ctcgctcaca tttaatgttg atgaaagctg gctacaggaa ggccagacgc gaattatttt    8220
tgatggcgtt ggaatt                                                   8236

<210> SEQ ID NO 23
<211> LENGTH: 6283
<212> TYPE: DNA
<213> ORGANISM: Artificial Sequence
<220> FEATURE:
<223> OTHER INFORMATION: pGEX-6P-1_NoGST_InaK-CBM

<400> SEQUENCE: 23
acgttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattctcc cctatactag gttattggaa aattaagggc cttgtgcaac     300
ccactcgact tcttttggaa tatcttgaag aaaaatatga gagcatttg tatgagcgcg     360 atgaaggtga taaatggcga aacaaaaagt ttgaattggg tttggagttt cccaatcttc     420
cttattatat tgatggtgat gttaaattaa cacagtctat ggccatcata cgttatatag     480
ctgacaagca aacatgttg ggtggttgtc aaaagagcg tgcagagatt caatgcttg       540 aaggagcggt tttggatatt agatacggtg tttcgagaat tgcatatagt aaagactttg     600
aaactctcaa agttgatttt cttagcaagc tacctgaaat gctgaaaatg ttcgaagatc     660
gtttatgtca taaacatat ttaaatgtg atcatgtaac ccatcctgac ttcatgttgt      720
atgacgctct tgatgttgtt ttatacatgg acccaatgtg cctggatgcg ttcccaaaat     780
tagtttgttt taaaaacgt attgaagcta tcccacaaat tgataagtac ttgaaatcca     840
gcaagtatat agcatggcct tgcagggct ggcaagccac gtttggtggt ggcgaccatc      900
ctccaaaatc ggatctggaa gttctgttcc aggggcccct gggatccatg gtcttagaca     960
aggcgctagt tctacgtacc tgcgctaata atatggccga tcactgcggc ttgatttggc    1020
ctgcctcagg gaccgtcgag tcaaggtatt ggcaatctac acgtcgtcac gagaacggac    1080
tggtaggtct tctttgggga gcaggaactt ctgctttctt gtcagtccat gcagacgccc    1140
gctggatcgt gtgcgaagtg gctgttgccg atattatctc cctagaggag cccggaatgg    1200
```

```
ttaaatttcc tcgggccgaa gtggtgcatg tgggcgatcg aatcagcgct tctcatttta    1260
tttcggcgcg gcaggcagat cccgcgagta cgagtacttc aacgtcgaca agtactctta    1320
ctcccatgcc cacggcaatc cccacccta tgccagcggt ggcgtcagtg acgttaccgg     1380
tggctgagca agcgcggcat gaggtgtttg atgtagctag tgtgagcgcc gcggctgctc    1440
ccgtgaacac tttacctgtc acgacacccc aaaacctcca gacggaaaac ctgtacttcc    1500
agggtgcgtc gtctggtcct gccggctgcc aagtcctttg gggcgtgaat cagtggaaca    1560
caggtttcac ggcgaatgtt accgtcaaga atacgtcctc cgctcctgtt gacggctgga    1620
ccttgacctt cagtttccca tcaggacaac aagtcactca agcctggtca tctaccgtga    1680
cccagagtgg atctgcggtc acagtacgta acgctccgtg gaacggttcg attcccgcgg    1740
gcgggactgc tcagttcggg tttaacggaa gccacactgg cactaatgct gcaccaactg    1800
ccttctcact taacggcacg ccgtgcaccg taggccacca tcaccatcac catgttcagc    1860
tggttgaaag cggtggtgca ctggttcagc ctggtggtag cctgcgtctg agctgtgcag    1920
caagcggttt tccggttaat cgttatagca tgcgttggta tcgtcaggca ccgggtaaag    1980
aacgtgaatg ggttgcaggt atgagcagtc cggtgatcg tagcagctac gaagatagcg     2040
ttaaaggtcg ttttaccatc agccgtgatg atgcacgtaa taccgtttat ctgcaaatga    2100
atagcctgaa accggaagat accgcagtgt attattgcaa cgttaacgtg ggctttgaat    2160
attgggtcca gggcacccag gttaccgtta gcagcaaact cgagcggccg catcgtgacg    2220
aacagaaact gattagcgaa gaagatctgt gagaattccc gggtcgactc gagcggccgc    2280
atcgtgactg actgacgatc tgcctcgcgc gtttcggtga tgacggtgaa aacctctgac    2340
acatgcagct cccggagacg gtcacagctt gtctgtaagc ggatgccggg agcagacaag    2400
cccgtcaggc gcgtcagcg ggtgttggcg ggtgtcgggg cgcagccatg acccagtcac     2460
gtagcgatag cggagtgtat aattcttgaa gacgaaaggg cctcgtgata cgcctatttt    2520
tataggttaa tgtcatgata taatggtttt cttagacgtc aggtggcact tttcggggaa    2580
atgtgcgcgg aaccctatt tgtttatttt tctaaataca ttcaaatatg tatccgctca     2640
tgagacaata accctgataa atgcttcaat aatattgaaa aaggaagagt atgagtattc    2700
aacatttccg tgtcgccctt attccctttt ttgcggcatt ttgccttcct gttttgctc     2760
acccagaaac gctggtgaaa gtaaaagatg ctgaagatca gttgggtgca cgagtgggtt    2820
acatcgaact ggatctcaac agcggtaaga tccttgagag ttttcgcccc gaagaacgtt    2880
ttccaatgat gagcactttt aaagttctgc tatgtggcgc ggtattatcc cgtgttgacg    2940
ccgggcaaga gcaactcggt cgccgcatac actattctca gaatgacttg gttgagtact    3000
caccagtcac agaaaagcat cttacggatg gcatgacagt aagagaatta tgcagtgctg    3060
ccataaccat gagtgataac actgcggcca acttacttct gacaacgatc ggaggaccga    3120
aggagctaac cgcttttttg cacaacatgg gggatcatgt aactcgcctt gatcgttggg    3180
aaccggagct gaatgaagcc ataccaaacg acgagcgtga ccacgatg cctgcagcaa     3240
tggcaacaac gttgcgcaaa ctattaactg gcgaactact tactctagct tcccggcaac    3300
aattaataga ctggatggag gcggataaag ttgcaggacc acttctgcgc tcggcccttc    3360
cggctggctg gtttattgct gataaatctg gagccggtga gcgtgggtct cgcggtatca    3420
ttgcagcact ggggccagat ggtaagccct cccgtatcgt agttatctac acgacgggga    3480
gtcaggcaac tatggatgaa cgaaatagac agatcgctga ataggtgcc tcactgatta    3540
agcattggta actgtcagac caagtttact catatatact ttagattgat ttaaaacttc    3600
```

```
atttttaatt taaaaggatc taggtgaaga tccttttga taatctcatg accaaaatcc    3660
cttaacgtga gttttcgttc cactgagcgt cagaccccgt agaaaagatc aaaggatctt    3720
cttgagatcc ttttttctg cgcgtaatct gctgcttgca acaaaaaaa ccaccgctac    3780
cagcggtggt ttgtttgccg gatcaagagc taccaactct ttttccgaag gtaactggct    3840
tcagcagagc gcagatacca atactgtcc ttctagtgta gccgtagtta ggccaccact    3900
tcaagaactc tgtagcaccg cctacatacc tcgctctgct aatcctgtta ccagtggctg    3960
ctgccagtgg cgataagtcg tgtcttaccg ggttggactc aagacgatag ttaccggata    4020
aggcgcagcg gtcgggctga acgggggggtt cgtgcacaca gcccagcttg gagcgaacga    4080
cctacaccga actgagatac ctacagcgtg agctatgaga aagcgccacg cttcccgaag    4140
ggagaaaggc ggacaggtat ccggtaagcg gcagggtcgg aacaggagag cgcacgaggg    4200
agcttccagg gggaaacgcc tggtatcttt atagtcctgt cgggtttcgc cacctctgac    4260
ttgagcgtcg atttttgtga tgctcgtcag ggggcggag cctatggaaa aacgccagca    4320
acgcggcctt tttacggttc ctggccttt gctggccttt tgctcacatg ttctttcctg    4380
cgttatcccc tgattctgtg gataaccgta ttaccgcctt tgagtgagct gataccgctc    4440
gccgcagccg aacgaccgag cgcagcgagt cagtgagcga ggaagcggaa gagcgcctga    4500
tgcggtattt tctccttacg catctgtgcg gtatttcaca ccgcataaat tccgacacca    4560
tcgaatggtg caaaacccttt cgcggtatgg catgatagcg cccggaagag agtcaattca    4620
gggtggtgaa tgtgaaacca gtaacgttat acgatgtcgc agagtatgcc ggtgtctctt    4680
atcagaccgt ttcccgcgtg gtgaaccagg ccagccacgt ttctgcgaaa acgcgggaaa    4740
aagtggaagc ggcgatggcg gagctgaatt acattcccaa ccgcgtggca caacaactgg    4800
cgggcaaaca gtcgttgctg attggcgttg ccacctccag tctggccctg cacgcgccgt    4860
cgcaaattgt cgcggcgatt aaatctcgcg ccgatcaact gggtgccagc gtggtggtgt    4920
cgatggtaga acgaagcggc gtcgaagcct gtaaagcggc ggtgcacaat cttctcgcgc    4980
aacgcgtcag tgggctgatc attaactatc cgctggatga ccaggatgcc attgctgtgg    5040
aagctgcctg cactaatgtt ccggcgttat ttcttgatgt ctctgaccag acacccatca    5100
acagtattat tttctcccat gaagacggta cgcgactggg cgtggagcat ctggtcgcat    5160
tgggtcacca gcaaatcgcg ctgttagcgg gcccattaag ttctgtctcg gcgcgtctgc    5220
gtctggctgg ctggcataaa tatctcactc gcaatcaaat tcagccgata gcggaacggg    5280
aaggcgactg gagtgccatg tccggttttc aacaaaccat gcaaatgctg aatgagggca    5340
tcgttcccac tgcgatgctg gttgccaacg atcagatggc gctgggcgca atgcgcgcca    5400
ttaccgagtc cgggctgcgc gttggtgcgg atatctcggt agtgggatac gacgataccg    5460
aagacagctc atgttatatc ccgccgtcaa ccaccatcaa acaggatttt cgcctgctgg    5520
ggcaaaccag cgtggaccgc ttgctgcaac tctctcaggg ccaggcggtg aagggcaatc    5580
agctgttgcc cgtctcactg gtgaaaagaa aaaccaccct ggcgcccaat acgcaaaccg    5640
cctctccccg cgcgttggcc gattcattaa tgcagctggc acgacaggtt tcccgactgg    5700
aaagcgggca gtgagcgcaa cgcaattaat gtgagttagc tcactcatta ggcacccag    5760
gctttacact ttatgcttcc ggctcgtatg ttgtgtggaa ttgtgagcgg ataacaattt    5820
cacacaggaa acagctatga ccatgattac ggattcactg gccgtcgttt tacaacgtcg    5880
tgactgggaa aaccctggcg ttacccaact taatcgcctt gcagcacatc ccccttcgc     5940
```

| | |
|---|---:|
| cagctggcgt aatagcgaag aggcccgcac cgatcgccct tcccaacagt tgcgcagcct | 6000 |
| gaatggcgaa tggcgctttg cctggtttcc ggcaccagaa gcggtgccgg aaagctggct | 6060 |
| ggagtgcgat cttcctgagg ccgatactgt cgtcgtcccc tcaaactggc agatgcacgg | 6120 |
| ttacgatgcg cccatctaca ccaacgtaac ctatcccatt acggtcaatc cgccgtttgt | 6180 |
| tcccacggag aatccgacgg gttgttactc gctcacattt aatgttgatg aaagctggct | 6240 |
| acaggaaggc cagacgcgaa ttattttttga tggcgttgga att | 6283 |

<210> SEQ ID NO 24
<211> LENGTH: 7198
<212> TYPE: DNA
<213> ORGANISM: Artificial Sequence
<220> FEATURE:
<223> OTHER INFORMATION: pGEX-6P-1_NoGST_InaK-Lipase

<400> SEQUENCE: 24

| | |
|---|---:|
| acgttatcga ctgcacggtg caccaatgct tctggcgtca ggcagccatc ggaagctgtg | 60 |
| gtatggctgt gcaggtcgta aatcactgca taattcgtgt cgctcaaggc gcactcccgt | 120 |
| tctggataat gttttttgcg ccgacatcat aacggttctg gcaaatattc tgaaatgagc | 180 |
| tgttgacaat taatcatcgg ctcgtataat gtgtggaatt gtgagcggat aacaatttca | 240 |
| cacaggaaac agtattctcc cctatactag gttattggaa aattaagggc cttgtgcaac | 300 |
| ccactcgact tcttttggaa tatcttgaag aaaaatatga gagcatttg tatgagcgcg | 360 |
| atgaaggtga taaatggcga aacaaaaagt ttgaattggg tttggagttt cccaatcttc | 420 |
| cttattatat tgatggtgat gttaaattaa cacagtctat ggccatcata cgttatatag | 480 |
| ctgacaagca aacatgttg ggtggttgtc caaagagcg tgcagagatt caatgcttg | 540 |
| aaggagcggt tttggatatt agatacgtg tttcgagaat tgcatatagt aaagactttg | 600 |
| aaactctcaa agttgatttt cttagcaagc tacctgaaat gctgaaaatg ttcgaagatc | 660 |
| gtttatgtca taaacatat ttaaatgtg atcatgtaac ccatcctgac ttcatgttgt | 720 |
| atgacgctct tgatgttgtt ttatacatgg acccaatgtg cctggatgcg ttcccaaaat | 780 |
| tagtttgttt taaaaaacgt attgaagcta tcccacaaat tgataagtac ttgaaatcca | 840 |
| gcaagtatat agcatggcct ttgcagggct ggcaagccac gtttggtggt ggcgaccatc | 900 |
| ctccaaaatc ggatctggaa gttctgttcc aggggcccct gggatccatg gtcttagaca | 960 |
| aggcgctagt tctacgtacc tgcgctaata atatggccga tcactgcggc ttgatttggc | 1020 |
| ctgcctcagg gaccgtcgag tcaaggtatt ggcaatctac acgtcgtcac gagaacggac | 1080 |
| tggtaggtct tctttgggga gcaggaactt ctgctttctt gtcagtccat gcagacgccc | 1140 |
| gctggatcgt gtgcgaagtg gctgttgccg atattatctc cctagaggag cccggaatgg | 1200 |
| ttaaatttcc tcgggccgaa gtggtgcatg tgggcgatcg aatcagcgct tctcatttta | 1260 |
| tttcggcgcg gcaggcagat cccgcgagta cgagtacttc aacgtcgaca agtactctta | 1320 |
| ctcccatgcc cacggcaatc cccaccccta tgccagcggt ggcgtcagtg acgttaccgg | 1380 |
| tggctgagca agcgcggcat gaggtgtttg atgtagctag tgtgagcgcc gcggctgctc | 1440 |
| ccgtgaacac tttacctgtc acgacacccc aaaacctcca gacggaaaac ctgtacttcc | 1500 |
| agggtaagtg ctgtcggatt atgtttgtgt tgctcggact gtggtttgtg ttcggcctat | 1560 |
| cggtcccggg agggcggacg gaagcggcat ccctacgcgc caacgacgca ccgattgtgc | 1620 |
| ttctccacgg gtttaccggc tggggacgag aggaaatgtt tggattcaag tattgggcg | 1680 |
| gcgtgcgcgg cgatatcgaa cagtggctga acgacaacgg ttatcgaacg tatacgctgg | 1740 |

```
cggtcggacc gctctcgagc aactgggacc gggcgtgtga agcgtacgct cagcttgtcg   1800
gcgggacggt cgattacggg gcagcccacg cggcaaagca cggccacgcg cggtttggcc   1860
gcacttatcc cggcctgttg ccggaattga aaaggggtgg ccgcatccat atcatcgccc   1920
acagccaagg ggggcagacg gcccgcatgc ttgtctcgct cctagagaac ggaagccaag   1980
aagagcggga gtacgccaag gcgcataacg tgtcgttgtc accgttgttt gaaggtggac   2040
atcattttgt gttgagtgtg acgaccatcg ccactcctca cgacgggacg acgcttgtca   2100
acatggttga tttcaccgat cgcttttttg acttgcaaaa agcggtgttg gaagcggcgg   2160
ctgtcgccag caacgtgccg tacacgagtc aagtatacga ttttaagctc gaccaatggg   2220
gactgcgccg ccagccgggt gaatcgttcg accattattt tgaacggctc aagcgctccc   2280
ctgtttggac gtccacagat accgcccgct acgatttatc cgtttccgga gctgagaagc   2340
tcaatcagtg ggtgcaagca agcccgaata cgtattattt gagtttctct acagaacgga   2400 cgtatcgcg agcgctcaca ggcaaccatt atcccgaact cggaatgaac gcattcagcg   2460
cggtcgtgtg cgctccgttt ctcggttcgt accgcaatcc gacgctcggc attgacgacc   2520
gttggttgga gaacgatggc attgtcaata cggtttccat gaacggtcca aagcgtggat   2580
caagcgatcg gatcgtgccg tatgacggga cgttgaaaaa aggggtttgg aacgatatgg   2640
gaacgtacaa cgtcgaccat ttggaaatca tcggcgttga cccgaatccg tcatttgata   2700
ttcgcgcctt ttatttgcgg cttgccgagc agttggcgag cttgcggcct caccatcacc   2760
atcaccatgt tcagctggtt gaaagcggtg gtgcactggt tcagcctggt ggtagcctgc   2820
gtctgagctg tgcagcaagc ggttttccgg ttaatcgtta tagcatgcgt tggtatcgtc   2880
aggcaccggg taaagaacgt gaatgggttg caggtatgag cagtgccggt gatcgtagca   2940
gctacgaaga tagcgttaaa ggtcgtttta ccatcagccg tgatgatgca cgtaataccg   3000
tttatctgca aatgaatagc ctgaaaccgg aagataccgc agtgtattat tgcaacgtta   3060
acgtgggctt tgaatattgg ggtcagggca cccaggttac cgttagcagc aaactcgagc   3120
ggccgcatcg tgacgaacag aaactgatta gcgaagaaga tctgtgagaa ttcccgggtc   3180
gactcgagcg gccgcatcgt gactgactga cgatctgcct cgcgcgtttc ggtgatgacg   3240
gtgaaaacct ctgacacatg cagctcccgg agacggtcac agcttgtctg taagcggatg   3300
ccgggagcag acaagcccgt cagggcgcgt cagcgggtgt tggcgggtgt cggggcgcag   3360
ccatgaccca gtcacgtagc gatagcggag tgtataattc ttgaagacga aagggcctcg   3420
tgatacgcct atttttatag gttaatgtca tgataataat ggtttcttag acgtcaggtg   3480 gcactttcg gggaaatgtg cgcggaaccc ctatttgttt attttctaa atacattcaa   3540 atatgtatcc gctcatgaga caataaccct gataaatgct tcaataatat tgaaaaagga   3600
agagtatgag tattcaacat ttccgtgtcg cccttattcc cttttttgcg cattttgcc   3660 ttcctgtttt tgctcaccca gaaacgctgg tgaaagtaaa agatgctgaa gatcagttgg   3720
gtgcacgagt gggttacatc gaactggatc tcaacagcgg taagatcctt gagagttttc   3780
gccccgaaga acgttttcca atgatgagca cttttaaagt tctgctatgt ggcgcggtat   3840
tatcccgtgt tgacgccggg caagagcaac tcggtcgccg catacactat tctcagaatg   3900
acttggttga gtactcacca gtcacagaaa agcatcttac ggatggcatg acagtaagag   3960
aattatgcag tgctgccata accatgagtg ataacactgc ggccaactta cttctgacaa   4020
cgatcggagg accgaaggag ctaaccgctt ttttgcacaa catgggggat catgtaactc   4080
```

```
gccttgatcg ttgggaaccg gagctgaatg aagccatacc aaacgacgag cgtgacacca    4140
cgatgcctgc agcaatggca acaacgttgc gcaaactatt aactggcgaa ctacttactc    4200
tagcttcccg gcaacaatta atagactgga tggaggcgga taaagttgca ggaccacttc    4260
tgcgctcggc ccttccggct ggctgggttta ttgctgataa atctggagcc ggtgagcgtg    4320
ggtctcgcgg tatcattgca gcactggggc cagatggtaa gccctcccgt atcgtagtta    4380
tctacacgac ggggagtcag gcaactatgg atgaacgaaa tagacagatc gctgagatag    4440
gtgcctcact gattaagcat tggtaactgt cagaccaagt ttactcatat atactttaga    4500
ttgatttaaa acttcatttt taatttaaaa ggatctaggt gaagatcctt tttgataatc    4560
tcatgaccaa aatcccttaa cgtgagtttt cgttccactg agcgtcagac cccgtagaaa    4620
agatcaaagg atcttcttga gatcctttttt ttctgcgcgt aatctgctgc ttgcaaacaa    4680
aaaaaccacc gctaccagcg gtggtttgtt tgccggatca agagctacca actcttttc    4740
cgaaggtaac tggcttcagc agagcgcaga taccaaatac tgtccttcta gtgtagccgt    4800
agttaggcca ccacttcaag aactctgtag caccgcctac atacctcgct ctgctaatcc    4860
tgttaccagt ggctgctgcc agtggcgata agtcgtgtct taccgggttg gactcaagac    4920
gatagttacc ggataaggcg cagcggtcgg gctgaacggg gggttcgtgc acacagccca    4980
gcttggagcg aacgacctac accgaactga gatacctaca gcgtgagcta tgagaaagcg    5040
ccacgcttcc cgaagggaga aaggcggaca ggtatccggt aagcggcagg gtcggaacag    5100
gagagcgcac gagggagctt ccaggggggaa acgcctggta tctttatagt cctgtcgggt    5160
ttcgccacct ctgacttgag cgtcgatttt tgtgatgctc gtcagggggg cggagcctat    5220
ggaaaaacgc cagcaacgcg gccttttttac ggttcctggc cttttgctgg ccttttgctc    5280
acatgttctt tcctgcgtta tcccctgatt ctgtggataa ccgtattacc gcctttgagt    5340
gagctgatac cgctcgccgc agccgaacga ccgagcgcag cgagtcagtg agcgaggaag    5400
cggaagagcg cctgatgcgg tattttctcc ttacgcatct gtgcggtatt tcacaccgca    5460
taaattccga caccatcgaa tggtgcaaaa cctttcgcgg tatggcatga tagcgcccgg    5520
aagagagtca attcagggtg gtgaatgtga accagtaaac gttatacgat gtcgcagagt    5580
atgccggtgt ctcttatcag accgtttccc gcgtggtgaa ccaggccagc cacgtttctg    5640
cgaaaacgcg ggaaaaagtg gaagcggcga tggcggagct gaattacatt cccaaccgcg    5700
tggcacaaca actggcgggc aaacagtcgt tgctgattgg cgttgccacc tccagtctgg    5760
ccctgcacgc gccgtcgcaa attgtcgcgg cgattaaatc tcgcgccgat caactgggtg    5820
ccagcgtggt ggtgtcgatg gtagaacgaa gcggcgtcga agcctgtaaa gcggcggtgc    5880
acaatcttct cgcgcaacgc gtcagtgggc tgatcattaa ctatccgctg gatgaccagg    5940
atgccattgc tgtggaagct gcctgcacta atgttccggc gttatttctt gatgtctctg    6000
accagacacc catcaacagt attatttttct cccatgaaga cggtacgcga ctgggcgtgg    6060
agcatctggt cgcattgggt caccagcaaa tcgcgctgtt agcgggccca ttaagttctg    6120
tctcggcgcg tctgcgtctg gctggctggc ataaatatct cactcgcaat caaattcagc    6180
cgatagcgga acgggaaggc gactggagtg ccatgtccgg ttttcaacaa accatgcaaa    6240
tgctgaatga gggcatcgtt cccactgcga tgctggttgc caacgatcag atggcgctgg    6300
gcgcaatgcg cgccattacc gagtccggGc tgcgcgttgg tgcggatatc tcggtagtgg    6360
gatacgacga taccgaagac agctcatgtt atatcccgcc gtcaaccacc atcaaacagg    6420
attttcgcct gctggggcaa accagcgtgg accgcttgct gcaactctct cagggccagg    6480
```

```
cggtgaaggg caatcagctg ttgcccgtct cactggtgaa aagaaaaacc accctggcgc   6540
ccaatacgca aaccgcctct ccccgcgcgt tggccgattc attaatgcag ctggcacgac   6600
aggtttcccg actggaaagc gggcagtgag cgcaacgcaa ttaatgtgag ttagctcact   6660
cattaggcac cccaggcttt acactttatg cttccggctc gtatgttgtg tggaattgtg   6720
agcggataac aatttcacac aggaaacagc tatgaccatg attacggatt cactggccgt   6780
cgttttacaa cgtcgtgact gggaaaaccc tggcgttacc caacttaatc gccttgcagc   6840
acatccccct ttcgccagct ggcgtaatag cgaagaggcc cgcaccgatc gcccttccca   6900
acagttgcgc agcctgaatg gcgaatggcg ctttgcctgg tttccggcac cagaagcggt   6960
gccggaaagc tggctggagt gcgatcttcc tgaggccgat actgtcgtcg tcccctcaaa   7020
ctggcagatg cacggttacg atgcgcccat ctacaccaac gtaacctatc ccattacggt   7080
caatccgccg tttgttccca cggagaatcc gacgggttgt tactcgctca catttaatgt   7140
tgatgaaagc tggctacagg aaggccagac gcgaattatt tttgatggcg ttggaatt     7198
```

<210> SEQ ID NO 25
<211> LENGTH: 21
<212> TYPE: DNA
<213> ORGANISM: Artificial Sequence
<220> FEATURE:
<223> OTHER INFORMATION: synthetic primer F2 minCKO

<400> SEQUENCE: 25
aacaacaata atgcgtgcca t                                               21

<210> SEQ ID NO 26
<211> LENGTH: 20
<212> TYPE: DNA
<213> ORGANISM: Artificial Sequence
<220> FEATURE:
<223> OTHER INFORMATION: synthetic primer R2 minCKO

<400> SEQUENCE: 26
gcgctggcga tgattaatag                                                 20

<210> SEQ ID NO 27
<211> LENGTH: 22
<212> TYPE: DNA
<213> ORGANISM: Artificial Sequence
<220> FEATURE:
<223> OTHER INFORMATION: synthetic primer F9 minCKO

<400> SEQUENCE: 27
agtaacaaca ataatgcgtg cc                                              22

<210> SEQ ID NO 28
<211> LENGTH: 16
<212> TYPE: DNA
<213> ORGANISM: Artificial Sequence
<220> FEATURE:
<223> OTHER INFORMATION: synthetic primer R9 minCKO

<400> SEQUENCE: 28
cgcgctggcg atgatt                                                     16

<210> SEQ ID NO 29
<211> LENGTH: 21
<212> TYPE: DNA
<213> ORGANISM: Artificial Sequence
<220> FEATURE:

<223> OTHER INFORMATION: synthetic primer F7 minDKO

<400> SEQUENCE: 29
ttccgcgaga gaaagaaatc g                                    21

<210> SEQ ID NO 30
<211> LENGTH: 23
<212> TYPE: DNA
<213> ORGANISM: Artificial Sequence
<220> FEATURE:
<223> OTHER INFORMATION: synthetic primer R7 minDKO

<400> SEQUENCE: 30
gaccgttcaa ccgttaaatt gat                                  23

<210> SEQ ID NO 31
<211> LENGTH: 20
<212> TYPE: DNA
<213> ORGANISM: Artificial Sequence
<220> FEATURE:
<223> OTHER INFORMATION: synthetic primer F10 minDKO

<400> SEQUENCE: 31
ctgtgttttt cttccgcgag                                      20

<210> SEQ ID NO 32
<211> LENGTH: 25
<212> TYPE: DNA
<213> ORGANISM: Artificial Sequence
<220> FEATURE:
<223> OTHER INFORMATION: synthetic primer R10 minDKO

<400> SEQUENCE: 32
tcaaccgtta aattgatccc ttttt                                25

<210> SEQ ID NO 33
<211> LENGTH: 20
<212> TYPE: DNA
<213> ORGANISM: Artificial Sequence
<220> FEATURE:
<223> OTHER INFORMATION: synthetic primer F6 minCDKO

<400> SEQUENCE: 33
tccgcgagag aaagaaatcg                                      20

<210> SEQ ID NO 34
<211> LENGTH: 17
<212> TYPE: DNA
<213> ORGANISM: Artificial Sequence
<220> FEATURE:
<223> OTHER INFORMATION: synthetic primer R6 minCDKO

<400> SEQUENCE: 34
cgcgctggcg atgatta                                         17

<210> SEQ ID NO 35
<211> LENGTH: 20
<212> TYPE: DNA
<213> ORGANISM: Artificial Sequence
<220> FEATURE:
<223> OTHER INFORMATION: synthetic primer F9 minCDKO

<400> SEQUENCE: 35
ctgtgttttt cttccgcgag                                      20

```
<210> SEQ ID NO 36
<211> LENGTH: 16
<212> TYPE: DNA
<213> ORGANISM: Artificial Sequence
<220> FEATURE:
<223> OTHER INFORMATION: synthetic primer R9 minCDKO

<400> SEQUENCE: 36
cgcgctggcg atgatt                                                       16

<210> SEQ ID NO 37
<211> LENGTH: 20
<212> TYPE: DNA
<213> ORGANISM: Artificial Sequence
<220> FEATURE:
<223> OTHER INFORMATION: synthetic primer 3'minCKO_1

<400> SEQUENCE: 37
ggccggataa aacttgtgct                                                   20

<210> SEQ ID NO 38
<211> LENGTH: 20
<212> TYPE: DNA
<213> ORGANISM: Artificial Sequence
<220> FEATURE:
<223> OTHER INFORMATION: synthetic primer 3'minCKO_2

<400> SEQUENCE: 38
agtcttcgga acatcatcgc                                                   20

<210> SEQ ID NO 39
<211> LENGTH: 20
<212> TYPE: DNA
<213> ORGANISM: Artificial Sequence
<220> FEATURE:
<223> OTHER INFORMATION: synthetic primer 5'minCKO_1

<400> SEQUENCE: 39
ccctttgccc gaagtaacaa                                                   20

<210> SEQ ID NO 40
<211> LENGTH: 20
<212> TYPE: DNA
<213> ORGANISM: Artificial Sequence
<220> FEATURE:
<223> OTHER INFORMATION: synthetic primer 5'minCKO_2

<400> SEQUENCE: 40
acggtgaaaa cctggcctat                                                   20

<210> SEQ ID NO 41
<211> LENGTH: 23
<212> TYPE: DNA
<213> ORGANISM: Artificial Sequence
<220> FEATURE:
<223> OTHER INFORMATION: synthetic primer minC_check_4_1

<400> SEQUENCE: 41
tcaatttaac ggttgaacgg tca                                               23

<210> SEQ ID NO 42
<211> LENGTH: 20
<212> TYPE: DNA
<213> ORGANISM: Artificial Sequence
<220> FEATURE:
<223> OTHER INFORMATION: synthetic primer minC_check_4_2
```

```
<400> SEQUENCE: 42
atgtcaaaca cgccaatcga                                               20

<210> SEQ ID NO 43
<211> LENGTH: 23
<212> TYPE: DNA
<213> ORGANISM: Artificial Sequence
<220> FEATURE:
<223> OTHER INFORMATION: synthetic primer minD_check_2_1

<400> SEQUENCE: 43
ttatcctccg aacaagcgtt tga                                           23

<210> SEQ ID NO 44
<211> LENGTH: 23
<212> TYPE: DNA
<213> ORGANISM: Artificial Sequence
<220> FEATURE:
<223> OTHER INFORMATION: synthetic primer minD_check_2_2

<400> SEQUENCE: 44
atggcacgca ttattgttgt tac                                           23
```